(12) United States Patent
Hafez et al.

(10) Patent No.: US 11,244,763 B2
(45) Date of Patent: *Feb. 8, 2022

(54) PREDICTING LIKELIHOOD AND SITE OF METASTASIS FROM PATIENT RECORDS

(71) Applicant: Tempus Labs, Inc., Chicago, IL (US)

(72) Inventors: Ashraf Hafez, Woodinville, WA (US); Martin Christian Stumpe, Belmont, CA (US); Nike Beaubier, Chicago, IL (US); Daniel Neems, Evanston, IL (US); Caroline Epstein, Chicago, IL (US); Adrian William George Lange, La Grange, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/373,451

(22) Filed: Jul. 12, 2021

(65) Prior Publication Data

US 2021/0343419 A1 Nov. 4, 2021

Related U.S. Application Data

(63) Continuation of application No. 17/227,120, filed on Apr. 9, 2021, now Pat. No. 11,145,416.

(Continued)

(51) Int. Cl.
*G16H 50/30* (2018.01)
*G16H 20/00* (2018.01)
(Continued)

(52) U.S. Cl.
CPC .......... *G16H 50/30* (2018.01); *G16B 20/00* (2019.02); *G16B 30/00* (2019.02); *G16H 10/60* (2018.01); *G16H 20/00* (2018.01); *G16H 50/20* (2018.01)

(58) Field of Classification Search
CPC .................................. G06Q 50/22–26
See application file for complete search history.

(56) References Cited

U.S. PATENT DOCUMENTS

2014/0127708 A1* 5/2014 Muraca ............ G01N 33/57434
435/7.1

FOREIGN PATENT DOCUMENTS

| WO | WO 2016/203262 A2 | 12/2016 |
| WO | WO 2019/152788 A1 | 8/2019 |
| WO | WO 2019/178283 A1 | 9/2019 |

OTHER PUBLICATIONS

Akagi, Ichiro, et al. "Combination of Protein Coding and Noncoding Gene Expression as a Robust Prognostic Classifier in Stage I Lung Adenocarcinoma", American Association for Cancer Research, 73 (13), Jul. 1, 2013, pp. 3821-3832.

(Continued)

*Primary Examiner* — Neal Sereboff
(74) *Attorney, Agent, or Firm* — Morgan, Lewis & Bockius LLP

(57) ABSTRACT

Systems and methods are provided for predicting metastasis of a cancer in a subject. A plurality of data elements for the subject's cancer is obtained, including sequence features comprising relative abundance values for gene expression in a cancer biopsy of the subject, optional personal characteristics about the subject, and optional clinical features related to the stage, histopathological grade, diagnosis, symptom, comorbidity, and/or treatment of the cancer in the subject, and/or a temporal element associated therewith. One or more models are applied to the plurality of data elements, determining one or more indications of whether the cancer will metastasize. A clinical report comprising the one or more indications is generated.

76 Claims, 24 Drawing Sheets

Related U.S. Application Data

(60) Provisional application No. 63/142,051, filed on Jan. 27, 2021, provisional application No. 63/007,874, filed on Apr. 9, 2020.

(51) Int. Cl.
    *G16H 50/20* (2018.01)
    *G16H 10/60* (2018.01)
    *G16B 30/00* (2019.01)
    *G16B 20/00* (2019.01)

(56) References Cited

OTHER PUBLICATIONS

Albain, Kathy S., et al. "Prognostic and predictive value of the 21-gene recurrence score assay in postmenopausal women with node-positive, oestrogen-receptor-positive breast cancer on chemotherapy: a retrospective analysis of a randomised trial", Lancet Oncol, Jan. 2010, vol. 11, pp. 55-65.

Amann, Joseph M., et al. "Genetic and Proteomic Features Associated with Survival after Treatment with Erlotinib in First-Line Therapy of Non-small Cell Lung Cancer in Eastern Cooperative Oncology Group 3503", Journal of Thoracic Oncology, vol. 5, No. 2, Feb. 2010, pp. 169-178.

Bueno-de-Mesquita, Jolien M., et al. "Use of 70-gene signature to predict prognosis of patients with node-negative breast cancer: a prospective community-based feasibility study (RASTER)", Lancet Oncol, 2007, vol. 8, pp. 1079-1087.

Buyse, Marc, et al. "Validation and Clinical Utility of a 70-Gene Prognostic Signature for Women With Node-Negative Breast Cancer", Journal of the National Cancer Institute, vol. 98, No. 17, Sep. 6, 2006, pp. 1183-1192.

Carbone, David P., et al. "VeriStrat® classifier for survival and time to progression in non-small cell lung cancer (NSCLC) patients treated with erlotinib and bevacizumab", Lung Cancer, vol. 69 (2010), pp. 337-340.

Cardoso, F., et al. "70-Gene Signature as an Aid to Treatment Decisions in Early-Stage Breast Cancer", The New England Journal of Medicine, Aug. 25, 2016, vol. 375, No. 8, pp. 717-729.

Chen, Er, et al. "Cost-Effectiveness of 70-Gene MammaPrint Signature in Node-Negative Breast Cancer".

Dowsett, Mitch, et al. "Prediction of Risk of Distant Recurrence Using the 21-Gene Recurrence Score in Node-Negative and Node-Positive Postmenopausal Patients With Breast Cancer Treated With Anastrozole or Tamoxifen: A TransATAC Study", Journal of Clinical Oncology, vol. 28, No. 11, Apr. 10, 2010, pp. 1829-1834.

Esserman, Laura J., et al. "Use of Molecular Tools to Identify Patients With Indolent Breast Cancers With Ultralow Risk Over 2 Decades", JAMA Oncology, Nov. 2017, vol. 3, No. 11, pp. 1503-1510.

Esteva, Francisco J., et al. "Prognostic Role of a Multigene Reverse Transcriptase-PCR Assay in Patients with Node-Negative Breast Cancer Not Receiving Adjuvant Systemic Therapy", Clinical Cancer Research, May 1, 2005, vol. 11, (9), pp. 3315-3319.

Gray, Richard G., et al. "Validation Study of a Quantitative Multigene Reverse Transcriptase-Polymerase Chain Reaction Assay for Assessment of Recurrence Risk in Patients With Stage II Colon Cancer", Journal of Clinical Oncology, vol. 29, No. 35, Dec. 10, 2011, pp. 4611-4619.

Habel, Laurel A., et al. "A population-based study of tumor gene expression and risk of breast cancer death among lymph node-negative patients", Breast Cancer Research, vol. 8, No. 3, pp. 1-15.

Kopetz, Scott, et al. "Genomic Classifier ColoPrint Predicts Recurrence in Stage II Colorectal Cancer Patients More Accurately Than Clinical Factors", The Oncologist, 2015, vol. 20, pp. 127-133.

Kratz, Johannes R., et al. "A practical molecular assay to predict survival in resected non-squamous, non-small-cell lung cancer: development and international validation studies", Lancet Mar. 3, 2012, vol. 379, pp. 823-832.

Kratz, Johannes R., et al "A Prognostic Assay to Identify Patients at High Risk of Mortality Despite Small, Node-Negative Lung Tumors ", JAMA, Oct. 24/31, 2012, vol. 308, No. 16, pp. 1629-1631.

Lee, Siow Ming, et al. "The clinical role of VeriStrat testing in patients with advanced non-small cell lung cancer considered unfit of r first-line platinum-based chemotherapy", European Journal of Cancer, 120 (2019), pp. 86-96.

Maak, Matthias, et al. "Independent Validation of a Prognostic Genomic Signature (ColoPrint) for Patients With Stage II Colon Cancer", Annals of Surgery, vol. 257, No. 6, Jun. 2013, pp. 1053-1058.

Mook, Stella, et al. "The 70-gene prognosis-signature predicts disease outcome in breast cancer patients with 1-3 positive lymph nodes in an independent validation study", Breast Cancer Res. Treat (2009), 116, pp. 295-302.

O'Connell, Michael J., et al. "Relationship Between Tumor Gene Expression and Recurrence in Four Independent Studies of Patients With Stage II/III Colon Cancer Treated With Surgery Alone or Surgery Plus Adjuvant Fluorouracil Plus Leucovorin", Journal of Clinical Oncology, vol. 28, No. 25, Sep. 1, 2010, pp. 3937-3944.

Pagès, Franck, et al. "International validation of the consensus Immunoscore for the classification of colon cancer: a prognostic and accuracy study", Lancet, May 26, 2018, vol. 391, pp. 2128-2139.

Paik, Soonmyung, et al. "Gene Expression and Benefit of Chemotherapy in Women With Node-Negative, Estrogen Receptor-Positive Breast Cancer", Journal of Clinical Oncology, vol. 24, No. 23, Aug. 10, 2006, pp. 3726-3734.

Paik, Soonmyung, et al. "A Multigene Assay to Predict Recurrence of Tamoxifen-Treated, Node-Negative Breast Cancer", The New England Journal of Medicine, 351; 27, Dec. 30, 2004, pp. 2817-2826.

Salazar, Ramon, et al. "Gene Expression Signature to Improve Prognosis Prediction of Stage II and III Colorectal Cancer", Journal of Clinical Oncology, vol. 29, No. 1, Jan. 1, 2011, pp. 17-24.

Sparano, J.A., et al. "Adjuvant Chemotherapy Guided by a 21-Gene Expression Assay in Breast Cancer", The New England Journal of Medicine, vol. 379, No. 2, pp. 111-121.

Tabernero, Josep, et al. "Clinical and technical validation of a genomic classifier (ColoPrint) for predicting outcome of patients with stage II colon cancer", Journal of Clinical Oncology, Abstract only, vol. 30, Issue 4, pp. 2.

Taguchi, Fumiko, et al. "Mass Spectrometry to Classify Non-Small-Cell Lung Cancer Patients for Clinical Outcome After Treatment With Epidermal Growth Factor Receptor Tyrosine Kinase Inhibitors: A Multicohort Cross-Institutional Study", JNCI, vol. 99, Issue 11, Jun. 6, 2007, pp. 838-846.

Toi, Masakazu, et al. "Clinical Significance of the 21-Gene Signature (Oncotype DX) in Hormone Receptor-Positive Early Stage Primary Breast Cancer in the Japanese Population", Cancer, Jul. 1, 2010, pp. 3112-3118.

Tsai, Michaela, et al. "Association of 70-Gene Signature Assay Findings With Physicians' Treatment Guidance for Patients With Early Breast Cancer Classified as Intermediate Risk by the 21-Gene Assay", JAMA Oncology, vol. 4, No. 1, Jan. 2018, pp. 7.

Van't Veer, Laura J., et al. "Gene expression profiling predicts clinical outcome of breast cancer", Nature, vol. 415, Jan. 31, 2002, pp. 530-536.

Venook, Alan P., et al. "Biologic Determinants of Tumor Recurrence in Stage II Colon Cancer: Validation Study of the 12-Gene Recurrence Score in Cancer and Leukemia Group B (CALGB) 9581", Journal of Clinical Oncology, vol. 31, No. 14, May 10, 2013, pp. 1775-1781.

Wittner, Ben S. et al., "Analysis of the MammaPrint Breast Cancer Assay in a Predominantly Postmenopausal Cohort", Clinical Cancer Research, 14, (10), May 15, 2008, pp. 2988-2993.

Woodard, Gavitt A. et al., "Prognostic Molecular Assay Might Improve Identification of Patients At Risk for Recurrence in Early-Stage NoneSmall-Cell Lung Cancer", Clinical Lung Cancer, vol. 15, No. 6, 2014, pp. 426-432.

Woodard, Gavitt A. et al., "Adjuvant chemotherapy guided by molecular profiling and improved outcomes in early stage, non-small cell lung cancer", Clinical Lung Cancer, Reference: CLLC 656, Accepted Manuscript Date: May 16, 2017, pp. 26.

(56) References Cited

OTHER PUBLICATIONS

Yamanaka, Takeharu et al., "12-Gene Recurrence Score Assay Stratifies the Recurrence Risk in Stage II/III Colon Cancer With Surgery Alone: The SUNRISE Study", Journal of Clinical Oncology, vol. 34, No. 24, Aug. 24, 2016, pp. 2906-2913.

Yothers, Greg, et al. "Validation of the 12-Gene Colon Cancer Recurrence Score in NSABP C-07 As a Predictor of Recurrence in Patients With Stage II and III Colon Cancer Treated With Fluorouracil and Leucovorin (FU/LV) and FU/LV Plus Oxaliplatin", Journal of Clinical Oncology, vol. 31, No. 36, Dec. 20, 2013, pp. 4512-4519.

Wikipedia—Dependent and independent variables, Apr. 3, 2020, XP055818482, pp. 1-6.

\* cited by examiner

| 1602 A method for predicting metastasis of a cancer in a subject. |
|---|

| 1604 Obtain, in electronic format, a plurality of data elements for the subject's cancer, comprising: |
|---|
| (1606) A first set of sequence features comprising relative abundance values for the expression of a plurality (e.g., at least 30) of genes in a biopsy of the cancer obtained from the subject. |
| (1608) One or more personal characteristics about the subject selected from the group consisting of age, gender, and race. |
| (1610) One or more clinical features related to the diagnosis or treatment of the cancer in the subject selected from the group consisting of a stage of the cancer, a histopathological grade of the cancer, a therapy administered to the subject, a symptom associated with cancer or metastasis thereof, and a comorbidity with the cancer. |
| (1611) One or more temporal features related to the diagnosis or treatment of the cancer in the subject selected from the group consisting of a first temporal element indicating a duration of time since a diagnosis for the cancer, a second temporal element indicating a duration of time since an administration of a therapy to the subject, a third temporal element indicating a duration of time since an experience of a symptom associated with cancer or metastasis thereof, and a fourth temporal element indicating a duration of time since an experience of a comorbidity with the cancer. |

| 1612 Apply, to the plurality of data elements for the subject's cancer, one or more models that are collectively trained to provide a respective one or more indications of whether the cancer will metastasize in the subject, thereby predicting whether the cancer will metastasize. |
|---|

| 1614 Generate a clinical report comprising the one or more indications of whether the cancer will metastasize. |
|---|

| 1616 When the one or more indications of whether the cancer will metastasize satisfy a first threshold risk for metastasis of the cancer, administer a first therapy tailored for treatment of metastatic cancer; and when the one or more indications of whether the cancer will metastasize do not satisfy the first threshold risk for metastasis of the cancer, administer a second therapy tailored for treatment of non-metastatic cancer. |
|---|

FIG. 16

PREDICTING LIKELIHOOD AND SITE OF METASTASIS FROM PATIENT RECORDS

CROSS REFERENCE TO RELATED APPLICATIONS

This application is a continuation of U.S. patent application Ser. No. 17/227,120, filed on Apr. 9, 2021, entitled "Predicting Likelihood and Site of Metastasis from Patient Records," which claims priority to U.S. Provisional Patent Application No. 63/007,874, filed on Apr. 9, 2020, entitled "Predicting Likelihood and Site of Metastasis from Patient Records," and U.S. Provisional Patent Application No. 63/142,051, filed on Jan. 27, 2021, entitled "Predicting Likelihood and Site of Metastasis from Patient Records," the disclosures of which are incorporated by reference herein, in their entireties, for all purposes.

FIELD OF THE INVENTION

The present disclosure relates to computer-implemented methods and systems for predicting a likelihood that a patient tumor metastasizes to another organ in the patient based on computational analysis of patient's medical records.

BACKGROUND

Precision oncology is the practice of tailoring cancer therapy to the unique genomic, epigenetic, and/or transcriptomic profile of an individual's cancer. Personalized cancer treatment builds upon conventional therapeutic regimens used to treat cancer based only on the gross classification of the cancer, e.g., treating all breast cancer patients with a first therapy and all lung cancer patients with a second therapy. This field was borne out of many observations that different patients diagnosed with the same type of cancer, e.g., breast cancer, responded very differently to common treatment regimens. Over time, researchers have identified genomic, epigenetic, and transcriptomic markers that improve predictions as to how an individual cancer will respond to a particular treatment modality.

There is growing evidence that cancer patients who receive therapy guided by their genetics have better outcomes. For example, studies have shown that targeted therapies result in significantly improved progression-free cancer survival. See, e.g., Radovich M. et al., Oncotarget, 7(35): 56491-500 (2016). Similarly, reports from the IMPACT trial—a large (n=1307) retrospective analysis of consecutive, prospectively molecularly profiled patients with advanced cancer who participated in a large, personalized medicine trial—indicate that patients receiving targeted therapies matched to their tumor biology had a response rate of 16.2%, as opposed to a response rate of 5.2% for patients receiving non-matched therapy. Tsimberidou A M et al., ASCO 2018, Abstract LBA2553 (2018).

In fact, therapy targeted to specific genomic alterations is already the standard of care in several tumor types, e.g., as suggested in the National Comprehensive Cancer Network (NCCN) guidelines for melanoma, colorectal cancer, and non-small cell lung cancer. In practice, implementation of these targeted therapies requires determining the status of the diagnostic marker in each eligible cancer patient. While this can be accomplished for the few, well known mutations associated with treatment recommendations in the NCCN guidelines using individual assays or small next generation sequencing (NGS) panels, the growing number of actionable genomic alterations and increasing complexity of diagnostic classifiers necessitates a more comprehensive evaluation of each patient's cancer genome, epigenome, and/or transcriptome.

For instance, cancer metastasis, which is the spread of a cancer from a primary site to other sites within the body, is a hallmark of an advanced cancer stage and is generally associated with poorer clinical outcomes. Metastatic cancers are more commonly treated with systemic therapies than are primary cancers without signs of metastasis, which are commonly treated with local therapy. For instance, a metastatic cancer may be treated with both a local therapy to address a particular tumor (e.g., a tumor at the primary site of cancer and/or a tumor at a metastasis site) and with a systemic adjuvant and/or neoadjuvant therapy to kill cancer cells that have spread to other parts of the body, thereby reducing the probability that further metastatic disease will develop. However, systemic treatments are generally more toxic to a patient's body than are local therapies, and are associated with side effects such as nausea, fatigue, low white blood cell count, myelosuppression, and nerve damage, which negatively impact a patient's quality of life. Because the ability to metastasize is not an inherent ability of all cancers, not all cancer patients will benefit from adjuvant therapy.

However, predicting which patients will most benefit from adjuvant therapy is difficult. For instance, Xu W. et al., BMC Medicine, 18:172 (2020) conducted an in-depth evaluation and cross-assessment of 34 risk factors and 12 prediction models for colorectal cancer metastasis and found convincing evidence for the association of only a single risk factor (vascular invasion) with colorectal cancer metastasis, and that association was limited to lymph node metastasis in pT1 tumors. As such, many cancer patients are unnecessarily treated with adjuvant therapies due in large part to the inability to accurately predict which cancers will ultimately metastasize and which cancers will not. van 't Veer L. J. et al., Nature, 415(6871):530-36 (2002).

Extracting meaningful medical features from an ever-expanding quantity of health information tabulated for a similarly expanding cohort of patients having a multitude of sparsely populated features is a difficult endeavor. Identifying which medical features, from the tens of thousands of features available in health information, are most probative to training and utilizing a prediction engine only compounds the difficulty. Features which may be relevant to predictions may only be available in a small subset of patients and features which are not relevant may be available in many patients. What is needed is a system that may ingest these impossibly comprehensive scope of available data across entire populations of patients to identify features which apply to the largest number of patients and establish a model for prediction of an objective. When there are multiple objectives to choose from, what is needed is a system which may curate the medical features extracted from patient health information to a specific model associated with the prediction of the desired objective. One relevant objective is to compute the likelihood that a patient's cancer will metastasize to a specifically identified organ in the patient's body within a defined period of time after one or more events, such as next-generation sequencing (NGS) of the patient's tumor.

SUMMARY

Given the above background, improved systems and methods are needed for predicting the likelihood that a patient's cancer will metastasize (e.g., to a specific tissue and/or within a specific time frame), for example to improve access to personalized therapies. Advantageously, the present disclosure provides solutions to these and other shortcomings in the art.

One aspect of the present disclosure provides a method for predicting metastasis of a cancer in a subject, at a computer system having one or more processors, and memory storing one or more programs for execution by the one or more processors. The method includes obtaining, in electronic format, a plurality of data elements for the subject's cancer.

The plurality of data elements includes a first set of sequence features comprising relative abundance values (e.g., expression values for a plurality of genes) for the expression of a plurality of genes (e.g., at least 30 genes) in a biopsy of the cancer obtained from the subject. In some embodiments, the plurality of data elements includes one or more personal characteristics about the subject selected from the group consisting of age, gender, and race. In some embodiments, the plurality of data elements further comprises one or more clinical features related to the diagnosis or treatment of the cancer in the subject selected from the group consisting of a stage of the cancer, a histopathological grade of the cancer, a therapy administered to the subject, a symptom associated with cancer or metastasis thereof, and a comorbidity with the cancer. In some embodiments, the plurality of data elements further comprises one or more temporal features related to the diagnosis or treatment of the cancer in the subject selected from the group consisting of a first temporal element indicating the duration of time since a diagnosis for the cancer (e.g., a diagnosis of the cancer, a grading of the cancer, and/or a histopathological grading of the cancer), a second temporal element indicating the duration of time since an administration of the therapy (e.g., since first administration, since last administration, and/or since completion of a first therapeutic regimen), a third temporal element indicating the duration of time since an experience of the symptom (e.g., since first experience of the symptom and/or since last experience of the symptom), and a fourth temporal element indicating the duration of time since an experience of the comorbidity (e.g., since the beginning of the comorbidity and/or since the resolution of the comorbidity).

The method includes applying, to the plurality of data elements for the subject's cancer, one or more models (e.g., predictive and/or classification models) that are collectively trained to provide a respective one or more indications (e.g., a binary indication, a likelihood and/or a probability) of whether the cancer will metastasize in the subject (e.g., to any tissue site within a respective single time horizon), thereby predicting whether the cancer will metastasize.

The method further includes generating a clinical report comprising the one or more indications of whether the cancer will metastasize (e.g., one or more indications of metastasis to any tissue site within a respective single time horizon).

In some embodiments, the method includes applying, to the plurality of data elements for the subject's cancer, a set of models (e.g., predictive and/or classification models) that are collectively trained to provide, for each respective tissue in a plurality of tissues (e.g., at different locations within a subject's body), a respective set of indications of whether the cancer will metastasize to the respective tissue in the subject (e.g., a binary indication, a likelihood and/or a probability). The respective set of indications includes a respective indication for each respective time horizon in a plurality of time horizons. Thus, in some such embodiments, the method determines a plurality of indications of whether the cancer will metastasize that includes, for each respective tissue in the plurality of tissues, a respective set of indications comprising, for each respective time horizon in a plurality of time horizons, a respective indication of whether the cancer in the subject will metastasize to the respective tissue within the respective time horizon.

In some embodiments, systems and methods are provided for generating and modeling predictions of patient objectives (e.g., generating, training, and applying models for predicting an objective based on features associated with a patient). The model(s) can be selected based on amount, type, and other properties of information available for a patient. The systems and methods provide techniques for computational processing of information in patient records (e.g., various semi-structured and unstructured data) to convert the information into a format suitable for use in the predictive models. Thus, in some embodiments, interactions are identified in a patient record, and, for every identified interaction, a prediction of an objective may be calculated. The prediction can relate to, for example, a likelihood of metastasis within a certain time from the respective interaction point and/or specific location(s) of the metastasis. The predictions are identified using a model that can be selected from a plurality of models based on the available patient information.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The figures described below depict various aspects of the system and methods disclosed herein. It should be understood that each figure depicts an example of aspects of the present systems and methods.

FIG. 16 provides a flow chart of processes and features for predicting metastasis of a cancer in a subject, in which optional blocks are indicated with dashed boxes, in accordance with some embodiments of the present disclosure.

DETAILED DESCRIPTION

Among other aspects, the present disclosure provides methods and systems for predicting whether a cancer will metastasize based on one or more characteristics of the subject. In some embodiments, the methods and systems described herein evaluate at least a portion of the transcriptome from a sample of the cancer tissue when predicting whether the cancer will metastasize. In some embodiments, the methods and systems further evaluate one or more personal characteristics of the subject, one or more clinical features of the cancer, one or more pathological features of the cancer, or one or more additional nucleic acid-based features of the cancer when predicting whether the cancer will metastasize. Also provided herein are methods for training models for predicting whether a cancer will metastasize.

Generating and Modeling Predictions of Patient Objectives.

Figure 1:
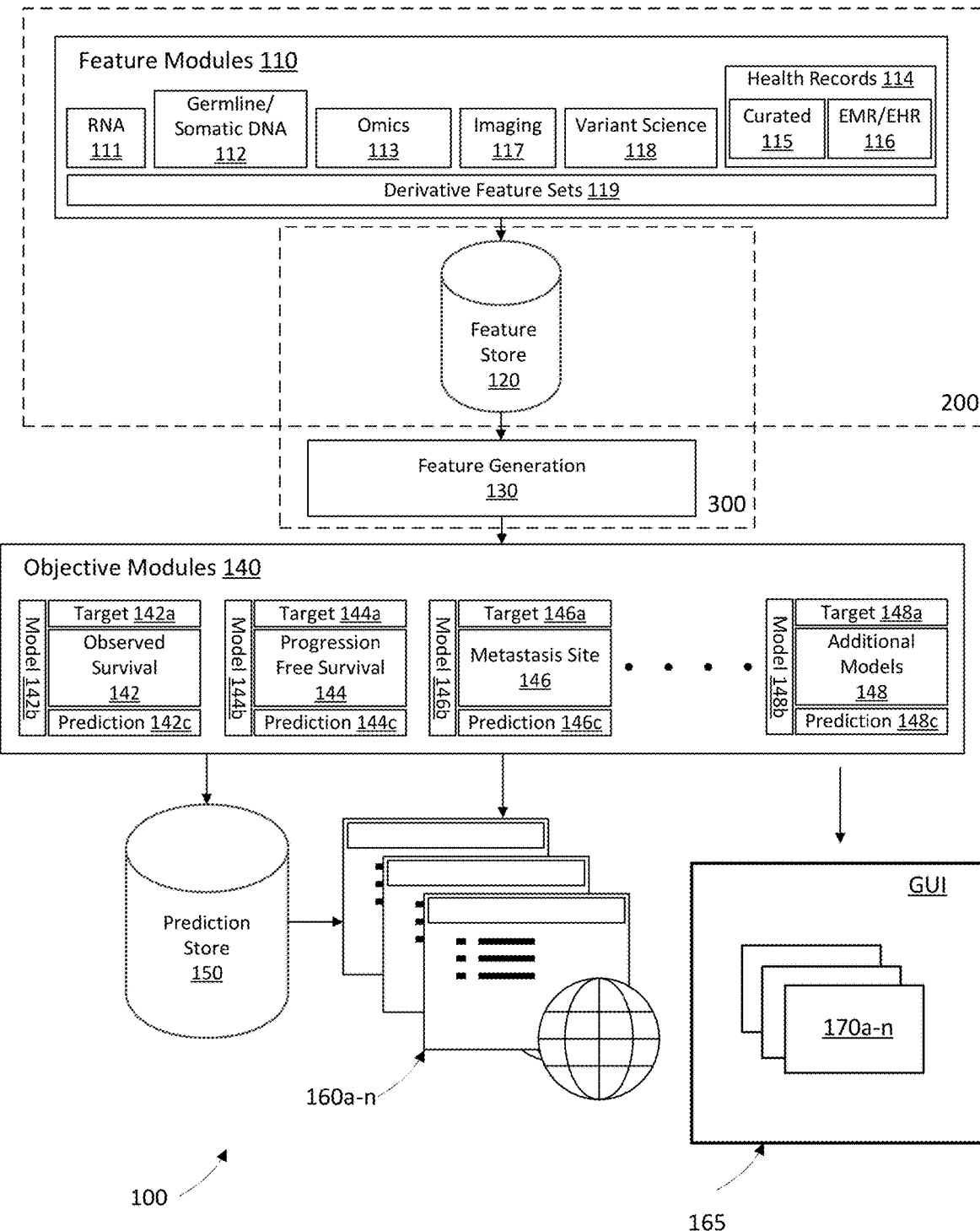
FIG. 1 is a block diagram illustrating a system for generating predictions of an objective from a plurality of patient features, in accordance with some embodiments of the present disclosure.

FIG. 1 illustrates an embodiment of a computer-implemented system 100 for generating and modeling predictions of patient objectives. Predictions may be generated from patient information represented by feature modules 110 implemented by the system architecture 100. The system 100 can be a content server (also referred to as a prediction engine), which is hardware or a combination of both hardware and software. A user, such as a health care provider or patient, is given remote access through the GUI to view, update, and analyze information about a patient's medical condition using the user's own local device (e.g., a personal computer or wireless handheld device). A user can interact with the system to instruct it to generate electronic records, update the electronic records, and perform other actions. The content server is configured to receive various information in different formats and it converts the information into the standardized format that is suitable for processing by modules operation on or in conjunction with the content server. Thus, information acquired from patients' electronic medical records (EMR), unstructured text, genetic sequencing, imaging, and various other information can be converted into features that are used for training a plurality of machine-learning models.

The information acquired, processed, and generated by the content server 100 is stored on one or more of the network-based storage devices. The user can interact with the content server to access the information stored in the network-based storage devices, and the content server can receive user-supplied information, apply the one or more models stored in the network-based storage to the information, and to provide, in an electronic form, results of the model application to the user on a graphical user interface of the user device. The electronic information is transmitted in a standardized format over the computer network to the users that have access to the information. In this way, the users can readily adapt their medical diagnostic and treatment strategy in accordance with the system's predictions which can be automatically generated. Moreover, the system generates recommendations to users regarding patient diagnosis and treatment.

In some embodiments, the described systems and methods are implemented as part of a digital and laboratory health care platform. The platform may automatically generate a molecular report as part of a targeted medical care precision medicine treatment. In some embodiments, the system in accordance with embodiments of the present disclosure operates on one or more micro-services, which can be micro-services of an order management system. In some embodiments, the system is implemented in conjunction with one or more micro-services of a cell-type profiling service.

The feature modules 110 may store a collection of features, or status characteristics, generated for some or all patients whose information is present in the system 100. These features may be used to generate and model predictions using the system 100. While feature scope across all patients is informationally dense, a patient's feature set may be sparsely populated across the entirety of the collective feature scope of all features across all patients. For example, the feature scope across all patients may expand into the tens of thousands of features, while a patient's unique feature set may include a subset of hundreds or thousands of the collective feature scope based upon the records available for that patient.

A plurality of features present in the feature modules 110 may include a diverse set of fields available within patient health records 114. Clinical information may be based upon fields which have been entered into an electronic medical record (EMR) or an electronic health record (EHR) 116, which can be done automatically or manually, e.g., by a physician, nurse, or other medical professional or representative. Other clinical information may be curated information (115) obtained from other sources, such as, for example, genetic sequencing reports (e.g., from molecular fields). Sequencing may include next-generation sequencing (NGS) and may be long-read, short-read, or other forms of sequencing a patient's somatic and/or normal genome. A comprehensive collection of features (status characteristics) in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, as shown in FIG. 1, a subset of features may comprise molecular data features, such as features derived from an RNA feature module 111 or a DNA feature module 112 sequencing.

As further shown in FIG. 1, another subset of features, imaging features from imaging feature module 117, may comprise features identified through review of a specimen by pathologist, such as, e.g., a review of stained H&E or IHC slides. As another example, a subset of features may comprise derivative features obtained from the analysis of the individual and combined results of such feature sets. Features derived from DNA and RNA sequencing may include genetic variants from variant science module 118, which can be identified in a sequenced sample. Further analysis of the genetic variants present in variant science module 118 may include steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology-related features.

Features derived from structured, curated, and/or electronic medical or health records 114 may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates associated with any of the above.

As shown in FIG. 1, the features 113 may be derived from information from additional medical- or research-based Omics fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features 117 derived from imaging data may further include reports associated with a stained slide, size of tumor, tumor size differentials over time including treatments during the period of change, as well as machine learning approaches for classifying PDL1 status, HLA status, or other characteristics from imaging data. Other features may include additional derivative features sets 119 derived using other machine learning approaches based at least in part on combinations of any new features and/or those listed above. For example, imaging results may need to be combined with MSI calculations derived from RNA expressions to determine additional further imaging features. As another example, a machine-learning model may generate a likelihood that a patient's cancer will metastasize to a particular organ or a patient's future probability of metastasis to yet another organ in the body. Additional derivative feature sets are discussed in more detail below with respect to FIG. 2. Other features that may be extracted from medical information may also be used. There are many thousands of features, and the above-described types of features are merely representative and should not be construed as a complete listing of features.

In addition to the above features and enumerated modules, the feature modules 110 may further include one or more of the modules that are described below and that can be included within respective modules of the Feature modules 110, as a sub-module or as a standalone module.

Continuing with FIG. 1, a germline/somatic DNA feature module 112 may comprise a feature collection associated with the DNA-derived information of a patient and/or a patient's tumor. These features may include raw sequencing results, such as those stored in FASTQ, BAM, VCF, or other sequencing file types known in the art; genes; mutations; variant calls; and variant characterizations. Genomic information from a patient's normal sample may be stored as germline and genomic information from a patient's tumor sample may be stored as somatic.

An RNA feature module 111 may comprise a feature collection associated with the RNA-derived information of a patient, such as transcriptome information. These features may include, for example, raw sequencing results, transcriptome expressions, genes, mutations, variant calls, and variant characterizations. Features may also include normalized sequencing results, such as those normalized by TMP.

The feature modules 110 can comprise various other modules. For example, a metadata module (not shown) may comprise a feature collection associated with the human genome, protein structures and their effects, such as changes in energy stability based on a protein structure.

A clinical module (not shown) may comprise a feature collection associated with information derived from clinical records of a patient, which can include records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

An imaging module, such as, e.g., the imaging module 117, may comprise a feature collection associated with information derived from imaging records of a patient. Imaging records may include H&E slides, IHC slides, radiology images, and other medical imaging information, as well as related information from pathology and radiology reports, which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

An epigenome module, such as, e.g., an epigenome module from Omics module 113, may comprise a feature collection associated with information derived from DNA modifications which are not changes to the DNA sequence and regulate the gene expression. These modifications can be a result of environmental factors based on what the patient may breathe, eat, or drink. These features may include DNA methylation, histone modification, or other factors which deactivate a gene or cause alterations to gene function without altering the sequence of nucleotides in the gene.

A microbiome module, such as, e.g., a microbiome module from Omics module 113, may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

A proteome module, such as, e.g., a proteome module from Omics module 113, may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) (not shown) may also be included in Omics module 113, such as a feature collection (which is a collection of status characteristics) associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's wellbeing, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous digital image sequence, or a video, can be interpreted as the capture of a single image evolving through time of mutations revealing patient insights.

In some embodiments, a robust collection of features may include all of the features disclosed above. However, predictions based on the available features may include models which are optimized and trained from a selection of fewer features than in an exhaustive feature set. Such a constrained feature set may include, in some embodiments, from tens to hundreds of features. For example, a prediction may include predicting the likelihood a patient's tumor may metastasize to the brain. A model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup. Examples of optimized feature sets are further discussed below, in connection with FIGS. 3-5.

The feature store 120 may enhance a patient's feature set through the application of machine learning and/or an artificial intelligence engine and analytics by selecting from any features, alterations, or calculated output derived from the patient's features or alterations to those features. One method for enhancing a patient's feature set may include dimensionality reduction, such as collapsing a feature set from tens of thousands of features to a handful of features. Performing dimensionality reduction without losing information may be approached in an unsupervised manner or a supervised manner. Unsupervised methods may include RNA Variational Auto-encoders, Singular Value Decomposition (SVD), PCA, KernelPCA, SparsePCA, DictionaryLearning, Isomap, Nonnegative Matrix Factorization (NMF), Uniform Manifold Approximation and Projection (UMAP), Feature agglomeration, Patient correlation clustering, KMeans, Gaussian Mixture, or Spherical KMeans. Performing dimensionality reduction in a supervised manner may include Linear Discriminant Analysis, Neighborhood Component Analysis, MLP transfer learning, or tree based supervised embedding.

In one embodiment, a grid search may be performed across a variety of encoding, such as the supervised and unsupervised approaches above, where each encoding is evaluated across a variety of hypertuning parameters to identify the encoding and hyperparameter set which generates the highest dimensionality reduction while retaining or improving accuracy.

In one embodiment, a grid search may identify a dimensionality reduction implemented with tree-based supervised embedding on RNA TPM feature sets for all patients. RNA TPM feature sets may be fit to a forest of decision trees, Such as a forest of decision trees generated from hyperparameters of minimum samples per leaf using a minimum number of 2, 4, 8, 16, 24, 100, or other selected number, a maximum feature set using a percentage of the features which should be used in each tree, the number of trees to be used in the forest, and the number of clusters which may be identified from the reduced dimensionality dataset. Each tree in the forest may randomly select up to the threshold percentage of features and with each selected feature identify the largest split between patients who have metastasis and do not have metastasis. When the feature set includes RNA TPM features, a random selection of genes may include identifying which genes are the most divisive of the random set of selected features, starting the branching from the most divisive gene and successively iterating down the gene list until either the minimum samples per leaf are not met or the maximum features are met. The leaf nodes for each tree include patients who meet the criteria at each branch and are correlated based upon their likelihood to metastasize. Patient membership of each leaf may be evaluated using one-hot KMeans cluster membership counts or a distance of each patient to each of the KMeans centroids/clusters.

In an example, the leaves of each tree are compared to identify which leaves include the same branches or equivalent branches, such as branches that result in the same patients because the genes, while different, are equivalent to each other. Equivalency may be determined when information related to the expression level of a gene may be correlated with, or predicted from, the expression level data associated with one or more other genes. When a gene may be correlated with, or predicted from, one or more other genes, the one or more other genes are defined as proxy genes. The terms proxy genes and equivalent genes may be used interchangeably herein. Identifying the number of same branches, or equivalent branches, for each leaf allows generation of membership for each leaf as it occurs within the individual trees of the forest. Similarly, when KMeans clusters are generated from the collection of leaves, a distance for each patient may be calculated for each patient. An array may be generated having the normalized inverse of each distance for each patient to each KMeans centroid. The array, at this point, may be stored as a reduced dimensionality feature set of RNA TPM features for the set of patients, and the features of reduced dimensionality may be used in any of the predictive methods described herein. In other words, the methods for identifying a prediction of a target/objective pair may be performed having the array of distances for each patient as an input into the artificial intelligence engine described below; including, for example, performing logistic regression to generate a predictive model for a target/objective pair.

The feature store 120 may generate new features from the original features found in feature module 110 or may identify and store insights or analysis derived using the features. The selections of features may be based upon an alteration or calculation to be generated, and may include the calculation of single or multiple nucleotide polymorphisms, insertion or deletions of the genome, a tumor mutational burden, a microsatellite instability, a copy number variation, a fusion, or other such calculations. In an example, an output of an alteration module which may inform future alterations or calculations may include a finding that patients having hypertrophic cardiomyopathy (HCM) express variants in MYH7 more commonly than patients without HCM. An exemplary approach may include the enrichment of variants and their respective classifications to identify a region in MYH7 that is associated with HCM. Any novel variants detected from patient's sequencing localized to this region would increase the patient's risk for HCM. Therefore, features which may be utilized in such an alteration detection include the structure of MYH7, the normal genome for MYH7, and classification of variants therein as impacting a patient's chances of having HCM. A model which focuses on enrichment may isolate such variants. Other variants may be isolated with respect to other illness, diseases, or diagnosis through an enrichment alteration module. The feature store selection, alteration, and calculations is discussed below in more detail with respect to FIG. 2.

The feature generation 130 may process features from the feature store 120 by selecting or receiving features from the feature store 120. The features may be selected based on a patient by patient basis, a target/objective by patient basis, or a target/objective by all patient basis, or a target/objective by cohort basis. In the patient by patient basis, features which occur a specified patient's timeline of medical history may be processed. In the target/objective by patient basis, features which occur in a specified patient's timeline which inform an identified target/objective prediction may be processed. In some examples, a model may be selected which optimizes the prediction based upon the features available to the prediction engine at the time of processing/generating a prediction for the patient or a prediction for all of the patients.

Targets/objectives may include a combination of an objective and a horizon, or time period, such as Progression within 6, 12, 24, 60 months, Death within 6, 12, 24, 60 months; Recurrence within 6, 12, 24, 60 months; First Administration of Medication within 7, 14, 21, or 28 days; First Occurrence of Procedure within 7, 14, 21, or 28 days; First Occurrence of Adverse Reaction within 6, 12, or 24 months of Initial Administration; Metastasis within 3 months; Metastasis to Organ within 3, 6, 9, 12, or 24 months; Metastasis from Primary Organ Site to Secondary Organ Site (localized metastasis to an organ) within 3, 6, 9, 12, or 24 months. The above listing of targets/objectives is not exhaustive, other objectives and horizons may be used based upon the predictions requested from the system. In one example, the prediction may be represented as $P(Y(t)|X)$, where P is the probability of developing a metastasis in organ Y at time t given the a patient's current medical state and history X. Where the P includes a target/objective, the X includes the patient features in the system. In the target/objective by all-patient basis, features which occur in each patient's timeline which inform an identified target/objective prediction may be processed for each patient until all patients have been processed. In the target/objective by cohort basis, features which occur in each patient's timeline which inform an identified target prediction may be processed for each patient until all patients of a cohort have been processed. A cohort may include a subset of patients having attributes in common with each other. For example, a cohort may be a collection of patients which share a common institution (such as a hospital or clinic), a common diagnosis (such as cancer, depression, or other illness), a common treatment (such as a medication or therapy), or common molecular characteristics (such as a genetic variation or alteration). Cohorts may be derived from any feature or characteristic included in the feature modules 110 or feature store 120. Feature generation may provide a prior feature set and/or a forward feature set to a respective objective module corresponding to the target/objective and/or prediction to be generated. Prior and forward feature sets will be disclosed in more detail with respect to FIGS. 3-5, below.

Objective Modules 140 may comprise a plurality of modules: Observed Survival 142, Progression Free Survival 144, Metastasis Site 146, and further additional models 148 which may include modules such as Medication or Treatment prediction, Adverse Response prediction, disease progression, disease recurrence, or other predictive models. Each module 142, 144, 146, and 148 may be associated with one or more targets 142a, 144a, 146a, and 148a. For example, observed survival module 142 may be associated with targets 142a having the objective "Death" and time periods "6, 12, 24, and 60 months." Progression free survival module 144 may be associated with targets 144a having the objective "Progression" and time periods "6, 12, 24, and 60 months." Metastasis Site module 146 may be associated with targets 146a having the objective "Metastasis, Metastasis to Organ, Metastasis from Primary Organ Site to Secondary Organ Site" and time periods "3/6/9/12/24 months." Additional models 148, such as a Propensity Module may be associated with targets 148a having an objective "Medications, Treatments, and Therapies" and time periods "7, 14, 21, and 28 days." Additional models 148, such as a Disease Progression Module and Disease Recurrence Module may be associated with targets 148a having an objective "Progression, Recurrence" and time periods "6, 12, 24, and 60 months." Each module 142, 144, 146, and 148 may be further associated with models 142b, 144b, 146b, and 148b. Models 142b, 144b, 146b, and 148b may be gradient boosting models, random forest models, neural networks (NN), regression models, Naive Bayes models, or machine learning algorithms (MLA). A MLA or a NN may be trained from a training dataset such as a plurality of matrices having a feature vector for each patient or images and features. In an exemplary prediction profile, a training dataset may include imaging, pathology, clinical, and/or molecular reports and details of a patient, such as those curated from an EHR or genetic sequencing reports. The training data may be based upon features such as the objective specific sets disclosed with respect to FIGS. 3-5, below.

MLAs include supervised algorithms (such as algorithms where the features/classifications in the dataset are annotated) using linear regression, logistic regression, decision trees, classification and regression trees, Naïve Bayes, nearest neighbor clustering; unsupervised algorithms (such as algorithms where no features/classification in the dataset are annotated) using Apriori, means clustering, principal component analysis, random forest, adaptive boosting; and semi-supervised algorithms (such as algorithms where an incomplete number of features/classifications in the dataset are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training dataset includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise.

Training may include providing optimized datasets as a matrix of feature vectors for each patient, labeling these traits as they occur in patient records as supervisory signals, and training the MLA to predict an objective/target pairing. Artificial NNs are powerful computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule-based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art.

In other MLAs, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the dataset. A single instance of the above models, or two or more such instances in combination, may constitute a model for the purposes of models 142b, 144b, 146, and 148b.

Models may also be duplicated for particular datasets which may be provided independently for each objective module 142, 144, 146, and 148. For example, the metastasis site objective module 146 may receive a DNA feature set, an RNA feature set, a combined RNA and DNA feature set, and observational feature set, or a complete dataset comprising all features for each patient. As another example, the metastasis site objective module 146 may receive imaging features extracted from various digital images acquired from analysis of a patient's sample. A model 146b may be generated for each of the potential feature sets or targets 146a. Each module 142, 144, 146, and 148 may be further associated with Predictions 142c, 144c, 146c, and 148c. A prediction may be a binary representation, such as a "Yes—Target predicted to occur" or "No—Target not predicted to occur." Predictions may be a likelihood representation such as "target predicted to occur with 83% probability/likelihood." Predictions may be performed on patient datasets having known outcomes to identify insights and trends which are unexpected. For example, a cohort of patients may be generated for patients with a common cancer diagnosis who have either remained progression free for five years after diagnosis, have progressed within five years after diagnosis, or who have passed away within five years of diagnosis. A prediction model may be associated with an objective for progression free survival (PFS) and a target of PFS within 2 years. The PFS model may identify every event in each patient's history and generate a prediction of whether the patient will be progression free within 2 years of that event. The cohort of patients may generate, for each event in a patient's medical file, the probability that the patient will remain progression free within the next two years and compare that prediction with whether the patient actually was progression free within two years of the event.

For example, a prediction that a patient may be progression free with a 74% likelihood but in fact progresses within two years may inform the prediction model that intervening events before the progression are worth reviewing or prompt further review of the patient record that lead to the prediction to identify characteristics which may further inform a prediction. An actual occurrence of a target is weighted to 1 and the non-occurrence of the event is weighted to 0, such that an event which is likely to occur but does not may be represented by the difference (0-0.73), an event which is not likely to occur but does may be represented by the difference (0.22-1), to provide a substantial difference in values in comparison to events which are closely predicted (0-0.12 or 1-0.89) having a minimal difference. Predictions will be discussed in further detail with respect to FIG. 6, below. For determining a prediction, each module 142, 144, 146, and 148 may be associated with a unique set of prior features, forward features, or a combination of prior features and forward features which may be received from feature generation 130. Selection of the unique set(s) of features will be disclosed in more detail with respect to FIGS. 3-5, below.

Prediction store 150 may receive predictions for targets/objectives generated from objective modules 140 and store them for use in the system 100. Predictions may be stored in a structured format for retrieval by a user interface such as, for example, a webform-based interactive user interface which, in some embodiments, may include webforms 160*a-n*. Webforms may support GUIs that can be displayed by a computer to a user of the computer system for performing a plurality of analytical functions, including initiating or viewing the instant predictions from objective modules 140 or initiating or adjusting the cohort of patients from which the objective modules 140 may perform analytics from. Electronic reports 170*a-n* may be generated and provided to the user via the graphical user interface (GUI) 165. It should be appreciated that the GUI 165 may be presented on a user device which is connected to the content server/prediction engine 100 via a network.

The reports 170 can be provided to the user as part of a network-based patient management system that collects, converts and consolidates patient information from various physicians and health-care providers (including labs) into a standardized format, stores it in network-based storage devices, and generates messages comprising electronic reports once the reports are generated in accordance with embodiments of the present disclosure. In this way, a user (e.g., a physician, oncologist, or any other health care provider, or a patient, receives computer-generated predictions related to a likelihood of a patient's tumor metastasizing, a predicted location of the metastasis, and/or an associated timeline.

In some embodiments, the electronic report may include a recommendation to a physician to treat the patient using a treatment that correlates with a magnitude of a determined degree of risk of the metastasis, a recommendation to a physician to de-escalate when the patient is low risk to reduce adverse events, save cost and improve health response, or a recommendation to a physician to elect a treatment which provides adjustments to the typical monitoring such as scanning, imaging, blood testing. Additionally or alternatively, the electronic report may include a recommendation for accelerated screening of the patient, a recommendation for consideration of additional monitoring. In some embodiments, an electronic report indicating that a patient may experience metastasis to one or more predicted organs results in researchers planning a clinical trial by predicting which groups of patients are most likely to respond to therapy that targets metastases or recurrences in general or metastases to specific organ sites. In some embodiments, a clinical trial may be performed by selecting patients who are predicted to be more likely or less likely to develop metastases or recurrences in general or metastases to specific organ site, using systems and methods in accordance with the present disclosure.

Figure 2:
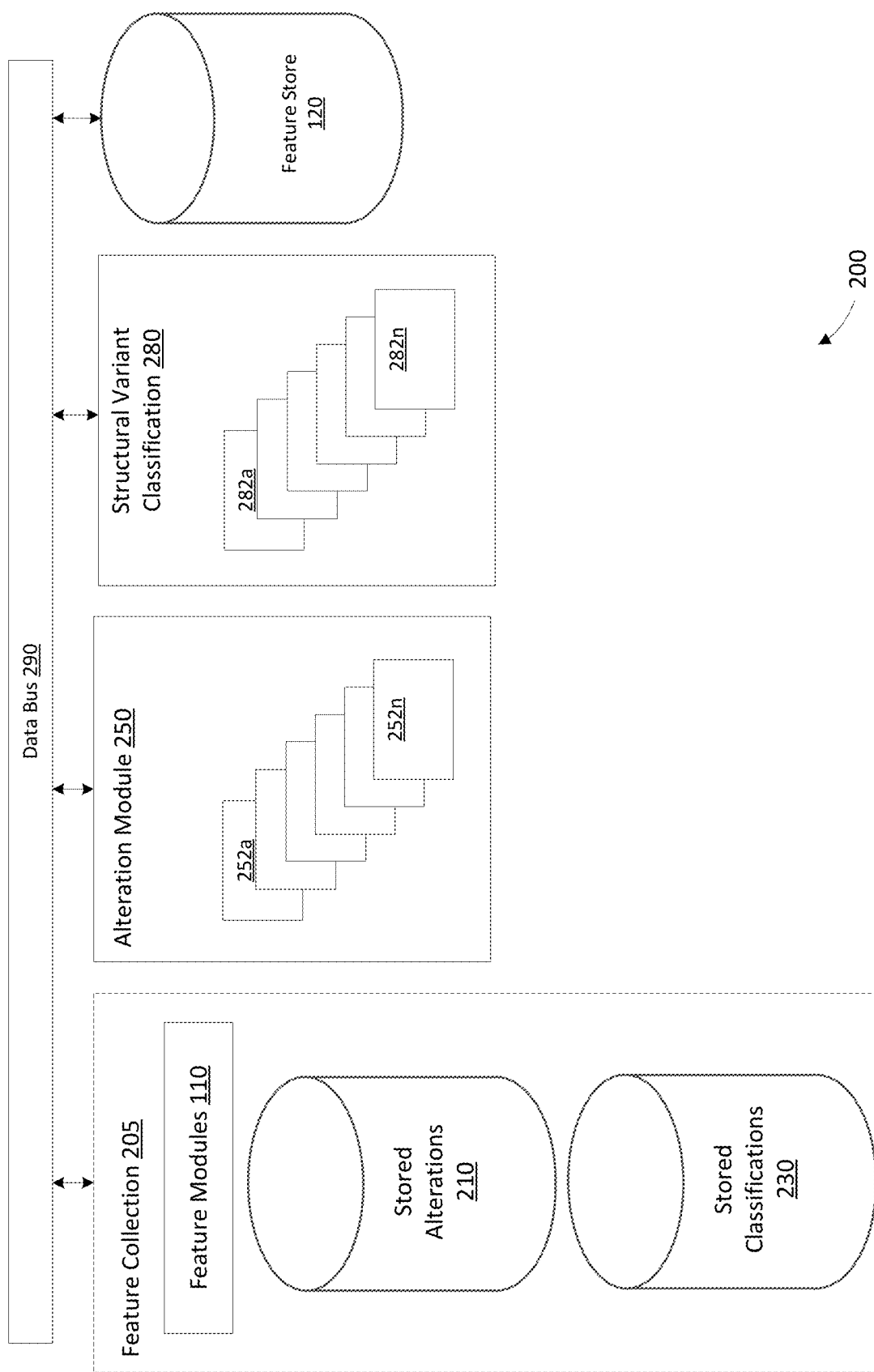
FIG. 2 is a block diagram illustrating a system for performing selection, alteration, and calculation of additional features from the patient features, in accordance with some embodiments of the present disclosure.

FIG. 2 illustrates the generation of additional derivative feature sets 119 of FIG. 1 and the feature store 120 using alteration modules. A feature collection 205 may comprise the modules of feature modules 110, stored alterations 210 from the alteration module 250 and stored classifications 230 from the structural variant classification 280. An alteration module 250 may be one or more microservices, servers, scripts, or other executable algorithms 252*a-n* which generate alteration features associated with de-identified patient features from the feature collection. Exemplary alterations modules may include one or more of the following alterations as a collection of alteration modules 252*a-n*. An SNP (single-nucleotide polymorphism) module may identify a substitution of a single nucleotide that occurs at a specific position in the genome, where each variation is present to some appreciable degree within a population (e.g., >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underline differences in susceptibility to a wide range of diseases (e.g., sickle-cell anemia, β-thalassemia and cystic fibrosis result from SNPs).

The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome. An InDels module may identify an insertion or deletion of bases in the genome of an organism classified among small genetic variations. While usually measuring from 1 to 10,000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites. An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint," each individual has microsatellites of a set length. The most common microsatellite in humans is a dinucleotide repeat of the nucleotides C and A, which occurs tens of thousands of times across the genome. Microsatellites are also known as simple sequence repeats (SSRs). A TMB (tumor mutational burden) module may identify a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials. A CNV (copy number variation) module may identify deviations from the normal genome and any subsequent implications from analyzing genes, variants, alleles, or sequences of nucleotides. CNV are the phenomenon in which structural variations may occur in sections of nucleotides, or base pairs, that include repetitions, deletions, or inversions.

A Fusions module may identify hybrid genes formed from two previously separate genes. It can occur as a result of: translocation, interstitial deletion, or chromosomal inversion. Gene fusion plays an important role in tumorgenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates the prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer.

In some embodiments, an IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyze a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated. For example, in some embodiments, the predictions may include PD-L1 prediction from H&E and/or RNA.

A Therapies module may identify differences in cancer cells (or other cells near them) that help them grow and thrive and drugs that "target" these differences. Treatment with these drugs is called targeted therapy. For example, many targeted drugs go after the cancer cells' inner "programming" that makes them different from normal, healthy cells, while leaving most healthy cells alone. Targeted drugs may block or turn off chemical signals that tell the cancer cell to grow and divide; change proteins within the cancer cells so the cells die; stop making new blood vessels to feed the cancer cells; trigger your immune system to kill the cancer cells; or carry toxins to the cancer cells to kill them, but not normal cells. Some targeted drugs are more "targeted" than others. Some might target only a single change in cancer cells, while others can affect several different changes. Others boost the way your body fights the cancer cells. This can affect where these drugs work and what side effects they cause.

In some embodiments, matching targeted therapies may include identifying the therapy targets in the patients and satisfying any other inclusion or exclusion criteria. A VUS (variant of unknown significance) module may identify variants which are called but cannot be classified as pathogenic or benign at the time of calling. VUS may be catalogued from publications regarding a VUS to identify if they may be classified as benign or pathogenic. A Trial module may identify and test hypotheses for treating cancers having specific characteristics by matching features of a patient to clinical trials. These trials have inclusion and exclusion criteria that must be matched to enroll which may be ingested and structured from publications, trial reports, or other documentation.

An Amplifications module may identify genes which increase in count disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another.

An Isoforms module may identify alternative splicing (AS), the biological process in which more than one mRNA (isoforms) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as the number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternative spliced isoforms.

A Pathways module may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations. A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing.

Structural variant classification 280 may evaluate features from feature collection 205, alterations from alteration module 250, and other classifications from within itself from one or more classification modules 282a-n. Structural variant classification 280 may provide classifications to stored classifications 230 for storage. An exemplary classification module may include a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules 282a-n. A classifier for clinical trials may include evaluation of variants identified from the alteration module 250 which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. Similar classifications may be performed for therapies, loss-of-function, gain-of-function, diagnosis, microsatellite instability, tumor mutational burden, indels, SNP, MNP, fusions, and other alterations which may be classified based upon the results of the alteration modules 252a-n.

Each of the feature collection 205, alteration module 250, structural variant 280 and feature store 120 may be communicatively coupled to data bus 290 to transfer data between each module for processing and/or storage. In another embodiment, each of the feature collection 205, alteration module 250, structural variant 280 and feature store 120 may be communicatively coupled to each other for independent communication without sharing data bus 290.

Figure 3:
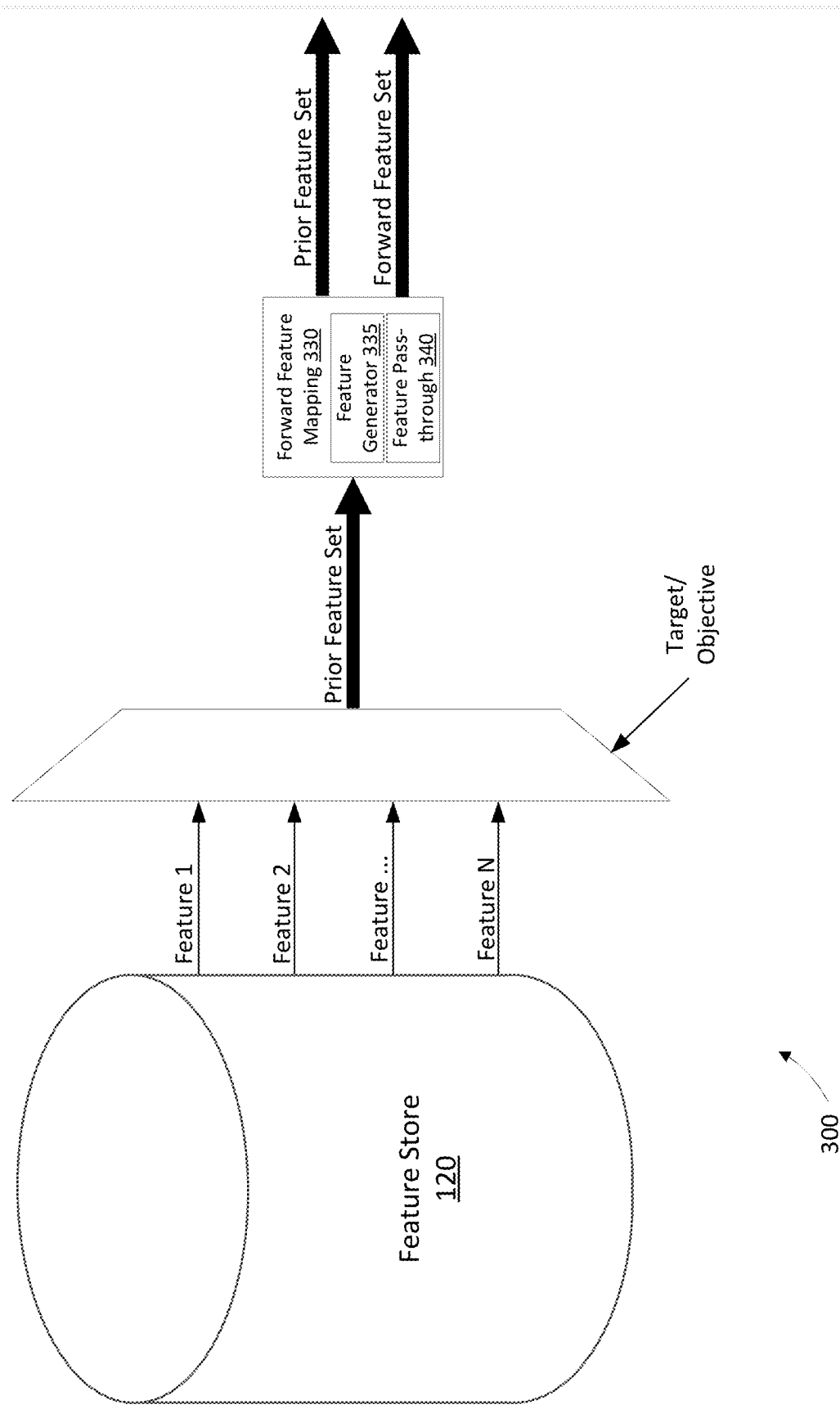
FIG. 3 is a schematic illustration of an example of a system for selecting a feature set for generating prior features and forward features based on a target/objective pair, in accordance with some embodiments of the present disclosure.
Figure 4:
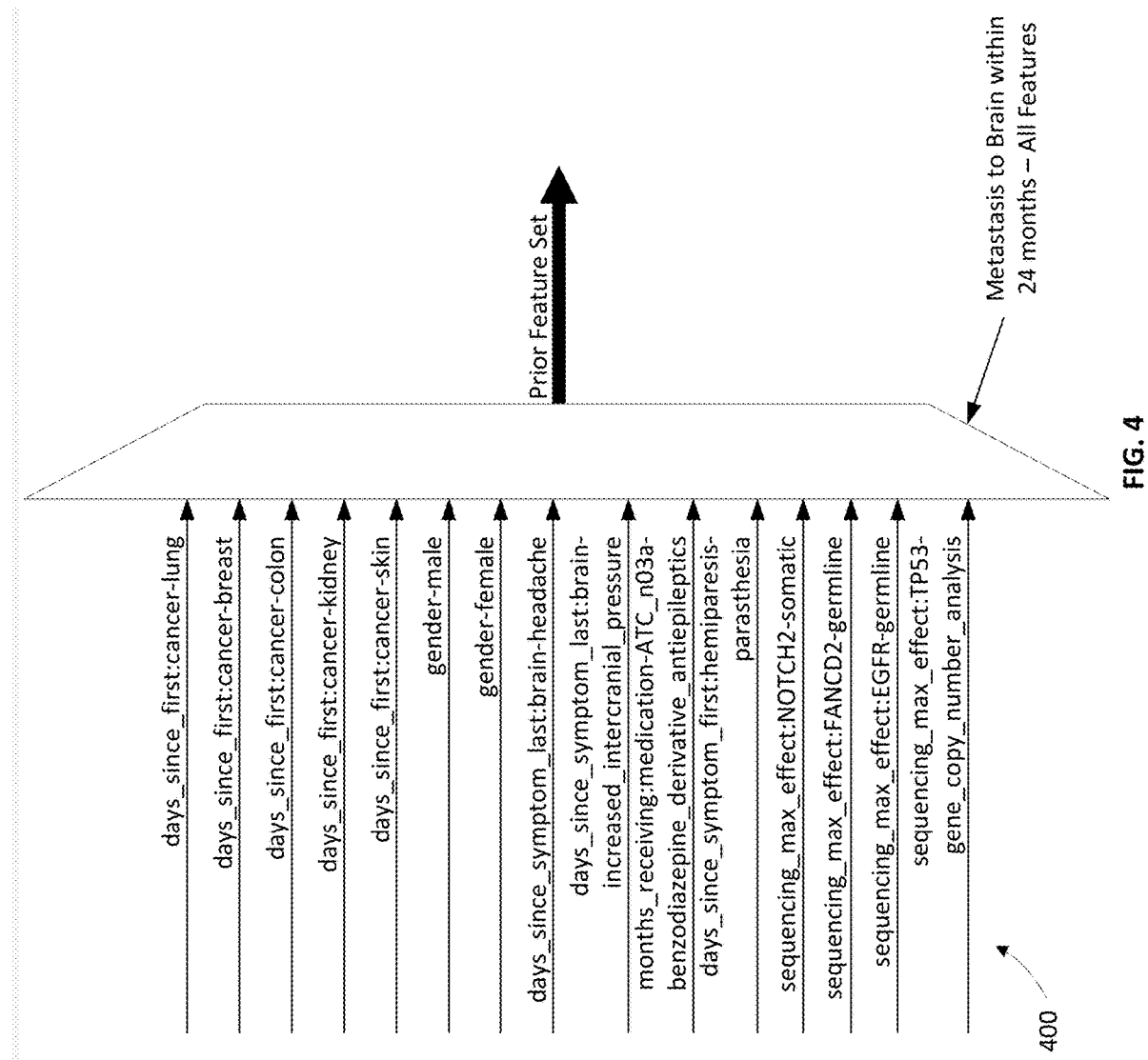
FIG. 4 is a schematic illustration of an example of a system for selecting a feature set for generating prior features based on predicting the likelihood that a patient's cancer will metastasize to a specifically identified organ in the patient's body within a defined period of time, in accordance with some embodiments of the present disclosure.
Figure 5:
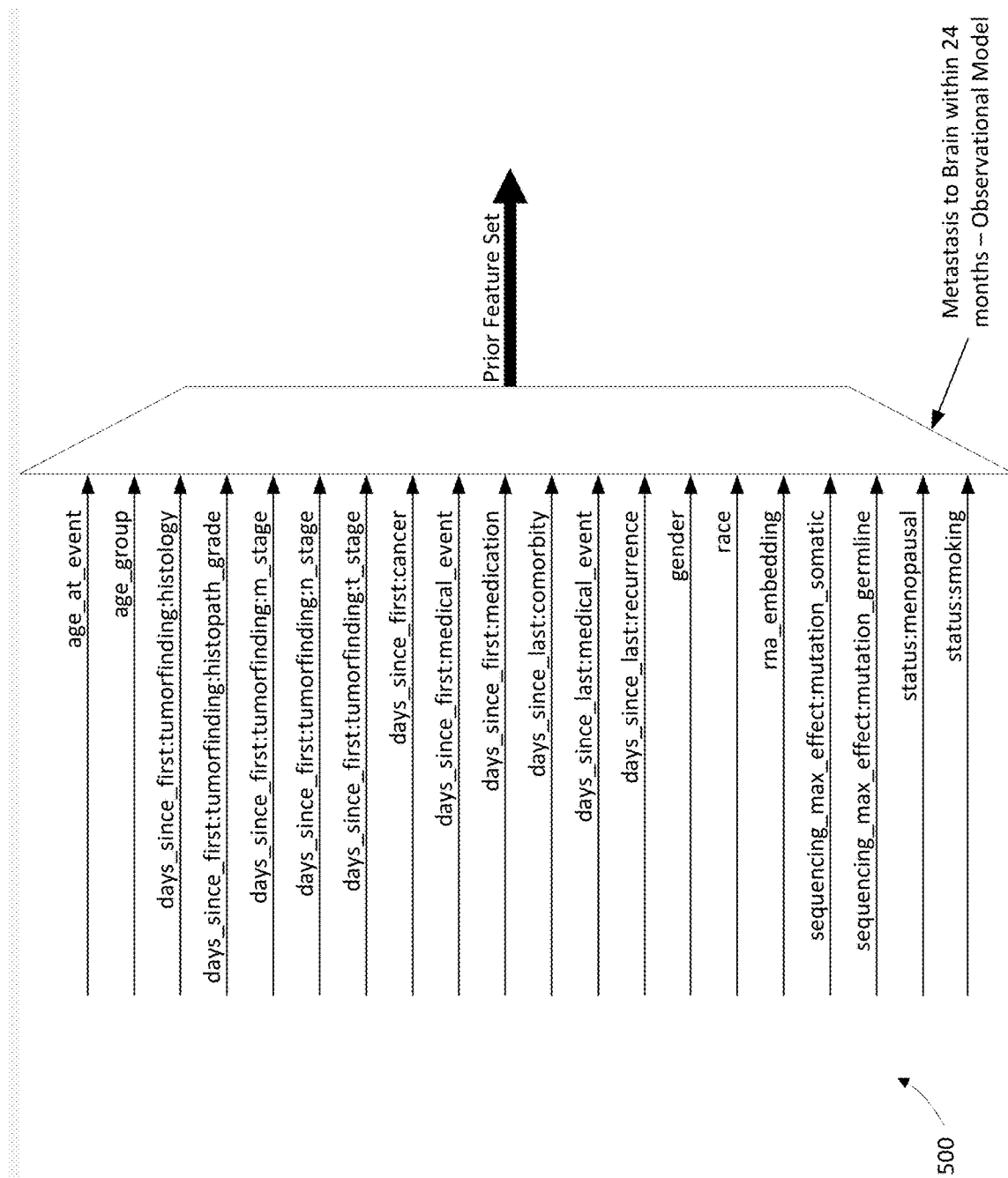
FIG. 5 is a schematic illustration of a system for selecting a feature set for generating prior features based from predicting the likelihood that a patient's cancer will metastasize to a specifically identified organ in the patient's body within a defined period of time, in accordance with some embodiments of the present disclosure.

FIGS. 3-5 illustrate the generation of feature sets from the feature store on a target/objective basis. FIG. 3 illustrates a system 300 for retrieving a first subset 1-N of features from the feature store 120. Different targets and objective modules may perform optimally on different feature sets. Feature selector and Prior feature set generator may select features 1-N based on the provided target and objective to produce an optimized, reduced feature set from which a patient-by-patient prior feature set may be generated. A prior feature set may be a collection of all features that occurred in a patient history before a specific date or may be an optimal collection of the best representative set of features satisfying the input requirements of a specific model, such as a model which has the best performance given the available features. For example, a patient with only DNA features may have a likelihood of metastasis to an organ predicted from a model trained only on DNA features, whereas a patient with both DNA and clinical features may have a likelihood of metastasis to an organ predicted from a model trained on both DNA and clinical features. In another example, a patient having sparsely populated features of numerous models, such as RNA, DNA, and clinical features, may evaluate expected performance from one or more combinations of the RNA, DNA, and clinical features alone and in combination to identify the best model and the set of features generated may be reduced to those that fit the optimal model. Other features, such as the specific date, may be selected from the current date at running of the model or any date in the past. In an exemplary likelihood that a patient's cancer will metastasize to a specifically identified organ in the patient's body within a defined period of time prediction model, the specific date may be an anchor point corresponding to the time of genetic sequencing at a laboratory, such as when a genetic sequencing laboratory provides results of tumor sequencing. In some embodiments, the prior feature set may be automatically analyzed and the most appropriate model may be selected based on the analysis.

Predictions may be effective tools for data science analytics to measure the impact of treatments on the outcome of a patient's diagnosis, compare the outcomes of patients who took a medication against patients who did not, or whether a patient will metastasize in a specified time period. It may be advantageous to separate a patient information into a collection of distinct prior feature sets and forward feature sets such that at every time point in the patient's history, predictions may be made and a more robust model generated that accurately predicts a patient's future satisfaction of a target/objective. A forward feature set may be advantageous when the predictive period for a target/objective combination begins to exceed a period of time that new information may be entered into the system 300. For example, a prediction that a patient may take a medication in the next 16-25 days has a limited window for new information from the date of prediction such that the prediction is unlikely to change based on information that becomes available within the next 16-25 days. However, a prediction that a patient's cancer will remain progression-free for the next 24 months may be greatly influenced by events that could happen in the next 24 months. Therefore, an exemplary system 300 may generate a forward feature set which looks to events that may occur during the prediction period at feature generator 335. In one embodiment, feature pass-through 340 may pass the prior feature set though the forward feature mapping 330 to objective modules 140 without generating an accompanying forward feature set, for example, when the prediction is unlikely to be improved by inclusion of a forward feature set.

As discussed above, the metastasis site objective module 146 may receive a DNA feature set, an RNA feature set, a combined RNA and DNA feature set, an observational feature set, partial subsets of features from the complete dataset, or a complete dataset comprising all features for each patient.

Various features may be generated and/or derived for a patient. For example, in some embodiments, the features can be related to RNA TPM (transcripts per million) count features. The feature space may comprise expression levels of the RNA for some or all of the coding genes in the sample. The expression is assayed by counting the number of RNA molecules (transcripts) that are present on a per gene basis. To standardize these counts across different experimental and technical conditions, the counts per gene can be corrected by a normalization factor. This factor standardizes the expression data to represent the number of RNA molecules that would be associated with a single gene in a pool of one million molecules, creating a TPM count.

In some embodiments, an input feature in a TPM space is a normalized count with a lower bound of 0, where the value represents the abundance of the transcript. Transcripts over the whole exome (nearly 19K genes) can be considered. For example, in some embodiments, the genes comprise DPM1, SCYL3, C1orf112, FGR, CFH, FUCA2, GCLC, NFYA, STPG1, NIPAL3, LAS1L, ENPP4, SEMA3F, CFTR, ANKIB1, CYP51A1, and KRIT1.

In some embodiments, the features generated for a patient may include RNA pathway features.

Previous experimental research has identified collections of functionally related genes, which are stored and collected in the MSigDB Molecular Signatures Database. RNA pathway features can be generated by performing single sample gene set enrichment analysis (ssGSEA) using the collections of gene sets and individual sample gene expression rankings. ssGSEA acts by ranking the RNA expression within a sample and then assigning a score to the gene set that is a function of that rank within the sample for the genes in the set. In practice, this functions to give high pathway scores to gene sets where all the genes in the set are highly expressed in the sample, and vice versa for lowly expressed genes. In practice, pathway scores serve to reduce some of the noise in the RNA expression feature space.

In an example, an input feature in RNA Pathway space is a numerical value between −1 and 1 indicating the coincident expression, either up-regulated or down-regulated, of all of the genes in the pathway grouping. Non-limiting examples of the pathways include: HALLMARK_ADIPOGENESIS, HALLMARK_ALLOGRAFT_REJECTION, HALLMARK_ANDROGEN_RESPONSE, HALLMARK_ANGIOGENESIS, HALLMARK_APICAL_JUNCTION, HALLMARK_APICAL_SURFACE, HALLMARK_APOPTOSIS, HALLMARK_BILE_ACID_METABOLISM, HALLMARK_CHOLESTEROL_HOMEOSTASIS, HALLMARK_COAGULATION, HALLMARK_COMPLEMENT, HALLMARK_DNA_REPAIR, HALLMARK_E2F_TARGETS, HALLMARK_EPITHELIAL_MESENCHYMAL_TRANSITION, HALLMARK_ESTROGEN_RESPONSE_EARLY, and HALLMARK_ESTROGEN_RESPONSE_LATE.

In some embodiments, additionally or alternatively, the features comprise imaging features extracted from digital images. In some embodiments, imaging features can be divided into two categories: biologically meaningful features and geometrically meaningful features. Biologically meaningful features can include tumor percentage (percentage of the detected tissue area on the slide classified as tumor, between 0 and 100), tumor cell percentage (percentage of the total cells that are tumor cells, as opposed to lymphocytes, between 0 and 100), tumor infiltrating lymphocytes percentage (calculated as total number of lymphocytes within the tumor region divided by total number cells in the tumor region, between 0 and 100), tumor budding features (specifically for colorectal cancer, represented as integer counts for number of detected tumor buds, or normalized by density within a given area), and more. Geometrically meaningful features include aggregation metrics (minimum, average, median, maximum) of tumor perimeter (to measure the perimeter of the tumor within a slide, given in pixels, where each pixel is 8 um by 8 um), average tumor cell circularity (calculated as cell area divided by the square of the perimeter, averaged over all cells, ranges between 0 and 1), average tumor cell length and aspect ratio (The eigenvalues are calculated for the cell shape, giving a relative, rotation independent, length and width of the cell; this is first done by identifying all pixels that are associated with the cell, and using the (x,y) pixel locations as points for a covariance matrix. The eigenvalues are then calculated, and the first component is taken as the length of the cell. The aspect ratio is calculated as the second divided by the first eigenvalues, ranges between 0 and 1).

Referring back to FIG. 1, a model 146b may be generated for each of the potential feature sets or targets 146a. FIG. 4 illustrates an exemplary prior feature set which may be generated for a target/objective combination for predicting metastasis to brain within 24 months where the inputs narrowed to the prior features based on the target/objective of "metastasis to brain within 24 months—all features." A sufficiently trained model may identify a combination of features including cancer site, date since diagnosis, gender, symptoms, and sequencing information as the most relevant features to predicting metastasis of a patient. In some instances, a patient's tumor may be more likely to metastasize to the brain when the originating tumor is an EGFR or HER2 positive lung cancer, a patient's tumor origin alone may influence metastasis when the origin is a primary neoplasm such as melanoma, lung, breast, renal, and colon cancer, the age of the patient may also play a role as children may be more likely to metastasize than adults, a male patient with lung cancer may be more likely to metastasize, a female patient with breast cancer may also be more likely to metastasize, symptoms implicating the brain from either neural discomfort such as headache, paresthesia or tingling in the patient's extremities, or a measurable increase in intercranial pressure may also increase the patient's likelihood for metastasis, and RNA/DNA sequencing results indicating a presence of a NOTCH2, FANCD2, EGFR, or TP53 variation or copy number change may increase a patient's likelihood for metastasis. Therefore, a predictive model may select a subset of features from the feature store 120 including each of these features, and more, as identified by the optimal model given a patient's (or collection of patients') feature set(s).

FIG. 5 illustrates a prior feature selection set for a target/objective pair metastasis to brain within 24 months using an observational model. In some embodiments, features of an observational model may be limited to features which may be observed from patient results from tests, progress notes, but not medications, procedures, therapies, or other proactive actions taken by a physician in treating the patient. General features in the observational feature set may include a patient's age at event for each event which may exist in the patient's record. Preprocessing steps may be performed on the ages available to reduce the dimensionality of the input features. For example, instead of having 100 points for ages of patients, the patient's age may be fitted into a group such as a range including 00 to 09, 10 to 19, 100 to 109, 110 to 119, 20 to 29, 30 to 39, 40 to 49, 50 to 59, 60 to 69, 70 to 79, 80 to 89, 90 to 99, or Unknown for each event in the patient's record. While a bin of ten years is exemplified, other bin sizes may be used. The reduction accomplished through binning features allows for a more robust analysis of the bins rather than the granular age. The patient's gender or race may be normalized so that different sources having different ethnicity options are binned into similar ethnicities. For example, a race of caucasian may be binned with white, a dataset including Japanese, Korean, Phillipean distinctions may be binned into Asian, a dataset with Hawaii, Guam, Tonga, Samoa, or Fiji may be binned into Pacific Islander, or a dataset with Cuban, Mexican, Puerto Rican, or South or Central American may be binned into Hispanic or Latino. Features which may be entered into the record by occurrence may be translated and tracked by a number of days since the first or last occurrence. Days since the first or last occurrence features may include a tumor finding by histology for tumors including acinar_cell_carcinoma, adenocarcinoma,_no_subtype, carcinoma,_no_subtype, infiltrating_duct_carcinoma, lobular_carcinoma, malignant_neoplasm,_primary, mucinous_adenocarcinoma, neuroendocrine_carcinoma, non_small_cell_carcinoma, otherGroup, small_cell_carcinoma, small_cell_neuroendocrine_carcinoma, squamous_cell_carcinoma,_no_icd_o_subtype, or transitional_cell_carcinoma. Other days since the first or last occurrence features may include tumor finding by histopathology grade or T-N-M stages including grade_1_(well_differentiated), grade_2_(moderately_differentiated), grade_3_(poorly_differentiated), grade_4_(undifferentiated), high_grade, m0, m1, mx, n0, n1, n2, n3, nx, pn0, pn1, pn2, pnx, stage_1, stage_2, stage_3, stage_4, pt1, pt2, pt3, pt4, t0, t1, t2, t3, t4, tx, or valg_stage-extensive.

Even other days since first or last occurrence features may include cancer type determinations or findings of breast, cervix_uteri, colon, head_and_neck, kidney, lung, lymphoid,_hemopoietic_and/or_related_tissue, otherGroup, ovary, pancreas, prostate, respiratory_tract, skin, skin_of_trunk, soft_tissues, stomach, tongue, unknown_site, or urinary_bladder. Still further days since first or last occurrence features may include medical events, prior medications, or comorbidity or recurrence events including emergency_room_admission, inpatient_stay, seen_in_hospital_outpatient_department, Abnormal_findings_on_diagnostic_imaging_of_breast, Administration_of_antineoplastic_agent, Anemia, Dehydration, Disorder_of_bone, Disorder_of_breast, Dyspnea, Essential_hypertension, Fatigue, Imaging_of_thorax_abnormal, Immunization_advised, Long_term_current_use_of_drug_therapy, Osteoporosis, Past_history_of_procedure, Screening_for_malignant_neoplasm_of_breast, chronic_obstructive_lung_disease, otherGroup, type_2_diabetes_mellitus, type_2_diabetes_mellitus_without_complication, emergency_room_admission, inpatient_stay, seen_in_hospital_outpatient_department, lung, otherGroup, or soft_tissues. DNA and RNA features which have been identified from a next generation sequencing (NGS) of a patient's tumor or normal specimen to identify germline or somatic variants include categorizations of RNA expression analysis from an RNA auto encoder, DNA related features (DNA variant calls) may include a calculation of the maximum effect a gene may have from sequencing results for the gene and source set forth in Table 1, fluorescence_in_situ_hybridization_(fish), gene_mutation_analysis, gene_rearrangement_analysis, or immunohistochemistry_(ihc) results. A patient's prior feature set may be selected from each of the above features identified within the patient's structured medical records available in the feature store 120. Prior feature sets from the feature generator may be provided to the corresponding model for the target/objective pair identified and predictions generated for the patient.

Figure 6:
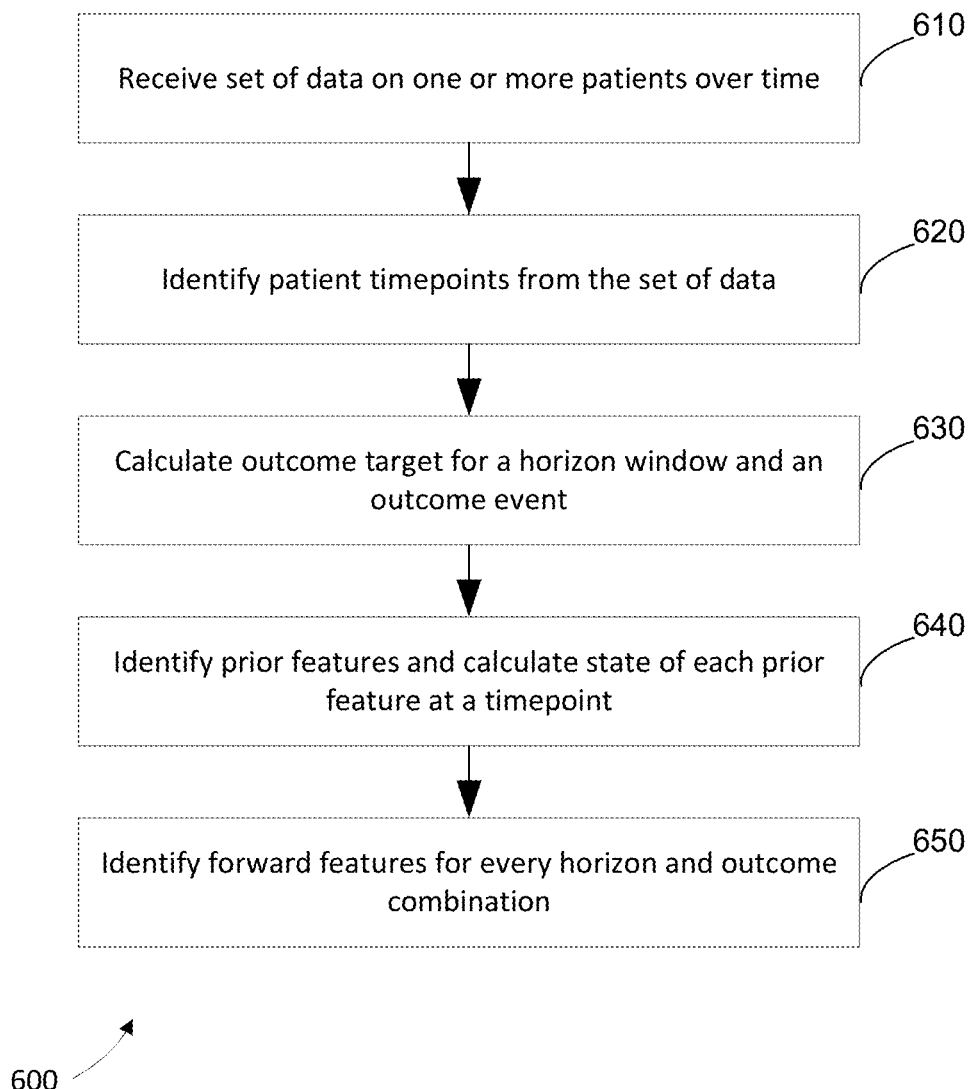
FIG. 6 is a flowchart illustrating a method for generating prior features and providing the prior features to a model for predicting the likelihood that a patient's cancer will metastasize to a specifically identified organ in the patient's body within a defined period of time, in accordance with some embodiments of the present disclosure.

FIG. 6 is a flow chart of a method 600 for generating prior feature sets and forward feature sets in accordance with some embodiments. At step 610, the system may receive a set of data relating to one or more patients, wherein the data can be obtained over time. The received set of data may include features from the feature generation 130 as a refined feature set described above with respect to FIGS. 4 and 5. Patient records are received which may span from a single entry to decades of medical records. While these records indicate the status of the patient over time, they may be received in a single transmission or a batch of transmissions. Each patient may have hundreds of records in the system. An exemplary set of records for a patient may include physician note entries from a routine doctor's visit where the doctor prescribed an antibiotic after determining the patient has a bacterial infection, a scheduling request to see a specialist after the patient complained about headaches, scheduling request to take an MRI scan, an MM report summarizing the radiologists findings of an unknown mass in the patient's lungs, a scheduling request to perform a biopsy of the mass, a pathologist's report of the cells present in the biopsy specimen, a prescription to begin a first line of therapy for lung cancer, an order for genetic sequencing of the biopsy specimen, and any subsequent next-generation sequencing (NGS) report for the biopsy specimen.

At step 620, the system may identify patient timepoints based on the set of data. Identified timepoints may include all timepoints from patient diagnosis up to the last entry or patient's death. In some target/objective pairs, the only timepoint for identification is the most recent timepoint in which the patient received genetic sequencing results, such as, e.g., results from a next-generation sequencer for the genomic composition of the patient's tumor biopsy. An exemplary timepoint selection for a metastasis to brain prediction may include only the date that the next-generation sequencing report for the biopsy specimen was performed. In another embodiment, timepoint selection for a patient's likelihood to take undergo a progression event (an event from which the cancer progresses such as metastasis, the tumor size increases, or other events known to those of ordinary skill in the art) may include timepoints from records: the pathologist's report of the cells present in the biopsy specimen, the prescription to begin a first line of therapy for lung cancer, the order for genetic sequencing of the biopsy specimen, and the subsequent next-generation sequencing report for the biopsy specimen.

At step 630, the system may calculate outcome targets for a horizon window and outcome event. Outcome events may be the objectives, and horizon windows may be the time periods such that an objective/target pair is calculated. An exemplary target/objective pair may be metastasis to brain (the objective) within 24 months (the target). The target/objective pair may also include the model from which the pair should be calculated. An exemplary model may be an observation model. Other target/objective pairs, datasets, and models are introduced above with respect to objective modules 140. At step 640, the system may identify prior features and calculate the state of the prior features at each timepoint. For example, for a target/objective pair "metastasis to brain within 24 months—observational model," as described above with respect to FIG. 5, the set of prior features may be calculated once, at the time of NGS. For a target objective pair "PFS within 2 years," the set of prior features may be calculated for each timepoint corresponding to the following records: the pathologist's report of the cells present in the biopsy specimen, the prescription to begin a first line of therapy for lung cancer, the order for genetic sequencing of the biopsy specimen, and the subsequent next-generation sequencing report for the biopsy specimen.

At step 650 of FIG. 6, the system may identify forward features for every horizon and outcome combination where the horizon is of a sufficient duration that an event happening after the anchor point but before the termination of the timeline may have a noticeable effect on the reliability of the prediction. A forward feature set may be calculated, at step 650, for horizons spanning months or years. In some embodiments, forward feature sets are calculated for horizons spanning a certain number of days. Forward features comprise the same feature sets as prior features but involve a conversion of the features from a backwards looking focus to a forwards looking focus. Exemplary forward features may include a computer-implemented determination of the following: "Will patient take medication A after date of anchor point and before date of endpoint," "Will patient experience headaches after date of anchor point and before date of endpoint," "Will patient progress after date of anchor point and before date of endpoint," or any other forward looking version of features in the prior feature set. Forward features may be predicted using another target/objective prediction, ensemble model first, and the predictions themselves added into the feature set to influence the final prediction. For example, a patient who is observing increased intercranial pressure may be predicted to experience headaches and a patient who experiences both increased intercranial pressure and headaches may be predicted to be more likely to have metastasis to the brain. A model which finds that a patient with an increase in intercranial pressure is likely to experience headaches within two weeks may provide additional features from which to inform the prediction of metastasis to the brain. While the example is hypothetical, models may be trained to predict occurrence of each feature.

Figure 7:
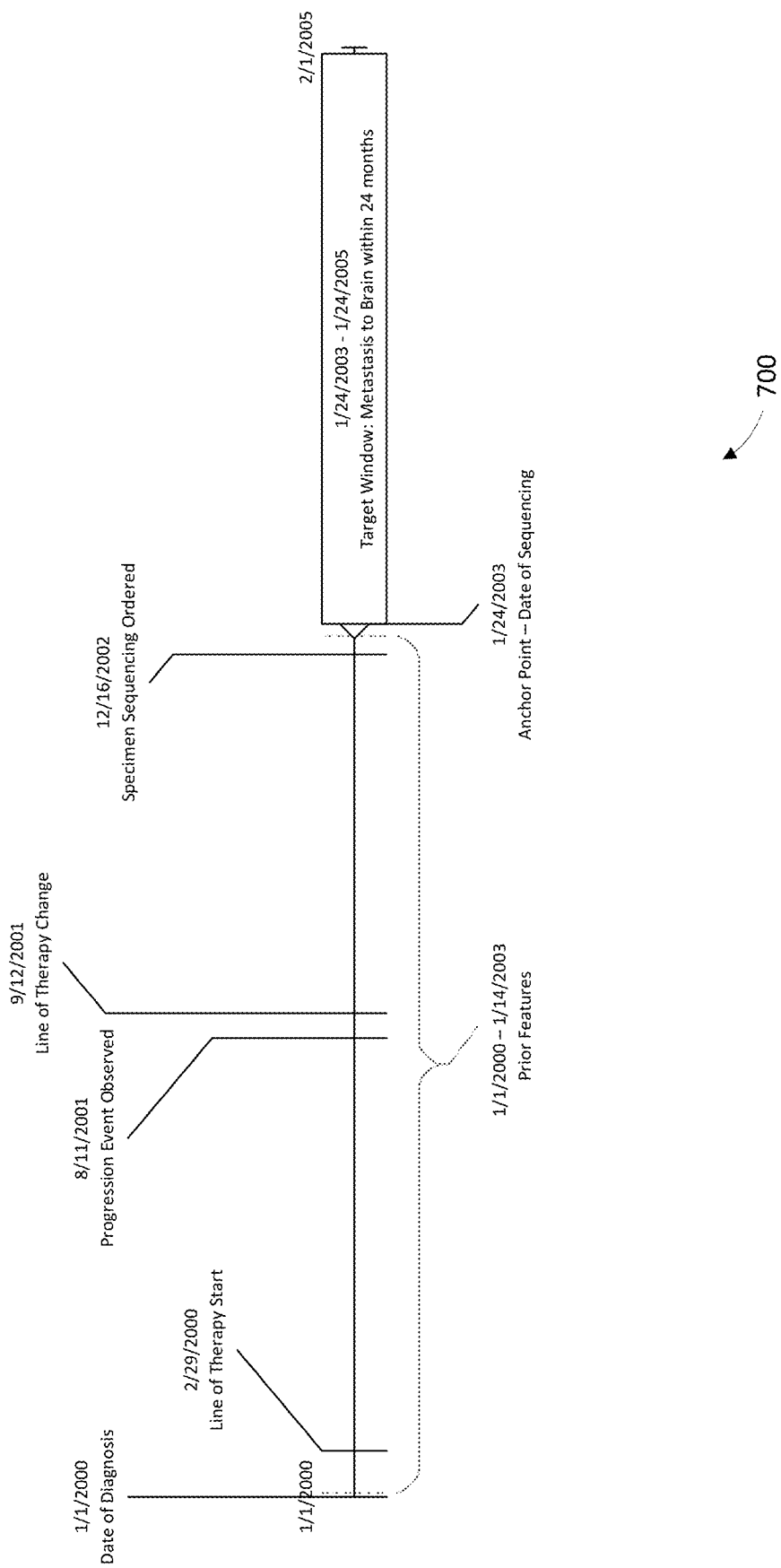
FIG. 7 is an illustration of an example of a patient timeline having events determining prior and forward features, in accordance with some embodiments of the present disclosure.

FIG. 7 illustrates an exemplary timeline of events in a patient's medical record which may provide prior features for a prior feature set.

A patient's medical record may have a unique series of events, or interactions, as they face the challenges of rigoring through treatment for a disease. In patients who are diagnosed with cancer, some of these events may provide important features to prediction of a site of origin of a metastatic tumor for the patient. For an exemplary patient, the first event informing their prior feature set may be a progress note from the date of diagnosis (Jan. 1, 2000) containing the patient's information, cancer type, cancer stage, and other features. The second event informing their prior feature set may be a prescription for medications of a first line of therapy (Feb. 29, 2000) containing the patient's medications, dosages, and expected administration frequency. A third and fourth event may be a progress note from a physician which notes that an imaging scan of the tumor (Aug. 11, 2001) shows that it has increased in size since the first line of therapy started and may prompt the physician to prescribe medications for a second line of therapy triggering another progress note (Sep. 12, 2001) containing the patient's new medications, dosages, and expected administration frequency.

The final events, or interactions, in the patient's medical record prior to triggering a prediction of the patient's site-specific prediction of metastasis may include a physician's order for sequencing a biopsy of the tumor (Dec. 16, 2002) and a subsequent sequencing report (Jan. 24, 2003) comprising the results of that sequencing. After a system, such as the system of FIGS. 1 and 5 processing site-specific metastatic predictions, including a metastasis to brain within 24 months, detects presence of a stored sequencing report, a model pipeline may trigger generation of the prediction. As another example, events, or interactions, which trigger generation of a prediction may include a physician's order for monitoring of the patient and a subsequent imaging report comprising the results of that imaging, including MM, X-Ray, radiology image, H&E slide, IHC Slide, or other imaging record.

In some embodiments, a model pipeline may include a plurality of models. When modeling with small sample sizes, random choice of specific patients for hold-out set evaluation can have a large impact on resulting performance. With different train-test patient assignments, a hold-out set ROC AUC score can be, in some implementations, of from 0.3 (considered to be worse than random) to 1.0 (considered to be a "perfect" model). In some embodiments, because of this large degree of variability, performance can be evaluated on a large number of different potential hold out sets, as opposed to relying on a single set of predefined train-test assignments.

In some embodiments, a modeling algorithm can include data preprocessing (log-transforming, one-hot encoding, imputing missing values, and in-line transformations such as z-scoring, dimensionality reduction methods, etc.), robust feature selection (a bootstrapped approach using lasso techniques, many different modifications of recursive feature elimination, Pearson correlation, correlated feature trimming, spectral biclustering, or other methods, hyper-parameter tuning (model selection from modifying the regularization strength in logistic regression, or number of estimators and maximum depth in a random forest, as examples), prediction generation (generating a probability between 0 and 1 for each patient at any given time horizon, from the tuned model), and feature importance evaluation (where features are identified which are driving, or correlated with the prediction). It should be appreciated, however, that any variations of the modeling algorithm are possible.

In some embodiments of the present disclosure, the entire modeling algorithm can be executed more than 100 times, each time with a different assignment of cross-validation folds and hold out set. This process results in over 100 out-of-fold cross validated scores on the training set and over 100 of hold-out (or test set) scores to allow for more robust evaluation of the model, given the chosen pipeline parameters, since it generates a distribution of performance metrics, as opposed to relying on single point estimates (which can have a large degree of variance). This approach improves both model development and understanding of model generalizability. For the model development, this allows us to more rigorously compare the potential benefit of change to the pipeline (e.g., a new feature selection method, modeling framework, etc.), by comparing the two distributions of model performance scores, instead of comparing two held-out score point estimates. In terms of model generalizability, the held-out score distribution gives a much better understanding of how the model can be expected to perform on completely unseen data.

Furthermore, the large number of sets of predictions can also allow making some estimate of confidence about each patient's predicted probability of metastasis, since the pipeline will generate the large number (e.g., at least 100, or at least 200, or at least 300, or at least 400, or at least 500, or at least 1000) different predictions for each patient, instead of only one single prediction. In addition, the repeated, multiple feature importance evaluations provide a more robust feature importance analysis, because such approach allows selecting most robust features based not only on one specific training set, but in a certain percentage of the large number of different training sets. A threshold can be used to determine which features are identified as robust.

Figure 8:
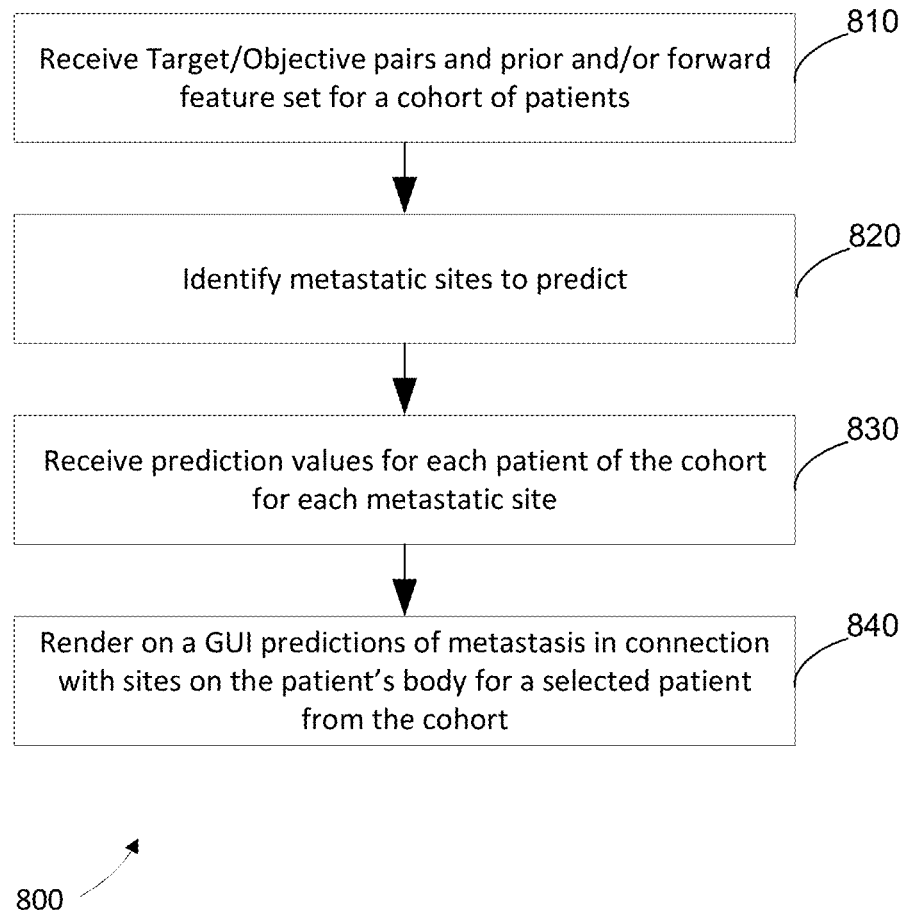
FIG. 8 is a flowchart illustrating a method for performing analytics in conjunction with application of a model for predicting site-specific metastasis in a patient, in accordance with some embodiments of the present disclosure.

FIG. 8 illustrates an exemplary flowchart of a process 800 for applying a model for predicting site-specific metastasis for a patient, in accordance with some embodiments of the present disclosure. The process 800 can be formed, for example, by the system 100 (FIG. 1) or by another suitable system.

At step 810, the system may receive target/objective pairs and prior feature set for a cohort of patients. The system may also receive a request to process one or more target/objective pairs from one or more prior and forward feature sets. Each target/objective pair may be matched with a specific combination of prior and/or forward feature sets based upon the requirements of a corresponding machine-learning model. At step 820, the system may identify metastatic sites to predict. In an embodiment, each of the target/objective pairs may reference a specific metastasis site which may be passed through to model selection directly. In other embodiments, a target/objective pair may not specify a metastasis site—e.g., the target/objective pair may define a request to predict metastasis within 60 months. The system may then select a model trained for prediction of a certain metastasis site within the available models, and it can pass the matched target/objective pair and combination of prior and/or forward features to the model. At step 830, the system may receive prediction values for each patient of the cohort for each metastatic site. The predictions may be stored in a prediction store such as, e.g., the prediction store 150 or the predictions may be passed to webforms for displaying prediction results for the patient on a graphical user interface of a computing device of a user. The user can be, e.g., a patient's physician, oncologist, or another medical professional. At step 840, the system may render, on the graphical user interface of the computing device, in a graphical form, predictions of metastasis for a patient of the cohort. The predictions of metastasis can be, e.g., in the format of a likelihood of metastasis to a certain part/site of the body within a certain time period from the current time. The predictions can be displayed on the user interface in association with a computer-implemented representation of the human body (or its parts), or in other suitable format.

In some embodiments, the graph, images, and/or other information may be generated in a corresponding webform for viewing the results of site-specific metastasis predictions. Metastasis predictions associated with the target/objective pair may be graphed on an image of a body and/or analytics may be viewed. Analytics may include the prediction percentages, survival curves of the cohort, or features which were driving factors in the prediction results generated. One example of a webform for displaying the graph is shown FIG. 9, discussed below.

Applications of predictions may include providing precision medicine results for a patient. For example, a sample obtained from a patient may be subjected to genetic sequencing during a course of treatment for a cancer diagnosis. Predictions may be generated based upon the patient's genetic sequencing results, which provide insights on the patients response to particular therapies. A physician may receive recommended considerations as a component of a reporting of the genetic sequencing as a precision medicine result for the patient. Results may include therapies which are expected to perform well for a patient having characteristics similar to the reported patient, clinical trials which may accept the patient, or results of the sequencing which may influence the physician's decisions. In one example, a patient may be prescribed a treatment which is considered aggressive for the treatment and prevention of metastasis. A prediction may be generated that the patient, based upon their particular genetics and clinical history, are unlikely to metastasize to any localized region within the next 60 months. A physician may then decide to suggest a less aggressive treatment to the patient which may reduce the negative side effects related to a harsher, more aggressive treatment and may be cheaper.

In another example, a patient may be prescribed an introductory treatment which is not considered aggressive just to see how the patient responds. A prediction may be generated that the patient, based upon their particular genetics, clinical history, and most recent imaging reports are likely to metastasize from a primary cancer site to another localized region within the next 6 months. A physician may then decide to suggest a more aggressive treatment to reduce the chance that the patient's tumor may metastasize to another localized region. Considerations made by the physician are not limited to treatments, as a physician may utilize predictions to schedule the frequency of monitoring for the patient, such as follow-up visits, additional scanning, screening, imaging, blood tests, or subsequent genetic sequencing. For example, a patient with a high prediction of metastasis may benefit from accelerated screening to detect changes as they occur rather than months after they occur and the patient is experiencing noticeable side effects. In another example, a pharmaceutical company testing a new drug may select potential test groups both off of their current inclusion and exclusion criteria and the probability that the patient will experience a predicted outcome.

In another example, a pharmaceutical company may retroactively analyze the predicted outcome of patients in a clinical trial against how they responded to identify patient characteristics which may be included as inclusion or exclusion criteria in a future clinical trial. For example, patients which responded well to treatment and had a high prediction for successful response to treatment may have features, or status characteristics, in common which are absent from the patients which did not respond well to treatment.

Figure 9:
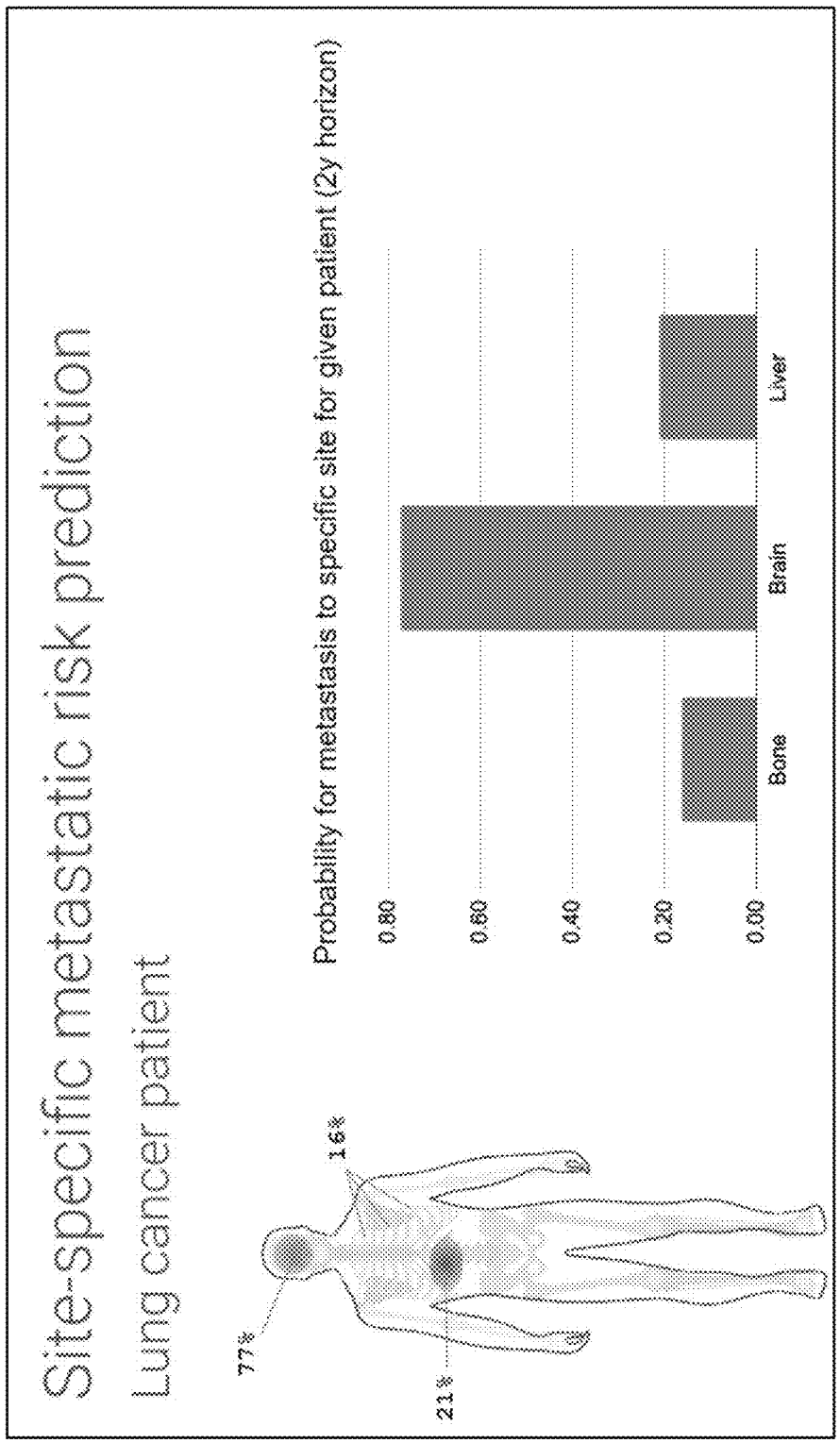
FIG. 9 illustrates an example of elements of a webform for viewing site-specific predictions of metastasis in a patient, in accordance with some embodiments of the present disclosure.

FIG. 9 illustrates an example of a webform for viewing site-specific predictions of metastasis in a single patient. The webform can be displayed on a GUI of a user device (e.g., the GUI 165 of FIG. 1).

An exemplary webform may provide a patient portal to a user, such as, e.g., a physician, oncologist, or patient, that may request predictions of metastasis based upon a target/objective scheme. For example, a user may request a prediction of metastasis to the brain in the next 12 months or a prediction of metastasis to any site in the next 60 months.

The system, such as system 100 of FIG. 1, may either calculate a prediction on the fly or retrieve a precalculated prediction from the prediction store 150 and provide the webform with the prediction information for display to the user. In one embodiment a user may request a prediction of metastasis to any site in 24 months. The webform may receive the predictions and display them to the user through the user interface of the webform.

The metastasis sites may be displayed in a number of different formats. A first format may include an image of a human body which regions having metastasis predictions highlighted therein. Highlighting for regions with predictions may be color coded based upon the value of the prediction. For example, elements/organs/sites of the human body which do not have predictions may not be referenced in the image, such as the breast or colon which are not referenced. A prediction falling below a threshold of 20% may receive a callout such as a line or other indicator linking the organ to the prediction threshold, such as the bones which are referenced in the image with lines to the prediction value 16%. A prediction falling between 20% and 50% may receive a callout linking the organ to the prediction threshold and a color coded shading over the region indicating the severity of the prediction, such as the liver which are referenced in the image with a line to the prediction value 21% and a green shading over the region where a liver would be in a human. A prediction falling between 50% and 75% may receive a callout linking the organ to the prediction threshold and a color coded shading over the region indicating the severity of the prediction, for example a yellow shading over the region where the metastasis site would be in a human. A prediction exceeding 75% may receive a callout linking the organ to the prediction threshold and a color coded shading over the region indicating the severity of the prediction, such as the brain which is referenced in the image with a line to the prediction value 77% and a red shading over the region where a brain would be in a human.

The above prediction ranges and combination of callout styles and color shading are provided for illustrative purposes and are not intended to limit the display to the user. Other combinations of prediction ranges, callout conventions, and/or coloring may be provided to the user without departing from the spirit of the disclosure. In addition to or as an alternative to the first format, a second format may include a histogram or bar chart which provides a side by side comparison of the predictions for differing metastatic sites. For example, a lung cancer patient may have metastasis predictions for bone, brain, and liver sites. A histogram may display the predicted values of each side-by-side to provide the user with a visual comparison of the likelihood of metastasis to each site. Other statistical, analytical, or graphical representations may be provided including charts, plots, and graphs such as prediction distribution Kernel Density Estimate (KDE) plots, violin plots, per patient time series line plots of predicted likelihood of metastasis to patient organs over time, etc.

Figure 10:
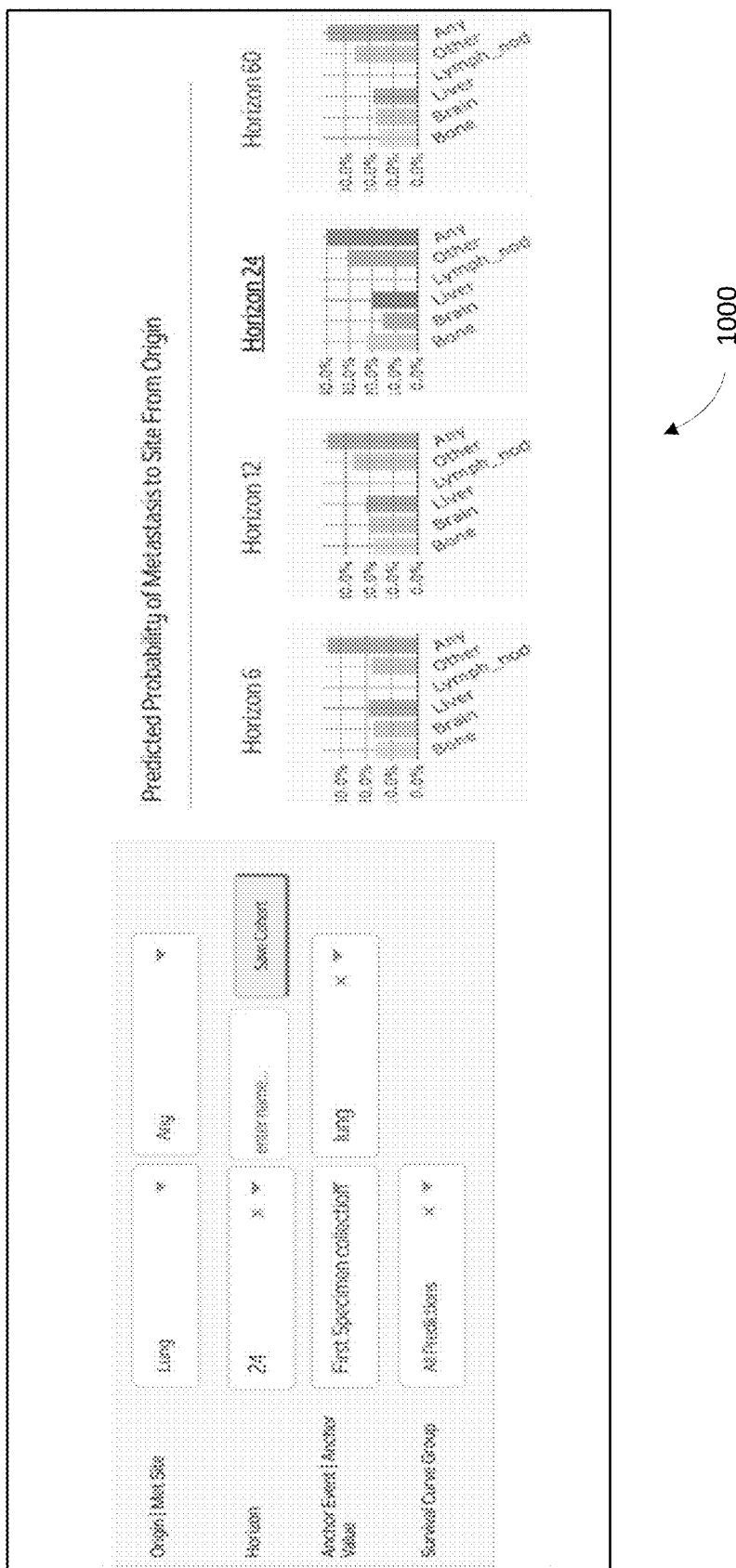
FIG. 10 illustrates an example of elements of a webform for viewing site-specific predictions of metastasis in a cohort of patients, in accordance with some embodiments of the present disclosure.

FIG. 10 illustrates elements of an exemplary webform 1000 for generating site-specific predictions of metastasis in a cohort of patients based on a user input received via the webform 1000.

An exemplary webform may provide a cohort portal to a user, such as a physician, oncologist, or researcher may request predictions of metastasis based upon a target/objective scheme across an entire cohort of patients. For example, a user may request a prediction of metastasis to the brain in the next 12 months or a prediction of metastasis to any site in the next 60 months. The system, such as system 100 of FIG. 1, may either calculate a prediction on the fly or retrieve a precalculated prediction from the prediction store 150 and provide the webform with the prediction information for display to the user. In one embodiment a user may request a prediction of metastasis to any site in 24 months. The webform may receive the predictions and display them to the user through the user interface of the webform. The receipt of the request may be facilitated through an aspect of the user interface containing one or more editable fields. For example, a first field may provide a text input or dropdown for selecting the origin site of cancer for patents of the cohort. The origin site may be selected from any diagnosable site of cancer, including: breast, lung, pancreas, prostate, colorectal, skin, brain, lymph nodes, and bone.

A second field may provide a text input or a drop down for selecting a metastasis site of cancer for patients in the cohort, including: breast, lung, pancreas, prostate, colorectal, skin, brain, lymph nodes, bone, and an "any" option to group all metastasis together. A third field may provide a text input or a drop down for selecting a horizon, or time period, within which to predict the likelihood of metastasis for patients in the cohort.

A fourth and fifth field may provide a text input or a drop down for selecting an anchor event and a corresponding anchor value. The anchor event being the event that must be common across all patients in the cohort and from which the prediction's horizon will toll. Anchor events and corresponding values (presented below as Event: Values) may include: First Primary Cancer Diagnosis: Any Cancer Site (breast, lung, pancreas, prostate, colorectal, skin, brain, lymph nodes, bone, etc.); First Stage: Any Cancer Stage (Stage 0, 1, 2, 3, 4); First medication: Any Medication (doxorubicin, cyclophosphamide, anastrozole, tamoxifen, dexamethasone, pegfilgrastim, etc.); First Radiotherapy: Any Radiotherapy Treatment (n-dimensional conformal radiation, cyberknife, external beam, image guided, intensity modulated, total body, radioactive isotope, etc.); First Procedure: Any Procedure (endoscopic, mastectomy, ablations, antrotomy, reconstructions, biopsies, excisions, resections, grafts, etc.); First Specimen Collection: Any Biopsy Site For Sequencing (breast, lung, pancreas, prostate, colorectal, skin, brain, lymph nodes, bone, etc.); First Alternative Grade: Any Grade (fuhrman stage 1-4, who stage i-iv, etc.); First Line of Therapy: Any Combination of LoT Medications (abiraterone+apalutamide+leuprolide, abiraterone+ascorbic acid, fluorouracil+oxaliplatin, capecitabine+fulvestrant, etc.); and other combinations of events and values which may occur in a patient's medical record. A sixth and seventh field may provide a text input box and a button that when activated stores a copy of the above selected cohort restraints under a name entered into the textbox. Alternative means for storing the cohort may be implemented in place of a text input field and button. For example, a single button may exist, which prompts a dialog box that navigates the file directory of the user's computer to select a location and name for which to store the selections or no location may be available if the user is restricted to only storing the saved cohort selections on the server for online-access only.

Selecting a cancer origin site, a cancer metastasis site, an anchor event, and/or a survival curve group may further filter the cohort to only patients which have the respective prerequisite event or outcome in their patient records, or those patients who receive the selected prediction.

The metastasis sites may be displayed in a number of different formats. In some embodiments, for example, a format may include an image of a human body which regions having metastasis predictions highlighted therein. Highlighting for regions with predictions may be color coded based upon the value of the prediction. For example, elements/organs/sites of the human body which do not have predictions may not be referenced in the image, such as the breast or colon which are not referenced. A prediction falling below a threshold of 20% may receive a callout such as a line or other indicator linking the organ to the prediction threshold, such as the bones which are referenced in the image with lines to the prediction value 16%.

A prediction falling between 20% and 50% may receive a callout linking the organ to the prediction threshold and a color coded shading over the region indicating the severity of the prediction, such as the liver which are referenced in the image with a line to the prediction value 21% and a green shading over the region where a liver would be in a human. A prediction falling between 50% and 75% may receive a callout linking the organ to the prediction threshold and a color coded shading over the region indicating the severity of the prediction, for example a yellow shading over the region where the metastasis site would be in a human.

A prediction exceeding 75% may receive a callout linking the organ to the prediction threshold and a color coded shading over the region indicating the severity of the prediction, such as the brain which is referenced in the image with a line to the prediction value 77% and a red shading over the region where a brain would be in a human. The above prediction ranges and combination of callout styles and color shading are provided for illustrative purposes and are not intended to limit the display of such to the user. Other combinations of prediction ranges, callout conventions, and/or coloring may be provided to the user without departing from the spirit of the disclosure. In addition to or as an alternative to the first format, a second format may include a histogram or bar chart which provides a side by side comparison of the predictions for differing metastatic sites. For example, a cohort of lung cancer patients may have metastasis predictions for bone, brain, liver, lymph node, other and any sites. A histogram may display the predicted values of each side-by-side to provide the user with a visual comparison of the likelihood of metastasis to each site. Additionally, a set of histograms may be viewed together, one for each of a set of horizons. For example, a first histogram may display the cohort average predictions for a horizon of 6 months, a second histogram for a horizon of 12 months, a third histogram for a horizon of 24 months, a fourth histogram for a horizon of 60 months, and so on. In addition to, or as an alternative to the first or second format, prediction distributions graphs, survival curves, or Kaplan Meier plots may be considered. Other statistical, analytical, or graphical representations may be provided including charts, plots, and graphs.

Once a user has accessed the webform, requested predictions of metastasis based upon a target/objective scheme across an entire cohort of patients, and obtained the displayed predictions via the user interface of the webform, the user may desire to understand which features shared by members of the cohort were most influential in driving the predictions and facilitate model interpretability. The most influential features can be, for example, features related to or derived from sequencing information, such as information on genes that are most informative of the generated predictions. An adaptive algorithm runs alongside the modeling to generate viable feature importance ranks exclusively on the selected sub-population of patients without needing to re-train the underlying models. An exemplary adaptive algorithm may: calculate population mean prediction across the patients in the cohort; encode categorical feature levels, including clustering/bucketing continuous features, as the difference/delta between the predicted value and the population mean prediction; aggregate average probability difference with the estimated percentage per categorical level and assign overall feature importance as the frequency-weighted sum of absolute value of all values; and assign an impact value representing each feature's co-occurrence with an observed deviation from prediction mean to explore the variation in impact per change in feature value. A graphical representation of the feature enrichment ranking results may be presented according to an embodiment of FIGS. 11 and 12.

Figure 11:
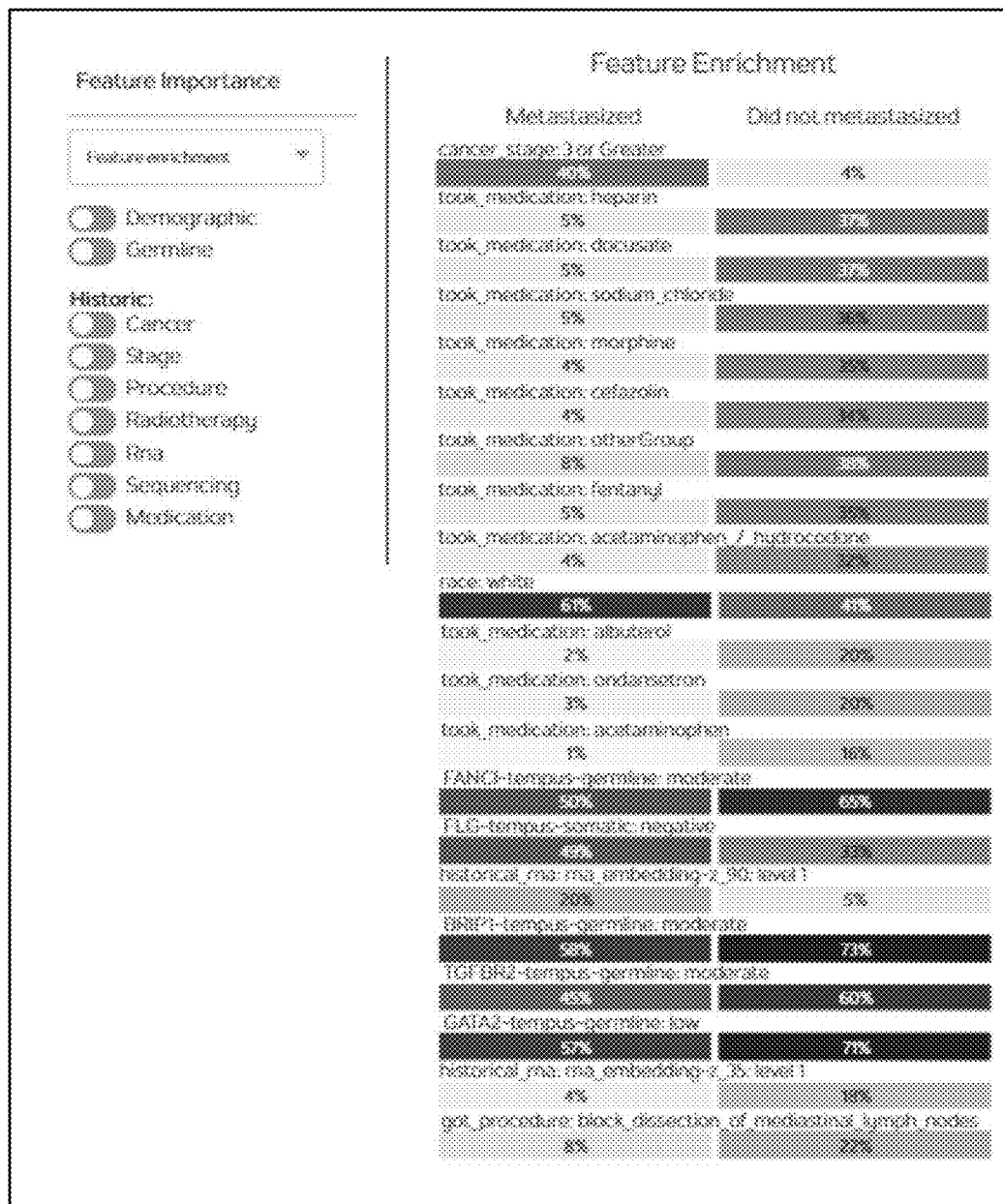
FIG. 11 illustrates an example of elements of a webform for viewing feature rankings of site-specific predictions of metastasis in a cohort of patients, in accordance with some embodiments of the present disclosure.

FIG. 11 illustrates elements of an exemplary webform for viewing feature importance rankings of site-specific predictions of metastasis in a cohort of patients.

A first field may provide a text input, radio button, toggle, or a drop down for selecting a feature importance ranking visualization method for selecting between a heatmap, feature enrichment presentation and a scaled, ranking bar feature importance representation. One or more additional radio buttons, toggles, or other feature selectors may be presented to the user to allow the selection of which features should be included in the feature importance model. Selectable features may include any level of categorization of the features in the input dataset, including patient demographics, germline results from sequencing, cancer types and/or stages, procedures or radiotherapies underwent by the patient, genomic or sequencing results of the patient's tumor or normal specimens, or medications taken by the patient. Selection of a selectable feature will trigger the inclusion or exclusion of the associated features from the feature importance calculations and the remaining features' weights will be recalculated to compensate for the adjustment to features.

An exemplary feature enrichment graphical representation may provide a heatmap of the feature importance to each model prediction of metastasized or did not metastasize. The heatmap may be selected between one or more colors such that if a single color is used in the heatmap visualization, the intensity of the color may vary to indicate a stronger or weaker importance of the feature in determining the model's prediction. The heatmap may be selected between two or more colors such that if multiple colors are used in the heatmap visualization, the color selection may vary to indicate a stronger or weaker importance of the feature in determining the model's prediction. The heatmap may be selected between two or more colors such that if multiple colors are used in the heatmap visualization, the color selection may vary to indicate a stronger or weaker importance of the feature in determining the model's prediction and the intensity of the color may further provide ranking visualizations within each classification of the feature importance. For example, a green color may be used for features which are most important to the model for predicting metastasize, a red color may be used for features which are most important to the model for predicting did not metastasize, and a yellow color may be used to features which were relevant to either metastasize or did not metastasize but were not the most significant of drivers in the prediction.

Further, within each classification color of green, red, and yellow, the intensity of the color may rank the importance of the features in each category such that light intensity corresponds with features of the least importance and bright, bold colors corresponds with features of the most importance. In addition to the color and intensity selection, a percentage of the patients in the cohort which presented the feature and were predicted to have metastasized or did not metastasized may be provided in the color coding of the feature. For example, a first column may be provided for prediction-metastasized features and a second column may be provided for prediction-did not metastasize features. Each row of the two columns may correspond to a single feature. The features hierarchically organized into the ranking of the features by importance to the predictions. A first feature may represent the greatest determining factor in the prediction of metastasized and did not metastasize and may be "cancer stage 3 or greater." 40% of the patients who were predicted to have metastasized had stage 3 cancer or greater while only 4% of patients who were not predicted to have metastasized had stage 3 cancer or greater. Because 40% is substantially greater than 4% the intensity of the coloring may be higher for the 40% heatmap and lower for the 4% heatmap. Another feature of the heatmap, "BRIP1-germline: moderate" may be one of the top 20 features relied on by the predictions with 58% of the patients who were predicted to have metastasized presenting the feature and 73% of the patients who were predicted to not metastasize presenting the feature. Because 58% is greater than 40% the intensity of the color may be even greater than the 40% heatmap and the intensity of the 73% even greater still.

Figure 12:
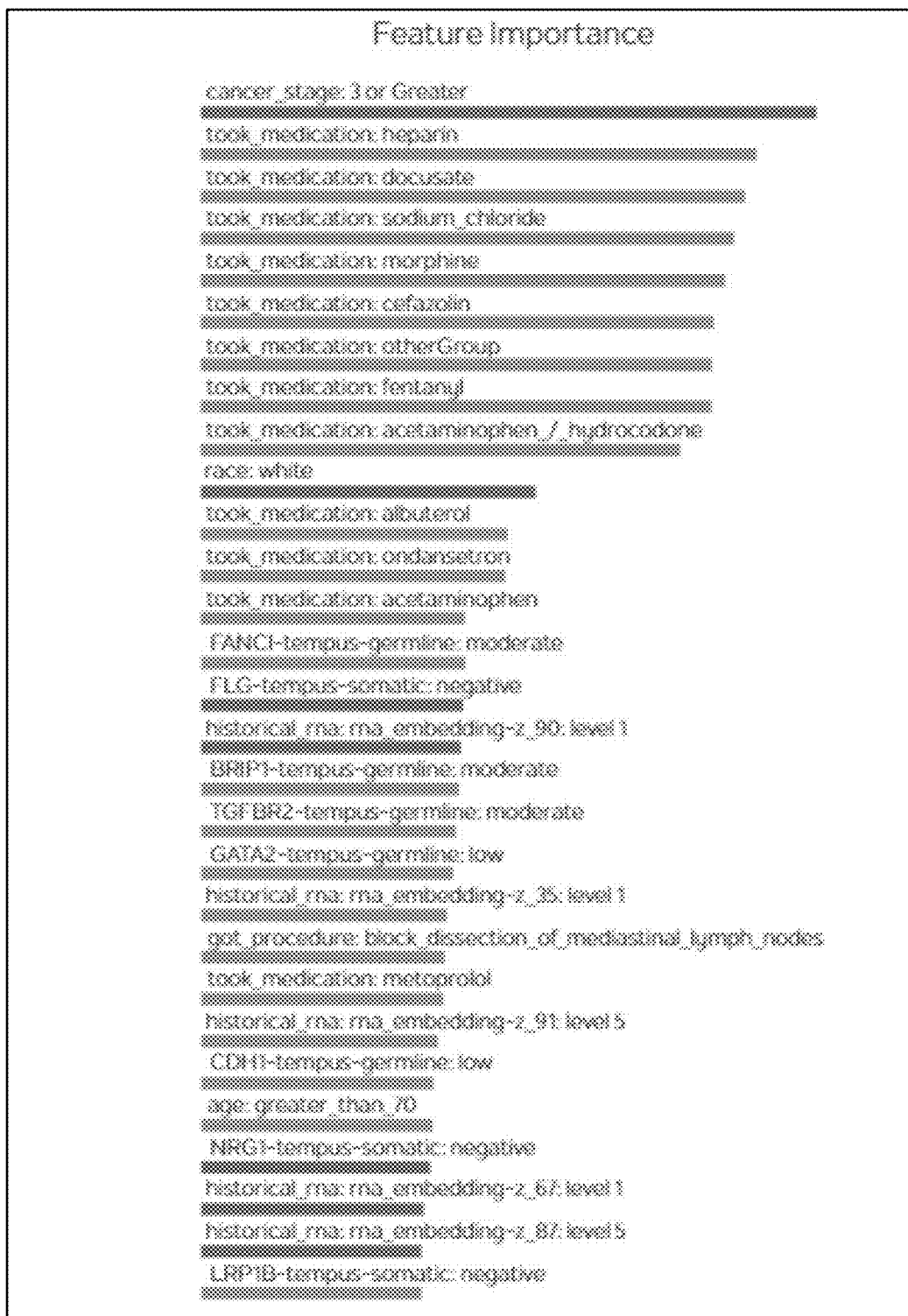
FIG. 12 illustrates an example of elements of a webform for viewing feature importance rankings of site-specific predictions of metastasis in a cohort of patients, in accordance with some embodiments of the present disclosure.

FIG. 12 illustrates elements of an exemplary webform for viewing feature importance rankings of site-specific predictions of metastasis in a cohort of patients.

When the first field for selecting a feature importance ranking visualization method has the scaled, ranking feature importance bar representation selected, an exemplary feature importance graphical representation may provide a ranked, bar chart of the feature importance to each model prediction of metastasized or did not metastasize. The bar chart may be selected between two colors, a first color for prediction-metastasized feature importance and a second color for prediction-did_not_metstasize feature importance. The length of the bar may correspond to the number of patients in the cohort which presented the feature and were predicted to have metastasized or did not metastasized. For example, each feature may be hierarchically organized by rows into the ranking of the features by importance to the predictions. A first color may identify features which are most important for predicting metastasized and a second color may identify features which are most important for predicting did not metastasize. A first row may identify the first feature and may represent the greatest determining factor in the prediction of metastasized and did not metastasize and may be "cancer stage 3 or greater." The feature may, based upon the results of the adaptive algorithm, have the bar with the greatest length to visually represent the feature's importance and the first color to indicate that the feature weighs most toward metastasized. A second row may identify the second feature and may represent the greatest determining factor in the prediction of metastasized and did not metastasize and may be "took_medication: heparin." The feature may, based upon the results of the adaptive algorithm, have the bar with the second greatest length to visually represent the feature's importance and the second color to indicate that the feature weighs most toward did not metastasize. Features continuing down the list may have increasingly shorter bars of either the first or second color to indicate their respective weights for or against the predictions for metastasized.

Figure 13:
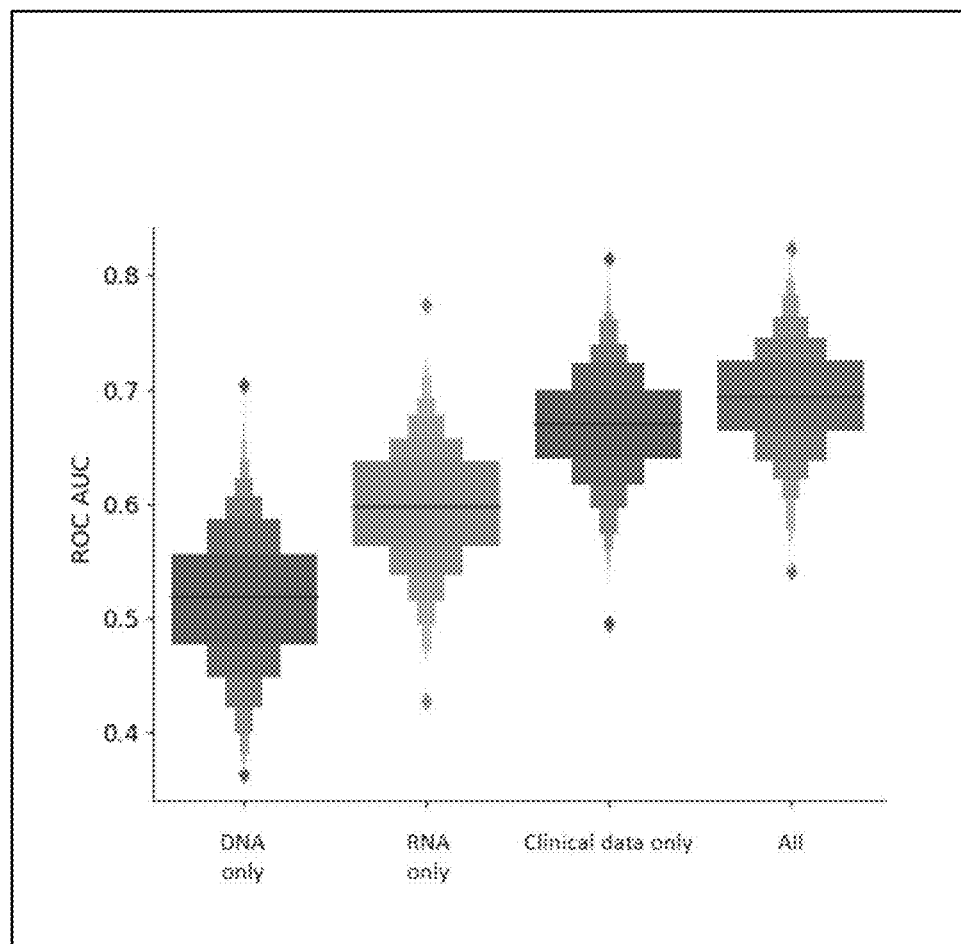
FIG. 13 is illustrates an example of aggregate measures of performance across classification thresholds of input datasets according to an objective of predicting the likelihood that a patient's cancer will metastasize to a specifically identified organ in the patient's body within a defined period of time, in accordance with some embodiments of the present disclosure.

FIG. 13 is an illustration 1300 of exemplary aggregate measures of performance across possible classification thresholds of input datasets according to an objective of predicting metastasis in lung cancer patients to any other cancer site within 24 months.

As discussed above with respect to FIG. 1, there are a number of models which may be selected and for each model there are a number of tuning parameters which may be considered. For an objective of metastasis prediction the collection of sites to which the patient will metastasize within the specified time horizon (24 months) at each time point may be used as the target of interest. The metastasis sites which may be considered include breast, colon, lung, liver, bone, brain and lymph node, with any other sites being grouped into a miscellaneous category. Other combinations of metastasis sites may be considered as well. During preprocessing, it may be advantageous to impose an additional requirement that each target must have more than one unique value within every cross validation fold in order to ensure the sites at which predictions are generated are variable depending on the origin cancer site.

Given a curated dataset with the five most common cancers in a cohort of all metastasized cancers being ovary, prostate, colon, breast, and lung, it may be advantageous to tune a multilabel random forest using 4 batches of 5 jobs, optimizing the average area under curve (AUC) across all target labels. In general, the models seem to prefer a large number of deep trees with heavy column sampling at each split, which could be used to improve future tuning jobs.

As an example, a random forest-based model may be instantiated using the following parameters:
range of max_depth: (5, 23)
n_estimators: (100, 1000)
min_samples_leaf: (20, 200)
max_features: (0.5, 0.8).

The following performance scores can be derived from the model based upon a set of patients for training according to cancer diagnosis.

An ovary objective scores by metastasis site may be:
Lymph node: 0.831445
Lung: 0.768152
An ovary predicted parameter set may be:
max_depth: 23
max_features: 0.70
min_samples_leaf: 58
n_estimators: 329
A prostate objective scores by metastasis site may be:
Lymph node: 0.784173
Other site: 0.784805
Bone: 0.878749
A prostate predicted parameter set may be:
max_depth: 15
max_features: 0.50
min_samples_leaf: 53
n_estimators: 748
A colon objective scores by metastasis site may be:
Lymph node: 0.836868
Liver: 0.877584
Other site: 0.840575
Lung: 0.885678
A colon predicted parameter set may be:
max_depth: 19
max_features: 0.57
min_samples_leaf: 55
n_estimators: 923
A breast objective scores by metastasis site may be:
Lymph node: 0.810405
Liver: 0.883235
Other site: 0.819709
Brain: 0.807003

Bone: 0.852316
Lung: 0.798472
A breast predicted parameter set may be:
max_depth: 23
max_features: 0.52
min_samples_leaf: 119
n_estimators: 821
A lung scores by metastasis site may be:
Lymph node: 0.725858
Liver: 0.840760
Other site: 0.771431
Brain: 0.791871
Bone: 0.724428
A lung predicted parameter set may be:
max_depth: 22
max_features: 0.51
min_samples_leaf: 111
n_estimators: 344

Given a known set of hyperparameters for each objective, such as those listed above, it may be advantageous to consider the impacts of a selected feature set for each objective. For example, a feature set for DNA related features (DNA variant calls) may include a calculation of the maximum effect a gene may have from sequencing results for the gene and source set forth in Table 1. A max effect calculation may include identifying an integer in a range from 0 to 7, wherein a 0 represents no effect and a 7 represents the highest effect a gene may impact a patient's cancer diagnosis. While the values 0-7 are used for illustrative purposes, other values may be used according to a desired resolution for measuring the effect. The values may be classified from a variant science pipeline based upon a characterization of the variant effect as pathogenic, benign, or unknown. In one example, a variant having a pathogenic classification may be assigned a value of 7 where a variant having a benign classification may be assigned a value of 0. Values of differing degrees may be awarded when mitigating or aggravating factors are present. For example, a variant which has substantial documentation within the medical committee for causing cancer may be assigned a higher value than a variant which has nominal documentation within the medical community for causing cancer. In one example, genetic variants are assigned a max effect value and a model may be trained on a variant by variant basis. A variant by variant model may be trained on variant max effects and a supervisory signal identifying patient metastasis. In another example, genetic variants are assigned a max effect value, but a model may be trained on a gene by gene basis. Converting variant max effect into gene max effect may include a number of approaches such as taking the highest max effect or applying customized weights to each max effect based upon the number of reads associated with the variant from sequencing of the patient's tumor. In one example, where the highest max effect is assigned, variants for each gene are compared to identify the highest max effect relating to the gene, and the highest max effect is assigned to the gene. Where the max effects are provided a customized weighting schema, each variant may be assigned a weight to scale the max effect and those max effects are combined into a gene max effect. For example, a gene with four identified variants may scale each max effect by 0.25 and sum the combined, scaled max effects into a gene max effect, effectively averaging the max effects. In another aspect, a gene with four variants having raw reads of 25, 100, 250, and 75 may scale each max effect by 25/450, 100/450, 250/450, and 75/450 respectively. A gene with no called variants (variants identified in the patient's genome) for a particular gene is assigned a max effect of 0.

TABLE 1

ABCB1-somatic
ACTA2-germline
ACTC1-germline
ALK-fluorescence_in_situ_hybridization_(fish)
ALK-immunohistochemistry_(ihc)
ALK-md_dictated
ALK-somatic
AMER1-somatic
APC-gene_mutation_analysis
APC-germline
APC-somatic
APOB-germline
APOB-somatic
AR-somatic
ARHGAP35-somatic
ARID1A-somatic
ARID1B-somatic
ARID2-somatic
ASXL1-somatic
ATM-gene_mutation_analysis
ATM-germline
ATM-somatic
ATP7B-germline
ATR-somatic
ATRX-somatic
AXIN2-germline
BACH1-germline
BCL11B-somatic
BCLAF1-somatic
BCOR-somatic
BCORL1-somatic
BCR-somatic
BMPR1A-germline
BRAF-gene_mutation_analysis
BRAF-md_dictated
BRAF-somatic
BRCA1-germline
BRCA1-somatic
BRCA2-germline
BRCA2-somatic
BRD4-somatic
BRIP1-germline
CACNA1S-germline
CARD11-somatic
CASR-somatic
CD274-immunohistochemistry_(ihc)
CD274-md_dictated
CDH1-germline
CDH1-somatic
CDK12-germline
CDKN2A-immunohistochemistry_(ihc)
CDKN2A-germline
CDKN2A-somatic
CEBPA-germline
CEBPA-somatic
CFTR-somatic
CHD2-somatic
CHD4-somatic
CHEK2-germline
CIC-somatic
COL3A1-germline
CREBBP-somatic
CTNNB1-somatic
CUX1-somatic
DICER1-somatic
DOT1L-somatic
DPYD-somatic
DSC2-germline
DSG2-germline
DSP-germline
DYNC2H1-somatic
EGFR-gene_mutation_analysis
EGFR-immunohistochemistry_(ihc)
EGFR-md_dictated
EGFR-germline
EGFR-somatic TABLE 1-continued EP300-somatic
EPCAM-germline
EPHA2-somatic
EPHA7-somatic
EPHB1-somatic
ERBB2-fluorescence_in_situ_hybridization_(fish)
ERBB2-immunohistochemistry_(ihc)
ERBB2-md_dictated
ERBB2-somatic
ERBB3-somatic
ERBB4-somatic
ESR1-immunohistochemistry_(ihc)
ESR1-somatic
ETV6-germline
FANCA-germline
FANCA-somatic
FANCD2-germline
FANCI-germline
FANCL-germline
FANCM-somatic
FAT1-somatic
FBN1-germline
FBXW7-somatic
FGFR3-somatic
FH-germline
FLCN-germline
FLG-somatic
FLT1-somatic
FLT4-somatic
GATA2-germline
GATA3-somatic
GATA4-somatic
GATA6-somatic
GLA-germline
GNAS-somatic
GRIN2A-somatic
GRM3-somatic
HDAC4-somatic
HGF-somatic
IDH1-somatic
IKZF1-somatic
IRS2-somatic
JAK3-somatic
KCNH2-germline
KCNQ1-germline
KDM5A-somatic
KDM5C-somatic
KDM6A-somatic
KDR-somatic
KEAP1-somatic
KEL-somatic
KIF1B-somatic
KMT2A-fluorescence_in_situ_hybridization_(fish)
KMT2A-somatic
KMT2B-somatic
KMT2C-somatic
KMT2D-somatic
KRAS-gene_mutation_analysis
KRAS-md_dictated
KRAS-somatic
LDLR-germline
LMNA-germline
LRP1B-somatic
MAP3K1-somatic
MED12-somatic
MEN1-germline
MET-fluorescence_in_situ_hybridization_(fish)
MET-somatic
MKI67-immunohistochemistry_(ihc)
MKI67-somatic
MLH1-germline
MSH2-germline
MSH3-germline
MSH6-germline
MSH6-somatic
MTOR-somatic
MUTYH-germline
MYBPC3-germline
MYCN-somatic
MYH11-germline
MYH11-somatic
MYH7-germline
MYL2-germline
MYL3-germline
NBN-germline
NCOR1-somatic
NCOR2-somatic
NF1-somatic
NF2-germline
NOTCH1-somatic
NOTCH2-somatic
NOTCH3-somatic
NRG1-somatic
NSD1-somatic
NTRK1-somatic
NTRK3-somatic
NUP98-somatic
OTC-germline
PALB2-germline
PALLD-somatic
PBRM1-somatic
PCSK9-germline
PDGFRA-somatic
PDGFRB-somatic
PGR-immunohistochemistly_(ihc)
PIK3C2B-somatic
PIK3CA-somatic
PIK3CG-somatic
PIK3R1-somatic
PIK3R2-somatic
PKP2-germline
PLCG2-somatic
PML-somatic
PMS2-germline
POLD1-germline
POLD1-somatic
POLE-germline
POLE-somatic
PREX2-somatic
PRKAG2-germline
PTCH1-somatic
PTEN-fluorescence_in_situ_hybridization_(fish)
PTEN-gene_mutation_analysis
PTEN-germline
PTEN-somatic
PTPN13-somatic
PTPRD-somatic
RAD51B-germline
RAD51C-germline
RAD51D-germline
RAD52-germline
RAD54L-germline
RANBP2-somatic
RB1-germline
RB1-somatic
RBM10-somatic
RECQL4-somatic
RET-fluorescence_in_situ_hybridization_(fish)
RET-germline
RET-somatic
RICTOR-somatic
RNF43-somatic
ROS1-fluorescence_in_situ_hybridization_(fish)
ROS1-md_dictated
ROS1-somatic
RPTOR-somatic
RUNX1-germline
RUNX1T1-somatic
RYR1-germline
RYR2-germline
SCN5A-germline
SDHAF2-germline
SDHB-germline
SDHC-germline
SDHD-germline
SETBP1-somatic
SETD2-somatic
SH2B3-somatic
SLIT2-somatic
SLX4-somatic

TABLE 1-continued

SMAD3-germline
SMAD4-germline
SMAD4-somatic
SMARCA4-somatic
SOX9-somatic
SPEN-somatic
STAG2-somatic
STK11-gene_mutation_analysis
STK11-germline
STK11-somatic
TAF1-somatic
TBX3-somatic
TCF7L2-somatic
TERT-somatic
TET2-somatic
TGFBR1-germline
TGFBR2-germline
TGFBR2-somatic
TMEM43-germline
TNNI3-germline
TNNT2-germline
TP53-gene_mutation_analysis
TP53-immunohistochemistry_(ihc)
TP53-md_dictated
TP53-germline
TP53-somatic
TPM1-germline
TSC1-germline
TSC1-somatic
TSC2-germline
TSC2-somatic
VHL-germline
WT1-germline
WT1-somatic
XRCC3-germline
ZFHX3-somatic In some examples, for a metastatic location prediction model trained on DNA features only, a resulting receiver operating characteristic (ROC) area under curve (AUC) may be approximately 0.52.

A feature set for RNA related features may include features associated with raw read counts for every transcriptome of the human genome, features associated with normalized read counts for every transcriptome of the human genome, or features associated with normalized, encoded read counts, such as encoded via an autoencoder or a dimensionality reducer. Raw read counts may be accompanied by a normal value, identifying the expected number of read counts should the transcriptome be normally expressed. Raw read counts exceeding the normal value may be considered over expressed, and raw read counts falling below the normal value may be considered under expressed. Normalized read counts may be normalized to ensure that while every transcriptome has its own normal value, the resulting normalized value falls within a desired range that accounts for the differences between each unnormalized transcriptoms normal. For example, RPKM (Reads Per Kilobase Million), FPKM (Fragments Per Kilobase Million), or TPM (Transcripts Per Kilobase Million) may be used for normalization. RPKM may be calculated by scaling the total RNA reads of a specimen by 1,000,000 to create a scaling factor, scaling the total reads for any read counts for each read by the scaling factor to create an RPM, and dividing the RPM by the length of the gene to create an RPKM. FPKM may be generated by performing the same steps, but when performing pair-end sequencing, accounting for the fact that some reads may be counted twice. TPM may be calculated by performing the same steps but in a different order. First creating a reads per kilobase (RPK) by dividing read counts by the length of each gene, creating the scaling factor, and then dividing the RPK by the scaling factor to create the TPM.

Other normalization methods may be applied as well, such as one or more of the RNA normalization methods disclosed in U.S. patent application Ser. No. 16/581,706, titled "Methods of Normalizing and Correcting RNA Expression Data," filed Sep. 24, 2019, the entire disclosure of which is hereby expressly incorporated by reference herein. Normalized, encoded read counts may be generated by first normalizing the RNA reads according to any of the above methods, and then passing the normalized read counts to an encoder or a dimensionality reducer, such as an autoencoder.

In one example, an autoencoder may reduce the dimensionality from 20,000+transcriptomes to 100 encoded features, creatively named: rna_embedding-z_1 through rna_embedding-z_100. In one example, RNA related features for each transcriptome are generated from a sequencing of a patient's tumor. The number of encoded features may be any number where identifying the optimal number may include performing encoding for each of 2-9999 total number of encoded features, calculating a performance metric of each, and selecting the number of encoded features to be the number with the highest performance metric. A performance metric may include the accuracy of predictions made from the model using each total number of encoded features. Raw read counts may be between 0 reads and tens of thousands of reads. Normalization of the raw read counts from sequencing may convert the raw read scores to a value between from −0.5 to 0.5 where 0 represents the mean, or a normal expression value and −0.5 is lowest expression and 0.5 is highest expression. The normalized value may represent the number of standard deviations the raw read was from the normal reads expected in a patient such that −0.5 represents a high standard deviation below normal and 0.5 represents a high standard deviation above normal. In one example, RNA may be calculated on a gene or transcriptome basis where variants are not included. In another example, variants may be included, similar to DNA above.

Encoding normalize RNA reads may include generating a standard population finding or autoencoding. In one example, autoencoding may include utilizing a variational autoencoder, such as Beta-VAE or TC-VAE, or dimensionality reducers, such as SVD, PCA, or UMap. Outputs from an encoder, autoencoder, or dimensionality reducer may be presented as a matrix, where each row is for each patient, and each column is a normal distributed variable which may be interpreted as a ratio of patient's makeup in each population, such as values −0.25 to 0.25 or a standard deviation of 1, centered at 0. A patient's vector of deviations from normal may be interpreted to identify the makeup of the patient according to each population identified in the respective encoder. The matrix of normalized, encoded values may be supplied to a model for prediction of metastasis without additional alterations.

Each of the models, raw RNA reads, normalized RNA reads, and normalized, encoded RNA reads may have differing operating characteristics, including speed and accuracy. For example, given the substantial reduced dimensionality from normalized, encoded RNA reads, one may expect the system to greatly improve processing speed at the cost of some degree of accuracy; however, the resulting ROC AUC may be approximately 0.60 which is greater than that of processing DNA features only.

A feature set for clinical data only may include: age_at_event (assigned a value equal to the patient's age), age_group {00 to 09, 10 to 19, 100 to 109, 110 to 119, 20 to 29, 30 to 39, 40 to 49, 50 to 59, 60 to 69, 70 to 79, 80 to 89, 90 to 99, Unknown} (assigned a binary, yes/no representation identifying which group the patient's age falls into), days_since_first:TumorFinding:histology {acinar_cell_carcinoma, adenocarcinoma, carcinoma, infiltrating_duct_carcinoma, lobular_carcinoma, malignant_neoplasm,_primary, mucinous_adenocarcinoma, neuroendocrine_carcinoma, non_small_cell_carcinoma, otherGroup, small_cell_carcinoma, small_cell_neuroendocrine_carcinoma, squamous_cell_carcinoma,_no_icd_o_subtype, transitional_cell_carcinoma} (assigned a value equal to the number of days), days_since_first:TumorFinding:histopath_grade {grade_1_(well_differentiated), grade_2_(moderately_differentiated), grade_3_(poorly_differentiated), grade_4_(undifferentiated), high_grade} (assigned a value equal to the number of days), days_since_first:TumorFinding:stage {m0, m1, mx, n0, n1, n2, n3, nx, pn0, pn1, pn2, pnx, stage_1, stage_2, stage_3, stage_4, pt1, pt2, pt3, pt4, t0, t1, t2, t3, t4, tx} (assigned a value equal to the number of days), days_since_first:cancer {breast, cervix_uteri, colon, head_and_neck, kidney, lung, lymphoid, hemopoietic_and/or_related_tissue, otherGroup, ovary, pancreas, prostate, respiratory_tract, skin, skin_of_trunk, soft_tissues, stomach, tongue, unknown_site, urinary_bladder} (assigned a value equal to the number of days), days_since_last:comorbidity {Abnormal_findings_on_diagnostic_imaging_of_breast, Administration_of_antineoplastic_agent, Anemia, Dehydration, Disorder_of_bone, Disorder_of_breast, Dyspnea, Essential_hypertension, Fatigue, Imaging_of_thorax_abnormal, Immunization_advised, Long_term_current_use_of_drug_therapy, Osteoporosis, Past_history_of_procedure, Pedal_cycle_accident, Screening_for_malignant_neoplasm_of_breast, chronic_obstructive_lung_disease, otherGroup, type_2_diabetes_mellitus, type_2_diabetes_mellitus_without_complication} (assigned a value equal to the number of days), gender {Missing, female, male} (assigned a binary, yes/no representation identifying gender of patient), and race {Missing, african race, american indian or alaska native, asian, pacific islander, black or african american, caucasian or white, hispanic, native hawaiian or other pacific islander, not hispanic or latino, other race, unknown or unknown racial group} (assigned a binary, yes/no representation identifying race of patient).

Clinical data features may be assigned weights manually when setting up the model for metastatic location prediction, may be assigned weights automatically via an external weighting model, or assigned weights automatically via model itself through a process called stacking.

The resulting ROC AUC may be approximately 0.67 which is greater than that of processing DNA features only and RNA features only.

Combining all of the above input feature sets together from the DNA model, RNA model, and Clinical data model above results in an ROC AUC of approximately 0.70 which is greater than any of the models individually.

In another example, an RNA normalized model using TPM normalization may be trained on breast cancer patients to predict metastasis to lung, brain, liver, or other organs and have an ROC AUC of approximately 0.92, which is greater than any of the previous models. Further optimizations may be pursued by adding in the additional feature sets.

Figure 14:
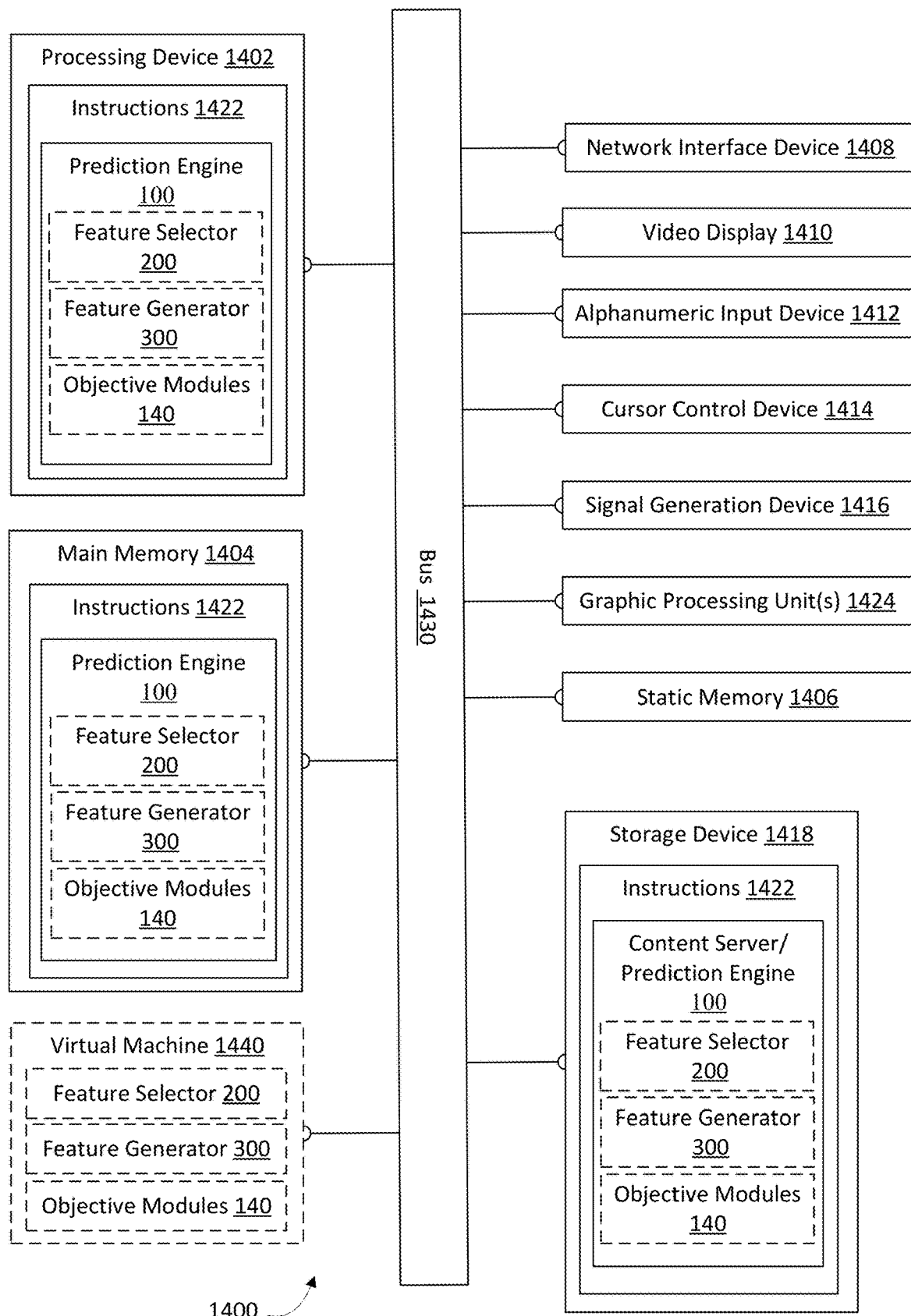
FIG. 14 is a block diagram of an example of a system in which some embodiments of the invention can be implemented.

FIG. 14 is an illustration of an example machine of a computer system 1400 within which a set of instructions, for causing the machine to perform any one or more of the methodologies discussed herein, may be executed. In some implementations, the machine may be connected (such as networked) to other machines in a LAN, an intranet, an extranet, and/or the Internet.

The machine may operate in the capacity of a server or a client machine in client-server network environment, as a peer machine in a peer-to-peer (or distributed) network environment, or as a server or a client machine in a cloud computing infrastructure or environment. The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1400 includes a processing device 1402, a main memory 1404 (such as read-only memory (ROM), flash memory, dynamic random access memory (DRAM) such as synchronous DRAM (SDRAM) or DRAM, etc.), a static memory 1406 (such as flash memory, static random access memory (SRAM), etc.), and a data storage device 1418, which communicate with each other via a bus 1430.

Processing device 1402 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1402 may also be one or more special-purpose processing devices such as an application specific integrated circuit (ASIC), a field programmable gate array (FPGA), a digital signal processor (DSP), network processor, or the like. The processing device 1402 is configured to execute instructions 1422 for performing the operations and steps discussed herein.

The computer system 1400 may further include a network interface device 1408 for connecting to the LAN, intranet, internet, and/or the extranet. The computer system 1400 also may include a video display unit 1410 (such as a liquid crystal display (LCD) or a cathode ray tube (CRT)), an alphanumeric input device 1412 (such as a keyboard), a cursor control device (such as, e.g., a mouse, joystick, or another control device, including a combination device), a signal generation device 1416 (such as, e.g., a speaker), and a graphic processing unit 1424 (such as, e.g., a graphics card).

The data storage device 1418 may be a machine-readable storage medium 1428 (also known as a computer-readable medium) on which is stored one or more sets of instructions or software 1422 embodying any one or more of the methodologies or functions described herein. The instructions 1422 may also reside, completely or at least partially, within the main memory 1404 and/or within the processing device 1402 during execution thereof by the computer system 1400, the main memory 1404 and the processing device 1402 also constituting machine-readable storage media.

In one implementation, the instructions 1422 include instructions for a prediction engine (such as the prediction engine 100 of FIGS. 1-3) and/or a software library containing methods that function as a prediction engine. The instructions 1422 may further include instructions for a feature selector 200 and generator 300 and objective modules 140. While the machine-readable storage medium 1428 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine-readable storage medium as a transitory storage medium or transitory machine-readable storage medium.

In another implementation, a virtual machine 1440 may include a module for executing instructions for a feature selector 200 and generator 300 and objective modules 140. In computing, a virtual machine (VM) is an emulation of a computer system. Virtual machines are based on computer architectures and provide functionality of a physical computer. Their implementations may involve specialized hardware, software, or a combination of hardware and software.

Artificial Intelligence Engine Training Pipeline

An exemplary AIE training pipeline may read in a configuration file (such as a JSON) with a number of operating parameters identified. Some parameters may be required while other parameters may be optional.

A pipeline may identify that one or more cohort files may be referenced for patient data such as a collection of metastatic site location data, diagnosis and metastasis sites location data, or optional extra evaluation sets. The pipeline may also load one or more patient cohort files containing information about patient metastasis details, including the date and occurrence from a diagnosis site to a metastasis site. The information may provide an indication, such as the date, or number of days since a patient metastasized to a site of interest. For a model of identifying metastasis from and/or to a specific organ, the information may include an indication that a patient metastasized and the time from biopsy collection to the metastasis. In another example, if there's no indication that the patient metastasized, an indicator may exist that there was no observed metastasis and the time from biopsy collection to the last time that a record exists which evaluated the patient's diagnosis (and still showed no metastasis) to generate a detailed metastasis record for each patient.

The pipeline may identify which feature set(s) are specified and queue up which feature set files for each patient may be loaded in order to access and use any relevant features. For example, if it specified that the pipeline is to train on a "staging" feature set, the pipeline may load a "Clinical" feature file, and subset all clinical data down to any staging features. If it is specified that the pipeline should use Cell Texture features, the pipeline may load an Imaging feature set and subset all imaging data down to any Cell Texture features. The pipeline may select from any of the patient features disclosed herein and further may also join the feature sets from multiple relevant targets into a combined training feature set.

The pipeline may identify an upfront preprocessing function specified in the configuration file to preprocess the combined training feature set using the identified preprocessing. In one example, a preprocessing function may include one-hot-encoding of categorical features, normalizing features (e.g., condensing separate feature entries for related features, such as pathologic N stage and clinical N stage, where condensing may include identifying the maximum of those two columns as the normalized feature), removing uninformative features (e.g., features that just indicate if a field is missing, such as "gender-missing", "race-missing", or other status-unknown entries), removing features known to be misleading or problematic (e.g., sequencing normalization read-throughs), drop features with no variance, imputing missing values from other data (e.g., when the imputation is reliable), or other preprocessing methods.

The pipeline may identify a number of folds for training and subset which features will be used per collection of training set folds. In one example, the identification of the number of folds and subsetting of features is based upon the combination of inline preprocessing method and feature selection method. In one example, a total of 5 folds may be selected, [0,1,2,3,4], one (e.g., fold 4) is kept as the hold out set, and the remaining 4 are used in training. Therefore, training sets may be identified for 5 total folds, including in one example:

[0,1,2] which will be used to generate predictions for fold 3

[0,1,3] which will be used to generate predictions for fold 2

[0,2,3] which will be used to generate predictions for fold 1

[1,2,3] which will be used to generate predictions for fold 0

[0,1,2,3] which will be used to generate predictions for the test set (fold 4)

Generating the combined feature sets for each fold, or the 5 different training sets defined above, may include, in one example, the following sequence of events:

1) Run the specified in-line preprocessing method using one or more of:
   a) Transformations to zero-center features (e.g., z-scoring)
   b) Transformations to scale features relative to the maximum observed value
   c) Dimensionality reduction (e.g., PCA)
   d) Subsetting to the top X correlated features to the target (where the target can be defined as the binary target, time until metastasis for only patients who metastasize, the log of that duration, or another format).

2) Run the specified feature selection method on the in-line processed data using one or more of:
   a) A custom feature selection approach using Lasso modeling such as by re-sampling with replacement a number of times (e.g., 100 times) from each training subset (e.g., folds [0,1,2]), and fitting a lasso model on each bootstrap. For each lasso model, storing the features that were used in the model, and the associated regression coefficients. The features that are most important for any given training subset are the ones that appear in the most bootstrapped models, have high (in magnitude) coefficients, and have stable coefficients across models (in terms of the sign of the coefficient). In one example, identifying feature selection sets may include selecting the features that are occur in more than a minimum percentage (e.g., 50%) of bootstraps, have the same sign of their coefficient at least some minimum percent (e.g., 90%) of the time that they are used.
b) A custom recursive feature elimination framework, such as by running a model on all features (or subset of features if defined in the inline preprocessing method), dropping the bottom (e.g., 10%) of features as ranked by their model coefficients, and repeating the feature elimination until a threshold number of features is met (e.g., 10, 50, 200, 5000). At each step of the process, each feature's rank is stored. At the end (once only Y features remain), the original combined feature set may be ranked, each by their average rank from this process, and only the top Z (e.g., 40) features may be selected as features for that training subset. Recursive feature elimination may include logistic regression, cox proportional hazards, early stopping, ranking/selection methods, and others.
3) Storing the selected features for use in each fold.
4) Optimizing hyperparameters, such as a gridsearch for the set of hyperparameters using one or more of:
   a) logistic regression
      i) identifying regularization strength the range 100, 10, 1, 0.1, 0.01, and 0.001.
   b) cox proportional hazards
   c) random forest
      i) number of trees, such as 20, 40, 60, or 80.
      ii) maximum depth of each tree, such as 2, 3, 4, 10, 20, 100, branches.
      iii) minimum samples per leaf, such as 5, 6, 7, 10, 100
      iv) The metric to optimize for. For example, ROC AUC or concordance index.
5) The pipeline may cycle through all the training subsets, for example, the four training subsets [0,1,2], [0,1,3], [0,2,3], and [1,2,3]), using the normalized and selected feature sets. Then, for each possible hyperparameter space, fitting the identified model on the training subset; predict on the remaining training fold; and storing the resulting the metric which is being optimized for (e.g., ROC AIX, concordance index) on the held out fold. Each search space (e.g., the combined training subset metric results) may then be associated with 4 out of fold metrics. The hyperparameter set that leads to the best average metric (averaged across those 4 out of fold estimates) is stored as the optimal hyperparameters of the model.
6) The pipeline may generate the final prediction on the test fold using the combined feature selected subset from each fold and the model identified with the optimal hyperparameters for the model to predict the output on the test fold and store the predictions.
7) Identify and store features which were most important in driving the predictions, based on the feature selection method(s) selected using one or more of:
   a) Spearman correlation between the feature and predictions,
   b) Pearson correlation between the feature and predictions,
   c) Kendall correlation between the feature and predictions,
   d) Custom subset aware feature effect correlation identification,
   e) Nulling-out method where all values of a feature may be set to 0, and compute the mean absolute deviation in resulting probabilities based on the rest of the features.
8) The prediction results may be stored in one or more patient information databases and all stored metrics may be saved to the pipeline as a model for predicting future metastatic site occurrence in a new patient.

Prediction of Colorectal Metastasis based on RNA

In one embodiment, the artificial intelligence engine may implement an RNA-based predictive algorithm to predict how likely a colorectal cancer patient is to develop a metastasis.

Training a model may include receiving sequencing results from 120,000 patients having a primary diagnosis of colorectal cancer wherein 10,000 patients have at least one tumor RNA sequencing result from a biopsy site of the colon. These 10,000 patients have been filtered from the 120,000 larger patient dataset to include only patients who are stage II or stage III only, excluding patients who have already metastasized and are stage IV at the time of the biopsy for the tumor tissue and in the event a patient may have multiple sequencing results, selecting the sequencing results that were biopsied from the colon at Stage III or Stage IV.

A training model pipeline may be initialized with the following parameters:
1) An input training dataset having all features for all patients, including TPM normalized, low pass, whole transcriptome RNA sequencing results for 120,000 patients.
2) A diagnosis site of interest of colorectal cancer. So that only patients whose tumor started in the colon are selected for model training.
3) A metastasis site of interest of any site. So that patients who metastasized after sequencing are included in the training set when any metastasis location is identified.
4) A horizon window of 24 months. So that only patients having records that extend through the period of the trained model prediction horizon are included. Patients who metastasized before the window closes may be included even if records fail to be present for the entire horizon.
5) A sample restriction of no Cancer Staging of I or IV at time of sequencing. So that patients whose sequencing results were generated from Stage I or Stage IV are excluded.
6) A data requirement of none. So that no data inclusion requirements are imposed on the patient set.
7) A modeling framework of logistic regression.
8) A hyperparameter space of regularization strength: C=[100,10,1,0.1,0.01,0.001]. So that matching hyperparameters for the logistic regression framework are selected.
9) A hyperparameter tuning optimization metric of ROC AUC.
10) A preprocessing option of RNA TPM.
11) An inline preprocessing of transforms.
12) A feature selection method of passthrough.
13) A feature importance method of spearman correlation.

A resulting pipeline run may generate a set of 5 folds, 4 training and one testing. The pipeline using a combined feature set of RNA TPM features with Lasso feature selection method may result in 359 features for training subset [0,1,2], 361 features for training subset [0,1,3], 347 features for training subset [0,2,3], 331 features for training subset [1,2,3], and 404 features for training subset [0,1,2,3]. In one example, all RNA TPM features may include over 20,000 genes or over 198,000 transcripts which may be mapped to genes. A complete feature set including all of the RNA TPM features which are selected during feature select may be optimized to include only 1030 genes and transcripts: A3GALT2, A4GNT, AADAC, AADACL2, ABCC1, ABTB2, ACAD9, ACHE, ACOT1, ACOT7, ACPL2, ACTR10, ACTR3B, ACVR2B, ADAM30, ADAMTS6, ADAP1, ADAT2, ADHFE1, ADIPOR1, ADORA2B, ADPRHL1, ADPRM, AFAP1, AGAP7, AGAP9, AGPAT6, AGPS, AGR2, AGTR2, AGXT, AHNAK, AHSA2, AIF1, AK1, AK2, AK3, AKR1B1, AKR1B15, AKR1C4, AKR7A3, ALDH1A3, ALG10, ALG14, ALG1L, ALKBH6, ALS2, AMIGO3, AMMECR1, ANAPC7, ANP32E, AOAH, APPL1, AQP8, ARHGAP1, ARHGDIB, ARHGEF35, ARMC4, ARSD, ASAH2, ASB8, ASH2L, ASMT, ASPG, ASPH, ASPRV1, ATF4, ATP13A1, ATP13A2, ATP5A1, ATP6V1C2, ATP6V1E2, ATRX, ATXN7L3B, AVEN, B2M, BAG2, BARD1, BBS9, BCL2L2, BEST4, BET1L, BHLHB9, BRMS1L, BTN2A1, BZRAP1, C10orf111, C10orf128, C11orf86, C12orf73, C14orf93, C15orf38, C16orf3, C16orf80, C17orf89, C19orf35, C19orf44, C1orf21, C1orf227, C1orf229, C1orf51, C1orf95, C1QL3, C1QTNF4, C1QTNF8, C21orf49, C22orf42, C2orf27B, C2orf48, C2orf72, C2orf91, C3, C3orf17, C3orf84, C4orf22, C4orf45, C4orf6, C5orf20, C5orf64, C6orf47, C6orf48, C6orf52, C6orf99, C7orf66, C7orf71, C8G, C8orf34, C8orf34-AS1, C9orf129, C9orf131, C9orf156, C9orf24, C9orf50, C9orf64, C9orf91, CA1, CABP2, CABP4, CACNA1E, CACNG4, CAPN2, CARTPT, CBR3, CCDC125, CCDC141, CCDC144A, CCDC17, CCDC175, CCDC183, CCDC25, CCDC78, CCDC81, CCDC89, CCIN, CCNA1, CCNE1, CCR6, CD151, CD200R1, CD247, CD28, CD4, CD9, CDA, CDIPT, CDK20, CDKN2AIP, CDNF, CEACAM16, CEACAM18, CEACAM3, CEACAM5, CEP76, CEP85, CFAP206, CHD5, CHKB, CHMP7, CKMT1B, CLDN10, CLDN22, CLDN23, CLDN34, CLEC18B, CLECL1, CLIC2, CLN8, CLP1, CLPB, CMSS1, CNBD1, CNOT6L, COA4, COCH, COMMD7, COMMD9, COPG2, COQ5, COX6A2, CPLX4, CRABP1, CRHR2, CRTC3, CRX, CRYBB2, CSK, CSNK2B, CTAGE6, CTBP2, CTTNBP2NL, CXorf38, CXXC1, CYLC2, CYorf17, CYP11B2, CYP27B1, CYP2C19, CYP2C8, CYP4A22, DAB1, DAZAP2, DAZL, DBF4, DCAF7, DCBLD1, DCLRE1B, DDHD1, DDHD2, DDO, DDR1, DDX4, DDX54, DDX56, DEFB127, DEFB134, DEGS2, DEXI, DGAT1, DGCR14, DHDDS, DHPS, DHRS4L2, DHRS7B, DIRC1, DNAH1, DNAH5, DNAJC27, DNAJC8, DND1, DOCK2, DPM2, DPPA3, DPY19L2, DRD1, DUS4L, DUSP27, DYNLL2, DYRK2, DYRK4, EBNA1BP2, ECHDC1, EDDM3A, EDDM3B, EFHC2, EFHD2, EIF3CL, ELANE, ELMOD1, EMID1, ENPP2, ENPP7, ENSG00000171282, ENSG00000173366, ENSG00000187461, ENSG00000187811, ENSG00000197665, ENSG00000203546, ENSG00000220032, ENSG00000241690, ENSG00000250232, ENSG00000251012, ENSG00000251606, ENSG00000254673, ENSG00000254943, ENSG00000254979, ENSG00000256100, ENSG00000258365, ENSG00000258881, ENSG00000259316, ENSG00000259649, ENSG00000260371, ENSG00000260836, ENSG00000260861, ENSG00000260869, ENSG00000266202, ENSG00000266956, ENSG00000267140, ENSG00000267157, ENSG00000267964, ENSG00000268170, ENSG00000268643, ENSG00000268702, ENSG00000268714, ENSG00000268950, ENSG00000269711, ENSG00000269846, ENSG00000272195, ENSG00000272617, ENSG00000272762, ENSG00000272822, ENSG00000272896, ENSG00000273217, ENSG00000273266, ENTPD3, EPHB1, EPM2AIP1, EPX, EQTN, ERCC6, ETNK1, ETS1, ETV2, ETV6, EVPLL, EXOC3L4, EYA1, FABP9, FAHD2B, FAM132B, FAM151A, FAM166A, FAM183A, FAM19A4, FAM219B, FAM21B, FAM228A, FAM24B, FAM26D, FAM71C, FAM72B, FAM83F, FAM98A, FBXL6, FBXO47, FBXW12, FDFT1, FDXR, FEZF2, FHIT, FKBP2, FKBP6, FKBPL, FNDC5, FOXD1, FRRS1L, FSCB, FSHR, FUS, FXR1, FZD10, G6PD, GABRR2, GAL3ST1, GAR1, GATSL1, GATSL3, GCSAML, GDF15, GGCT, GGNBP2, GGT1, GIMAP2, GLS2, GMEB1, GNRHR, GOLGA6L1, GOLGA7, GOLGA8O, GOLM1, GPATCH1, GPATCH2L, GPC2, GPR112, GPR115, GPR143, GPR152, GPR19, GPR55, GRAPL, GRIP1, GRK7, GRM2, GSG1L, GSPT2, GSTT1, GTF2A1L, GTF2H2C, GTF3A, GTF3C6, GUCA2B, GVQW3, GZF1, H2AFB1, HACE1, HACL1, HAL, HBD, HBZ, HCN1, HCRTR1, HDDC3, HEBP1, HINT3, HIRA, HIRIP3, HLA-DMB, HLA-DPB1, HLA-DQB1, HLA-DRB1, HLA-G, HMX3, HNF4G, HNRNPA2B1, HNRNPCL1, HNRNPR, HOMEZ, HORMAD1, HORMAD2, HOXA1, HOXA11, HOXA13, HOXA3, HR, HRNR, HS6ST2, HSCB, HSD17B13, HSD17B8, HSPA8, HTATSF1, HTR5A-AS1, HTR6, ID2, IDH2, IFIT1, IFNA2, IFRD2, IFT172, IGF2BP2, IGFN1, IGSF3, IL12A, IL12B, IL17RB, IL18R1, IL2, IL4, IL9, INPP5A, INSR, IPO4, IPO9, IQCF6, IQCK, IREB2, ISCA1, IVD, KCNA10, KCNS3, KCTD18, KDM5C, KIAA1211, KIAA1467, KIAA1683, KIF21B, KIF26A, KIF5A, KLF11, KLHDC10, KLHL10, KLHL40, KLK2, KLRD1, KRT12, KRT24, KRT40, L3MBTL4, LANCL1, LDHD, LENG9, LHCGR, LILRB2, LILRB4, LIMS1, LIN7A, LMBR1L, LONRF3, LRAT, LRP8, LRR1, LRRC57, LRRC59, LRRFIP1, LSM14A, LTBP2, LUZP1, LUZP2, LY6G5C, LY6G6F, LY86, LYG1, M6PR, MAGEB5, MAGIX, MAL2, MAN1A1, MAP4K2, MAPK15, MAPKBP1, MARK3, MASP2, MC2R, MCOLN3, MDGA2, ME3, MECR, MED9, MESDC2, METTL11B, MFSD2B, MFSD9, MIB1, MICALL2, MINOS1, MKS1, MLF2, MLLT4, MLPH, MMP17, MOB1B, MPL, MPP3, MPP5, MPP7, MPZL1, MRPL38, MS4A8, MSH5, MSL3, MT1F, MTCP1, MTDH, MTUS1, MTX3, MX1, MYBPC3, MYCBP, MYH15, MYH2, MYLK4, MYO1A, MYO9A, N4BP1, NDUFA3, NDUFC2, NEUROD1, NFRKB, NFXL1, NGRN, NHLH2, NKAIN2, NKAPL, NLRP9, NME2, NMNAT1, NOL7, NOXRED1, NPC1L1, NPHS2, NPIPA8, NPIPB 15, NPRL3, NPTX2, NPY4R, NPY5R, NR2C2, NRG4, NRTN, NT5DC4, NTSR1, NTSR2, NUCB1, NUDC, NUDT8, NUTM2B, NWD1, OAZ2, OBP2A, ODAM, OLFM4, OPCML, OPLAH, OPTN, OR10A2, OR10A5, OR10P1, OR13F1, OR1E1, OR2AE1, OR2AK2, OR2H1, OR2M4, OR2T12, OR2T2, OR2T27, OR2Y1, OR4F15, OR5111, OR52B6, OR52D1, OR5AC2, OR5H6, OR5K3, OR6A2, OR6B3, OR6C76, OR7D4, OR7G3, ORC6, OSBPL3, OTOP2, OXER1, P2RY8, P4HB, PABPC1, PABPC3, PACS1, PACSIN2, PADI3, PALM3, PANK4, PAPOLB, PAQR6, PARD6G-AS1, PARL, PARP11, PARVB, PAX8, PCCA, PCDH19, PCDHB5, PCDHGA2, PCDHGB1, PCGF2, PCNP, PDE10A, PDE8B, PDZD8, PECR, PEX2, PFN3, PHC1, PHF20L1, PHTF1, PIH1D2, PIK3C2G, PINX1, PIWIL1, PIWIL3, PKNOX1, PLEKHO1, PLK5, PLSCR5, PLXNA2, PNMA2, PNP, PODXL, POGLUT1, POLD3, POLG2, POLR3F, POM121, POM121C, PPAPDC1B, PPIAL4A, PPIAL4B, PPIAL4G, PPM1J, PPP1CA, PPP1R1C, PPP1R36, PPP2R2D, PPP2R5B, PPY, PRAIVIEF12, PRAIVIEF21, PRB1, PRDM10, PRDM12, PRKG2, PROSC, PRPF38B, PRPF39, PRPH, PRR4, PRRT2, PRSS21, PRSS46, PRSS53, PSMD9, PSMF1, PSPC1, PTDSS2, PTER, PTGES3L, PTPN20B, PTPRG, PTPRQ, PVRL3, PXDNL, QDPR, RAB11FIP1, RAB1B, RAB40AL, RABGGTA, RAD23A, RAD50, RAET1E, RANBP1, RAPH1, RASEF, RASGEF1B, RBCK1, RBM11, RBM23, RBM34, RCAN3, RCVRN, RD3L, RDH8, REG1B, RELN, RFTN2, RFX3, RGS14, RGS6, RHOXF1, RHPN2, RIN3, RIPK1, RIPPLY1, RLN1, RNASE11, RNASE9, RNF214, RNF25, RNF31, ROBO3, ROS1, RPA4, RPAIN, RPEL1, RPF1, RPGR, RPL36, RPL39L, RPRM, RPS3, RPS6KB2, RRS1, RSPH4A, RTN4R, RTP1, RUVBL2, SAE1, SAP25, SAPCD1, SBSPON, SCIN, SCN4A, SCP2D1, SCPEP1, SDCBP2, SEC23IP, SECISBP2, SELENOF, SEMA4G, SEPW1, SERINC3, SERP2, SETMAR, SF3B2, SFN, SFTPD, SGCZ, SH3BGR, SHISA4, SIK2, SIM2, SIRPD, SLC10A6, SLC11A1, SLC13A5, SLC22A31, SLC22A7, SLC24A2, SLC25A2, SLC25A26, SLC25A47, SLC25A53, SLC2A12, SLC34A3, SLC35E1, SLC35G5, SLC3A2, SLC44A5, SLC4A9, SLC6A12, SLC6A8, SLC7A7, SLC9A7, SMAD2, SMAD5, SMCR8, SMIM11, SMIM13, SMIM5, SMR3A, SNAP29, SNIP1, SNRPA1, SNTG1, SNX2, SNX31, SNX32, SOCS2, SOX8, SPACA5B, SPAG1, SPAG4, SPATA22, SPATA3, SPATA31D1, SPDYC, SPOCK2, SPPL3, SPRED1, SPRED2, SPTBN1, SPTLC3, SRSF12, SRSF3, SSTR5, ST6GAL2, ST8SIA3, ST8SIA6, STAG3, STMN4, STMND1, STPG2, STRN3, SULT1A2, SUMF1, SUMF2, SUPT5H, SUV420H2, SYNDIG1L, SYT17, SYT2, TAAR8, TAC3, TACC1, TACC2, TACR1, TAF12, TAMM41, TAP2, TAS2R31, TAS2R39, TAS2R43, TAS2R46, TAS2R8, TBC1D2B, TBC1D30, TBCCD1, TBRG1, TCAP, TCEB3CL2, TCN2, TCTA, TCTN1, TDRD9, TEDDM1, TEPP, TERF1, TEX14, TEX30, TEX33, TEX40, TFIP11, TGM2, THAP8, TIMM22, TIMMDC1, TINAGL1, TM6SF2, TM7SF2, TMC4, TMED2, TMEM107, TMEM125, TMEM132C, TMEM151B, TMEM155, TMEM170B, TMEM178B, TMEM180, TMEM206, TMEM220, TMEM248, TMEM249, TMEM33, TMEM54, TMEM55B, TMPRSS11A, TMPRSS11D, TMSB4Y, TNNI3, TNNI3K, TOE1, TP53I11, TP53TG3D, TPPP, TPPP3, TPR, TRDMT1, TRIM16, TRIM16L, TRIM24, TRIM36, TRIM46, TRIM6, TRIM64C, TRMT1, TRMT2A, TRPC3, TRPC6, TRPC7, TSC1, TSEN34, TSNAXIP1, TSSC1, TSSK4, TSTA3, TTC21A, TTC29, TTC6, TTYH2, TUBA3E, TUBAE, TUBB8, TXK, TXLNB, TXN2, U2AF1L4, UBE2E3, UBE2G2, UBE2V1, UBFD1, UBQLNL, UBXN10, UCN, UGT3A1, ULK4, UMP5, UNC13B, UPRT, UQCC1, URGCP, URI1, USP41, VANGL1, VANGL2, VAPB, VAX2, VBP1, VCPKMT, VIMP, VPS11, VTI1B, VTN, WASF3, WBSCR16, WDR63, WDR74, WDR91, YBX2, YDJC, YKT6, ZBBX, ZBTB7B, ZC2HC1B, ZC4H2, ZCCHC17, ZDHHC19, ZDHHC5, ZFAND2A, ZIC5, ZNF114, ZNF266, ZNF284, ZNF317, ZNF329, ZNF460, ZNF554, ZNF561, ZNF576, ZNF606, ZNF662, ZNF692, ZNF705B, ZNF705G, ZNF98, ZP3, ZSCAN20, ZSCAN30, ZSWIM2, and ZSWIM7.

A lasso model input feature set may be further limited to only genes and transcripts which are most impactful in the prediction, including 404 genes and transcripts: A4GNT, ABTB2, ACHE, ACOT1, ACOT7, ACTR10, ACTR3B, ACVR2B, ADHFE1, ADIPOR1, ADPRHL1, AGPAT6, AGTR2, AGXT, AHNAK, AIM1L, AK2, AKR1B1, AKR1C4, ALDH1A3, ALG14, ALG1L, ALKBH6, AMIGO3, AMMECR1, ANP32E, AOAH, ARHGDIB, ARMC4, ARSD, ASAH2, ASB8, ASPG, ASPH, ATP13A1, ATP13A2, ATP6V1E2, ATRX, ATXN7L3B, BET1L, BTN2A1, BZRAP1, C12orf73, C14orf93, C15orf38, C16orf3, C19orf35, C1orf227, C1orf229, C1QL3, C2orf27B, C2orf48, C2orf91, C3orf84, C4orf45, C5orf20, C6orf47, C6orf52, C8G, C8orf34, C9orf129, C9orf156, C9orf91, CABP4, CACNG4, CBR3, CCDC125, CCDC141, CCDC144A, CCDC183, CCDC25, CCDC78, CCDC89, CD51, CD200R1, CD247, CDA, CEACAM18, CEACAM5, CKMT1B, CLDN10, CLDN34, CLEC18B, CLPB, COCH, COMMD7, COMMD9, COPG2, COQ5, COX6A2, CPLX4, CTBP2, CXorf38, DAB1, DBF4, DCBLD1, DDHD1, DEFB134, DEGS2, DHDDS, DHRS4L2, DIRC1, DPM2, DUSP27, DYRK4, ECHDC1, EDDM3A, ELMOD1, EMID1, ENSG00000187461, ENSG00000187811, ENSG00000197665, ENSG00000203546, ENSG00000250232, ENSG00000254673, ENSG00000256100, ENSG00000260836, ENSG00000266956, ENSG00000267140, ENSG00000267157, ENSG00000268714, ENSG00000268950, ENSG00000269846, ENSG00000272617, ENSG00000272762, ENSG00000273217, EPHB1, EQTN, ERCC6, ETS1, ETV2, ETV6, EYA1, FABP9, FAHD2B, FAM21B, FAM72B, FAM83F, FBXO47, FDFT1, FEZF2, FHIT, FKBP2, FOXD1, FRRS1L, FSHR, FUS, FXR1, G6PD, GATSL3, GDF15, GGT1, GLS2, GMEB1, GOLGA6L1, GOLGA8O, GOLM1, GPATCH2L, GPR112, GPR115, GPR19, GPR55, GRK7, GSPT2, GTF2A1L, GVQW3, HDDC3, HIRA, HIRIP3, HLA-DMB, HLA-DPB1, HLA-DQB1, HMX3, HORMAD1, HOXA11, HOXA13, HRNR, HS6ST2, HSD17B13, HTR6, IFRD2, IGF2BP2, INPP5A, ISCA1, KCNS3, KIAA1467, KIAA1683, KIF21B, KIF5A, KLHDC10, KLK2, KRT12, KRT40, L3MBTL4, LDHD, LHCGR, LILRB2, LILRB4, LMBR1L, LONRF3, LRAT, LRR1, LRRC57, LRRC59, LUZP1, LY6G5C, M6PR, MAGEB5, MAGIX, MAPKBP1, MARK3, MEDS, METTL11B, MFSD9, MIB1, MICALL2, MKS1, MLPH, MMP17, MPL, MPP3, MPP7, MSH5, MT1F, MTCP1, MTDH, MTUS1, MYBPC3, MYCBP, MYH2, MYLK4, MYO1A, NDUFA3, NFXL1, NGRN, NLRP9, NME2, NMNAT1, NPC1L1, NPRL3, NPY5R, NRG4, NRTN, NUCB1, NUDC, NWD1, OAZ2, OBP2A, OLFM4, OPLAH, OR2AE1, OR4F15, OR52B6, OR5AC2, ORC6, OSBPL3, OXER1, PADI3, PALM3, PANK4, PAPOLB, PAQR6, PARD6G-AS1, PCDH19, PCDHB5, PCDHGA2, PCNP, PDE10A, PDE8B, PEX2, PHF20L1, PIK3C2G, PLK5, PLSCR5, PLXNA2, POLR3F, POM121C, PPIAL4A, PPP1R36, PPP2R2D, PRAMEF21, PRKG2, PROSC, PRR4, PRSS53, PSPC1, PTER, PTPN20B, RAB40AL, RABGGTA, RAD50, RASEF, RASGEF1B, RBCK1, RCAN3, RCVRN, RD3L, RELN, RGS14, RGS6, RIN3, RNASE11, RNF25, ROBO3, RPA4, RPAIN, RPEL1, RPGR, RPL39L, RPS3, SAP25, SAPCD1, SBSPON, SCIN, SDCBP2, SETMAR, SH3BGR, SHISA4, SIRPD, SLC24A2, SLC35E1, SLC7A7, SLC9A7, SMAD5, SMIM11, SNRPA1, SNTG1, SOCS2, SOX8, SPATA22, SPATA3, SPOCK2, SPRED1, SPRED2, SPTBN1, SRSF12, ST8SIA6, STPG2, STRN3, SULT1A2, TAC3, TACC1, TAF12, TAS2R31, TAS2R43, TAS2R46, TBC1D2B, TBC1D30, TBCCD1, TCTN1, TDRD9, TEDDM1, TERF1, TEX40, TFIP11, TIMMDC1, TM6SF2, TMC4, TMEM107, TMEM125, TMEM151B, TMEM155, TMEM180, TMEM206, TMEM249, TNNI3, TPR, TRDMT1, TRIM16L, TRIM36, TRIM6, TRMT1, TRMT2A, TRPC3, TSC1, TSEN34, TSNAXIP1, TSSC1, TTC21A, TTC29, TTYH2, TUBA3E, TXK, U2AF1L4, UBE2V1, UBFD1, UBQLNL, UGT3A1, UMP5, UNC13B, URI1, VAPB, VAX2, VTI1B, WASF3, WBSCR16, YKT6, ZBTB7B, ZCCHC17, ZDHHC19, ZNF266, ZNF284, ZNF705B, and ZNF705G.

In another example, a resulting pipeline run may generate a set of 5 folds, 4 training and one testing. The pipeline using a combined feature set of RNA TPM features with recursive feature elimination feature selection method may result in 40 features for training subset [0,1,2], 40 features for training subset [0,1,3], 40 features for training subset [0,2,3], 40 features for training subset [1,2,3], and 40 features for training subset [0,1,2,3]. In one example, all RNA TPM features may include over 20,000 genes or over 198,000 transcripts which may be mapped to genes. A complete feature set including all of the RNA TPM features which are selected during feature select may be optimized to include only 112 genes and transcripts: ALG10, ANKH, ART1, BRK1, C10orf71, C11orf73, C14orf177, C1orf167, CACNG1, CCER1, CCZ1, CHRNA2, CNIH1, CNOT8, COPG2, CRKL, CYLC2, DEFB4B, DLL3, DPPA2, ENSG00000254943, ENSG00000255439, ENSG00000258881, ENSG00000269881, ESD, FAM163A, FAM180B, FEZF2, GRK7, GRM6, GTPBP1, HAT1, HCRTR1, HRK, KCNK4, LAPTM4A, LCE1A, LCE6A, LGALS16, LOR, LPCAT3, LY6L, MAGOHB, MFSD2B, MPZL1, MRGPRX3, MTRNR2L10, NDUFA4, NDUFB1, NDUFC2, NDUFS4, NUP133, OPN1MW, OR10G3, OR10G4, OR1I1, OR2G6, OR2T34, OR6C76, OR8S1, PABPC1L2A, PIGF, PLG, PON2, PRDM12, PRDX6, RDH8, RHO, RLBP1, ROM1, RPL10A, RPL41, RPS27, RSL24D1, SF3A1, SIM1, SLC17A2, SLC17A6, SLC38A2, SMARCC1, SMDT1, SOX15, SPACA1, SPIN1, SPPL3, SRSF3, SSX2B, STX17, TECRL, TEX261, TEX33, THUMPD1, TM2D1, TMEM167A, TMEM251, TMEM258, TRAPPC10, TRIM49, TRIML1, TRIT1, TRMT2A, TULP1, UBE2E1, UBE2Q1, UNC50, UPRT, VMA21, YPEL5, ZC3H7A, ZNF311, and ZP1.

A recursive feature elimination model input feature set may be further limited to only the top 40 genes and transcripts which are most impactful in the prediction, including: CACNG1, CNIH1, CRKL, CYLC2, DEFB4B, ENSG00000258881, ENSG00000269881, ESD, FAM163A, FAM180B, GRM6, HAT1, LAPTM4A, LCE6A, MFSD2B, MPZL1, MTRNR2L10, NDUFA4, NUP133, OR6C76, OR8S1, PABPC1L2A, PIGF, PLG, PRDM12, ROM1, RPL41, RPS27, SLC38A2, SMDT1, SOX15, SPIN1, SRSF3, STX17, THUMPD1, TMEM167A, TMEM258, TRIT1, YPEL5, and ZNF311.

In another embodiment, the lasso and/or recursive feature elimination feature selection models above may select a trained model input from 5 or more, 10 or more, 25 or more, 50 or more, 75 or more, 125 or more, or another selected number of features from the feature sets identified above. In one example, embodiments including a selected number of features may be used when whole transcriptome results are not available.

In another embodiment, information related to the expression level of a gene may be correlated with or predicted from the expression level data associated with one or more other genes. When a gene may be predicted from one or more other genes, the one or more other genes are defined as proxy genes. In one example, a gene of a trained model may be replaced by its proxies or predicted from the proxies and the prediction fed in its place.

One or more of the final models may be used to predict patient metastasis from cancers having a diagnosis of colorectal to any other site/organ.

The methods and systems described above may be implemented as a component of various practical applications. For example, a person may experience symptoms such as, e.g., unexpected weight loss and a cough that persists for several weeks. Concerned for their overall wellbeing, they may seek a diagnosis from a physician. The physician may recognize the person's symptoms as indicative of lung cancer and schedule imaging of the patient's lung with a Computed Tomography (CT) scan of the chest. Imaging results may come back identifying a suspected tumor in the person's lung. The person, now patient of an oncologist (also called the physician), may have a biopsy performed which identifies the tumor as malignant. The physician may then send a biopsy to a pathologist for diagnosis and to have the tumor sequenced to identify any drivers of the patient's lung cancer. The pathologist may identify the lung cancer as non-small cell lung cancer (NSCLC).

In some embodiments, a tumor specimen and blood sample may be sent to a next-generation sequencing laboratory for Tumor-Normal sequencing. The DNA and RNA may be isolated from the tumor tissue specimen and sequencing may be performed on an Illumina sequencer. As used herein, "Matched Tumor-Normal," "Tumor-Normal Matched," and "Tumor-Normal Sequencing" defines processing genomic information from a subject's normal sample, such as saliva, blood, urine, stool, hair, healthy tissue, or other collections of cells or fluids from the subject, and genomic information from a subject's tumor sample, such as smears, biopsies or other collections of cells or fluids from a subject which contain tumor tissue, cells, or DNA. DNA and RNA features which have been identified from a next generation sequencing (NGS) of a subject's tumor or normal specimen may be cross-referenced to remove genomic mutations and/or variants which appear as part of a subject's germline from the somatic analysis. The use of a somatic and germline dataset leads to substantial improvements in mutation identification and a reduction in false positive rates. Tumor-Normal Matched Sequencing provides a more accurate variant calling due to improved germline mutation filtering. For example, generating a variant call based at least in part on the germline and somatic specimen may include identifying common mutations and removing them. In such a manner, variant calls from the germline are removed from variant calls from the somatic as non-driver mutations. A variant call that occurs in both the germline and the somatic specimen may be presumed to be normal to the patient and removed from further bioinformatics calculations.

The same procedure may be performed on the blood sample as the normal sequencing so that results from the RNA and DNA results of both tumor and normal sequencing may be analyzed. A sequencer, such as the sequencer generating results for the Tumor-Normal sequencing, may generate a FASTQ file having a plurality of reads from the sequencing. After generation of a FASTQ file, the file may be uploaded to a cloud-based platform or processed locally. Reads may be aligned to a reference genome using paired-end reads to increase the accuracy. Aligned reads may be stored as a BAM file. A bioinformatics pipeline may receive the BAM file and identify variant calls, gene mutations, fusions, alterations, copy number states, and other alterations as described above. In an example, the sequencing and subsequent processing of RNA and/or DNA obtained from the patient sample may identify a variant in one of the following genes: kirsten rat sarcoma viral oncogene (KRAS), anaplastic lymphoma kinase receptor (ALK), human epidermal growth factor receptor 2 (HER2), v-raf murine sarcoma viral oncogene homolog B1 (BRAF), PI3K catalytic protein alpha (PI3KCA), AKT1, MAPK kinase 1 (MAP2K1 or MEK1), or MET, which encodes the hepatocyte growth factor receptor (HGFR). In one example, mutations may be identified in the EGFR gene. A report may be generated, summarizing the results from the bioinformatics pipeline, including clinical trials and therapies that are determined to be most relevant to the patient's particular genome.

As part of the report generation, predictions may be generated by an artificial intelligence engine, such as an engine included in the system in accordance with the present disclosure and configured to perform the described processes. In one example, a prediction may be generated as to the likelihood that the patient's lung cancer may metastasize to another organ, such as the brain, liver, or bone. A report, summarizing the findings from the pathologist and subsequent sequencing may be generated for the physician. The report can be used by a physician to consider the prediction provided by the report. For example, the generated prediction can be that the patient is likely to metastasize to the brain in the next 12 months. This information may allow making a decision regarding whether to schedule a surgery for the patient, a combination of surgery and endobronchial therapy, surgery and radiation therapy, surgery and chemotherapy, or cytotoxic chemotherapy in combination with EGFR tyrosine kinase inhibitors. In one example, the physician may elect for surgery with increased monitoring afterwards, such as by regularly CT imaging and 18F-FDG positron-emission tomography (PET) scanning. In another example, the physician may elect a combination of cytotoxic chemotherapy in combination with EGFR tyrosine kinase inhibitors to aggressively treat the patient. The patient, because of the selected therapy, may experience a substantially improved response and outcome to treatment. The patient's NSCLC may go into remission and the patient may remain progression free until the patient's natural death of old age. A physician may schedule regular monitoring through CT imaging or PET scanning. The power of the reporting, including a prediction of the patient's likelihood to metastasis to another organ, is in allowing the physician to provide the most expedient, affordable care to the patient by applying the benefits of precision medicine over a one-size fits all care regimen.

In furtherance of the above patient timeline, generation of the predictions may be performed in accordance with the method and systems disclosed above. The system, such as, e.g., the system 100 for generating and modeling predictions of patient objectives (FIG. 1), may generate the predictions to be included in the report to the physician. In one example, an artificial intelligence engine or a component thereof, such as, for example, the metastasis site objective module 146 of Objective Modules 140, may generate the prediction from patient records.

In an example, the artificial intelligence engine may be initiated for a Target/Objective of Metastasis from Lung to Brain within 12 months. A model 146b may be trained on labeled RNA feature data. The labeled RNA feature data may be labeled with information about whether the patient from whom the RNA feature data was derived had a form of lung cancer that metastasized to the brain. The label information may include the organ, such as brain, to which the cancer metastasized, the period of time from initial diagnosis to metastasis diagnosis, such as a binary yes or no to within the 12 months after sequencing, the staging information, tumor state such as TNM and so forth. RNA feature data may be presented in a format representing raw reads from sequencing, raw reads ma RPKM, FPKM, TPM, or other methods as described above.

As an example, the artificial intelligence engine may be initiated for a Target/Objective of Metastasis from Lung to Liver within 24 months. A model 146b may be trained on labeled DNA feature data. The labeled DNA feature data may be labeled with information about whether the patient from whom the DNA feature data was derived had a form of lung cancer that metastasized to the liver. The label information may include the organ, such as liver, to which the cancer metastasized, the period of time from initial diagnosis to metastasis diagnosis, such as a binary yes or no to within the 24 months after sequencing, the staging information, tumor state such as TNM and so forth. In an example, the DNA feature data may include features which are labeled on a structural variant by variant basis or features which are labeled on a gene by gene basis. One such example of a gene-by-gene basis includes the features of Table 1, above.

In an example, the physician may order sequencing of a tumor specimen and blood sample from a laboratory where the ordering includes identification of which tests the physician would like the laboratory to perform on the specimen and blood sample in addition to a report of the patient's genomic profile. Tests may include MSI, TMB, CNV, Fusions, activated or deactivated pathways, or other alterations as described above with respect to alteration module 250. Tests may also include predictions from an artificial intelligence engine, such as system 100 for generating and modeling predictions of patient objectives, or more specifically the metastasis site objective module 146 of Objective Modules 140. A physician may order sequencing with only genetic results and their implications reported or sequencing with genetic results and subsequent alteration tests, including a prediction of patient's likelihood for metastasis, reported together. In an example, a physician may order predictions without sequencing, such as when another laboratory sequences the patient's tumor. The physician may submit the patient's EMR or sequencing results for abstraction, and predictions may be performed on the sequencing results only or the sequencing results and any abstracted patient features obtained from the EMR. Sequencing results from another lab may include DNA, RNA, or Immunology related features.

In an example, a tumor specimen may be difficult to obtain, such as from the brain or lung or when a patient is undergoing recurring sequencing and a physician may not desire to repeatedly biopsy the patient's tumor. In place of sampling the patient's tumor in some instances, a sample of blood may be processed using a cell-free DNA, cfDNA, approach or sequencing of proteins using protein sequencers.

In an example, a patient may be identified as high risk for metastasis based upon the patient's circumstances and a test for likelihood of metastasis may not be ordered. High risk circumstances may include NSCLC recurrence, lack of actionable targeted mutations, expression of EGFR, EGFR T790M, ALK, ROS1, RET, BRAF, NTRK mutations which are typically more likely to metastasize, certain high risk combinations of cancer types and patient features including colorectal cancer and high microsatellite instability, or based upon staging of the cancer.

As described above, models may be generated for any combination of features based upon the best performance to patients having a representative selection of features a model has been trained on. Each patient has a unique feature set based upon their interactions with the medical system and length of time in the medical system. While it is impossible to exhaustively list every combination of features, patients tend to bin into a set of feature sets. As the medical industry advances and more feature sets are curated for more patients, the models listed here may be increased. Accordingly, a patient may be selected for a model comprising features wherein the patient features include: raw RNA reads, normalized RNA reads, autoencoded RNA reads, RNA related features, any RNA related features with any other RNA related features, DNA reads, normalized DNA reads, autoencoded DNA reads, DNA related features, any DNA related features with any other DNA related features, any RNA related features with any DNA related features, RNA and DNA reads, RNA and DNA related features, RNA reads and imaging features, RNA related features and imaging features, DNA reads and imaging features, DNA related features and imaging features, cfDNA reads, cfDNA related features, cfDNA reads and imaging features, cfDNA related features and imaging features, cfDNA reads and clinical features, cfDNA related features and clinical features, cfDNA reads and combined clinical and imaging features, cfDNA related features and combined clinical and imaging features, cfDNA related features and RNA related features, cfDNA related features and DNA related features, combined RNA and DNA reads and imaging features, combined RNA and DNA related features and imaging features, RNA reads and clinical features, RNA related features and clinical features, DNA reads and clinical features, DNA related features and clinical features, imaging features and clinical features, RNA reads and combined imaging and clinical features, RNA related features and combined imaging and clinical features, DNA reads and combined imaging and clinical features, DNA related features and combined imaging and clinical features, combined RNA and DNA reads and combined imaging and clinical features, any combined RNA and DNA related features and combined imaging and clinical features, any RNA related features with any proteomic features, and DNA related features with any proteomic features, combined RNA and DNA related features with any proteomic features, any DNA related features combined with imaging features and proteomic features, any DNA related features combined with clinical features and proteomic features, any RNA related features combined with imaging features and proteomic features, any RNA related features combined with clinical features and proteomic features, and any combined RNA and DNA related features combined with combined clinical and imaging features and proteomic features. While some combinations have been inadvertently left out of the above listing of combinations of features, it should be appreciated that a full combinatorial listing of features from each of the above features to each other of the above features is attempted and desired. It should also be appreciated that a full combinatorial listing of the features from feature store 120 is similarly disclosed as applicable models to the artificial intelligence engine as disclosed herein.

It should be understood that RNA related features may include raw RNA reads, normalized RNA reads, and autoencoded RNA reads and that DNA related features may include raw DNA reads, normalized DNA reads, and autoencoded DNA reads. Therefore combined RNA and DNA related features may include any combination raw RNA reads to raw DNA reads, normalized DNA reads, and autoencoded DNA reads, normalized RNA reads to raw DNA reads, normalized DNA reads, and autoencoded DNA reads, autoencoded RNA reads to raw DNA reads, normalized DNA reads, and autoencoded DNA reads and vice versa.

The methods and systems described above may be utilized in combination with or as part of a digital and laboratory health care platform that is generally targeted to medical care and research, and in particular, generating a molecular report as part of a targeted medical care precision medicine treatment or research. It should be understood that many uses of the methods and systems described above, in combination with such a platform, are possible. An example of such a platform is described in U.S. patent application Ser. No. 16/657,804, titled "Data Based Cancer Research and Treatment Systems and Methods" (hereinafter "the '804 application"), which is incorporated herein by reference in its entirety for all purposes. In some aspects, a physician or other individual may utilize an artificial intelligence engine, such as the system 100 for generating and modeling predictions of patient objectives, in connection with one or more expert treatment system databases shown in FIG. 1 of the '804 application. The artificial intelligence engine of system 100 may operate on one or more micro-services operating as part of systems, services, applications, and integration resources database, and the methods described herein may be executed as one or more system orchestration modules/resources, operational applications, or analytical applications. At least some of the methods (e.g., microservices) can be implemented as computer readable instructions that can be executed by one or more computational devices, such as the artificial intelligence engine of system 100. For example, an implementation of one or more embodiments of the methods and systems as described above may include microservices included in a digital and laboratory health care platform that can generate predictions of a patient's likelihood to metastasis to an organ within a time period based upon the patient's available features and sequencing results.

In some embodiments, a system may include a single microservice for executing and delivering the predictions or may include a plurality of microservices, each microservice having a particular role which together implement one or more of the embodiments above. In an example, a first microservice may include extracting patient information from one or more patients, identifying one or more interactions for each of the one or more patients based at least in part on the received patient information; generating, for one or more targets at each one or more interactions, one or more timeline metrics identifying whether each of the one or more targets occurs within a time period of an occurrence of the interaction; identifying, for each timeline metric of the one or more timeline metrics, whether a patient will be associated with one or more status characteristics within the time period; training a target prediction model for each of the one or more targets based at least in part on the one or more status characteristics; and associating predictions for each patient from the target prediction model for each of the one or more targets with a respective one or more timeline metrics of the one or more timeline metrics. A second microservice may include listening for an order to generate a prediction using the artificial intelligence engine of system 100 for a new patient using the trained model. Similarly, the second microservice may include providing the received information to the trained prediction model for the identified target/objective and generating a prediction so that the artificial intelligence engine of system 100 may provide the prediction in response to the order according to an embodiment, above.

The artificial intelligence engine of system 100 may be utilized as a source for automated data generation of the kind identified in FIG. 59 of the '804 application. For example, the artificial intelligence engine of system 100 may interact with an order intake server to receive an order for a test, such as a test that provides predictions with respect to a patient. Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above.

For example, continuing with the above first and second microservices, an order management system may notify the first microservice that an order for a test has been received and is ready for processing. The first microservice may include executing and notifying the order management system once the delivery of any patient information for the second microservice is ready, including one or more interactions, one or more timeline metrics, and a target/objective pair. Furthermore, the order management system may identify that execution parameters (prerequisites) for the second microservice are satisfied, including that the first microservice has completed, and notify the second microservice that it may continue processing the order to provide the prediction from the artificial intelligence engine of system 100 according to an embodiment, above. While two microservices are utilized for illustrative purposes, patient information extraction, interaction identification, status characteristic identification, model training, and patient predictions may be split up between any number of microservices in accordance with performing embodiments herein.

The digital and laboratory health care platform further includes one or more insight engines shown in FIG. 272 of the '804 application. Exemplary insight engines may include a tumor of unknown origin engine, a human leukocyte antigen (HLA) loss of homozygosity (LOH) engine, a tumor mutational burden (TMB) engine, a PD-L1 status engine, a homologous recombination deficiency (HRD) engine, a cellular pathway activation report engine, an immune infiltration engine, a microsatellite instability engine, a pathogen infection status engine, and so forth as described with respect to FIGS. 189, 199-200, and 266-270 of the '804 application. In an aspect, a model may be trained on and subsequently receive as an input for predictions, features including diagnosis of the patient as to an insight engine such as HLA LOH, TMB, PD-L1, HRD, active pathway, or other insight status. The artificial intelligence engine of system 100 may identify a patient having features from an insight engine and select an appropriate model and feature set to utilize the features in a prediction.

When the digital and laboratory health care platform further includes a molecular report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ via a genetic analyzer. The report may further include therapies and/or clinical trials matched based on a portion or all of the genetic profile or insight engine findings and summaries shown in FIGS. 271 and 302 of the '804 application.

It should be understood that the examples given above are illustrative and do not limit the uses of the systems and methods described herein in combination with a digital and laboratory health care platform.

Predicting Metastasis of Cancer in a Subject.

Example System Embodiments

Figure 15:
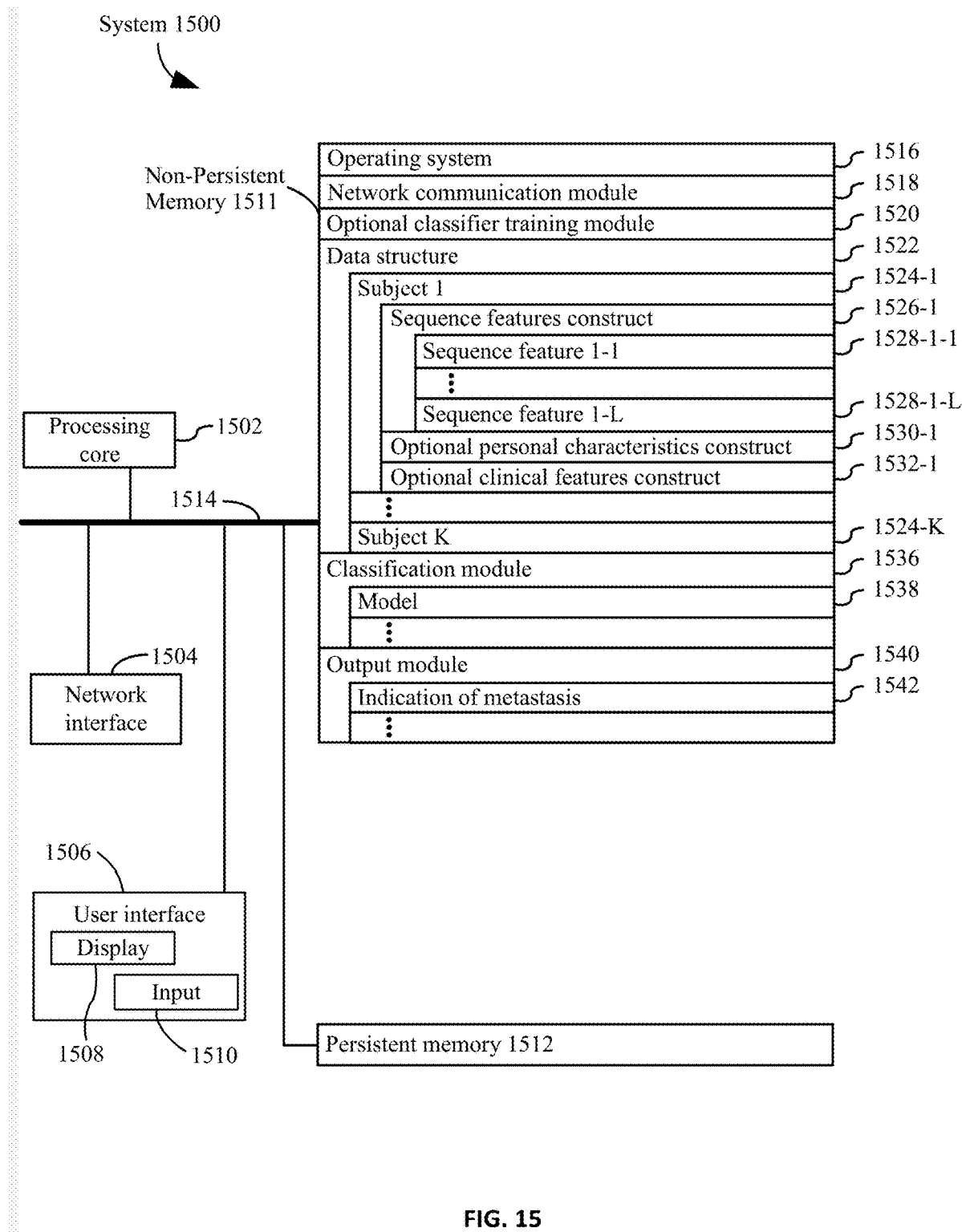
FIG. 15 illustrates a block diagram of an example computing device, in accordance with some embodiments of the present disclosure.

Now that an overview of some aspects of the present disclosure have been provided, details of an exemplary system are described in conjunction with FIG. 15. FIG. 15 is a block diagram illustrating a system 1500 in accordance with some implementations.

The system 1500 in some implementations includes one or more processing units CPU(s) 1502 (also referred to as processors), one or more network interfaces 104, a user interface 106 including (optionally) a display 1508 and an input system 1510, a non-persistent memory 1511, a persistent memory 1512, and one or more communication buses 1514 for interconnecting these components. The one or more communication buses 1514 optionally include circuitry (sometimes called a chipset) that interconnects and controls communications between system components. The non-persistent memory 1511 typically includes high-speed random access memory, such as DRAM, SRAM, DDR RAM, ROM, EEPROM, flash memory, whereas the persistent memory 1512 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 1512 optionally includes one or more storage devices remotely located from the CPU(s) 1502. The persistent memory 1512, and the non-volatile memory device(s) within the non-persistent memory 1512, comprise non-transitory computer readable storage medium.

In some implementations, as illustrated in FIG. 15, the non-persistent memory 1511 or alternatively the non-transitory computer readable storage medium stores the following programs, modules and data structures, or a subset thereof, sometimes in conjunction with the persistent memory 1512:

- an optional operating system 1516, which includes procedures for handling various basic system services and for performing hardware dependent tasks;
- an optional network communication module (or instructions) 1518 for connecting the system 1500 with other devices and/or a communication network 1504;
- an optional classifier training module 1520 for training one or more models (e.g., predictive and/or classification models) to provide one or more indications of whether the cancer will metastasize in the subject;
- a data structure 1522 comprising a plurality of data elements for a cancer of a subject 1524 (e.g., optionally, a plurality of subjects 1524-1, . . . , 1524-K), the data structure 1522 comprising:
    - a sequence features data construct 1526 (e.g., 1526-1) comprising a first set of sequence features 1528 (e.g., 1528-1-1, . . . , 1528-1-L) (e.g., relative abundance values for the expression of a plurality of genes (e.g., at least 30 genes) in a biopsy of the cancer obtained from the subject);

optionally, a personal characteristics data construct 1530 (e.g., 1530-1) comprising one or more personal characteristics about the subject (e.g., age, gender, and/or race); and optionally, a clinical features data construct 1532 (e.g., 1532-1) comprising one or more clinical features related to the diagnosis or treatment of the cancer in the subject and/or one or more temporal elements associated with the one or more clinical features;

a classification module 1536 comprising one or more models 1538 (e.g., optionally, a set of models) that are trained to provide one or more indications of whether the cancer will metastasize in the subject; and an output module 1540 comprising one or more indications 1542 of whether the cancer will metastasize in the subject (e.g., optionally, for each respective tissue in a plurality of tissues, a respective set of indications for each respective time horizon in a plurality of time horizons).

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 1511 optionally stores a subset of the modules and data structures identified above. Furthermore, in some embodiments, the memory stores additional modules and data structures not described above. In some embodiments, one or more of the above identified elements is stored in a computer system, other than that of system 1500, that is addressable by system 1500 so that system 1500 may retrieve all or a portion of such data when needed.

Although FIG. 15 depicts a "system 1500," the figure is intended more as a functional description of the various features that may be present in computer systems than as a structural schematic of the implementations described herein. In practice, and as recognized by those of ordinary skill in the art, items shown separately could be combined and some items could be separated. Moreover, although FIG. 15 depicts certain data and modules in non-persistent memory 1511, some or all of these data and modules instead may be stored in persistent memory 1512 or in more than one memory. For example, in some embodiments, at least data structure 1522 is stored in a remote storage device which can be a part of a cloud-based infrastructure. In some embodiments, at least data structure 1522 is stored on a cloud-based infrastructure. In some embodiments, data structure 1522, the classifier training module 1520, the classification module 1536, and/or the output module 1540 can also be stored in the remote storage device(s). In some embodiments, any of the features of the system 1500 can be used in conjunction with any of the features of any one or more of system 100, system 200, system 300, system 400, system 500, and/or system 1400, as depicted in FIGS. 1-5 and 14, and/or any combinations thereof as will be apparent to one skilled in the art. For instance, data structure 1522 can comprise any of the example features listed in systems 400 and 500 or can further be associated with any one or more of feature collection 205, feature module 110, feature store 120, feature selector 200, and feature generator 300.

Classification Methods

While a system in accordance with the present disclosure has been disclosed with reference to FIG. 15 (e.g., alone or in combination with any one or more of FIGS. 1-5 and 14), methods in accordance with the present disclosure are now detailed with reference to FIGS. 16 and 17.

Referring to FIG. 16, the present disclosure provides a method 1602 for predicting metastasis of a cancer in a subject. In particular, in some embodiments, the systems and methods described herein utilize at least relative abundance values determined from RNA molecules in a sample from the subject to determine at least a first indication (e.g., a binary indication and/or a probability) of whether the cancer will metastasize in the subject. In some embodiments, the systems and methods described herein are used to determine an indication (e.g., a binary indication and/or a probability) of whether the cancer will metastasize to a respective tissue in the subject, for each tissue in a plurality of tissues. In some embodiments, the systems and methods described herein are used to determine an indication of whether the cancer will metastasize within a respective time horizon (e.g., a period of time following a temporal element such as a clinical event), for each time horizon in a plurality of time horizons. In some embodiments, the systems and methods disclosed herein are used to determine an indication (e.g., a binary indication and/or a probability) of whether the cancer will metastasize to any given tissue within any given time horizon, for each respective tissue in a plurality of tissues and each time horizon in a plurality of time horizons. In some such embodiments, any possible combination of tissue and time horizon that will be apparent to one skilled in the art is contemplated for the determination and/or provision of metastasis predictions.

Benefit.

In some embodiments, the systems and methods described herein provide predictions of the likelihood, location, and/or projected timeline of cancer metastasis that are used to improve patient diagnosis, clinical reporting, monitoring of cancer progression, assessments of treatment efficacy, recommendations of personalized therapies, and/or administration of personalized therapies (e.g., targeted cancer therapies). For example, conventional methods of cancer therapy are based upon generalized standard of care guidelines that are applicable across a wide variety of patients and clinical histories (e.g., a one-size-fits-all care regimen). By contrast, predictions of metastasis improve upon conventional methods of cancer therapy by considering patient-specific molecular, demographics, and/or clinical features to determine a personalized mode of treatment that is designed to treat not only the current stage or type of cancer, but also to anticipate and treat, prevent, and/or ameliorate metastatic cancers.

As such, predictions of the likely occurrence, time, and/or location of cancer metastasis allows patients to access (e.g., via a physician or medical provider) more expedient, affordable care as part of the benefits of precision medicine. Furthermore, as described above, applications of predictions of cancer metastasis based on such inputs as genetic and molecular sequencing, personal characteristics and/or clinical data can be used to identify therapies which are expected to perform well for a patient having characteristics similar to the reported patient, clinical trials which may accept the patient, or other personalized analysis results which may influence the physician's decisions. Notably, a prediction of cancer metastasis can be used as the basis for prescribing a treatment which is considered aggressive for the treatment and prevention of metastasis. Alternatively, a prediction that metastasis is unlikely within an extended target window (e.g., the next 60 months) can be used as the basis for suggesting a less aggressive treatment to the patient which may be more cost effective and/or cause less severe, or avoid altogether, adverse effects associated with more aggressive treatment regimen.

The benefits of predicting the likelihood of cancer metastasis are not limited to treatments, but can be used to schedule the frequency of monitoring for the patient, such as follow-up visits, additional scanning, screening, imaging, blood tests, or subsequent genetic sequencing. For example, a patient with a high prediction of metastasis may benefit from accelerated screening to detect changes at regular intervals, allowing early intervention before the onset of severe, advanced, and/or noticeable side effects. Additionally, metastasis predictions can be used to determine enrollment in drug trials and/or clinical trials (e.g., by a pharmaceutical company) based on the intersection between inclusion and exclusion criteria and the probability that the patient will experience a predicted outcome, and to provide valuable data, upon analysis, as to the underlying genetic, demographic, and/or clinical basis for positive or negative responses to experimental treatment.

In some embodiments, the systems and methods described herein support a clinical tool for assisting with clinical care, such as a graphical user interface (GUI) and/or tool for determination, reporting, and visualization of one or more indications of cancer metastasis. In some embodiments, the use of a cancer metastasis prediction tool informs users (e.g., clinicians, researchers, and/or patients) as to likely events throughout cancer progression and further provides guidance for decision-making with respect to standard of care therapy recommendations, clinical trial enrollment, and reimbursement for therapies.

It should be noted that details of other processes described herein (as in the above sections, "Generating and Modeling Predictions of Patient Objectives") are also applicable in an analogous manner to the methods described below with reference to FIGS. 16 and 17. For example, details relating to features (e.g., types of features, feature selection methodologies, RNA transcripts, genes, and/or dimensionality reduction), model selection, model training (e.g., artificial intelligence training pipeline), reporting (e.g., graphical user interfaces), etc., described below with reference to method 1602 optionally have one or more of the characteristics of the features, model selection, model training, reporting, etc., described herein with reference to the above sections (e.g., "Generating and Modeling Predictions of Patient Objectives"). For brevity, these details are not repeated here.

Cancer Conditions.

In some embodiments, the subject is a human. In some embodiments, the subject is a patient diagnosed with a cancer condition (e.g., a presence or absence of cancer, a stage of cancer, a cancer type, a cancer subtype, a tissue of origin, a cancer grade, and/or a histopathological grade). In some embodiments, the subject has a cancer having one or more other cancer characteristics (e.g., a homologous recombination deficiency status, a microsatellite stability status, a mutational burden, a genomic alteration (e.g., SNPs/indels, fusions, copy number variations, amplifications, deletions, and/or variant allelic ratios), and/or a genomic marker status (e.g., associated with an actionable therapy)), which are further utilized to determine at least the first indication of whether the cancer will metastasize in the subject. Methods for determining cancer characteristics are known in the art, as described in U.S. patent application Ser. No. 15/930,234, filed May 12, 2020, entitled "Systems and Methods for Multi-Label Cancer Classification," which is hereby incorporated by reference in its entirety.

In some embodiments, the subject's cancer type has been determined. In some such embodiments, a classifier trained specifically to predict metastasis for that type of cancer is used. In other such embodiments, a multi-label classifier that uses cancer type as an input feature is used. In yet other such embodiments, a pan-cancer classifier that does not consider the type of cancer is used. In some embodiments, the subject's cancer has not been identified, e.g., the subject has been diagnosed with a cancer of unknown origin. Accordingly, in some such embodiments, a pan-cancer classifier that does not consider the type of cancer is used.

Generally, the methods and systems described herein are useful for predicting metastasis for any type of cancer. In some embodiments, a classifier used in the methods and systems described herein is trained to predict metastasis for a single type of cancer. In other embodiments, the classifier is a multi-label classifier, that is trained to predict metastasis for multiple types of cancer, e.g., which may or may not use the subject's cancer type as an input. In yet other embodiments, the classifier is a pan-cancer classifier that does not consider the subject's cancer type when predicting metastasis for a subject.

In some embodiments, the cancer is colorectal cancer, non-small cell lung cancer (NSCLC), breast cancer, or ovarian cancer.

In some embodiments, the cancer is selected from Acute Lymphoblastic Leukemia (ALL), Acute Myeloid Leukemia (AML), Adolescents, Cancer in, Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Appendix Cancer, Astrocytomas, Childhood (Brain Cancer), Atypical Teratoid/Rhabdoid Tumor, Childhood, Central Nervous System (Brain Cancer), Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors (Lung Cancer), Burkitt Lymphoma, Carcinoid Tumor (Gastrointestinal), Carcinoma of Unknown Primary, Cardiac (Heart) Tumors, Childhood, Central Nervous System, Atypical Teratoid/Rhabdoid Tumor, Childhood (Brain Cancer), Medulloblastoma and Other CNS Embryonal Tumors, Childhood (Brain Cancer), Germ Cell Tumor, Childhood (Brain Cancer), Primary CNS Lymphoma, Cervical Cancer, Childhood Cancers, Cancers of Childhood, Unusual, Cholangiocarcinoma, Chordoma, Childhood (Bone Cancer), Chronic Lymphocytic Leukemia (CLL), Chronic Myelogenous Leukemia (CML), Chronic Myeloproliferative Neoplasms, Colorectal Cancer, Craniopharyngioma, Childhood (Brain Cancer), Cutaneous T-Cell Lymphoma, Ductal Carcinoma In Situ (DCIS), Childhood (Brain Cancer), Endometrial Cancer (Uterine Cancer), Ependymoma, Childhood (Brain Cancer), Esophageal Cancer, Esthesioneuroblastoma (Head and Neck Cancer), Ewing Sarcoma (Bone Cancer), Extracranial Germ Cell Tumor, Childhood, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST) (Soft Tissue Sarcoma), Germ Cell Tumors, Childhood Central Nervous System Germ Cell Tumors (Brain Cancer), Childhood Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Childhood, Hepatocellular (Liver) Cancer, Histiocytosis, Langerhans Cell, Hodgkin Lymphoma, Hypopharyngeal Cancer (Head and Neck Cancer), Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell, Small Cell, Pleuropulmonary Blastoma, and Tracheobronchial Tumor), Lymphoma, Male Breast Cancer, Malignant Fibrous Histiocytoma of Bone and Osteosarcoma, Melanoma, Melanoma, Intraocular (Eye), Merkel Cell Carcinoma (Skin Cancer), Mesothelioma, Malignant, Metastatic Cancer, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, Chronic (CIVIL), Myeloid Leukemia, Acute (AML), Myeloproliferative Neoplasms, Chronic, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Osteosarcoma and Malignant Fibrous Histiocytoma of Bone, Ovarian Cancer, Pancreatic Cancer, Pancreatic Neuroendocrine Tumors (Islet Cell Tumors), Papillomatosis (Childhood Laryngeal), Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma (Lung Cancer), Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Childhood (Soft Tissue Sarcoma), Salivary Gland Cancer (Head and Neck Cancer), Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Soft Tissue Sarcoma, Uterine Sarcoma, Sézary Syndrome (Lymphoma), Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, T-Cell Lymphoma, Lymphoma (Mycosis Fungoides and Sezary Syndrome), Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Tracheobronchial Tumors (Lung Cancer), Transitional Cell Cancer of the Renal Pelvis and Ureter (Kidney (Renal Cell) Cancer), Ureter and Renal Pelvis, Transitional Cell Cancer (Kidney (Renal Cell) Cancer, Urethral Cancer, Uterine Cancer, Endometrial, Uterine Sarcoma, Vaginal Cancer, Vascular Tumors (Soft Tissue Sarcoma), and/or Vulvar Cancer.

In some embodiments, the cancer is selected from brain non-glioma (ependymoma, hemangioblastoma, medulloblastoma, meningioma), breast (breast ductal, breast lobular), colon, endometrial (endometrial, endometrial serous, endometrial stromal sarcoma), gastroesophageal (esophageal adenocarcinoma, gastric), gastrointestinal stromal tumor, glioma (Glioma, oligodendroglioma), head and neck adenocarcinoma, hematological (acute lymphoblastic leukemia, acute myeloid leukemia, b cell lymphoma, chronic lymphocytic leukemia, chronic myeloid leukemia, rosai dorfman, T-cell lymphoma), hepatobiliary (cholangiocarcinoma, gallbladder, liver), lung adenocarcinoma, melanoma, mesothelioma, neuroendocrine (gastrointestinal neuroendocrine, high grade neuroendocrine lung, low grade neuroendocrine lung, pancreatic neuroendocrine, skin neuroendocrine), ovarian (ovarian clear cell, ovarian granulosa, ovarian serous), pancreas, prostate, renal (renal chromophobe, renal clear cell, renal papillary), sarcoma (chondrosarcoma, chordoma, ewing sarcoma, fibrous sarcoma, leiomyosarcoma, liposarcoma, osteosarcoma, rhabdomyosarcoma, synovial sarcoma, vascular sarcoma), squamous (cervical, esophageal squamous, head and neck squamous, lung squamous, skin squamous/basal), thymic, thyroid, and/or urothelial cancers.

In some embodiments, the cancer is any one or more entries of the ICD-10-CM, or the International Classification of Disease. The ICD provides a method of classifying diseases, injuries, and causes of death. The World Health Organization (WHO) publishes the ICDs to standardize the methods of recording and tracking instances of diagnosed disease, including cancer. For example, in some embodiments, the cancer is selected from the classifications from any chapter of the ICD or cancers from Chapter 2, C and D codes. C codes include Neoplasm of Lip, Oral Cavity and Pharynx (C00-C14), Neoplasm of Digestive Organs (C15-C26), Neoplasm of Respiratory System and Intrathoracic Organs (C30-C39), Neoplasm of Mesothelial and Soft Tissue (C45), Neoplasm of Bones, Joints and Articular Cartilage (C40-C41), Neoplasm of Skin (Melanoma, Merkel Cell, and Other Skin Histologies) (C43, C44, C4a), Kaposi Sarcoma (46), Neoplasm of Peripheral Nerves and Autonomic nervous system, Retroperitoneum, Peritoneum, and Soft Tissues (C47, C48, C49), Neoplasm of Breast and Female Genital Organs (C50-C58), Neoplasm of Male Genital Organs (C60-C63), Neoplasm of Urinary Tract (C64-C68), Neoplasms of Eye, Brain and Other Parts of the Central Nervous System (C69-C72), Neoplasm of Thyroid, Other Endocrine Glands, and Ill-defined Sites (C73-C76), Malignant Neuroendocrine Tumors (C7a._), Secondary Neuroendocrine Tumors (C7B), Neoplasm of other and ill-defined sites (C76-80), Secondary and unspecified malignant neoplasm of lymph nodes (C77), Secondary Cancers of respiratory and digestive organs, other and unspecified sites (C78-80), Malignant Neoplasm without specification of site (C80), Malignant neoplasms of lymphoid, and/or hematopoietic and related tissue (C81-C96).

In some embodiments, the cancer is any broadly construed categorization to a cohort class. Exemplary cohort classes include, but are not limited to, Blood Cancer, Bone Cancer, Brain Cancer, Bladder Cancer, Breast Cancer, Colon and Rectal Cancer, Endometrial Cancer, Kidney Cancer, Leukemia, Liver Cancer, Lung Cancer, Melanoma, Non-Hodgkin Lymphoma, Pancreatic Cancer, Prostate Cancer, Thyroid Cancer, and/or other tissue-based or organ-based classifications.

In some embodiments, the cancer is a site of biopsy for a biopsy specimen (e.g., a sample from a subject) such as one or more ICD-03 codes, including but not limited to lip, base of tongue, tongue, gum, floor of mouth, other mouth, salivary gland, oropharynx, nasopharynx, posterior wall of nasopharynx, hypopharynx, pharynx, esophagus, stomach, small intestine, large intestine, appendix, rectum, anal canal and/or anus, liver, intrahepatic bile ducts, gallbladder and/or extrahepatic bile ducts, pancreas, unspecified digestive organs, nasal cavity (including nasal cartilage), middle ear, sinuses, accessory sinus, nose, larynx, trachea, lung and/or bronchus, thymus, heart, mediastinum, pleura, respiratory, bones and/or joints, bones of skull and face, mandible, blood, bone marrow, hematopoietic system, spleen, reticuloendothelial, skin, peripheral nerves, retroperitoneum and/or peritoneum, connective and/or soft tissue, breast, vagina and/or labia, vulva, cervix uteri, corpus uteri, uterus, ovary, fallopian tube, other female genital, placenta, penis, prostate gland, testis, epididymis, spermatic cord, male genital, scrotum, kidney, renal pelvis, ureter, urinary bladder, other urinary organs, orbit and/or lacrimal gland, retina, eyeball, eye, nose, meninges (e.g., cerebral and spinal), brain, cranial nerves, spinal cord, ventricle, cerebellum, other nervous system, thyroid gland, adrenal glands, parathyroid gland, pituitary gland, craniopharyngeal duct, pineal gland, other endocrine glands, and/or lymph nodes.

In some embodiments, the cancer is one of a plurality of tumor and/or tissue types having common cell lineages. In some embodiments, the cancer is one of a plurality of metastasis sites and/or a metastasis site of origin (e.g., a liver metastasis of pancreatic origin, upper gastrointestinal origin, or cholangio origin; a breast metastasis of salivary gland origin, squamous origin, or ductile origin; a brain metastasis of glioblastoma, oligodendroglioma, astrocytoma, or medulloblastoma; a lung metastasis of NSCLC adenocarcinoma or squamous, etc.).

Data Elements.

Generally, the methods and systems described herein use several different types of characteristics about the subject's cancer and/or the subject themselves, to predict whether the subject's cancer will metastasize. In some embodiments, these characteristics include at least one type of sequence feature determined from sequencing of nucleic acids from the subject's cancer (e.g., DNA and/or RNA from the subject's cancer). As described above, different types of biological samples from the subject can provide such nucleic acids, including biopsies of the cancerous tissue and blood samples which contain circulating tumor DNA (ctDNA). In some embodiments, these characteristics include one or more personal characteristics about the subject (e.g., age, gender, race, and others described herein). In some embodiments, these characteristics include one or more clinical features related to the diagnosis and/or treatment of the cancer (e.g., including temporal and/or non-temporal clinical features).

Referring to Block 1604, in some embodiments, the method includes obtaining, in electronic format, a plurality of data elements for the subject's cancer. The plurality of data elements includes a first set of sequence features (1606) e.g., relative abundance values for the expression of a plurality of genes (e.g., at least 30 genes) in a biopsy of the cancer obtained from the subject. For example, in some embodiments, the plurality of data elements is stored in a data structure 1522 in a system 1500, and the first set of sequence features (1606) comprises a plurality of sequence features 1528 stored in a sequence features construct 1526. Additionally, as illustrated in FIG. 17 and discussed in further detail below, in some embodiments, the first set of sequence features includes nucleic acid-based features (e.g., RNA expression, tumor purity, germline genomics, and/or cancer genomics).

Figure 17:
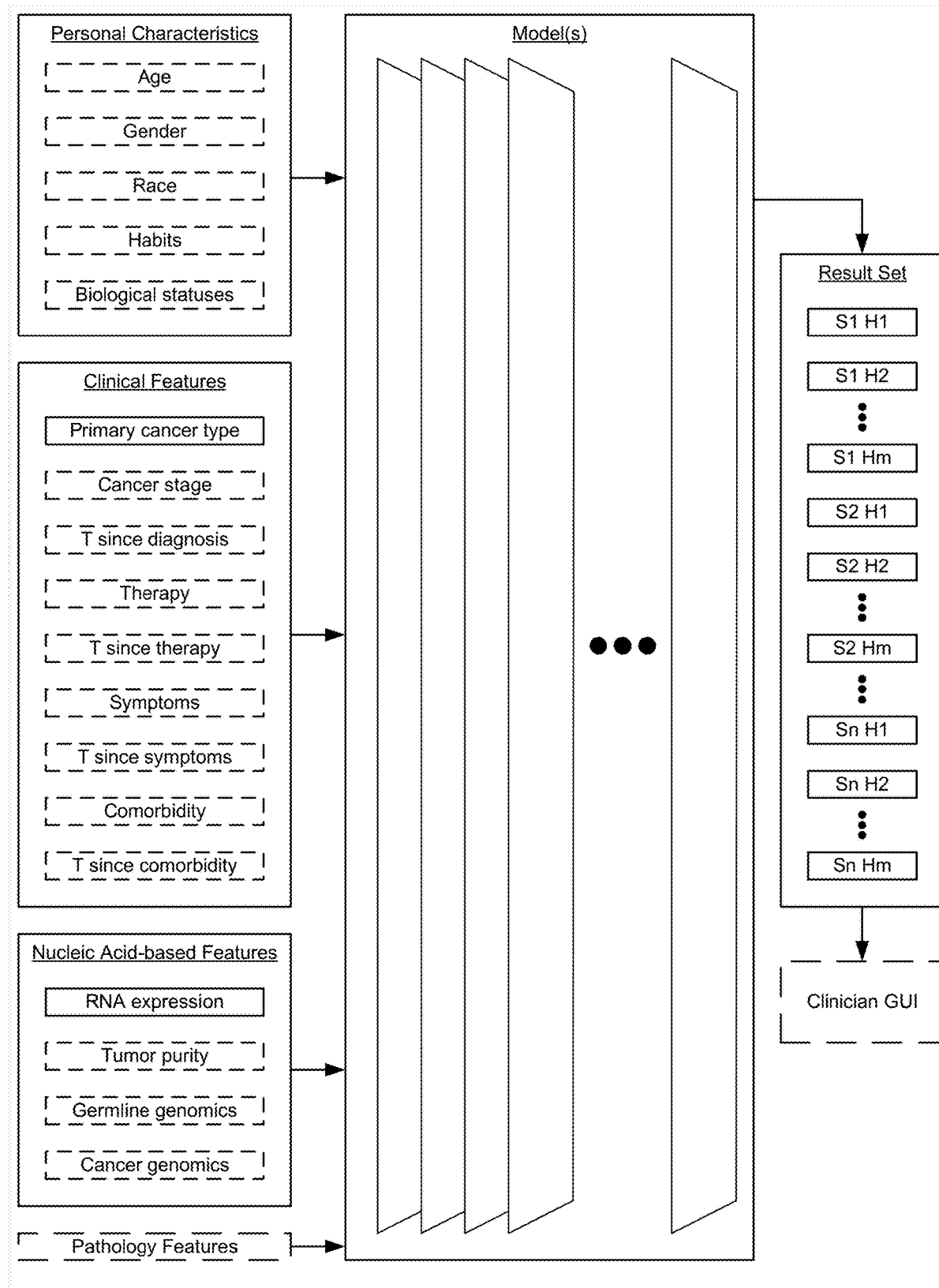
FIG. 17 illustrates a schematic of one or more classification models for predicting metastasis of a cancer in a subject, in which optional features are indicated with dashed boxes, in accordance with some embodiments of the present disclosure.

In some embodiments, the plurality of data elements includes one or more personal characteristics (1608) about the subject (e.g., age, gender, race, habits, and/or biological statuses; see also FIG. 17). In some embodiments, the one or more personal characteristics is stored in an optional personal characteristics construct 1530 in a data structure 1522.

In some embodiments, the plurality of data elements includes one or more clinical features (1610) related to the diagnosis or treatment of the cancer in the subject (e.g., a stage of the cancer, a histopathological grade of the cancer, a diagnosis for the cancer, a therapy administered to the subject, a symptom associated with cancer or metastasis thereof, a comorbidity with the cancer, and/or one or more temporal elements associated therewith). In some embodiments, the plurality of data elements includes one or more temporal features (1611) related to the diagnosis or treatment of the cancer in the subject (e.g., a first temporal element indicating a duration of time since a diagnosis for the cancer, a second temporal element indicating a duration of time since an administration of a therapy to the subject, a third temporal element indicating a duration of time since an experience of a symptom associated with cancer or metastasis thereof, and/or a fourth temporal element indicating a duration of time since an experience of a comorbidity with the cancer). For example, as illustrated in FIG. 17, in some embodiments, the one or more clinical features includes characteristics of cancer (e.g., primary cancer type, cancer stage, therapy, symptoms, and/or comorbidity) and one or more temporal elements associated therewith (e.g., time since diagnosis, time since therapy, time since symptoms, and/or time since comorbidity). In some embodiments, the one or more clinical features including characteristics of cancer and temporal elements are stored in an optional clinical features construct 1532 in a data structure 1522.

Sequence features 1606.

In some embodiments, the plurality of data elements includes a first set of sequence features (1606) (e.g., stored in a sequence features construct 1526) determined from sequencing of nucleic acids from the subject's cancer.

In some embodiments, the nucleic acids are from a biopsy of the cancer obtained from the subject. Methods for biopsy collection are known in the art, including, but not limited to, macrodissected formalin fixed paraffin embedded (FFPE) tissue sections, surgical biopsy, skin biopsy, punch biopsy, prostate biopsy, bone biopsy, bone marrow biopsy, needle biopsy, CT-guided biopsy, ultrasound-guided biopsy, fine needle aspiration, aspiration biopsy, fresh tissue and/or blood samples. In some embodiments, the biopsy is a solid sample of a cancerous tissue from the subject. In some embodiments, the biopsy is a liquid sample of a blood cancer. In some embodiments, the biopsy is a liquid sample containing ctDNA from a solid cancerous tissue of the subject. In some embodiments, sequence features are determined using both a cancerous biopsy and a tumor-matched sample of non-cancerous tissue from the subject.

In some embodiments, the first set of sequence features includes at least 25, at least 30, at least 40, at least 50, at least 75, at least 100, at least 150, at least 200, at least 250, at least 300, at least 400, at least 500, at least 600, at least 700, at least 800, at least 900, at least 1000, or more sequence features. In some embodiments, the first set of sequence features for the subject includes at least 100, at least 200, at least 300, at least 400, at least 500, at least 600, at least 700, at least 800, at least 900, at least 1000, at least 1500, at least 2000, at least 2500, at least 3000, at least 4000, at least 5000, at least 7500, at least 10,000, at least 15,000, at least 20,000, at least 25,000, at least 30,000 or more sequence features.

In some embodiments, the first set of sequence features includes no more than 50, no more than 75, no more than 100, no more than 150, no more than 200, no more than 250, no more than 300, no more than 400, no more than 500, no more than 600, no more than 700, no more than 800, no more than 900, or no more than 1000 sequence features. In some embodiments, the first set of sequence features for the subject includes no more than 100, no more than 200, no more than 300, no more than 400, no more than 500, no more than 600, no more than 700, no more than 800, no more than 900, no more than 1000, no more than 1500, no more than 2000, no more than 2500, no more than 3000, no more than 4000, no more than 5000, no more than 7500, no more than 10,000, no more than 15,000, no more than 20,000, no more than 25,000, or no more than 30,000 sequence features.

In some embodiments, the first set of sequence features includes from 25 to 5000 sequence features. In some embodiments, the first set of sequence features includes from 50 to 1000 sequence features. In some embodiments, the first set of sequence features includes from 75 to 500 sequence features. In some embodiments the first set of sequence features falls within another range starting no lower than 25 sequence features and ending no higher than 30,000 sequence features.

In some embodiments, the first set of sequence features are determined from a first plurality of sequence reads obtained from a sequencing reaction of nucleic acids from a biopsy of a cancerous tissue from the subject. In some embodiments, the first plurality of sequence reads is obtained by any suitable sequencing method, including but not limited to next-generation sequencing, whole genome sequencing, targeted panel sequencing, RNA sequencing, mRNA sequencing, whole exome sequencing, microarrays, and/or quantitative reverse transcription polymerase chain reaction. For example, methods of next-generation sequencing for use in accordance with the methods described herein are disclosed in Shendure, 2008, *Nat. Biotechnology* 26:1135-1145 and Fullwood et al., 2009, *Genome Res.* 19:521-532, each of which is hereby incorporated herein by reference in its entirety. Next generation sequencing methods well known in the art include synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In some embodiments, the first set of sequence features includes a plurality of features based on mRNA expression values for the cancerous tissue of the subject. That is, in some embodiments, a first plurality of sequence reads is obtained from sequencing RNA molecules in a biopsy of the cancerous tissue of the subject, and features are formed based on expression values for mRNA species. In some embodiments, these features include abundance values for individual mRNA species, e.g., relative expression values for individual genes, which may be normalized and/or bias corrected relative to raw abundance values obtained for each mRNA species, as described herein. In some embodiments, these features include arithmetic combinations of abundance values for more than one mRNA species, such as dimension-reduction component values. For instance, as illustrated in FIG. 17, in some embodiments, the first set of sequence features includes a set of nucleic acid-based features comprising RNA expression for the subject.

Generally, any methodology for measuring RNA expression (e.g., determining an mRNA expression profile) can be used in conjunction with the methods described herein, including nucleic acid sequencing methodologies (e.g., of mRNA molecules directly or cDNA generated from mRNA), comparative hybridization (e.g., using microarrays), and/or quantitative PCR. In some embodiments, nucleic acid sequencing provides advantages over other RNA expression profiling methodologies, such as the ability to generate other types of genomic information from the same reaction, for example, genomic variant information (e.g., SNPs, MNPs, indels, small inversions, translocations, etc.).

Methods for RNA sequencing are well known in the art. For example, methods of RNA-seq for use in accordance with the methods described herein are disclosed in Nagalakshmi et al., 2008, Science 320, 1344-1349; and Finotell and Camillo, 2014, *Briefings in Functional Genomics* 14(2), 130-142, each of which is hereby incorporated herein by reference in its entirety. In some embodiments, RNA sequencing is performed by whole exome sequencing (WES), as disclosed in, for example, Serrati et al., 2016, Onco Targets Ther. 9, 7355-7365 and Cieslik, M. et al., 2015 *Genome Res.* 25, 1372-81, each of which is hereby incorporated herein by reference in its entirety, for all purposes. In some embodiments, the RNA sequencing is performed by nanopore sequencing. A review of the use of nanopore sequencing techniques on the human genome can be found in Jain et al., 2018, Nature 36(4), 338-345.

Methods for comparative hybridization (e.g., microarrays) are also known in the art. Such methods are disclosed in Wang et al., 2009, *Nat Rev Genet* 10, 57-63; Roy et al., 2011, *Brief Funct Genomic* 10:135-150; Shendure, 2008, *Nat Methods* 5, 585-587; Cloonan et al., 2008, "Stem cell transcriptome profiling via massive-scale mRNA sequencing," Nat Methods 5, 613-619; Mortazavi et al., 2008, "Mapping and quantifying mammalian transcriptomes by RNA-Seq," Nat Methods 5, 621-628; and Bullard et al., 2010, "Evaluation of statistical methods for normalization and differential expression in mRNA-Seq experiments," BMC Bioinformatics 11, p. 94, each of which is hereby incorporated herein by reference in its entirety.

This list is not exhaustive of the RNA sequencing methods that may be used in accordance with the methods described herein. In some embodiments, the RNA sequencing is performed according to any one or more sequencing methods known in the art. See, for example, a review of RNA sequencing methods disclosed Kukurba et al., 2015, *Cold Spring Harb Protoc.* 11: 951-969, which is hereby incorporated herein by reference in its entirety.

In some embodiments, the first plurality of sequence reads obtained from the sequencing of the biopsy, e.g., RNA sequence reads, includes at least 1000, at least 5000, at least 10,000, at least 50,000, at least 100,000, at least 500,000, at least 1 million, at least 5 million, at least 10 million, or more sequence reads. In some embodiments, the first plurality of sequence reads is no more than 50,000, no more than 100,000, no more than 500,000, no more than 1 million, no more than 5 million, no more than 10 million, or no more than 50 million sequence reads. In some embodiments, the first plurality of sequence reads is from 1000 sequence reads to 100 million sequence reads, from 10,000 sequence reads to 50 million sequence reads, or from 100,000 sequence reads to 50 million sequence reads. In some embodiments, the first plurality of sequence reads falls within another range starting no lower than 1000 sequence reads and ending no higher than 500 million sequence reads.

In some embodiments, a measure of central tendency (e.g., mean, median, etc.) for the length of the sequence reads in the first plurality of sequence reads is at least 15 nucleotides, at least 50 nucleotides, at least 100 nucleotides, at least 250 nucleotides, at least 500 nucleotides, at least 1000 nucleotides, or longer.

In some embodiments, the first plurality of sequence reads is mapped (e.g., to a reference sequence), quantified, normalized, scaled, deconvoluted, cleaned, filtered and/or otherwise preprocessed for analysis. For example, in some embodiments, sequence reads are mapped to a reference construct (e.g., a reference exome or genome comprising a plurality of target gene sequences, or a similar reference map, e.g., representing divergent sequences at particular loci across a species). In some embodiments, the number of sequence reads aligned to each region of the reference construct (e.g., each gene) gives a measure of its level of expression (e.g., abundance). In some embodiments, the mapping is an alignment (e.g., an alignment performed via STAR and/or a k-mer hashing-based pseudoalignment performed via Kallisto). In some embodiments, mRNA expression levels are normalized (e.g., to correct for GC content, sequencing depth, and/or gene or transcript length). For example, in some embodiments, raw read counts are quantile-normalized. In some embodiments, RNA expression levels are normalized relative to the total number of transcripts in the first plurality of sequence reads and presented as transcripts per million. Methods for preprocessing sequence reads, including mapping raw RNA sequence reads to the transcriptome, quantifying gene counts, normalization of gene counts, and/or deconvolution are known in the art, as described in U.S. Patent Application No. 62/735,349, entitled "Methods of Normalizing and Correcting RNA Expression Data," filed on Sep. 24, 2018, and in U.S. patent application Ser. No. 16/732,229, entitled "Transcriptome Deconvolution of Metastatic Tissue Samples," filed on Dec. 31, 2019, each of which is hereby incorporated herein by reference in its entirety.

In some embodiments, the first set of sequence features from the biopsy of the subject includes relative RNA abundance values (e.g., mRNA expression values normalized to account for one or more of, e.g., a total number of transcripts in a sample, a GC content of the transcripts, length of the transcripts, etc.) for a plurality of genes. In some embodiments, one or more sequence features is a combination of relative RNA abundance values for two or more of the genes, e.g., a linear or non-linear combination. In some embodiments, one or more sequence features is a dimension reduction component value based on relative RNA abundance values for two or more of the genes. In some embodiments, each sequence feature in the first set of sequence features for the subject is an abundance value (e.g., a raw abundance value, normalized abundance value, standardized abundance value, scaled abundance value, or a combination thereof) for a single gene.

Generally, a sequence feature based on one or more RNA abundance values (e.g., mRNA abundance values) may take a variety of forms, including without limitation, an absolute expression value (e.g., transcript number), a relative expression value (e.g., relative fluorescent units, transcriptome analysis, and/or gene set expression analysis (GSEA)), a compound or aggregated expression value, a transformed expression value (e.g., log 2 and/or log 10 transformed), a change (e.g., fold- or log-change) relative to a reference (e.g., a normal tissue sample of the subject, a tumor-normal matched sample, a tissue sample from a healthy subject, a reference dataset comprising expression values from a cohort of healthy subjects, a housekeeping gene, and/or a reference standard), a measure of central tendency (e.g., mean, median, mode, weighted mean, weighted median, and/or weighted mode), a measure of dispersion (e.g., variance, standard deviation, and/or standard error), an adjusted expression value (e.g., normalized, scaled, and/or error-corrected), and/or a dimension-reduced expression value (e.g., principal component vectors and/or latent components). Methods for obtaining sequence features using dimension reduction techniques are known in the art, including but not limited to principal component analysis, factor analysis, linear discriminant analysis, multi-dimensional scaling, isometric feature mapping, locally linear embedding, hessian eigenmapping, spectral embedding, t-distributed stochastic neighbor embedding, and/or any substitutions, additions, deletions, modification, and/or combinations thereof as will be apparent to one skilled in the art. See, for example, Sumithra et al., 2015, "A Review of Various Linear and Non Linear Dimensionality Reduction Techniques," Int J Comp Sci and Inf Tech, 6(3), 2354-2360, which is hereby incorporated herein by reference in its entirety. Other methods for obtaining abundance values for gene expression are contemplated, as disclosed in U.S. Provisional Patent Application No. 63/007,874, entitled "Predicting Likelihood and Site of Metastasis from Patient Records," filed on Apr. 9, 2020, which is incorporated by reference herein in its entirety.

In some embodiments, the first set of sequence features includes relative abundance values for the expression of a plurality of genes. In some embodiments, the first set of features includes relative abundance values for the expression of at least 25 genes. In some embodiments, the first set of features includes relative abundance values for the expression of at least 50 genes. In some embodiments, the first set of features includes relative abundance values for the expression of at least 75 genes. In some embodiments, the first set of features includes relative abundance values for the expression of at least 100 genes. In some embodiments, the first set of features includes relative abundance values for the expression of at least 250 genes. In some embodiments, the first set of features includes relative abundance values for the expression of at least 150 genes, at least 200 genes, at least 300 genes, at least 400 genes, at least 500 genes, at least 750 genes, at least 1000 genes, or more.

In some embodiments, the first set of features includes relative abundance values for the expression of no more than 4000 genes. In some embodiments, the first set of features includes relative abundance values for the expression of no more than 3000 genes. In some embodiments, the first set of features includes relative abundance values for the expression of no more than 2000 genes. In some embodiments, the first set of features includes relative abundance values for the expression of no more than 1000 genes. In some embodiments, the first set of features includes relative abundance values for the expression of no more than 900 genes, no more than 800 genes, no more than 700 genes, no more than 600 genes, no more than 500 genes, no more than 400 genes, no more than 250 genes. In some embodiments, the plurality of genes is no more than 1000 genes, no more than 750 genes, no more than 500 genes, no more than 400 genes, no more than 300 genes, no more than 250 genes, no more than 200 genes, no more than 175 genes, no more than 150 genes, no more than 125 genes, no more than 100 genes, no more than 75 genes, no more than 50 genes, no more than 40 genes, or less.

In some embodiments, the first set of features includes relative abundance values for the expression of from 25 to 4000 genes. In some embodiments, the first set of features includes relative abundance values for the expression of from 50 to 2000 genes. In some embodiments, the first set of features includes relative abundance values for the expression of from 50 to 1000 genes. In some embodiments, the first set of features includes relative abundance values for the expression of from 75 to 500 genes. In some embodiments, the first set of features includes relative abundance values for the expression of another range starting no lower than 25 genes and ending no higher than 4000 genes.

In some embodiments, the first set of features includes relative abundance values for the expression of at least 5, at least 10, at least 20, at least 25, at least 30, at least 40, at least 50, at least 75, or all of the genes disclosed herein in the above sections (see, "Prediction of Colorectal Metastasis based on RNA").

In some embodiments, the plurality of genes includes at least 20 of the genes listed in Table 2. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 2. In some embodiments, the plurality of genes includes at least 50%, at least 55%, at least 60%, at least 70%, at least 75%, at least 80%, at least 85%, at least 90%, at least 95%, or all of the genes listed in Table 2.

In some embodiments, the plurality of genes includes at least 20 of the genes listed in Table 3. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 3.

In some embodiments, the plurality of genes includes at least 20 of the genes listed in Table 3 that were used in at least 150 iterations of the model. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 3 that were used in at least 150 iterations of the model. In some embodiments, the plurality of genes includes at least 50%, at least 55%, at least 60%, at least 70%, at least 75%, at least 80%, at least 85%, at least 90%, at least 95%, of all of the genes listed in Table 3 that were used in at least 150 iterations of the model.

In some embodiments, the plurality of genes includes at least 20 of the genes listed in Table 3 that were used in at least 160 iterations of the model. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 3 that were used in at least 160 iterations of the model. In some embodiments, the plurality of genes includes at least 50%, at least 55%, at least 60%, at least 70%, at least 75%, at least 80%, at least 85%, at least 90%, at least 95%, of all of the genes listed in Table 3 that were used in at least 160 iterations of the model.

In some embodiments, the plurality of genes includes at least 20 of the genes listed in Table 3 that were used in at least 165 iterations of the model. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 3 that were used in at least 165 iterations of the model. In some embodiments, the plurality of genes includes at least 50%, at least 55%, at least 60%, at least 70%, at least 75%, at least 80%, at least 85%, at least 90%, at least 95%, of all of the genes listed in Table 3 that were used in at least 165 iterations of the model.

In some embodiments, the plurality of genes includes at least 20 of the genes listed in Table 3 that were used in at least 165 iterations of the model. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 3 that were used in at least 165 iterations of the model. In some embodiments, the plurality of genes includes at least 50%, at least 55%, at least 60%, at least 70%, at least 75%, at least 80%, at least 85%, at least 90%, at least 95%, of all of the genes listed in Table 3 that were used in at least 165 iterations of the model.

In some embodiments, the plurality of genes includes at least 20 of the genes listed in Table 3 that were used in at least 171 iterations of the model. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 3 that were used in at least 171 iterations of the model. In some embodiments, the plurality of genes includes at least 50%, at least 55%, at least 60%, at least 70%, at least 75%, at least 80%, at least 85%, at least 90%, at least 95%, of all of the genes listed in Table 3 that were used in at least 171 iterations of the model.

In some embodiments, the plurality of genes includes at least 20 of the genes listed in Table 3 that were used in at least 172 iterations of the model. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 3 that were used in at least 172 iterations of the model. In some embodiments, the plurality of genes includes at least 50%, at least 55%, at least 60%, at least 70%, at least 75%, at least 80%, at least 85%, at least 90%, at least 95%, of all of the genes listed in Table 3 that were used in at least 172 iterations of the model.

In some embodiments, the plurality of genes includes at least 20 of the genes listed in Table 3 that were used in all 173 iterations of the model. In some embodiments, the plurality of genes includes at least 20, at least 25, at least 30, at least 35, at least 40, at least 50, at least 75, at least 100, at least 125, at least 150, at least 175, at least 200, at least 250, at least 300, at least 350, at least 400, at least 450, or all of the genes listed in Table 3 that were used in all 173 iterations of the model. In some embodiments, the plurality of genes includes at least 50%, at least 55%, at least 60%, at least 70%, at least 75%, at least 80%, at least 85%, at least 90%, at least 95%, of all of the genes listed in Table 3 that were used in all 173 iterations of the model.

In some embodiments, the first set of sequence features includes a plurality of dimension reduction component values determined from relative abundance values for a plurality of genes. For instance, Example 1 describes an instance where relative expression values for the 500 most correlated genes are used to generate 40 sequence features using singular value decomposition, which are the basis for a prediction model. Accordingly, in some embodiments, the first set of sequence features include a plurality of dimension reduction component values determined from relative abundance values for at least 25, at least 50, at least 75, at least 100, at least 150, at least 200, at least 250, at least 500, at least 750, at least 1000, or more genes. In some embodiments, the first set of sequence features include a plurality of dimension reduction component values determined from relative abundance values for no more than 2000 genes, no more than 1500 genes, no more than 1000 genes, no more than 750 genes, no more than 500 genes, or less. In some embodiments, the first set of sequence features include a plurality of dimension reduction component values determined from relative abundance values for from 25 to 2000 genes, from 50 to 1000 genes, or from 100 to 750 genes.

Thus, for example, referring again to FIG. 16, in some embodiments the method includes obtaining a plurality of data elements for the subject's cancer, where the plurality of data elements includes a first set of sequence features comprising relative abundance values for the expression of a plurality of genes (e.g., at least 30 genes) in a biopsy of the cancer obtained from the subject. In some embodiments, obtaining the first set of sequence features includes obtaining a plurality of at least 10,000 sequence reads, where the plurality of sequence reads is obtained from a plurality of RNA molecules from the biopsy of the cancer obtained from the subject, and determining, from the plurality of sequence reads, relative abundance values for the plurality of genes. For example, in some embodiments, the determining includes mapping (e.g., alignment via STAR and/or pseudo-alignment via Kallisto) the plurality of at least 10,000 sequence reads to a reference construct comprising a plurality of target gene sequences (e.g., mRNA sequences) and counting the number of sequence reads aligned to each gene of interest. In some embodiments, the determining further includes normalizing the plurality of sequence reads (e.g., for GC content, transcript length, library depth, etc.).

In some embodiments, the plurality of data elements further includes additional sequence features, including but not limited to RNA-based features (including mRNA and derivatives of RNA such as cDNA and/or proteins), DNA-based features, tumor purity features, germline genomics features, cancer genomics features, transcript (splice) isoforms, expression values for gene copies (e.g., a wild-type copy of a gene, a variant copy of the gene, or an arithmetic combination thereof), epigenetic features, methylation-based features, homologous recombination deficiency status, microsatellite stability status, microsatellite repeat length, tumor mutation burden, SNPs, SNVs, indels, fusions, copy number variations, amplifications, deletions, variant allelic ratios, genomic marker status (e.g., associated with an actionable therapy), pathway features (e.g., RNA pathway features, gene set enrichment analysis, functional pathway features, etc.), and/or any combination thereof. In some embodiments, sequence features are obtained by any sequencing method (e.g., RNAseq, mRNA sequencing, DNA sequencing, microarrays, etc.) and sequencing processing methods (e.g., normalization, error-correction, deconvolution, etc.) disclosed herein. As illustrated in FIG. 17, in some instances, the plurality of data elements includes additional nucleic acid-based features such as tumor purity, germline genomics, and/or cancer genomics features. In some embodiments, the first set of sequence features includes any of the features described in the feature modules disclosed in the above sections (see, "Generating and Modeling Predictions of Patient Objectives").

For example, in some embodiments, the plurality of data elements further includes a mutational status for one or more genes in the genome of the cancer. In some embodiments, the plurality of data elements further includes a mutational status for one or more genes in the genome of a non-cancerous tissue of the subject. In some embodiments, the plurality of data elements further includes a copy number status for one or more genomic regions (e.g., one or more genes) of the cancer.

In some embodiments, the plurality of data elements further includes a single-sample gene set enrichment analysis (ssGSEA) score for the transcriptional profile of the cancer. Methods for obtaining ssGSEA scores are described in the above sections (see, "Generating and Modeling Predictions of Patient Objectives") and in Subramanian et al., 2005, PNAS 102, 15545-15550 and Liberzon et al., 2015, Cell Systems 23; 1(6): 417-425, each of which is hereby incorporated herein by reference in its entirety.

Other methods for obtaining sequence features are contemplated, as disclosed in U.S. Provisional Patent Application No. 63/007,874, entitled "Predicting Likelihood and Site of Metastasis from Patient Records," filed on Apr. 9, 2020, which is incorporated by reference herein in its entirety.

Selection of sequence features. In some embodiments, the first set of sequence features is selected using a first training plurality of sequence reads (e.g., a training dataset), where the first training plurality of sequence reads is obtained from one or more samples obtained from each respective training subject in a first plurality of training subjects. In some embodiments, a set of selected sequence features (e.g., a panel of genes of interest) and any corresponding values for the set of selected sequence features (e.g., gene expression values) obtained from the training dataset are used as input for training a model (e.g., a set of models). In some embodiments, the first training plurality of sequence reads is obtained by a sequencing method and/or preprocessed by, for example, any of the methods for obtaining the first set of sequence features disclosed herein.

In some embodiments, feature selection is performed based on the informative quality of the respective features. For example, as described below, in some embodiments a feature is considered "informative" if it exhibits a variable characteristic that can be used to predict metastasis of a cancer in a subject. For instance, in some embodiments, a feature is considered informative if it has at least a threshold variance (e.g., statistical variance and/or standard deviation) or a threshold level of abundance (e.g., absolute or relative abundance, differential gene expression, and/or fold change). In some embodiments, a feature is considered "uninformative" if it does not exhibit a characteristic that can be used to predict metastasis of a cancer in a subject.

In some embodiments, feature selection is performed using one or more models, including any of the models disclosed in the above sections (see, "Generating and Modeling Predictions of Patient Objectives"). Feature selection is performed by generating predictions using the training dataset and evaluating (e.g., scoring) the importance of features based on the generated predictions, thus identifying features that drive and/or are correlated with such predictions. For example, in some embodiments, a feature selection method is performed by executing a prediction generation more than 100 times on a classification model, each time with a different assignment of cross-validation folds and hold out set. This process results in over 100 out-of-fold cross validated scores on the training set and over 100 of hold-out (or test set) scores. A distribution of performance metrics is generated based on the scores of the predictions. By assessing the distribution of performance metrics in the over 100 different training subsets, features that generate high-scoring predictions across a high percentage of training runs and performance metrics can be identified, rather than relying on single point estimates (which can have a large degree of variance). Such methods allow for more robust feature importance evaluation and improved feature selection. Other methods for feature selection are known in the art, as reviewed, for example, in Saeys et al., 2007, "A review of feature selection techniques in bioinformatics," Bioinformatics 23:19, 2507-2517; doi: 10.1093/bioinformatics/btm344, which is hereby incorporated herein by reference in its entirety.

Personal Characteristics 1608.

In some embodiments, the plurality of data elements includes one or more personal characteristics (1608) about the subject (e.g., stored in an optional personal characteristics construct 1530) selected from the group consisting of age, gender, and/or race.

In some embodiments, as illustrated in FIG. 17, the one or more personal characteristics includes, but is not limited to, age, gender, race, personal habits (e.g., smoking, drinking, diet, etc.), weight, biological statuses (e.g., high blood pressure, dry skin, other diseases and/or other pertinent medical conditions), and/or other demographic features. In some embodiments, the one or more personal characteristics include smoking status and/or menopausal status. In some embodiments, the one or more personal characteristics include one or more demographic features that is associated with the respective cancer condition of the subject (e.g., a smoking status and/or a menopausal status in conjunction with a lung cancer, breast cancer, and/or an ovarian cancer. Other, non-limiting examples of personal characteristics that may be used in the disclosed metastasis models are described above in the section titled "Generating and Modeling Predictions of Patient Objectives."

Clinical Features 1610.

In some embodiments, the plurality of data elements includes one or more clinical features related to the diagnosis or treatment of the cancer in the subject (e.g., stored in an optional clinical features construct 1532).

In some embodiments, the one or more clinical features related to the diagnosis or treatment of the cancer in the subject is selected from the group consisting of a stage of the cancer, grading of the cancer, a histopathological grade of the cancer, presence and/or absence of cancer, a cancer type, a cancer subtype, a tissue of origin, a therapy administered to the subject, a symptom associated with cancer or metastasis thereof, and a comorbidity with the cancer. Other, non-limiting examples of clinical features that may be used in the disclosed metastasis models are described in FIGS. 4, 5, 11, 12, and 17, and discussed in detail above in the section titled "Generating and Modeling Predictions of Patient Objectives."

Temporal Features 1611.

In some embodiments, the plurality of data elements includes one or more temporal features related to the diagnosis or treatment of the cancer in the subject (e.g., stored in an optional clinical features construct 1532).

In some embodiments, the one or more clinical features includes the one or more temporal features. In some embodiments, the one or more temporal features is any temporal feature associated with any clinical feature in the one or more clinical features. In some embodiments, the one or more temporal features includes a first temporal element indicating the duration of time since a diagnosis for the cancer (e.g., a diagnosis of the cancer, including presence, absence, stage, type, subtype, grade, histopathological grade, and/or tissue of origin), a second temporal element indicating the duration of time since an administration of the therapy (e.g., since first administration, since last administration, and/or since completion of a first therapeutic regimen), a third temporal element indicating the duration of time since an experience of the symptom (e.g., since first experience of the symptom and/or since last experience of the symptom), and a fourth temporal element indicating the duration of time since an experience of the comorbidity (e.g., since the beginning of the comorbidity and/or since the resolution of the comorbidity). Other, non-limiting examples of clinical features that may be used in the disclosed metastasis models are described in FIGS. 4, 5, 11, 12, and 17, and discussed in detail above in the section titled "Generating and Modeling Predictions of Patient Objectives."

Additional Data Elements.

In some embodiments, the plurality of data elements further includes one or more pathological features, one or more viral features, one or more metabolomic features, one or more microbiome features, and/or any combination thereof.

For example, in some embodiments, the plurality of data elements further includes one or more physical characteristics of the biopsy of the cancer. In some embodiments, the one or more physical characteristics of the biopsy of the cancer are obtained from a biological imaging of the biopsy of the cancer. In some embodiments, the biological image includes biologically meaningful features and geometrically meaningful features, both of which can be included as features in the plurality of data elements.

For example, in some embodiments, the one or more physical characteristics of a biopsy of a cancer includes a tumor percentage (e.g., a percentage of the detected tissue area on the slide classified as tumor, e.g., indicated as a value between 0 and 100).

In some embodiments, the one or more physical characteristics includes a tumor cell percentage (e.g., a percentage of the total cells that are tumor cells, as opposed to lymphocytes, e.g., indicated as a value between 0 and 100).

In some embodiments, the one or more physical characteristics includes a tumor infiltrating lymphocytes percentage (e.g., calculated as total number of lymphocytes within the tumor region divided by total number cells in the tumor region, e.g., indicated as a value between 0 and 100).

In some embodiments, the one or more physical characteristics includes tumor budding features (e.g., for colorectal cancer. In some embodiments, tumor budding features are represented as integer counts for a number of detected tumor buds. In some embodiments, tumor budding features are normalized by density within a given area.

In some embodiments, geometrically meaningful features include aggregation metrics (e.g., a minimum, average, median, and/or maximum) of tumor perimeter. For example, in some embodiments, geometrically meaningful features are used to measure the perimeter of a tumor biopsy within a slide, given in pixels, where each pixel has fixed dimensions (e.g., 8 um by 8 um).

In some embodiments, geometrically meaningful features include average tumor cell circularity (e.g., calculated as cell area divided by the square of the perimeter, averaged over all cells, e.g., indicated as a value ranging between 0 and 1).

In some embodiments, geometrically meaningful features include average tumor cell length and/or aspect ratio. In some such embodiments, aspect ratio is determined by calculating the eigenvalues for the cell shape of a cell in the tumor biopsy, giving relative, rotation-independent values for the length and width of the cell. Specifically, all pixels that are associated with the cell are first identified, using the (x,y) pixel locations as points for a covariance matrix. Eigenvalues are then calculated, and the first component is taken as the length of the cell. The aspect ratio is calculated by dividing the second eigenvalues by the first eigenvalues. In some embodiments, the aspect ratio is indicated as a value ranging between 0 and 1.

Imaging features, including biologically meaningful features and geometrically meaningful features, are further described in the above sections of the present disclosure (see, "Generating and Modeling Predictions of Patient Objectives").

Figure 18:
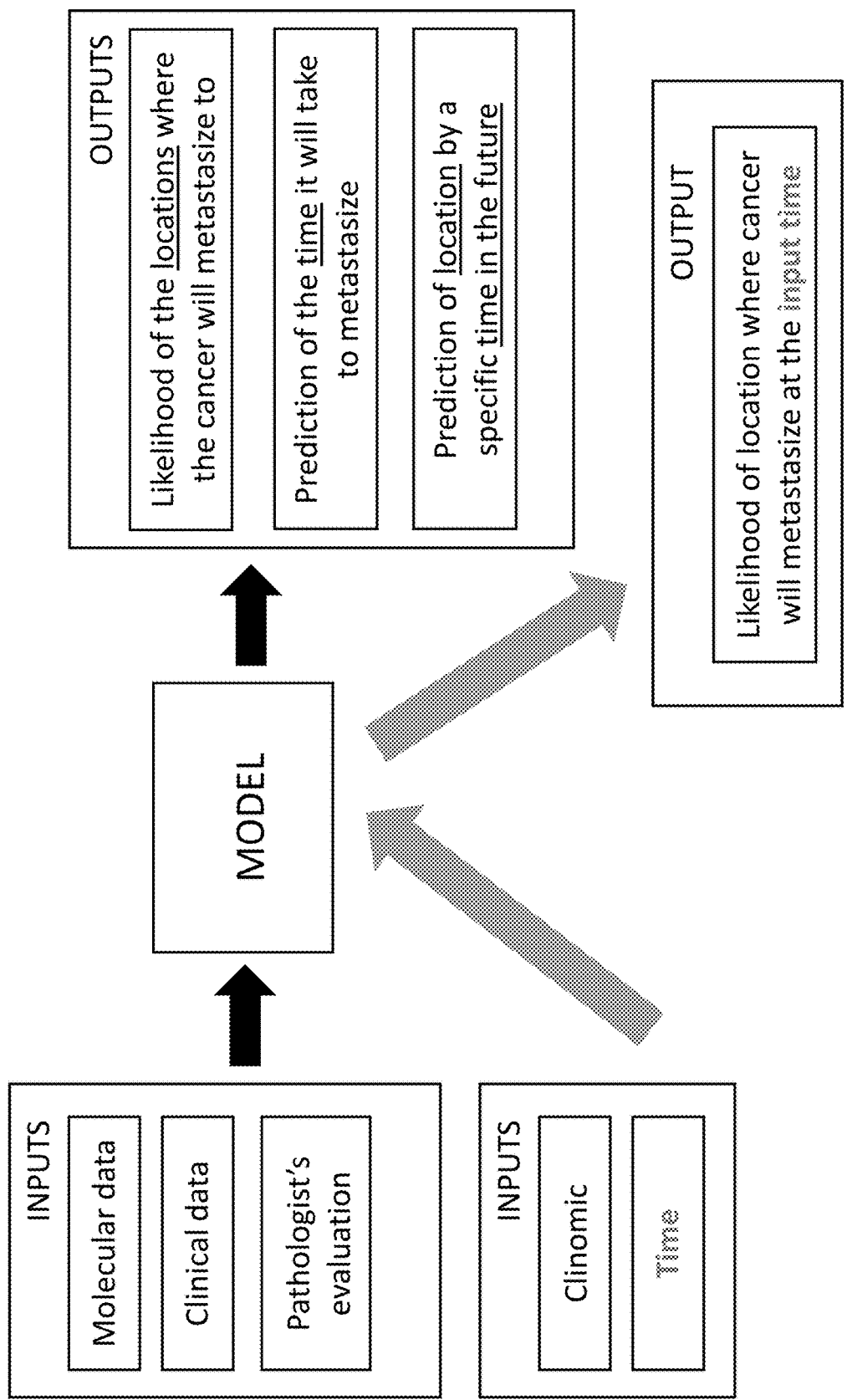
FIG. 18 illustrates a schematic of a classification model for predicting metastasis of a cancer in a subject, in accordance with some embodiments of the present disclosure.

Example inputs for models for predicting metastasis of a cancer in a subject are illustrated in FIGS. 17 and 18. In some embodiments, inputs include personal characteristics, clinical features (e.g., clinical data and/or clinomic data), nucleic acid-based features (e.g., molecular data), pathology features (e.g., pathologist evaluation), and/or temporal data (e.g., time since clinical events as illustrated, for example, in FIG. 7).

Additional features to be used as inputs for using a trained model (e.g., a predictive and/or classification model) to predict metastasis of a cancer in a subject are contemplated, as illustrated in FIGS. 4, 5, 11 and 12 and further described in the above sections of the present disclosure (see, "Generating and Modeling Predictions of Patient Objectives"). In some embodiments, any of the features disclosed herein are obtained from a feature collection 205, a feature module 110, a feature store 120, a feature selector 200, a feature generator 300, and/or a data structure 1522, as illustrated in FIGS. 1-3, 14, and 15 and described in detail herein (see, "Generating and Modeling Predictions of Patient Objectives"). Suitable features also include any substitutions, additions, deletions, modifications, and/or combinations of any of the embodiments disclosed herein, as will be apparent to one skilled in the art.

Obtaining Indications of Metastasis.

One or more metastasis models are then applied to the data elements identified for the subject. In some embodiments, a single model providing an indication of whether the cancer will metastasize (e.g., to any tissue within the subject) is applied to the data elements. For example, in some embodiments, the one or more models is a single model that provides one or more indications (e.g., predictions) on whether a cancer will metastasize, to any or an unspecified tissue, within a single or an unspecified duration of time. The one or more models can be one or more models 1538 stored in a classification module 1536, as part of a system 1500 depicted in FIG. 15. Furthermore, the one or more indications can be one or more indications 1542 stored in an output module 1540 in the system 1500.

In other embodiments, multiple metastasis models are applied to the data elements. For example, in some embodiments, separate models are applied to provide an indication of whether the cancer will metastasize to each of a plurality of tissues, that is, one or more model is applied for each tissue of interest. Similarly, in some embodiments, separate models are applied to provide an indication of whether the cancer will metastasize (to a specific tissue or at all) within each of a plurality of time horizons, that is, one or more model is applied for each time horizon of interest.

Accordingly, in some embodiments, referring to Block 1612, the method further includes applying, to the plurality of data elements for the subject's cancer, one or more models that are collectively trained to provide a respective one or more indications of whether the cancer will metastasize in the subject, thereby predicting whether the cancer will metastasize. In some embodiments, the one or more indications of whether the cancer will metastasize in the subject predicts whether the cancer will metastasize to any tissue in the subject (e.g., does not specify the metastasis site). In some embodiments, the one or more indications of whether the cancer will metastasize in the subject predicts whether the cancer will metastasize at any time horizon (e.g., does not specify the time period for metastasis). In some embodiments, the one or more indications of whether the cancer will metastasize in the subject predicts whether the cancer will metastasize within a single time horizon.

In some embodiments, the method further includes applying, to the plurality of data elements for the subject's cancer, a set of models that are collectively trained to provide, for each respective tissue in a plurality of tissues, a respective set of indications of whether the cancer will metastasize to the respective tissue in the subject, wherein the respective set of indications includes a respective indication for each respective time horizon in a plurality of time horizons, thereby determining a plurality of indications of whether the cancer will metastasize comprising, for each respective tissue in the plurality of tissues, a respective set of indications comprising, for each respective time horizon in a plurality of time horizons, a respective indication of whether the cancer in the subject will metastasize to the respective tissue within the respective time horizon.

Metastasis Sites.

In some embodiments, the method includes obtaining an indication of whether the cancer of the subject will metastasize to one or more tissues in a plurality of tissues (e.g., one or more potential metastasis sites). In some embodiments, the indication is a determination that the cancer will or will not metastasize (e.g., a binary indication), and/or a likelihood that the cancer will metastasize (e.g., a probability).

In some embodiments, the plurality of tissues (e.g., potential metastasis sites) includes lymph tissue (e.g., proximal lymph tissue and/or distal lymph tissue), liver tissue, and/or lung tissue. In some embodiments, the plurality of tissues includes two or more similar tissue types found in different locations within the body (e.g., proximal lymph tissue and distal lymph tissue).

In some embodiments, the plurality of tissues includes one or more tissues selected from cardiovascular (e.g., heart, blood, and/or blood vessels), lymphatic (e.g., lymph, lymph nodes, and/or lymph vessels), digestive (e.g., mouth, salivary glands, esophagus, stomach, liver, gallbladder, exocrine pancreas, small intestine, and/or large intestine), endocrine (e.g., pituitary, pineal, thyroid, parathyroids, endocrine pancreas, adrenals, testes, and/or ovaries), integumentary (e.g., skin, hair, and/or nails), muscular (e.g., skeletal, cardiac, and/or smooth muscles), nervous (e.g., brain, spinal cord, nerves, sensory organs, eyes, ears, tongue, skin, and/or nose), reproductive (e.g., fallopian tubes, uterus, vagina, ovaries, mammary glands, testes, vas deferens, seminal vesicles, prostate, and/or penis), respiratory (e.g., mouth, nose, pharynx, larynx, trachea, bronchi, lungs, and/or diaphragm), skeletal (e.g., bones, cartilage, joints, tendons, and/or ligaments), urinary (e.g., kidneys, ureters, urinary bladder, and/or urethra) and/or immune (e.g., leukocytes, tonsils, adenoids, thymus, and/or spleen).

In some embodiments, the plurality of tissues includes one or more tissues selected based on the cancer of the subject. For example, in some embodiments, the cancer of the subject is bladder, and the plurality of tissues includes bone, liver, and/or lung. In some embodiments, the cancer of the subject is breast, and the plurality of tissues includes bone, brain, liver, and/or lung. In some embodiments, the cancer of the subject is colon, and the plurality of tissues includes liver, lung, and/or peritoneum. In some embodiments, the cancer of the subject is kidney, and the plurality of tissues includes adrenal gland, bone, brain, liver, and/or lung. In some embodiments, the cancer of the subject is lung, and the plurality of tissues includes adrenal gland, bone, brain, liver, and/or lung. In some embodiments, the cancer of the subject is melanoma, and the plurality of tissues includes bone, brain, liver, lung, skin, and/or muscle. In some embodiments, the cancer of the subject is ovary, and the plurality of tissues includes liver, lung, and/or peritoneum. In some embodiments, the cancer of the subject is pancreas, and the plurality of tissues includes liver, lung, and/or peritoneum. In some embodiments, the cancer of the subject is prostate, and the plurality of tissues includes adrenal gland, bone, liver, and/or lung. In some embodiments, the cancer of the subject is rectal, and the plurality of tissues includes liver, lung, and/or peritoneum. In some embodiments, the cancer of the subject is stomach, and the plurality of tissues includes liver, lung, and/or peritoneum. In some embodiments, the cancer of the subject is thyroid, and the plurality of tissues includes bone, liver, and/or lung. In some embodiments, the cancer of the subject is uterus, and the plurality of tissues includes bone, liver, lung, peritoneum, and/or vagina.

In some embodiments, the plurality of tissues includes at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, at least 100, at least 125, at least 150, at least 175, or at least 200 tissues (e.g., potential metastasis sites).

In some embodiments, the plurality of tissues includes no more than 200, no more than 175, no more than 150, no more than 125, no more than 100, no more than 80, no more than 60, no more than 50, no more than 40, no more than 30, or no more than 20 tissues (e.g., metastasis sites). In some embodiments, the plurality of tissues is from 2 and 200 tissues. In some embodiments, the plurality of tissues is from 3 and 100 tissues, from 10 and 70 tissues, from 20 to 200 tissues, from 2 to 20 tissues, or from 50 to 100 tissues. In some embodiments, the plurality of tissues falls within another range starting no lower than 2 tissues and ending no higher than 200 tissues (e.g., potential metastasis sites).

Time horizons. In some embodiments, the method includes obtaining an indication of whether the cancer of the subject will metastasize in the subject (e.g., to one or more tissues in the plurality of tissues) within a respective time horizon. For example, in some embodiments, the method includes obtaining an indication (e.g., a prediction) that the cancer will metastasize within a given period of time within the subject's clinical timeline (e.g., after an occurrence of a clinical event). In some embodiments, the method includes obtaining an indication of whether the cancer of the subject will metastasize in the subject (e.g., to one or more tissues in the plurality of tissues) within a respective time horizon in a plurality of time horizons.

In some embodiments, a time horizon is a period of time (e.g., a duration of time). For example, in some embodiments a time horizon is a period of time comprising at least 1, at least 2, at least 3, or at least 4 weeks. In some embodiments, a time horizon is a period of time comprising at least 1, at least 2, at least 3, at least 4, at least 5, at least 6, at least 7, at least 8, at least 9, at least 10, at least 11, or at least 12 months. In some embodiments, a time horizon is a period of time comprising at least 1, at least 2, at least 3, at least 4, at least 5, at least 6, at least 7, at least 8, at least 9, at least 10, at least 15, at least 20, at least 25, at least 30, at least 35, at least 40, at least 50, at least 60, at least 70, at least 80, at least 90, or at least 100 years. In some embodiments, a time horizon is about 1, about 2, about 3, about 4, about 5, about 6, about 7, about 8, about 9, about 10, about 11, or about 12 months. In some embodiments, a time horizon is a period of time comprising about 1, about 2, about 3, about 4, about 5, about 6, about 7, about 8, about 9, about 10, about 15, about 20, about 25, about 30, about 35, about 40, about 50, about 60, about 70, about 80, about 90, or about 100 years. In some embodiments, a time horizon is from 1 month to 3 months, from 1 month to 6 months, from 3 months to 1 year, from 6 months to 5 years, from 1 year to 10 years, or from 2 years to 50 years.

In some embodiments, a time horizon in the plurality of time horizons is a period of time extending from a temporal element (e.g., a time since a first diagnosis, a time since a subsequent diagnosis other than the first diagnosis, a time since first administration of a therapy, a time since a last administration of a therapy, a time since a completion of a first therapeutic regimen, a time since a first experience of a symptom, a time since a last experience of a symptom, a time since a first experience of a comorbidity, and/or a time since a resolution of a comorbidity).

In some embodiments, a time horizon is a period of time that is any of the above durations (e.g., weeks, months, and/or years) following any of the above temporal elements (e.g., any period of time starting from a clinical event in the subject's timeline). Examples of time horizons are further illustrated in FIG. 7 (e.g., "anchor point" indicates a starting temporal element; "target window" indicates a time horizon following the starting temporal element).

In some embodiments, the plurality of time horizons for a respective set of indications (e.g., for a respective tissue) includes at least 2, at least 3, at least 4, at least 5, at least 6, at least 7, at least 8, at least 9, at least 10, at least 15, at least 20, at least 25, at least 30, at least 35, at least 40, at least 50, at least 60, at least 70, at least 80, at least 90, or at least 100 time horizons (e.g., target windows). In some embodiments, the plurality of time horizons includes no more than 100, no more than 80, no more than 60, no more than 50, no more than 40, no more than 30, no more than 20, no more than 15, or no more than 10 time horizons. In some embodiments, the plurality of time horizons is from 2 to 100 time horizons. In some embodiments, the plurality of time horizons is from 2 to 10, between 5 and 50, between 10 and 20, or between 10 and 100 time horizons.

In some embodiments, each time horizon in the plurality of time horizons includes the same duration of time (e.g., 6 months). In some embodiments, a first time horizon in the plurality of time horizons includes a different duration of time from a second time horizon in the plurality of time horizons (e.g., 6 months and 12 months). In some embodiments, a first time horizon overlaps with a second time horizon in the plurality of time horizons. For example, in some embodiments, the plurality of time horizons includes a first time horizon of 6 months after a first temporal element (e.g., a cancer diagnosis) and a second time horizon of 12 months after the respective first temporal element, where the first 6 months in the second time horizon of 12 months overlaps with the first time horizon of 6 months. As another example, in some embodiments, the plurality of time horizons includes a first time horizon spanning the period between months 6 and 18 after a temporal element (e.g., a cancer diagnosis), and a second time horizon spanning the period between months 12 and 24 after the respective temporal element. In some embodiments, a first time horizon in the plurality of time horizons does not overlap with a second time horizon in the plurality of time horizons (e.g., each time horizon encompasses a distinct epoch of time (e.g., months 6-12, years 1-2, years 2-3, years 3-6, etc.)).

In some embodiments, the plurality of time horizons for each respective set of indications in a plurality of sets of indications (e.g., for each respective tissue in a plurality of tissues) includes the same number and/or durations of time horizons (e.g., such that indications are provided for each tissue in a plurality of tissues across a uniform set of time horizons). In some embodiments, the plurality of time horizons for each respective set of indications in a plurality of sets of indications (e.g., for each respective tissue in a plurality of tissues) includes different numbers and/or durations of time horizons.

In some embodiments, the number and/or duration of time horizons in the plurality of time horizons is predetermined (e.g., fixed). In some embodiments, each time horizon in the plurality of time horizons is selectable and/or adjustable by a user or practitioner (e.g., such that indications are provided for any desired target window and/or any point of interest in a subject's clinical timeline). In some embodiments, the selection and/or adjustment of time horizons is performed via a user affordance (e.g., a typed-in command and/or a scrollable bar in an interactive graphical representation).

Indications. In some embodiments, predictions of cancer metastasis provide information on whether a cancer will metastasize, to any or an unspecified tissue, within a single or an unspecified duration of time (e.g., as one or more indications of metastasis 1542 provided by a corresponding one or more models 1538).

Additional example predictions of cancer metastasis are further illustrated with reference to FIGS. 17 and 18. For example, FIG. 18 illustrates that an indication of cancer metastasis, in some embodiments, provides information on the location to which the cancer will metastasize (e.g., predicted location, within a single or unspecified duration of time). In some embodiments, an indication of cancer metastasis provides information on the time until metastasis is expected to occur in the subject (e.g., predicted time horizon, to any and/or unspecified tissue). In some embodiments, an indication of cancer metastasis further provides information on a specific location to which the cancer will metastasize by a specific time in the future (e.g., specific tissue and time horizon). FIG. 17 further illustrates an example of a plurality of indications of whether the cancer will metastasize (e.g., where the plurality of indications includes, for each respective tissue in the plurality of tissues, a respective set of indications for each respective time horizon in the plurality of time horizons). Thus, for example, for a plurality of N tissues S and a plurality of M time horizons H, the plurality of indications can include all possible combinations of N tissues and M time horizons from $S_1H_1$ to $S_NH_M$. In some embodiments, the plurality of indications includes separate indications for similar tissue types found in different locations within the body (e.g., proximal lymph tissue and distal lymph tissue).

In some embodiments, an indication of whether the cancer of the subject will metastasize is a binary output (e.g., "yes" or "no" and/or "likely" or "not likely"). In some embodiments, an indication of whether the cancer of the subject will metastasize is a likelihood or a probability (e.g., a value between 0 and 1 and/or a percentage between 0 and 100). In some embodiments, the indication is transformed and/or scaled (e.g., from a percentage to a probability).

In some embodiments, the one or more models (e.g., comprising predictive and/or classification models) provides both a binary and a non-binary indication of whether the cancer of the subject will metastasize. For example, in some embodiments, an output from the one or more models includes a probability value between 0 and 1 and a binary output based on an interpretation of the probability value (e.g., whether the probability value satisfies a likelihood cutoff threshold). Thus, if the one or more models provides a probability of 0.98 that the cancer will metastasize (e.g., to a respective tissue within a respective time horizon, or to any tissue at any time), and the probability threshold for a positive indication is 0.95, then the one or more models would provide both the probability (0.98) and a binary indication ("yes"). In some embodiments, the likelihood cutoff threshold (e.g., the probability threshold for a positive indication) is a hyperparameter. In some embodiments, a hyperparameter is predetermined. In some embodiments, a hyperparameter is provided by a user or practitioner. In some embodiments, a hyperparameter is adjustable and/or is inputted by a user or practitioner. In some embodiments, a hyperparameter is optimized based on one or more optimization analyses. In some embodiments, optimization of a hyperparameter is performed to increase or decrease the stringency of the classification.

In some embodiments, where the one or more indications is a plurality of indications corresponding to a plurality of time horizons and/or a plurality of tissues, an indication of whether the cancer of the subject will metastasize includes a ranking for a respective tissue and/or a respective time horizon (e.g., of a ranked likelihood that the cancer will metastasize to the respective tissue and/or within the respective time horizon). For example, in some embodiments, the plurality of indications includes, for each respective tissue in the plurality of tissues, a ranking of the likelihood that the cancer will metastasize to the respective tissue within each respective time horizon in the plurality of time horizons. In some embodiments, the ranking is performed by comparing between all possible combinations of tissues and time horizons (e.g., from $S_1H_1$ to $S_NH_M$) in order to generate a ranked list.

In some embodiments, the one or more models further provide a confidence measure for the one or more indications of whether the cancer of the subject will metastasize. In some embodiments, the confidence measure is a p-value, a confidence interval, a standard deviation, a variance, a standard error, and/or a distribution.

In some embodiments, each indication in the one or more indications (e.g., for a respective one or more combinations of possible time horizons and/or tissues) are the same or different.

In some embodiments, each model in the one or more model provides a different indication in the corresponding one or more indications (e.g., each respective model in the one or more models provides a respective indication in the one or more indications). In some embodiments, the one or more models collectively provide the one or more indications. In some embodiments, the one or more models collectively provide a single indication. In some embodiments, the one or more models is a single model that provides a single indication.

Models. In some embodiments, a model in the one or more models 1538 (e.g., set of models) is a predictive model and/or a classification model.

In some embodiments, a model in the one or more models includes an algorithm selected from the group consisting of a neural network algorithm, a support vector machine algorithm, a Naive Bayes algorithm, a nearest neighbor algorithm, a boosted regression decision tree ensemble algorithm, a random forest decision tree ensemble algorithm, and a multinomial logistic regression algorithm. In some embodiments, the model is a multinomial logistic regression algorithm comprising a regularization parameter (e.g., an L1 or an L2 (e.g., ridge) regularization penalty).

Logistic regression classifiers are disclosed in Agresti, An Introduction to Categorical Data Analysis, 1996, Chapter 5, pp. 103-144, John Wiley & Son, New York, which is hereby incorporated by reference. In some embodiments, the logistic regression classifier includes at least 10, at least 20, at least 50, at least 100 weights, or at least 1000 weights and requires a computer to calculate because it cannot be mentally solved.

A k-nearest neighbor classifier is a non-parametric machine learning method in which the input consists of the k closest training examples in feature space. The output is a class membership. An object is classified by a plurality vote of its neighbors, with the object being assigned to the class most common among its k nearest neighbors (k is a positive integer, typically small). If k=1, then the object is simply assigned to the class of that single nearest neighbor. See, Duda et al., 2001, Pattern Classification, Second Edition, John Wiley & Sons, which is hereby incorporated by reference. In some embodiments, the number of distance calculations needed to solve the k-nearest neighbor classifier is such that a computer is used to solve the classifier for a given input because it cannot be mentally performed.

A deep neural network classifier includes an input layer, a plurality of individually weighted convolutional layers, and an output scorer. The weights of each of the convolutional layers as well as the input layer contribute to the plurality of weights associated with the deep neural network classifier. In some embodiments, at least 100 weights, at least 1000 weights, at least 2000 weights or at least 5000 weights are associated with the deep neural network classifier. As such, deep neural network classifiers require a computer to be used because they cannot be mentally solved. In other words, given an input to the classifier, the classifier output needs to be determined using a computer rather than mentally in such embodiments. See, for example, Krizhevsky et al., 2012, "Imagenet classification with deep convolutional neural networks," in Advances in Neural Information Processing Systems 2, Pereira, Burges, Bottou, Weinberger, eds., pp. 1097-1105, Curran Associates, Inc.; Zeiler, 2012 "ADADELTA: an adaptive learning rate method," CoRR, vol. abs/1212.5701; and Rumelhart et al., 1988, "Neurocomputing: Foundations of research," ch. Learning Representations by Back-propagating Errors, pp. 696-699, Cambridge, Mass., USA: MIT Press, each of which is hereby incorporated by reference.

SVM classifiers are described in Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data training set with a hyper-plane that is maximally distant from the labeled data. For cases in which no linear separation is possible, SVMs can work in combination with the technique of "kernels," which automatically realizes a non-linear mapping to a feature space. The hyper-plane found by the SVM in feature space corresponds to a non-linear decision boundary in the input space. In some embodiments, the plurality of weights associated with the SVM define the hyper-plane. In some embodiments, the hyper-plane is defined by at least 10, at least 20, at least 50, or at least 100 weights and the SVM classifier requires a computer to calculate because it cannot be mentally solved.

Decision tree classifiers are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, Pattern Classification, John Wiley & Sons, Inc., New York, pp. 396-408 and pp. 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety. In some embodiments, the decision tree classifier includes at least 10, at least 20, at least 50, or at least 100 weights (decisions) and requires a computer to calculate because it cannot be mentally solved.

A Naive Bayes classifier is any classifier in a family of "probabilistic classifiers" based on applying Bayes' theorem with strong (naïve) independence assumptions between the features. In some embodiments, they are coupled with Kernel density estimation. See, for example, Hastie et al., 2001, "The elements of statistical learning: data mining, inference, and prediction," eds. Tibshirani and Friedman, Springer, New York, which is hereby incorporated by reference.

In some embodiments, the model is a trained survival function, also known as a complementary cumulative distribution function. Survival functions relate the time that passes, before some event occurs (e.g., metastasis), to one or more covariates (e.g., features formed from RNA expression data, somatic mutation data, clinical data, imaging data, etc.) associated with that quantity of time. Non-limiting examples of survival functions include the Kaplan-Meier estimator, proportional hazards models such as the Cox proportional hazards model (Cox, David R (1972). "Regression Models and Life-Tables". Journal of the Royal Statistical Society, Series B. 34 (2): 187-220. JSTOR 2985181. MR 0341758, the content of which is hereby incorporated by reference), poisson regression models, accelerated failure time models, first-hitting-time models, and the like. For more information on survival functions, see, for example, Kleinbaum, David G.; Klein, Mitchel (2012), Survival analysis: A Self-learning text (Third ed.), Springer, ISBN 978-1441966452, the content of which is hereby incorporated by reference.

In some embodiments, the one or more models includes at least 2, at least 3, at least 4, at least 5, at least 6, at least 7, at least 8, at least 9, at least 10, at least 15, at least 20, at least 25, at least 30, at least 35, at least 40, at least 50, at least 60, at least 70, at least 80, at least 90, or at least 100 models.

In some embodiments, the one or more models includes at least 50, at least 100, at least 200, at least 300, at least 400, at least 500, at least 600, at least 700, at least 800, at least 900, or at least 1000 models, or more. In some embodiments, the one or more models includes no more than 500, no more than 400, no more than 300, no more than 200, no more than 100, no more than 75, no more than 50, no more than 25, or no more than 10 models, or less. In some embodiments, the one or more models includes from 2 to 1000 models, from 10 to 500 models, from 10 to 200 models, from 5 to 100 models, from 5 to 50 models, from 100 to 200 models, or from 100 to 1000 models. In some embodiments the one or more models falls within another range starting no lower than 2 models and ending no higher than 1000 models.

In some embodiments, the one or more models is a set of models, each model in the set of models corresponding to a respective different combination of a respective tissue in a plurality of tissues and a respective time horizon in a plurality of time horizons for the respective tissue.

For example, in some embodiments, the set of models includes, for each respective tissue in the plurality of tissues, a respective subset of models, where each respective model, in the respective subset of models, is trained to provide a respective indication of whether the cancer in the subject will metastasize to the respective tissue in the subject within a single respective time horizon in the respective plurality of time horizons (e.g., separate models for each combination of tissue and time horizon). For example, referring to FIG. 17, in some such embodiments, the set of models includes N×M models for each combination of N tissues and M time horizons, where each model provides a single indication for the nth tissue at the mth time horizon.

In some embodiments, the respective plurality of time horizons for each respective tissue in the plurality of tissues is the same, and the set of models includes, for each respective time horizon in the plurality of time horizons, a respective model trained to provide, for each respective tissue in the plurality of tissues, a respective indication of whether the cancer in the subject will metastasize to the respective tissue in the subject within the respective time horizon (e.g., separate multi-label models indicating a plurality of tissues for each time horizon). For example, referring again to FIG. 17, in some such embodiments, the set of models includes M models for each of M time horizons, where each model provides N indications for each of N tissues.

In some embodiments, the set of models includes, for each respective tissue in the plurality of tissues, a respective model trained to provide, for each respective time horizon in the plurality of time horizons, a respective indication of whether the cancer in the subject will metastasize to the respective tissue in the subject within the respective time horizon (e.g., separate multi-label models indicating a plurality of time horizons for each tissue). Thus, referring again to FIG. 17, in some such embodiments, the set of models includes N models for each of N tissues, where each model provides M indications for each of M time horizons.

In some embodiments, the set of models includes a respective model trained to provide, for each respective time horizon in a plurality of time horizons, a respective indication of whether the cancer will metastasize to any tissue in the subject, and the plurality of indications of whether the cancer will metastasize includes, for each respective time horizon in a plurality of time horizons, a respective indication of whether the cancer will metastasize to any tissue in the subject (e.g., likelihood or metastasis to any tissue in the subject). Thus, in some embodiments, a model in the set of models provides a prediction of cancer metastasis within one or more periods of time, but without specifying a predicted metastasis site.

In some embodiments, the one or more models are collectively trained by a process comprising obtaining, in electronic format, for each respective training subject in a plurality of training subjects, a respective plurality of data elements. Each respective training subject in the plurality of training subjects has a respective cancer, and for each respective training subject in the plurality of training subjects, the respective plurality of data elements comprises a first set of sequence features comprising relative abundance values for the expression of a plurality of genes (e.g., at least 30 genes) in a biopsy of the cancer obtained from the training subject. In some embodiments, a respective training subject in the plurality of training subjects, including associated cancer conditions, data elements, sequence features, and/or genes, comprises any of the embodiments for subjects, cancer conditions, data elements, sequence features, and genes described in the above sections (see, "Cancer conditions" and "Data elements," above).

In some embodiments, the training the one or more models comprises training one or more untrained or partially untrained models using the respective plurality of data elements for each respective training subject in the plurality of training subjects as input, thus obtaining one or more corresponding trained models that are collectively trained to provide a respective one or more indications of whether a cancer will metastasize in a subject.

For instance, another aspect of the present disclosure provides a method for predicting metastasis of a cancer in a subject, comprising at a computer system having one or more processors, and memory storing one or more programs for execution by the one or more processors, obtaining, in electronic format, for each respective training subject in a plurality of training subjects, a respective plurality of data elements. Each respective training subject in the plurality of training subjects has a respective cancer, and for each respective training subject in the plurality of training subjects, the respective plurality of data elements comprises a first set of sequence features comprising relative abundance values for the expression of a plurality of genes (e.g., at least 30 genes) in a biopsy of the cancer obtained from the training subject. The method comprises training one or more untrained or partially untrained models using the respective plurality of data elements for each respective training subject in the plurality of training subjects as input, thus obtaining one or more corresponding trained models, and using the one or more trained models to collectively provide a respective one or more indications of whether a cancer will metastasize in a test subject, thereby predicting whether the cancer will metastasize.

In some embodiments, a model in the one or more models is trained and implemented using any of the methods and/or embodiments for model training and implementation described in the above sections (see, "Artificial Intelligence Engine Training Pipeline," and "Prediction of Colorectal Metastasis based on RNA"). In some embodiments, the one or more models is trained using an optional classifier training module 1520 comprising any of the training subjects, training data, associated cancer conditions, data elements, sequence features, and/or genes disclosed herein.

Suitable methods and/or embodiments for training models, including feature selection, identification of prior features, identification of forward features, target and objective selection, and/or model training, include but are not limited to any of the methods and/or embodiments for training models, including feature selection, identification of prior features, identification of forward features, target and objective selection, and/or model training described in the present disclosure (see, for example, "Generating and Modeling Predictions of Patient Objectives" and FIGS. 6-8), and any substitutions, additions, deletions, modifications, and/or combinations thereof as will be apparent to one skilled in the art.

In some embodiments, the one or more models, including trained, untrained, and/or partially untrained models, includes any of the embodiments disclosed herein, including any substitutions, additions, deletions, modifications, and/or combinations thereof as will be apparent to one skilled in the art.

Reporting.

Referring to Block 1614, in some embodiments, the method further includes generating a clinical report comprising the one or more indications of whether the cancer will metastasize. In some embodiments, where multiple indications are provided (as described in detail in the foregoing sections), the one or more indications are presented as a list of tissues, a list of time horizons, and/or a list of possible combinations of tissues and time horizons, where each entry in the respective list includes a corresponding indication of whether the cancer will metastasize for the respective tissue, time horizon, and/or combination of tissue and time horizon. In some embodiments, the one or more indications are presented as a table, a chart, and/or a graphical representation. In some embodiments, the one or more indications are presented in an interactive format.

In some embodiments, the method further includes displaying the clinical report in a graphical user interface (GUI), wherein the GUI includes an anatomical representation of a body and a first affordance configured for switching between respective time horizons in the plurality of time horizons. The displaying includes displaying a first rendering of metastatic predictions comprising, for each respective tissue in the plurality of tissues, a respective visual representation of the respective indication, in the plurality of indications, corresponding to whether the cancer in the subject will metastasize to the respective tissue within a first respective time horizon in the plurality of time horizons, where the rendering is superposed upon the anatomical representation of the body. Responsive to receiving a user input corresponding to the first affordance on the GUI, the method includes replacing the display of the first rendering of metastatic predictions with a display of a second rendering of metastatic predictions comprising, for each respective tissue in the plurality of tissues, a respective visual representation of the respective indication, in the plurality of indications, corresponding to whether the cancer in the subject will metastasize to the respective tissue within a second respective time horizon in the plurality of time horizons, where the rendering is superposed upon the anatomical representation of the body.

In some embodiments, the graphical user interface is a prediction tool such as a webform, as described in detail in the present disclosure and with reference to FIGS. 9-12 (see, "Generating and Modeling Predictions of Patient Objectives").

Referring to Block 1616, in some embodiments, the method further includes, when the one or more indications of whether the cancer will metastasize satisfy a first threshold risk for metastasis of the cancer, administering a first therapy tailored for treatment of metastatic cancer, and when the one or more indications of whether the cancer will metastasize do not satisfy the first threshold risk for metastasis of the cancer, administering a second therapy tailored for treatment of non-metastatic cancer. For example, in some embodiments, the first threshold risk for metastasis is an indication that the cancer of the subject will metastasize (e.g., has above a threshold probability of metastasizing) to any one or more tissues within a first time horizon (e.g., within 6 months, within 1 year, within 2 years, within 3 years, within 4 years, within 5 years, within 10 years, and/or within greater than 10 years). In some embodiments, the first threshold risk for metastasis is an indication that the cancer of the subject will metastasize (e.g., has above a threshold probability of metastasizing) to a respective tissue (e.g., a specific metastasis site), in a plurality of tissues, within a first time horizon.

In some embodiments, the subject is administered an anti-cancer agent selected from lenalidomid, pembrolizumab, trastuzumab, bevacizumab, rituximab, ibrutinib, human papillomavirus quadrivalent (types 6, 11, 16, and 18) vaccine, pertuzumab, pemetrexed, nilotinib, nilotinib, denosumab, abiraterone acetate, promacta, imatinib, everolimus, palbociclib, erlotinib, bortezomib, and bortezomib. In some embodiments, the first therapy is an anti-cancer agent that is selected based on the identity of one or more tissues, in the plurality of tissues, predicted for metastasis. In some embodiments, the first therapy and/or the second therapy is administered in accordance with the NCCN standard of care guidelines (available online at www.nccn.org). In some embodiments, the subject is administered with a combination therapy. For example, in some embodiments, the first therapy and/or the second therapy is administered in conjunction with a radiation therapy and/or a surgical treatment.

Additional Embodiments

Another aspect of the present disclosure provides a method for predicting metastasis of a cancer in a subject, comprising obtaining, in electronic format, a plurality of data elements for the subject's cancer. In some embodiments, the cancer is colorectal cancer, non-small cell lung cancer (NSCLC), breast cancer, or ovarian cancer. In some embodiments, the cancer is colon cancer. In some embodiments, the cancer is rectosigmoid junction cancer. In some embodiments, the cancer is colon or rectosigmoid junction cancer.

In some embodiments, the plurality of data elements includes a first set of sequence features based on relative abundance values for the expression of a plurality of genes (e.g., at least 30 genes) in a biopsy of the cancer obtained from the subject.

In some embodiments, the plurality of data elements also includes one or more personal characteristics about the subject (e.g., selected from the group consisting of age, gender, and race).

In some embodiments, the plurality of data elements further includes one or more clinical features related to the diagnosis or treatment of the cancer in the subject selected from the group consisting of a stage of the cancer, a histopathological grade of the cancer, a therapy administered to the subject, a symptom associated with cancer or metastasis thereof, and a comorbidity with the cancer.

In some embodiments, the plurality of data elements further includes one or more temporal features (e.g., associated with any of the clinical features in the one or more clinical features) related to the diagnosis or treatment of the cancer in the subject selected from the group consisting of a first temporal element indicating the duration of time since a diagnosis for the cancer, a second temporal element indicating the duration of time since an administration of the therapy, a third temporal element indicating the duration of time since an experience of the symptom, and a fourth temporal element indicating the duration of time since an experience of the comorbidity.

Suitable methods and/or embodiments for obtaining the plurality of data elements, including sequence features (e.g., collecting biopsies, sequencing methods, sequence reads, preprocessing methods, determining abundance values, and/or selection of sequence features), personal characteristics, clinical features, and/or additional data elements, include but are not limited to any of the methods and/or embodiments for obtaining a plurality of data elements described in the present disclosure, including sequence features (e.g., collecting biopsies, sequencing methods, sequence reads, preprocessing methods, determining abundance values, and/or selection of sequence features), personal characteristics, clinical features, and/or additional data elements (see, "Classification Methods: Data elements"), and any substitutions, additions, deletions, modifications, and/or combinations thereof as will be apparent to one skilled in the art.

For example, in some embodiments, obtaining the first set of sequence features includes obtaining a plurality of at least 10,000 sequence reads, where the plurality of sequence reads is obtained from a plurality of RNA molecules from the biopsy of the cancer obtained from the subject, and determining, from the plurality of sequence reads, relative abundance values for a plurality of genes. In some embodiments, the plurality of genes comprises at least 20 genes selected from the group consisting of the genes listed in Table 2. In some embodiments, the plurality of genes is no more than 250 genes.

In some embodiments, the first set of sequence features includes relative abundance values for the expression of a plurality of genes. In some embodiments, the first set of features includes relative abundance values for the expression of at least 25 genes. In some embodiments, the first set of features includes relative abundance values for the expression of at least 50 genes. In some embodiments, the first set of features includes relative abundance values for the expression of at least 75 genes. In some embodiments, the first set of features includes relative abundance values for the expression of at least 100 genes. In some embodiments, the first set of features includes relative abundance values for the expression of at least 250 genes. In some embodiments, the first set of features includes relative abundance values for the expression of at least 150 genes, at least 200 genes, at least 300 genes, at least 400 genes, at least 500 genes, at least 750 genes, at least 1000 genes, or more.

In some embodiments, the first set of sequence features includes a plurality of dimension reduction component values determined from relative abundance values for a plurality of genes. For instance, Example 1 describes an instance where relative expression values for the 500 most correlated genes are used to generate 40 sequence features using singular value decomposition, which are the basis for a prediction model. Accordingly, in some embodiments, the first set of sequence features include a plurality of dimension reduction component values determined from relative abundance values for at least 25, at least 50, at least 75, at least 100, at least 150, at least 200, at least 250, at least 500, at least 750, at least 1000, or more genes. In some embodiments, the first set of sequence features include a plurality of dimension reduction component values determined from relative abundance values for no more than 2000 genes, no more than 1500 genes, no more than 1000 genes, no more than 750 genes, no more than 500 genes, or less. In some embodiments, the first set of sequence features include a plurality of dimension reduction component values determined from relative abundance values for from 25 to 2000 genes, from 50 to 1000 genes, or from 100 to 750 genes.

In some embodiments, the plurality of data elements further includes a single-sample gene set enrichment analysis (ssGSEA) score for the transcriptional profile of the cancer.

In some embodiments, the plurality of data elements further includes a mutational status for one or more genes in the genome of the cancer (e.g., where the mutational status is for a gene selected from the group consisting of the genes listed in Table 2). In some embodiments, the plurality of data elements further includes a mutational status for one or more genes in the genome of a non-cancerous tissue of the subject. In some embodiments, the plurality of data elements further includes a copy number status for one or more genomic regions (e.g., one or more genes) of the cancer.

In some embodiments, the plurality of data elements further includes a personal characteristic. In some embodiments, the one or more personal characteristics include smoking status or menopausal status (e.g., associated with lung cancer, breast cancer, and/or ovarian cancer). In some embodiments, the plurality of data elements further includes a clinical feature for the subject.

In some embodiments, the plurality of data elements further includes a physical characteristic of the biopsy of the cancer. For example, in some embodiments, the plurality of data elements includes tumor percentage, tumor cell percentage, tumor infiltrating lymphocytes percentage, tumor budding features, biologically meaningful features, and/or geometrically meaningful features (e.g., aggregation metrics (e.g., minimum, average, median, maximum) of tumor perimeter, average tumor cell circularity, average tumor cell length and/or aspect ratio).

The method further includes applying, to the plurality of data elements for the subject's cancer, a model (e.g., a predictive and/or classification model) that is collectively trained to provide an indication (e.g., binary, likelihood, and/or probability) of whether the cancer will metastasize in the subject, thus predicting whether the cancer will metastasize. Thus, in some embodiments, the present disclosure provides a single model that provides a single indication of whether the cancer will metastasize in the subject to any tissue site in the subject within a particular time horizon.

Suitable methods and/or embodiments for predicting whether the cancer will metastasize using a model, including tissues, time horizons, indications, types of models, training models, and/or outputs, include but are not limited to any of the methods and/or embodiments for obtaining indications described in the present disclosure, including tissues, time horizons, indications, types of models, training models, and/or outputs (see, "Classification Methods: Obtaining indications of metastasis"), and any substitutions, additions, deletions, modifications, and/or combinations thereof as will be apparent to one skilled in the art.

In some embodiments, the method comprises applying, to the plurality of data elements for the subject's cancer, a set of models that are collectively trained to provide, for each respective tissue in a plurality of tissues, a respective set of indications in the one or more indications of whether the cancer will metastasize to the respective tissue in the subject, where the respective set of indications includes a respective indication for each respective time horizon in a plurality of time horizons, thus determining a plurality of indications of whether the cancer will metastasize comprising, for each respective tissue in the plurality of tissues, a respective set of indications comprising, for each respective time horizon in a plurality of time horizons, a respective indication of whether the cancer in the subject will metastasize to the respective tissue within the respective time horizon.

In some embodiments, the set of models comprises, for each respective tissue in the plurality of tissues, a respective subset of models, where each respective model, in the respective subset of models, is trained to provide a respective indication of whether the cancer in the subject will metastasize to the respective tissue in the subject within a single respective time horizon in the respective plurality of time horizons.

In some embodiments, the respective plurality of time horizons for each respective tissue in the plurality of tissues is the same, and the set of models comprises, for each respective time horizon in the plurality of time horizons, a respective model trained to provide, for each respective tissue in the plurality of tissues, a respective indication of whether the cancer in the subject will metastasize to the respective tissue in the subject within the respective time horizon.

In some embodiments, the set of models comprises, for each respective tissue in the plurality of tissues, a respective model trained to provide, for each respective time horizon in the plurality of time horizons, a respective indication of whether the cancer in the subject will metastasize to the respective tissue in the subject within the respective time horizon.

In some embodiments, the set of models comprises a respective model trained to provide, for each respective time horizon in a plurality of time horizons, a respective indication of whether the cancer will metastasize to any tissue in the subject, and the plurality of indications of whether the cancer will metastasize includes, for each respective time horizon in a plurality of time horizons, a respective indication of whether the cancer will metastasize to any tissue in the subject.

In some embodiments, the plurality of tissues comprises lymph tissue, liver tissue, and lung tissue.

In some embodiments, the one or more trained models are collectively trained by a process comprising obtaining, in electronic format, for each respective training subject in a plurality of training subjects, a respective plurality of data elements. Each respective training subject in the plurality of training subjects has a respective cancer, and for each respective training subject in the plurality of training subjects, the respective plurality of data elements comprises a first set of sequence features comprising relative abundance values for the expression of a plurality of genes (e.g., at least 30 genes) in a biopsy of the cancer obtained from the training subject. The method includes training one or more untrained or partially untrained models using the respective plurality of data elements for each respective training subject in the plurality of training subjects as input, thus obtaining one or more corresponding trained models that are collectively trained to provide a respective one or more indications of whether a cancer will metastasize in a subject.

Suitable methods and/or embodiments for training models, including feature selection, identification of prior features, identification of forward features, target and objective selection, and/or model training, include but are not limited to any of the methods and/or embodiments for training models, including feature selection, identification of prior features, identification of forward features, target and objective selection, and/or model training described in the present disclosure (see, for example, "Generating and Modeling Predictions of Patient Objectives," with reference to FIGS. 6-8, and "Classification Methods: Obtaining indications of metastasis"), and any substitutions, additions, deletions, modifications, and/or combinations thereof as will be apparent to one skilled in the art.

The method further includes generating a clinical report comprising the indication of whether the cancer will metastasize.

In some embodiments, the method further includes displaying the clinical report in a graphical user interface (GUI), where the GUI comprises an anatomical representation of a body and a first affordance configured for switching between respective time horizons in the plurality of time horizons. The displaying comprises displaying a first rendering of metastatic predictions comprising, for each respective tissue in the plurality of tissues, a respective visual representation of the respective indication, in the plurality of indications, corresponding to whether the cancer in the subject will metastasize to the respective tissue within a first respective time horizon in the plurality of time horizons, where the rendering is superposed upon the anatomical representation of the body. Responsive to receiving a user input corresponding to the first affordance on the GUI, the method includes replacing display of the first rendering of metastatic predictions with display of a second rendering of metastatic predictions comprising, for each respective tissue in the plurality of tissues, a respective visual representation of the respective indication, in the plurality of indications, corresponding to whether the cancer in the subject will metastasize to the respective tissue within a second respective time horizon in the plurality of time horizons, where the rendering is superposed upon the anatomical representation of the body.

In some embodiments, the method further includes, when the indication of whether the cancer will metastasize satisfies a first threshold risk for metastasis of the cancer, administering a first therapy tailored for treatment of metastatic cancer, and when the indication of whether the cancer will metastasize does not satisfy the first threshold risk for metastasis of the cancer, administering a second therapy tailored for treatment of non-metastatic cancer.

In some embodiments, the generating a clinical report and/or administering therapies using the single model method includes any of the methods and/or embodiments for a set of models described in the present disclosure, above (see, "Classification Methods: Obtaining indications of metastasis: Reporting"), and any substitutions, additions, deletions, modifications, and/or combinations thereof as will be apparent to one skilled in the art.

In some embodiments, any of the presently disclosed methods and/or embodiments are performed at a computer system having one or more processors, and memory storing one or more programs for execution by the one or more processors.

Another aspect of the present disclosure provides a computer system having one or more processors, and memory storing one or more programs for execution by the one or more processors, the one or more programs comprising instructions for performing any of the methods disclosed herein.

Another aspect of the present disclosure provides a non-transitory computer readable storage medium storing one or more programs configured for execution by a computer, the one or more programs comprising instructions for carrying out any of the methods disclosed herein.

Example Models for Predicting Whether a Cancer Will Metastasize.

Advantageously, the present disclosure describes several classes of features that are informative for predicting whether a cancer will metastasize. For instance, among other aspects, the present disclosure describes improvements in generating predictions of whether a cancer will metastasize using (i) sequence features comprising relative abundance values for the expression of a plurality of genes (e.g., at least 30 genes) in a biopsy of the cancer obtained from the subject, (ii) one or more personal characteristics about the subject, (iii) one or more clinical features related to the diagnosis or treatment of the cancer in the subject, (iv) one or more temporal features related to the diagnosis or treatment of the cancer in the subject and/or (v) one or more pathological features of the cancer tissue. It is contemplated that various combinations of these improvements, as well as other non-conventional aspects described herein, may be integrated into a common classification module 1536 (e.g., a prediction analysis pipeline) for indicating whether a cancer will metastasize. For instance, in some embodiments, a classification module integrates one, two, three, four, or all five of these feature types for improved predictions of cancer metastasis. Examples of various combinations of improvements that may be combined into a single classification module (e.g., comprising one or more models), methods associated thereof, systems for performing such methods, and/or non-transitory computer readable media for executing such methods are described below. It will be appreciated that these combinations can be performed with any other preparatory or classification steps described in the other methods described herein, e.g., methods 600, 800, and 1602 as illustrated in FIGS. 6, 8, and 16, and further described above.

In some embodiments, a classification module for predicting metastasis of a cancer in a subject is provided that integrates at least a first set of sequence features comprising relative abundance values for the expression of a plurality of genes, as described above in the section entitled "Sequence features."

Accordingly, in some embodiments, a method is provided for predicting metastasis of a cancer in a subject that includes (A) obtaining, in electronic format, a plurality of data elements for the subject's cancer comprising a first set of sequence features comprising relative abundance values for the expression of a plurality of genes (e.g., at least 30 genes) in a biopsy of the cancer obtained from the subject, as described above in the section entitled "Sequence features," (B) applying, to the plurality of data elements for the subject's cancer, one or more models that are collectively trained to provide a respective one or more indications of whether the cancer will metastasize in the subject, thereby predicting whether the cancer will metastasize, and (C) generating a clinical report comprising the one or more indications of whether the cancer will metastasize. In some embodiments, the method includes, when the one or more indications of whether the cancer will metastasize satisfies a first threshold risk for metastasis of the cancer, administering a first therapy tailored for treatment of metastatic cancer, and when the one or more indications of whether the cancer will metastasize does not satisfy the first threshold risk for metastasis of the cancer, administering a second therapy tailored for treatment of non-metastatic cancer, as described in the above section entitled "Reporting."

In some embodiments, the plurality of data elements including the relative abundance values for the expression of the plurality of genes also includes one or more personal characteristics about the subject, e.g., as described above in the section entitled "Personal characteristics." In some embodiments, the plurality of data elements including the relative abundance values for the expression of the plurality of genes also includes the age of the subject. In some embodiments, the plurality of data elements including the relative abundance values for the expression of the plurality of genes also includes the gender of the subject. In some embodiments, the plurality of data elements including the relative abundance values for the expression of the plurality of genes also includes a race of the subject. In some embodiments, the plurality of data elements including the relative abundance values for the expression of the plurality of genes also includes a habit of the subject (e.g., a smoking status, alcohol consumption status, dietary status, etc.). In some embodiments, the plurality of data elements including the relative abundance values for the expression of the plurality of genes also includes a physiological characteristic of the subject (e.g., a blood pressure status, a dermatological condition, a co-morbidity, etc.).

In some embodiments, the classification module integrating at least a first set of sequence features comprising relative abundance values for the expression of a plurality of genes also integrates one or more clinical features related to the diagnosis or treatment of the cancer in the subject, as described above in the section entitled "Clinical features." In some embodiments, the classification module integrating at least a first set of sequence features comprising relative abundance values for the expression of a plurality of genes also integrates one or more temporal features related to the diagnosis or treatment of the cancer in the subject, as described above in the section entitled "Temporal features."

In some embodiments, the classification module integrating at least a first set of sequence features comprising relative abundance values for the expression of a plurality of genes also integrates one or more personal characteristics about the subject, as described above in the section entitled "Personal characteristics," and further integrates one or more clinical features related to the diagnosis or treatment of the cancer in the subject, as described above in the section entitled "Clinical features." In some embodiments, the classification module integrating at least a first set of sequence features comprising relative abundance values for the expression of a plurality of genes also integrates one or more personal characteristics about the subject, as described above in the section entitled "Personal characteristics," and further integrates one or more temporal features related to the diagnosis or treatment of the cancer in the subject, as described above in the section entitled "Temporal features." In some embodiments, the classification module integrating at least a first set of sequence features comprising relative abundance values for the expression of a plurality of genes also integrates one or more clinical features related to the diagnosis or treatment of the cancer in the subject, as described above in the section entitled "Clinical features," and further integrates one or more temporal features related to the diagnosis or treatment of the cancer in the subject, as described above in the section entitled "Temporal features."

In some embodiments, the classification module integrating at least a first set of sequence features comprising relative abundance values for the expression of a plurality of genes also integrates one or more personal characteristics about the subject, as described above in the section entitled "Personal characteristics," further integrates one or more clinical features related to the diagnosis or treatment of the cancer in the subject, as described above in the section entitled "Clinical features," and further integrates one or more temporal features related to the diagnosis or treatment of the cancer in the subject, as described above in the section entitled "Temporal features."

In some embodiments, a classification module for predicting metastasis of a cancer in a subject is provided that integrates at least a first set of sequence features comprising relative abundance values for the expression of a plurality of genes, as described above in the section entitled "Sequence features," and one or more personal characteristics about the subject, as described above in the section entitled "Personal characteristics."

Accordingly, in some embodiments, a method is provided for predicting metastasis of a cancer in a subject that includes (A) obtaining, in electronic format, a plurality of data elements for the subject's cancer comprising (i) a first set of sequence features comprising relative abundance values for the expression of a plurality of genes (e.g., at least 30 genes) in a biopsy of the cancer obtained from the subject, as described above in the section entitled "Sequence features," and (ii) one or more personal characteristics about the subject selected from the group consisting of age, gender, and race, as described above in the section entitled "Personal characteristics," (B) applying, to the plurality of data elements for the subject's cancer, one or more models that are collectively trained to provide a respective one or more indications of whether the cancer will metastasize in the subject, thereby predicting whether the cancer will metastasize, and (C) generating a clinical report comprising the one or more indications of whether the cancer will metastasize. In some embodiments, the method includes, when the one or more indications of whether the cancer will metastasize satisfies a first threshold risk for metastasis of the cancer, administering a first therapy tailored for treatment of metastatic cancer, and when the one or more indications of whether the cancer will metastasize does not satisfy the first threshold risk for metastasis of the cancer, administering a second therapy tailored for treatment of non-metastatic cancer, as described in the above section entitled "Reporting."

In some embodiments, the classification module integrating at least a first set of sequence features comprising relative abundance values for the expression of a plurality of genes and one or more personal characteristics about the subject, also integrates one or more clinical features related to the diagnosis or treatment of the cancer in the subject, as described above in the section entitled "Clinical features." In some embodiments, the classification module integrating at least a first set of sequence features comprising relative abundance values for the expression of a plurality of genes and one or more personal characteristics about the subject, also integrates one or more temporal features related to the diagnosis or treatment of the cancer in the subject, as described above in the section entitled "Temporal features."

In some embodiments, the classification module integrating at least a first set of sequence features comprising relative abundance values for the expression of a plurality of genes and one or more personal characteristics about the subject, also integrates one or more clinical features related to the diagnosis or treatment of the cancer in the subject, as described above in the section entitled "Clinical features," and further integrates one or more temporal features related to the diagnosis or treatment of the cancer in the subject, as described above in the section entitled "Temporal features."

In some embodiments, a classification module for predicting metastasis of a cancer in a subject is provided that integrates at least a first set of sequence features comprising relative abundance values for the expression of a plurality of genes, as described above in the section entitled "Sequence features," and one or more clinical features related to the diagnosis or treatment of the cancer in the subject, as described above in the section entitled "Clinical features."

Accordingly, in some embodiments, a method is provided for predicting metastasis of a cancer in a subject that includes (A) obtaining, in electronic format, a plurality of data elements for the subject's cancer comprising (i) a first set of sequence features comprising relative abundance values for the expression of a plurality of genes (e.g., at least 30 genes) in a biopsy of the cancer obtained from the subject, as described above in the section entitled "Sequence features," and (ii) one or more clinical features related to the diagnosis or treatment of the cancer in the subject selected from the group consisting of a stage of the cancer, a histopathological grade of the cancer, a therapy administered to the subject, a symptom associated with cancer or metastasis thereof, and a comorbidity with the cancer, as described above in the section entitled "Clinical features," (B) applying, to the plurality of data elements for the subject's cancer, one or more models that are collectively trained to provide a respective one or more indications of whether the cancer will metastasize in the subject, thereby predicting whether the cancer will metastasize, and (C) generating a clinical report comprising the one or more indications of whether the cancer will metastasize. In some embodiments, the method includes, when the one or more indications of whether the cancer will metastasize satisfies a first threshold risk for metastasis of the cancer, administering a first therapy tailored for treatment of metastatic cancer, and when the one or more indications of whether the cancer will metastasize does not satisfy the first threshold risk for metastasis of the cancer, administering a second therapy tailored for treatment of non-metastatic cancer, as described in the above section entitled "Reporting."

In some embodiments, the classification module integrating at least a first set of sequence features comprising relative abundance values for the expression of a plurality of genes and one or more clinical features related to the diagnosis or treatment of the cancer in the subject, also integrates one or more personal characteristics about the subject, as described above in the section entitled "Personal characteristics." In some embodiments, the classification module integrating at least a first set of sequence features comprising relative abundance values for the expression of a plurality of genes and one or more clinical features related to the diagnosis or treatment of the cancer in the subject, also integrates one or more temporal features related to the diagnosis or treatment of the cancer in the subject, as described above in the section entitled "Temporal features."

In some embodiments, the classification module integrating at least a first set of sequence features comprising relative abundance values for the expression of a plurality of genes and one or more clinical features related to the diagnosis or treatment of the cancer in the subject, also integrates one or more personal characteristics about the subject, as described above in the section entitled "Personal characteristics," and further integrates one or more temporal features related to the diagnosis or treatment of the cancer in the subject, as described above in the section entitled "Temporal features."

In some embodiments, a classification module for predicting metastasis of a cancer in a subject is provided that integrates at least a first set of sequence features comprising relative abundance values for the expression of a plurality of genes, as described above in the section entitled "Sequence features," and one or more temporal features related to the diagnosis or treatment of the cancer in the subject, as described above in the section entitled "Temporal features."

Accordingly, in some embodiments, a method is provided for predicting metastasis of a cancer in a subject that includes (A) obtaining, in electronic format, a plurality of data elements for the subject's cancer comprising (i) a first set of sequence features comprising relative abundance values for the expression of a plurality of genes (e.g., at least 30 genes) in a biopsy of the cancer obtained from the subject, as described above in the section entitled "Sequence features," and (ii) one or more temporal features related to the diagnosis or treatment of the cancer in the subject selected from the group consisting of a first temporal element indicating a duration of time since a diagnosis for the cancer, a second temporal element indicating a duration of time since an administration of a therapy to the subject, a third temporal element indicating a duration of time since an experience of a symptom associated with cancer or metastasis thereof, and a fourth temporal element indicating a duration of time since an experience of a comorbidity with the cancer, as described above in the section entitled "Temporal features," (B) applying, to the plurality of data elements for the subject's cancer, one or more models that are collectively trained to provide a respective one or more indications of whether the cancer will metastasize in the subject, thereby predicting whether the cancer will metastasize, and (C) generating a clinical report comprising the one or more indications of whether the cancer will metastasize. In some embodiments, the method includes, when the one or more indications of whether the cancer will metastasize satisfies a first threshold risk for metastasis of the cancer, administering a first therapy tailored for treatment of metastatic cancer, and when the one or more indications of whether the cancer will metastasize does not satisfy the first threshold risk for metastasis of the cancer, administering a second therapy tailored for treatment of non-metastatic cancer, as described in the above section entitled "Reporting."

In some embodiments, the classification module integrating at least a first set of sequence features comprising relative abundance values for the expression of a plurality of genes and one or more temporal features related to the diagnosis or treatment of the cancer in the subject, also integrates one or more personal characteristics about the subject, as described above in the section entitled "Personal characteristics." In some embodiments, the classification module integrating at least a first set of sequence features comprising relative abundance values for the expression of a plurality of genes and one or more temporal features related to the diagnosis or treatment of the cancer in the subject, also integrates one or more clinical features related to the diagnosis or treatment of the cancer in the subject, as described above in the section entitled "Clinical features."

In some embodiments, the classification module integrating at least a first set of sequence features comprising relative abundance values for the expression of a plurality of genes and one or more temporal features related to the diagnosis or treatment of the cancer in the subject, also integrates one or more personal characteristics about the subject, as described above in the section entitled "Personal characteristics," and further integrates one or more clinical features related to the diagnosis or treatment of the cancer in the subject, as described above in the section entitled "Clinical features."

Specific Embodiments

The following clauses describe specific embodiments of the disclosure.

Clause 1. A method, comprising receiving patient information comprising result of analysis of a first plurality of nucleic acids derived from a somatic specimen and a second plurality of nucleic acids derived from a germline specimen of a plurality of patients; identifying one or more interactions for each of the plurality of patients based at least in part on the received patient information; generating, for one or more targets associated with each interaction of the one or more interactions, one or more timeline metrics identifying whether each of the one or more targets occurs within a time period of an occurrence of the interaction; determining, for each timeline metric of the one or more timeline metrics, a probability that a patient will be associated with one or more status characteristics within the time period; training a target prediction model for each of the one or more targets based at least in part on the one or more status characteristics thereby generating a plurality of trained target prediction models; and associating predictions for each patient, wherein the predictions are generated by the target prediction model for each of the one or more targets, with a respective timeline metric from the one or more timeline metrics.

Clause 2. The method of clause 1, further comprising rendering, on a graphical user interface of a computing device, a representation of the predictions in association with the respective timeline metric.

Clause 3. The method of clause 1, further comprising receiving second information associated with a new patient; identifying at least one interaction from the second information; selecting a target prediction model from the plurality of trained target prediction models based on a type of the received second information; and applying the selected target prediction model to the second information to generate predictions for each target from the one or more targets, wherein each target corresponds to an interaction from the at least one interaction, and wherein each target is associated with a timeline metric from the one or more timeline metrics.

Clause 4. The method of clause 3, further comprising rendering, on a graphical user interface of a computing device, a representation of the predictions for each target in association with the respective timeline metric.

Clause 5. The method of any one of clauses 1 to 4, wherein the patient information includes information acquired from an electronic medical record (EMR) and/or free-text progress notes for each patient.

Clause 6. The method of any one of clauses 1 to 5, wherein the patient information includes one or more of clinical information, information obtained using immunohistochemistry (IHC), and information obtained using fluorescence in situ hybridization (FISH).

Clause 7. The method of any one of clauses 1 to 5, wherein the patient information includes one or more of clinical information, information obtained from pathology reports, and information obtained from radiology reports.

Clause 8. The method of any one of clauses 1 to 7, wherein the one or more targets comprise one or more of metastasis to an organ of the patient, a measure of cancer progression in the patient, cancer local recurrence in the patient, and cancer regional recurrence in the patient.

Clause 9. The method of any one of clauses 1 to 8, wherein the organ is the brain, lung, breast, liver, pancreas, colon, skin, lymph nodes, and bones.

Clause 10. The method of any one of clauses 1 to 9, wherein the time period is measured in days, month, or years.

Clause 11. The method of any one of clauses 1 to 10, wherein the one or more interactions comprise a record from a patient's medical history, a record of a diagnosis, a record of a prescribed medication, a record of a taken medication, a record of an administered treatment, a record of a cancer progression, a record of a cancer recurrence, a record of a cancer localized metastasis, a record of a genetic sequencing, or a record of a digital image acquisition.

Clause 12. The method of clause 11, wherein the record of the administered treatment comprises a record of one or more of surgery, therapy, or procedure.

Clause 13. The method of clause 11, wherein the record of the digital image acquisition is information obtained from an H&E slide, IHC slide, or a radiology image.

Clause 14. The method of any one of clauses 1 to 13, wherein the one or more status characteristics comprise a prior occurrence of an interaction or a prior result of a laboratory test.

Clause 15. The method of any one of clauses 1 to 14, wherein the one or more status characteristics are measured as a time since occurrence of one or more prior interaction.

Clause 16. The method of any one of clauses 1 to 15, wherein the patient is a cancer patient.

Clause 17. The method of clause 16, wherein the cancer comprises adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

Clause 18. The method of any one of clauses 1 to 17, further comprising automatically generating an electronic report including the predictions generated for the one or more targets, and respective timeline metrics.

Clause 19. The method of clause 18, comprising transmitting the electronic report to a user over a computer network in real time, so that the user has immediate access to the electronic report.

Clause 20. The method of any one of clauses 1 to 17, further comprising receiving an anchor point; identifying one or more subsets of patients from the plurality of patients for which targets associated with respective predictions, at the anchor point, deviate from observed target occurrence for a control cohort of patients; and automatically generating an electronic report indicating a likelihood of a patient, from the one or more subsets of patients, experiencing metastasis to one or more organs.

Clause 21. The method of clause 20, wherein the anchor point is an occurrence of next generation genetic sequencing of the patient's tumor.

Clause 22. The method of clause 21, wherein the next generation genetic sequencing of the patient's tumor includes tumor-normal matched sequencing, full transcriptome sequencing, tumor-only sequencing, or cell-free DNA sequencing of the patient's blood.

Clause 23. The method of clause 18 or 20, wherein the electronic report is generated as part of a precision medicine result delivery for the patient.

Clause 24. The method of clause 18 or 20, wherein the electronic report comprises a recommendation to a physician to treat the patient using a treatment that correlates with a magnitude of a determined degree of risk of the metastasis.

Clause 25. The method of clause 18 or 20, wherein the electronic report comprises a recommendation to a physician to select a treatment which provides adjustments to a typical monitoring including one or more of scanning, imaging, and blood testing.

Clause 26. The method of clause 18 or 20, wherein the electronic report comprises a recommendation of accelerated screening.

Clause 27. The method of any one of clauses 1 to 26, wherein the method operates as part of a digital and laboratory health care platform.

Clause 28. The method of clause 27, wherein the digital and laboratory health care platform generates a molecular report as part of a targeted medical care precision medicine treatment.

Clause 29. The method of any one of clauses 1 to 26, wherein the method operates on one or more micro-services.

Clause 30. The method of any one of clauses 1 to 26, wherein the method is performed in conjunction with one or more micro-services of an order management system.

Clause 31. The method of any one of clauses 1 to 26, wherein the method is performed in conjunction with one or more micro-services of a cell-type profiling service.

Clause 32. The method of any one of clauses 1 to 26, wherein the method is performed in conjunction with a variant calling engine and/or an insight engine.

Clause 33. The method of any one of clauses 1 to 32, wherein the one or more status characteristics comprise a plurality of features.

Clause 34. The method of clause 33, comprising applying a dimensionality reduction algorithm to the plurality of features to generate a reduced set of a plurality of features.

Clause 35. The method of any one of clauses 1 to 32, wherein the patient information comprises a plurality of patient features.

Clause 36. The method of clause 33, comprising applying a dimensionality reduction algorithm to the plurality of patient features to generate a reduced set of a plurality of features.

Clause 37. The method of clause 34 or 36, wherein the dimensionality reduction algorithm comprises a supervised algorithm.

Clause 38. The method of clause 37, wherein the supervised algorithm comprises one or more of Linear Discriminant Analysis, Neighborhood Component Analysis, MLP transfer learning, and tree-based supervised embedding.

Clause 39. The method of clause 34 or 36, wherein the dimensionality reduction algorithm comprises an unsupervised algorithm.

Clause 40. The method of clause 39, wherein the unsupervised algorithm comprises one or more of an RNA Variational Auto-encoder, Singular Value Decomposition (SVD), PCA, KernelPCA, SparsePCA, DictionaryLearning, Isomap, Nonnegative Matrix Factorization (NMF), Uniform Manifold Approximation and Projection (UMAP), feature agglomeration, patient correlation clustering, KMeans, Gaussian Mixture, and Spherical KMeans.

Clause 41. The method of any one of clauses 33 to 40, wherein at least some of the plurality of features and the plurality of patient features are used in training the target prediction model to generate the plurality of trained target prediction models.

Clause 42. The method of any one of clauses 1 to 41, wherein information on the first plurality of nucleic acids is obtained from a corresponding plurality of sequence reads derived from a respective patient sample by targeted or whole transcriptome RNA sequencing.

Clause 43. The method of any one of clauses 1 to 42, wherein information on the second plurality of nucleic acids is obtained from a corresponding plurality of sequence reads derived from a respective patient sample by targeted or whole transcriptome RNA sequencing.

Clause 44. The method of clause 42 or clause 43, wherein the whole transcriptome sequencing comprises next-generation sequencing.

Clause 45. A method of any one of clauses 33 to 44, comprising displaying, at least in part, the predictions on a graphical user interface of a computing device.

Clause 46. The method of clause 45, wherein the predictions are displayed on the graphical user interface in association with information on at least some features from the plurality of features and/or the plurality of patient features.

Clause 47. The method of clause 46, comprising receiving, via the graphical user interface, a request to display ranking information associated with the at least some features, the ranking information comprising a score associated with each feature of the at least some features.

Clause 48. The method of clause 47, wherein the request comprises a threshold for scores associated with the features of the at least some features, and wherein the method comprises displaying the information on the at least some features based on the threshold.

Clause 49. The method of clause 48, wherein the information on the at least some features comprises information on most influential genes and/or transcripts selected from the first plurality of nucleic acids and/or the second plurality of nucleic acids.

EXAMPLES

Example 1—Leave-One-Out Modeling Pipeline

Metastasis models were trained for each training subject in a training cohort of 162 subjects with available whole exome expression data. Briefly, the data from a single patient was removed from the training cohort and a model was fit. The process was then repeated for all the patients within the cohort. The results of this is the establishment of one model for every patient in the training cohort, and one prediction for every patient in the training cohort. A Cox's proportional hazard model (CoxPHFitter) was used in a grid search searching over a set of parameters for the model with the best concordance index scores.

Briefly, RNA expression data was normalized to transcripts per million (TPM) for all genes. The top 500 most correlated genes were then identified for each training run by Spearman Rank correlation. Singular Value Decomposition (SVD) was then performed for each training run, using the identified set of 500 genes. From the resulting SVD matrix, the first 40 components (columns) were then used as features in the model.

From the 162 runs of the training pipeline (one for each subject in the training cohort), the total number of times each gene was identified in the top 500 most correlated genes was determined. Table 2 lists those genes that were identified in the top 500 genes for at least 80 of the 162 training runs.

TABLE 2

Most frequently identified genes, listed from most commonly identified to least commonly identified (column 1 = most frequently identified; column 5 = least frequently identified).

| Column 1 | Column 2 | Column 3 | Column 4 | Column 5 |
|---|---|---|---|---|
| IGF1R | TM2D1 | RNF130 | C10orf32 | NDUFB8 |
| ELOVL1 | C17orf49 | ARHGAP6 | YY1AP1 | TSG101 |
| ACP2 | PGAM1 | C5orf22 | LAPTM4A | TMCO1 |
| NDUFA7 | SAMD13 | CREB3 | CHI3L1 | CCND3 |
| MT2A | ENSG00000272617 | MTFP1 | PRKAA2 | NELFCD |
| CRIP2 | NQO2 | IGFN1 | NDUFV2 | MANF |
| ZNHIT1 | NIPSNAP3A | TMEM185A | DNAJC15 | SLC46A3 |
| ATOX1 | CD63 | FAM118A | HCST | GHRL |
| GBA | NINJ1 | LILRA6 | RTN3 | CYBA |
| PEF1 | CD151 | COX7B | TIMM21 | ABHD1 |
| DHX37 | HLA-DPA1 | CBWD2 | COPS8 | HIST1H1C |
| POLR2L | TIMMDC1 | SCAMP4 | USMG5 | BCL2 |
| PHPT1 | CAP1 | NFXL1 | ISCA2 | SKP1 |
| ARF1 | APOBR | UMPS | DHFR | UBE2D1 |
| MPC1 | MLANA | C3orf35 | DNAJA2 | ZNF619 |
| YARS | NOMO3 | YIPF3 | NGRN | PSPC1 |
| SEC61B | TMEM258 | IFI30 | RNF181 | APPBP2 |
| GPR108 | MTRNR2L9 | ATP8B1 | ACTR1A | RAB10 |
| TPP1 | PDE6G | CLTCL1 | UBL5 | CMTM6 |
| SERHL2 | MRPL23 | BTF3L4 | OR2T5 | PCGF6 |
| TMX1 | FUCA1 | S100A1 | A3GALT2 | OR51S1 |
| CHRNG | NDUFB1 | CEPT1 | EIF2B5 | HSD11B1 |
| CD4 | UBE2L6 | LMF2 | OR4F4 | C9orf78 |
| DPAGT1 | TLN2 | OR52D1 | GABARAP | FLRT1 |
| ZMAT2 | MAP4K3 | FAM180B | PEX16 | CHAD |
| TAF10 | TMEM107 | C1orf85 | HPD | NPRL2 |
| RPS19BP1 | INO80 | C2orf76 | ANKRD61 | SCARF1 |
| TUBA3E | MRPL40 | APOBEC3C | SPCS3 | HGD |
| KRTCAP2 | WBSCR22 | MRO | CTPS1 | HIST2H2AA3 |
| PEBP1 | B3GAT3 | SCAMP3 | RNF17 | IFLTD1 |
| ARIH1 | CCDC36 | PPARG | PHC2 | GEMIN2 |
| RBFOX2 | TTC3 | MFSD1 | C1orf50 | ZNF146 |
| TMBIM6 | SLC38A2 | RPL41 | SF3A3 | GPR64 |
| PIN1 | SHISA4 | AKAP13 | CENPA | GNPTG |
| TMED9 | TRIM17 | TMX2 | PHKG1 | WDR13 |
| IFRD2 | CATSPERG | LYPLA2 | BECN1 | POLD4 |

TABLE 2-continued

Most frequently identified genes, listed from most commonly identified to least commonly identified (column 1 = most frequently identified; column 5 = least frequently identified).

| Column 1 | Column 2 | Column 3 | Column 4 | Column 5 |
|---|---|---|---|---|
| NDUFS2 | S100A11 | SERPINB6 | TUBA3C | MLF2 |
| INIP | CCL4L2 | C7orf55 | MRPL27 | ARRDC4 |
| CDK5RAP3 | NDUFC2 | HYPK | CCNH | RIMBP3 |
| SDHB | DERL2 | MT1X | IL10RB | RPS10 |
| XPNPEP1 | GNS | SRGN | TSEN15 | NEU4 |
| HSPB11 | RNF121 | PABPC1 | LSM2 | ZSWIM7 |
| C18orf32 | GSTP1 | ZBTB8OS | DHRS7B | LILRB1 |
| MRPL38 | DNAJC1 | ENSG00000268643 | MAN2A2 | ARF5 |
| SRSF3 | MTRNR2L10 | AP1S1 | CCDC53 | SV2A |
| SCPEP1 | RNF220 | ANKRD24 | HEXA | PLD3 |
| DXO | UROD | VKORC1 | PHYKPL | LRRC34 |
| RGS14 | PIGK | CYB5R1 | EFCAB3 | POPDC3 |
| CD40 | VMA21 | SYNGR4 | SOX2 | LMBRD1 |
| TNFSF12 | DRAP1 | NDUFS3 | SNAPC5 | ENSG00000269871 |
| OR52B6 | DDX41 | PTRH1 | CNPY2 | HDDC3 |
| IER3IP1 | CCNDBP1 | LPCAT3 | FSCN2 | PRPF39 |
| FANCG | SLC25A35 | RFXANK | OPCML | FIS1 |
| RPA2 | SPRY2 | UBR7 | TMEM179B | CPNE1 |
| SOSTDC1 | ENSG00000206044 | URI1 | COQ10A | NDFIP1 |
| PSMG4 | YPEL5 | HPR | EMD | NKAIN1 |
| CUTA | MUM1L1 | TSPAN9 | SF3B6 | CUEDC2 |
| DHRS1 | NDUFS7 | CHRNB1 | TRAK1 | MRPL33 |
| HSPA1A | SATB1 | NUTM2G | SSX2 | CHURC1 |
| HM13 | RUVBL2 | CEBPA | AGAP9 | PRDX1 |
| C15orf38 | LRTOMT | CTSA | PTTG1 | MIF |
| CA5B | UIMC1 | DDX54 | RAB4B | FPGT |
| ENSG00000267954 | C9orf89 | TRAPPC1 | FPR1 | PLEKHG4 |
| UQCRC1 | ALKBH4 | BBS4 | APOC2 | HPSE |
| SPCS1 | DEPDC7 | NEDD8 | KPTN | ASB1 |
| PEMT | TRIT1 | PIGY | NMT1 | GADD45A |
| C19orf68 | C9orf16 | TUBB | RAB5B | DBNDD1 |
| POLR3D | H2AFZ | CREBZF | TSSK4 | ZNF774 |
| SLC10A1 | ZMPSTE24 | SC5D | PDZD11 | OCEL1 |
| UQCR11 | CCDC137 | DUSP18 | RBFOX3 | ANXA5 |
| MLXIP | GIMAP5 | MECR | COMMD1 | GSK3A |
| SCP2 | LSM14A | ZNF587B | FCER1G | SCO1 |
| TMEM208 | PSAP | AMT | SNRPC | ATXN2 |
| SYCP3 | HDAC10 | CYSTM1 | ZNF337 | POU5F1 |
| C6orf48 | AGA | COX6A1 | NHP2 | STRA13 |
| HEXB | PRKACB | NDUFS4 | LAMTOR5 | ALKBH6 |
| SRSF2 | MDK | CTSS | A4GNT | FASTKD3 |
| GOLGA6L10 | PHF12 | ATP6V1E1 | ALG3 | PPP2R2D |
| TSC22D2 | ENSG00000260537 | CCL4L1 | HIST2H2AA4 | NUDT13 |
| WDR45B | NPNT | HN1 | PGBD1 | PRDX6 |
| POGLUT1 | EIF5A2 | PFKM | SUMO1 | TMEM45B |
| RABL2A | MRPL22 | DPM3 | HFE | NKD2 |
| RIN3 | SYVN1 | NDUFA4 | MAP4K2 | PGLYRP1 |
| CAPZA1 | TMEM41B | CCL3 | WLS | SFN |
| EIF3I | MRPS36 | PRICKLE4 | COMMD9 | LRP6 |
| ATP2A1 | TBC1D3G | WIBG | ARHGEF35 | DAPK2 |
| NPC2 | MAGOH | NRM | FBN3 | FADS2 |
| HMGN2 | RNASEK | MOB1A | RTN4RL2 | C8orf76 |
| RBX1 | CKLF | POLR2J | ZNF462 | TXNDC9 |
| AMELX | PFDN6 | NATI | CPA2 | BYSL |
| SPRED1 | CNDP2 | MRPS7 | JKAMP | ENSG00000260342 |
| DCAF7 | HOXB7 | ICAM2 | DAD1 | RAB17 |
| CD82 | TTC4 | HIST1H2BC | ZACN | PSMB2 |
| SLC35B1 | GSTM4 | ZNF259 | TRIM2 | EDRF1 |
| GALNS | C6orf226 | SSBP1 | ATG4A | PLEKHO1 |
| MAN1B1 | POP5 | CCL4 | KLRC4 | TIMM23 |
| MCCC1 | SLC31A1 | UBE2E1 | HINT1 | CXCL3 |
| CCL26 | ERP44 | SOWAHC | ARHGAP28 | ENTPD3 |
| GNB2L1 | MR1 | HLA-DPB1 | NKG7 | VAMP5 |
| C5orf15 | CTSD | EMC6 | ATF4 | SNRNP25 |

Example 2—RNA Expression-Based Predication Model for Metastasis of Colorectal Cancer RNA expression data obtained from tumor samples from 317 subjects with colorectal cancer was used to train a Cox Proportional Hazard model for time without metastasis of the cancer. Briefly, the inclusion criteria for selection of the training subjects was: the subject had a primary colorectal cancer diagnosis, RNA sequence data from tissue collected from the primary colorectal tumor was available, the primary colorectal cancer was not a recurrence, subjects with positive margins were excluded, subjects with metastases recorded within 30 days of sample collection were excluded, subjects staged with stage 4 cancer were excluded, patients without evidence of future metastasis must have at least two years of follow-up medical records available, and fresh-frozen tissue samples were excluded.

Briefly, a Cox Proportional Hazard model was trained by regression. RNA expression features were prepared by log-transforming expression data from each tumor sample according to log(RNA+1). Zero variance columns of the RNA expression data were dropped. Features were cross-validated by dropping the lowest quartile of variance columns, keeping the top 100 features most correlated (Spearman) with metastasis, and standard scaling. Stratified K-fold feature selection was performed using 5-folds. Hyperparameters of the model were searched via grid search of a spline space defined as [0.2, 0.02, 0.002, 0.0002]. Model performance was evaluated by repeated stratified k-fold cross-validation using 10-folds repeated 10 times. A brief summary of model training is shown below:

Model description:
CV framework:
    Model Performance Evaluation:
        RepeatedStratifiedKFold, 10 Folds, 10 Times.
    Feature Selection:
        StratifiedKFold, 5 Folds
Feature Generation
    Overall
        Drop Zero Variance Columns, log(RNA+1) Transform
    Cross-Validated:
        Drop Lowest Quartile of Variance Columns
        Keep Top 100 Features Most correlated (Spearman) with metastasis,
        Standard Scaling
Model type: Cox Proportional Hazard Regression
Hyperparameter search method and space
    Method: Grid Search
    Space: Spline=[0.2, 0.02, 0.002, 0.0002]

Figure 19A:
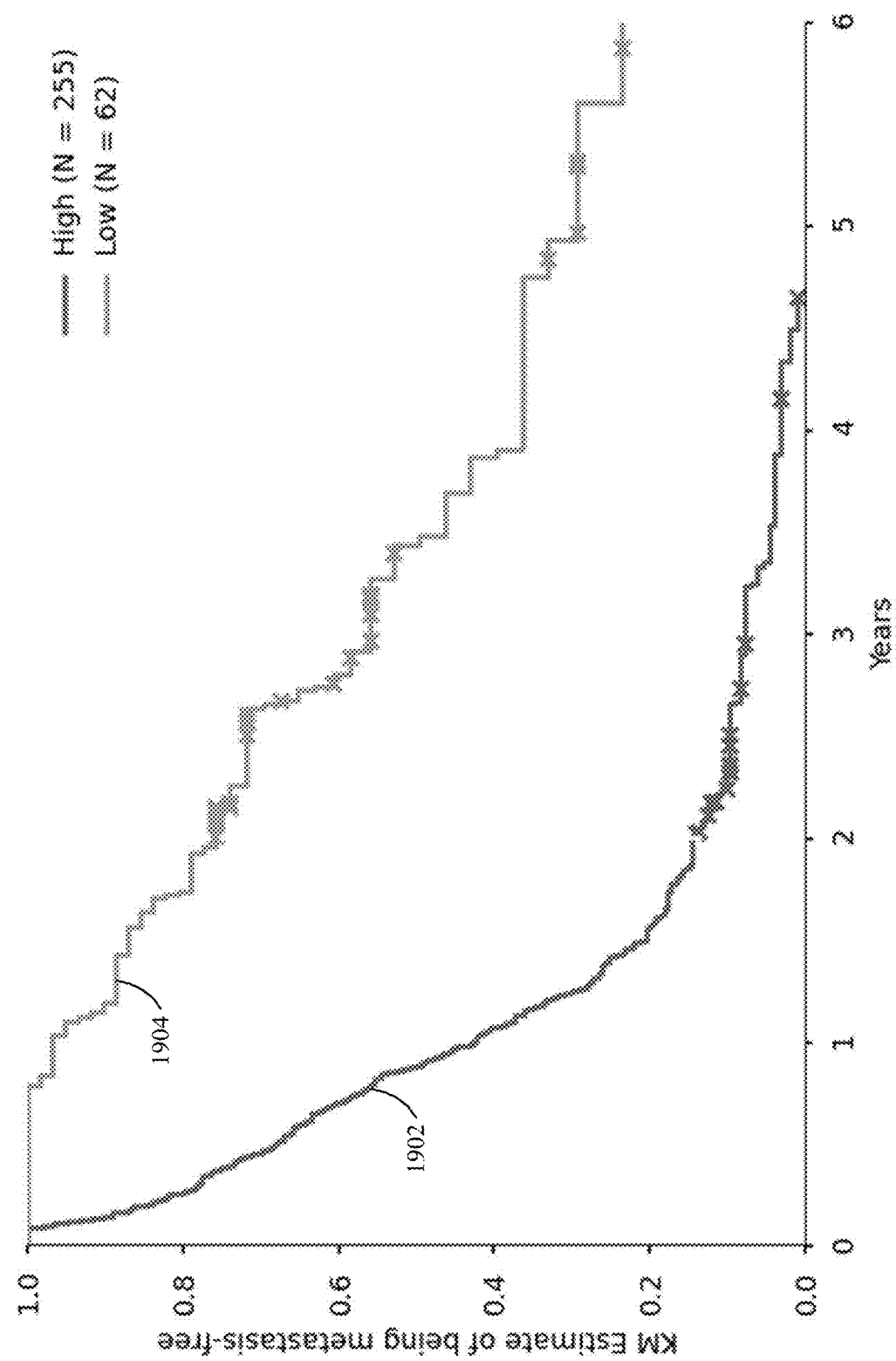
FIG. 19A illustrates survival curves of a survival model showing predicted metastasis-free survival for high-risk patients (1902) and low-risk patients (1904), in accordance with some embodiments of the present disclosure.

Survival curves of the model showing predicted metastasis-free survival for high-risk patients (1902) and low-risk patients (1904) are illustrated in FIG. 19A. The hazard ratio comparing the predicted high-risk group to the low-risk group is 5.3 (3.73-8.17).

Figure 19B:
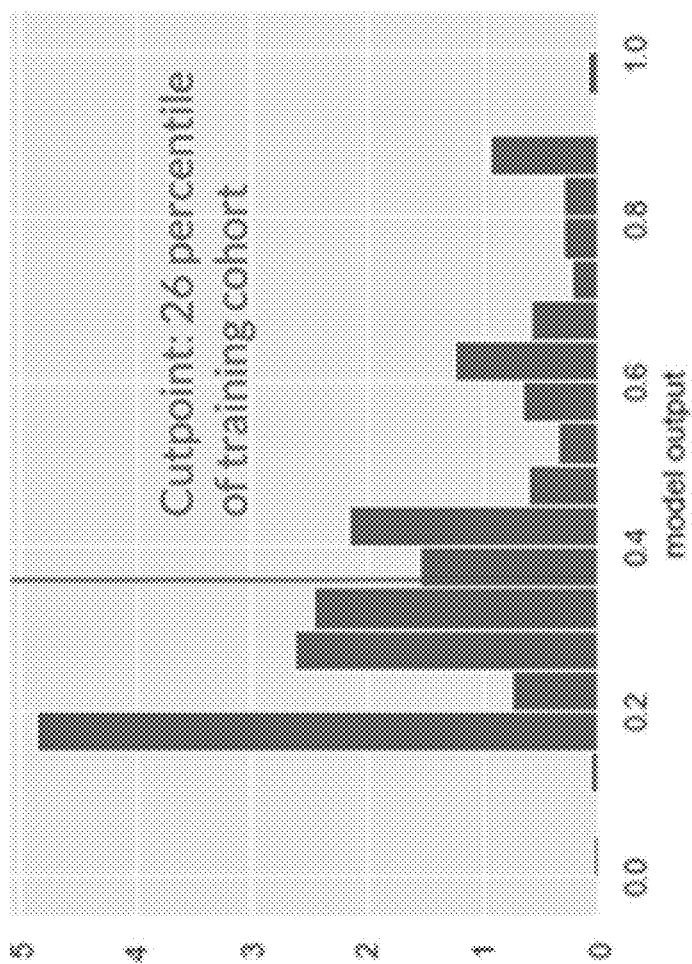
FIG. 19B illustrates a histogram of model scores output from an entire training cohort, in accordance with some embodiments of the present disclosure.

The risk status for a patient was determined using a risk score threshold, which can be selected between 0% and 100% of the total possible model output (e.g., 0 to 1 for a model in which 1 represents 100% chance of metastasis). In this example, the risk threshold was determined by using the percentile from ranked predictions that corresponds to the metastasis rate of the training cohort. That is, if 74% of patients in the cohort experienced metastasis, the risk threshold is set as the predicted probability at the $26^{th}$ percentile. For instance, FIG. 19B illustrates a histogram of model scores output from an entire training cohort in which 74% of the training subjects experienced metastasis. The model score at the $26^{th}$ percentile (between 0.3 and 0.4) is set as the risk threshold.

Example 3—Prediction Model for Metastasis of Colon and Rectosigmoid Junction Cancers RNA expression data obtained from tumor samples from 173 subjects with colon or rectosigmoid junction cancer was used to train a Cox Proportional Hazard model for time without metastasis of the cancer. Briefly, the inclusion criteria for selection of the training subjects was: the subject had a primary colon or rectosigmoid junction cancer diagnosis, RNA sequence data from tissue collected from the primary colorectal tumor was available, the primary colorectal cancer was not a recurrence, subjects with positive margins were excluded, subjects with metastases recorded within 30 days of sample collection were excluded, subjects staged with stage 4 cancer were excluded, patients without evidence of future metastasis must have at least two years of follow-up medical records available from members of the subject's cancer treatment team, fresh-frozen tissue samples were excluded, subjects staged with stage 1 cancer were excluded, non-adenocarcinomas were excluded, samples taken from biopsies were excluded (only samples obtained from resections were used), subjects with metastases recorded within 90 days of sample collection or who were determined to be likely metastatic at the time of sample collection were excluded, and subjects undergoing systematic treatment for an additional primary cancer within two years of the colon cancer diagnosis were excluded.

Metastasis models were trained for each training subject in a training cohort of 162 subjects with available whole exome expression data. Briefly, the data from a single patient was removed from the training cohort and a model was fit. The process was then repeated for all the patients within the cohort. The results of this is the establishment of one model for every patient in the training cohort, and one prediction for every patient in the training cohort. A Cox's proportional hazard model (CoxPHFitter) was used in a grid search searching over a set of parameters for the model with the best concordance index scores.

Figure 20:
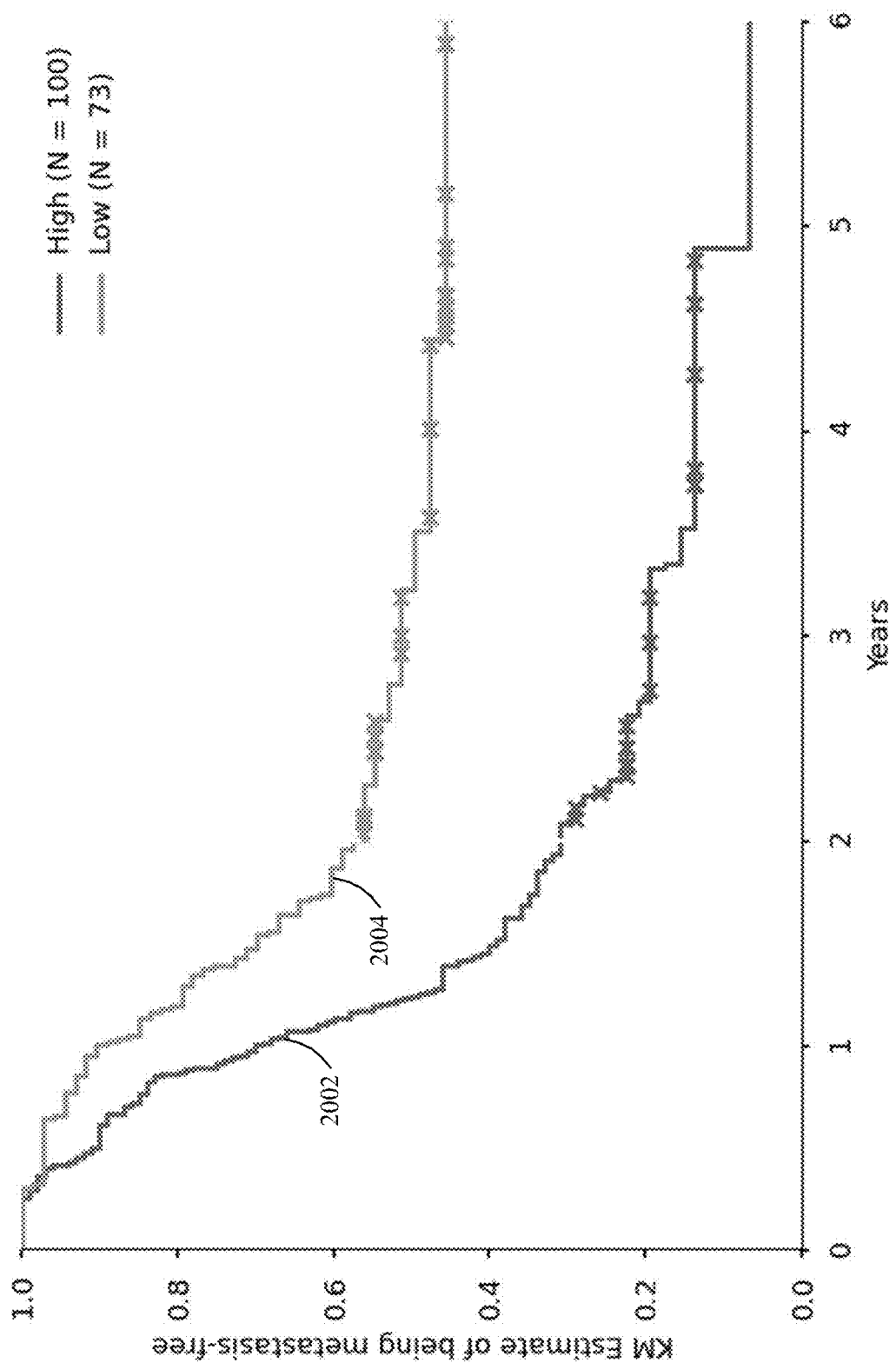
FIG. 20 illustrates survival curves of a survival model showing predicted metastasis-free survival for high-risk patients (2002) and low-risk patients (2004), in accordance with some embodiments of the present disclosure.

Briefly, RNA expression data was normalized to transcripts per million (TPM) for all genes. The top 500 most correlated genes were then identified for each training run by Spearman Rank correlation. Singular Value Decomposition (SVD) was then performed for each training run, using the identified set of 500 genes. From the resulting SVD matrix, the first 40 components (columns) were then used as features in the model. A brief summary of model training is shown below:

Model Description:
CV framework:
    Model Performance Evaluation:
        LeaveOneOut: 173 Splits
    Feature Selection:
        SurvivalSplitter, 5 Splits
Feature Generation:
    Overall:
        Drop Column with Zero Variance
    Cross-Validated
        Drop Lowest Quartile of Variance Columns
        Keep Top 500 Features Most correlated (Spearman) with metastasis
        Feature Space
        StandScaler
        Singular Value Decomposition, Keeping First 40 Columns
        StandardScaler
Model type:
    Cox Proportional Hazard Regression
Hyperparameter search method and space:
    None Survival curves of the model showing predicted metastasis-free survival for high-risk patients (2002) and low-risk patients (2004) are illustrated in FIG. 20. The hazard ratio comparing the predicted high-risk group to the low-risk group is 2.58 (1.74-3.82).

The risk status for a patient was determined using a risk score threshold, which can be selected between 0% and 100% of the total possible model output (e.g., 0 to 1 for a model in which 1 represents 100% chance of metastasis). In this example, the risk threshold was determined by using the percentile from ranked predictions that corresponds to the metastasis rate of the training cohort. That is, if 74% of patients in the cohort experienced metastasis, the risk threshold is set as the predicted probability at the $26^{th}$ percentile. For instance, FIG. 19B illustrates a histogram of model scores output from an entire training cohort in which 74% of the training subjects experienced metastasis. The model score at the $26^{th}$ percentile (between 0.3 and 0.4) is set as the risk threshold.

From the 173 runs of the training pipeline (one for each subject in the training cohort), the total number of times each gene was identified in the top 500 most correlated genes was determined. Table 3 lists all the genes identified in the top 500 most correlated genes and denotes how many times the gene was identified in that list.

TABLE 3

Frequency of genes appearing in the top 500 most correlated genes.

| Gene Name | #of times used | Gene Name | #of times used | Gene Name | #of times used | Gene Name | #of times used | Gene Name | #of times used |
|---|---|---|---|---|---|---|---|---|---|
| MBNL2 | 173 | GJC3 | 173 | TUBGCP3 | 162 | SCPEP1 | 12 | CSDC2 | 1 |
| NAPB | 173 | GLIPR2 | 173 | CSNK2A2 | 162 | ETFDH | 12 | IGSF3 | 1 |
| C1orf111 | 173 | CDX2 | 173 | KDELR3 | 162 | EMR2 | 12 | LACTB | 1 |
| MPZL3 | 173 | GNS | 173 | RAC3 | 162 | MAMSTR | 12 | ARRB2 | 1 |
| MR1 | 173 | GOLGA6L2 | 173 | SH3D19 | 160 | GAD1 | 12 | CRLS1 | 1 |
| MROH5 | 173 | GPR143 | 173 | RILP | 160 | GPR183 | 12 | RAB27B | 1 |
| MRPL22 | 173 | SCG5 | 173 | BLVRB | 160 | ZNF251 | 12 | ATP4B | 1 |
| MT1X | 173 | BSG | 173 | LRRC71 | 159 | MYOM3 | 12 | PILRA | 1 |
| MT2A | 173 | STARD13 | 173 | AK1 | 159 | HVCN1 | 11 | PHOSPHO2 | 1 |
| MTHFS | 173 | ACADSB | 173 | VAMP5 | 159 | TMEM150B | 11 | PEX5 | 1 |
| C1QBP | 173 | YAP1 | 173 | CD59 | 158 | LGMN | 11 | PARP2 | 1 |
| NAA16 | 173 | WNT11 | 173 | NCOA6 | 158 | DENND2D | 11 | BRCA2 | 1 |
| NAPG | 173 | STK24 | 173 | HLA-G | 158 | IF135 | 11 | OVGP1 | 1 |
| MPHOSPH8 | 173 | STK35 | 173 | AQP12B | 158 | KANK1 | 11 | NUDT6 | 1 |
| C19orf80 | 173 | STMND1 | 173 | ZMYM2 | 157 | FXYD7 | 11 | NQO2 | 1 |
| NCF1 | 173 | STON2 | 173 | NCF2 | 157 | FBF1 | 11 | LGALS9 | 1 |
| C15orf65 | 173 | WDR76 | 173 | SOX14 | 157 | FAM186A | 11 | NARS | 1 |
| NDFIP2 | 173 | SYNJ2 | 173 | PAGE2B | 157 | SYCE2 | 11 | MRAP | 1 |
| NEURL1B | 173 | TCN1 | 173 | ABHD6 | 157 | EPHA8 | 11 | MPI | 1 |
| NKD2 | 173 | SYNPR | 173 | IFNA1 | 156 | GAPDHS | 11 | MERTK | 1 |
| NKG7 | 173 | VWA8 | 173 | OSCP1 | 156 | IVD | 10 | ZSWIM4 | 1 |
| NLRP11 | 173 | TAF4 | 173 | FAM211B | 156 | HAL | 10 | MAPRE3 | 1 |
| NR1I2 | 173 | AIRE | 173 | SFXN1 | 155 | URGCP | 10 | LUC7L | 1 |
| C11orf84 | 173 | TASP1 | 173 | GPR18 | 155 | CHD7 | 10 | LRRN3 | 1 |
| C1orf85 | 173 | TBC1D4 | 173 | HEATR6 | 154 | ZKSCAN1 | 10 | LRRC16B | 1 |
| MPDU1 | 173 | TCF20 | 173 | SPIRE2 | 154 | BPHL | 9 | ZSWIM7 | 1 |
| NRP1 | 173 | SSUH2 | 173 | DCUN1D2 | 154 | RPS7 | 9 | | |
| LRCH1 | 173 | AKR1B1 | 173 | DYX1C1 | 153 | KPTN | 9 | | |
| CARS2 | 173 | ALDH3A2 | 173 | ZNF852 | 152 | BRI3 | 9 | | |
| CARKD | 173 | SPRY2 | 173 | KLRD1 | 152 | SYT7 | 9 | | |
| LGALS3BP | 173 | SLC9A7 | 173 | CPSF4L | 152 | ZNF287 | 9 | | |
| LHPP | 173 | ZNF133 | 173 | TEX9 | 152 | SAT2 | 9 | | |
| LILRA6 | 173 | SLX4IP | 173 | NXPH1 | 152 | CHPT1 | 9 | | |
| LIPA | 173 | ZMYND8 | 173 | MPP3 | 151 | CSNK2A3 | 8 | | |
| LITAF | 173 | ANKRD10 | 173 | CD82 | 151 | SLC39A6 | 8 | | |
| LMAN1 | 173 | SNTB1 | 173 | HDHD2 | 149 | RARG | 8 | | |
| C9orf50 | 173 | SNX32 | 173 | CLDN16 | 148 | GSTM4 | 8 | | |
| C9orf116 | 173 | ALX3 | 173 | CLCF1 | 148 | KNOP1 | 8 | | |
| C8orf33 | 173 | ZIC2 | 173 | CLHC1 | 148 | EID1 | 8 | | |
| MICAL3 | 173 | SP140L | 173 | RPS27L | 148 | MDK | 8 | | |
| LRRTM4 | 173 | ZFHX3 | 173 | N4BP2L2 | 148 | TMEM110 | 8 | | |
| C6orf25 | 173 | SPATA13 | 173 | FAM83C | 148 | LRP6 | 8 | | |
| LY6G6D | 173 | ZC3H13 | 173 | TMCO1 | 147 | MAP2K4 | 8 | | |
| LY6G6F | 173 | ZBTB10 | 173 | SLC39A4 | 146 | TSACC | 8 | | |
| MANBA | 173 | SPIN2B | 173 | RNF113B | 146 | OASL | 7 | | |
| MAPK12 | 173 | AGTRAP | 173 | FPR2 | 145 | HS6ST2 | 7 | | |
| MAZ | 173 | TEAD4 | 173 | ADPRM | 144 | PCDHGA11 | 7 | | |
| C2orf54 | 173 | ZNF263 | 173 | MAP2K3 | 144 | TYROBP | 7 | | |
| C20orf196 | 173 | TNFSF13 | 173 | GLTPD2 | 143 | RCOR2 | 7 | | |
| MEST | 173 | ADNP | 173 | ASPDH | 143 | KRT4 | 7 | | |
| NR6A1 | 173 | TSR1 | 173 | PLEKHG6 | 142 | MIS12 | 7 | | |
| NUTM2B | 173 | TMPRSS11A | 173 | ALDH6A1 | 140 | PGD | 7 | | |
| KSR2 | 173 | ADCY10 | 173 | MYCBP2 | 140 | EPOR | 7 | | |
| ASAH1 | 173 | TMPRSS11D | 173 | CAMKV | 139 | CEL | 6 | | |
| PRSS56 | 173 | TMPRSS6 | 173 | TMCO3 | 139 | RRAD | 6 | | |
| PSAP | 173 | TMTC4 | 173 | FBL | 137 | FAT3 | 6 | | |
| PTAFR | 173 | TNNC2 | 173 | EMR3 | 137 | MACROD1 | 6 | | |
| PTTG2 | 173 | ACP5 | 173 | ZBTB44 | 137 | PNPLA3 | 6 | | |
| QSOX1 | 173 | ADM | 173 | TIMP1 | 136 | MLPH | 6 | | |
| R3HDML | 173 | TSPO2 | 173 | HOXA5 | 135 | MOGAT3 | 6 | | |
| RAB3A | 173 | TRIM13 | 173 | ARL15 | 135 | ARSA | 6 | | |

TABLE 3-continued

Frequency of genes appearing in the top 500 most correlated genes.

| Gene Name | # of times used | Gene Name | # of times used | Gene Name | # of times used | Gene Name | # of times used | Gene Name | # of times used |
|---|---|---|---|---|---|---|---|---|---|
| RALY | 173 | TSPAN7 | 173 | IGFN1 | 134 | CMTM4 | 6 | | |
| ASIP | 173 | TSC22D1 | 173 | SLC30A2 | 133 | OR2A7 | 6 | | |
| RAP2A | 173 | ADCY3 | 173 | SETD6 | 133 | COX7A2 | 5 | | |
| RBM26 | 173 | TSPAN13 | 173 | ADIRF | 133 | C1QC | 5 | | |
| PROM1 | 173 | TTYH1 | 173 | MOCOS | 132 | CD244 | 5 | | |
| RDH10 | 173 | TUBG1 | 173 | HFE | 131 | ANKRD27 | 5 | | |
| RDH11 | 173 | TMEM61 | 173 | ZNF506 | 131 | ASS1 | 5 | | |
| REPS2 | 173 | TMEM254 | 173 | MRPL38 | 130 | A3GALT2 | 5 | | |
| ARID3A | 173 | VKORC1 | 173 | FAM107B | 128 | RPL7 | 5 | | |
| RNF144B | 173 | VAPA | 173 | COL2A1 | 128 | RPS3 | 5 | | |
| ARHGEF35 | 173 | TFDP1 | 173 | RPL3 | 124 | TRIM29 | 5 | | |
| RPA2 | 173 | USP14 | 173 | SMIM14 | 124 | SQRDL | 5 | | |
| RPGR | 173 | ACSL6 | 173 | ANTXR2 | 122 | SRCRB4D | 5 | | |
| RSL1D1 | 173 | ACSS1 | 173 | DBX1 | 121 | SORL1 | 5 | | |
| RTDR1 | 173 | UPF3A | 173 | CRYZ | 120 | LIPM | 5 | | |
| PROSER1 | 173 | UMODL1 | 173 | RNASEH2B | 119 | RBP5 | 5 | | |
| PRLR | 173 | ANXA10 | 173 | SOX4 | 119 | SOAT1 | 5 | | |
| CPNE6 | 173 | ULK2 | 173 | TOR1B | 119 | PPP1R32 | 5 | | |
| PFKP | 173 | TMEM139 | 173 | CTH | 118 | FGFR2 | 5 | | |
| OTX1 | 173 | UFM1 | 173 | YIPF1 | 118 | OSBPL2 | 5 | | |
| P2RX4 | 173 | TMEM178A | 173 | NT5M | 116 | FAM101A | 5 | | |
| PABPC3 | 173 | AGA | 173 | URB1 | 113 | HMGCL | 5 | | |
| PAPD5 | 173 | TXNDC17 | 173 | TPP1 | 113 | FAM162A | 5 | | |
| PBX2 | 173 | ZNF232 | 173 | ARHGEF19 | 113 | PLA2G4A | 4 | | |
| PCCB | 173 | TSPAN12 | 173 | PSMG2 | 110 | CD27 | 4 | | |
| PCID2 | 173 | SESN1 | 173 | ZNF730 | 109 | HLTF | 4 | | |
| PDIA3 | 173 | ABHD12 | 173 | TCF7 | 107 | NR2E1 | 4 | | |
| PDS5B | 173 | SLC31A1 | 173 | ZFP28 | 107 | TGM1 | 4 | | |
| PEMT | 173 | SLC17A7 | 173 | RNF217 | 105 | MPPE1 | 4 | | |
| BCORL1 | 173 | SLC16A14 | 173 | HNF4A | 104 | MESP2 | 4 | | |
| PRDX3 | 173 | SLC25A35 | 173 | CLCN2 | 103 | CFTR | 4 | | |
| BCL11A | 173 | SHROOM4 | 173 | AGR3 | 101 | SSX4 | 4 | | |
| PIGL | 173 | AADAT | 173 | NEK3 | 97 | PLK5 | 4 | | |
| PKP1 | 173 | ABHD3 | 173 | ATG9B | 96 | RPS10-NUDT3 | 4 | | |
| ATP7B | 173 | SHMT1 | 173 | ALDH1L1 | 82 | FCAMR | 4 | | |
| ATP11A | 173 | ZNF396 | 173 | GMDS | 81 | VMO1 | 4 | | |
| ASXL1 | 173 | SERPINB6 | 173 | ABHD10 | 74 | RPTN | 3 | | |
| POLR1D | 173 | ZNRF2 | 173 | CTTNBP2 | 55 | GJA5 | 3 | | |
| PPP4R1 | 173 | ANO9 | 173 | PSMA5 | 53 | LCP2 | 3 | | |
| PRB1 | 173 | ZNF3 | 173 | HCST | 47 | CNOT1 | 3 | | |
| PRB4 | 173 | SIGLEC11 | 173 | IDH1 | 47 | RBBP8 | 3 | | |
| CASS4 | 173 | SIGLEC8 | 173 | PRRT2 | 46 | KRTAP10-8 | 3 | | |
| CCL26 | 173 | SIM2 | 173 | UBR5 | 45 | RHOC | 3 | | |
| APCDD1L | 173 | FAM151A | 172 | RBBP8NL | 45 | CCR9 | 3 | | |
| ELF3 | 173 | TSPY1 | 172 | FCGR3A | 43 | OCEL1 | 3 | | |
| DNAH6 | 173 | OSBP2 | 172 | ZFC3H1 | 41 | KCNIP2 | 3 | | |
| COBLL1 | 173 | C18orf42 | 172 | MDH1 | 41 | GALK1 | 3 | | |
| DNAJC28 | 173 | SLC25A11 | 172 | ANKRD45 | 40 | ERBB3 | 3 | | |
| DNASE2 | 173 | APOL1 | 172 | SPATA2 | 39 | CYB5D2 | 3 | | |
| DPEP1 | 173 | YWHAE | 172 | NKD1 | 38 | VPS4B | 3 | | |
| DRD2 | 173 | KIAA1279 | 172 | CDCP1 | 38 | PLCH1 | 3 | | |
| DUSP16 | 173 | SYDE2 | 172 | CD74 | 37 | MPL | 3 | | |
| ECI2 | 173 | ZNRF3 | 172 | RPS12 | 36 | TMEM63C | 3 | | |
| CNDP2 | 173 | DUSP8 | 172 | PLA2G12B | 36 | BCL3 | 3 | | |
| EIF5A | 173 | KCTD17 | 172 | TRAF5 | 35 | PMP22 | 3 | | |
| EMP3 | 173 | SERPINB1 | 172 | C3orf33 | 35 | ACVR1B | 3 | | |
| DLX3 | 173 | KCNRG | 172 | ADRBK2 | 35 | TUFT1 | 3 | | |
| ENGASE | 173 | ARHGEF7 | 172 | AKAP1 | 35 | GJC2 | 3 | | |
| CLEC4E | 173 | IZUMO3 | 172 | DOCK8 | 33 | NCK2 | 3 | | |
| F3 | 173 | GRTP1 | 172 | TSC22D4 | 33 | MTIF3 | 2 | | |
| F7 | 173 | MGA | 172 | SECTM1 | 32 | RIIAD1 | 2 | | |
| CLDN7 | 173 | MINK1 | 172 | TLE2 | 30 | RNASET2 | 2 | | |
| FAM57A | 173 | DAPK2 | 172 | RRS1 | 30 | RANBP6 | 2 | | |
| FARP1 | 173 | SLC6A12 | 172 | OR56B4 | 30 | NCKAP5 | 2 | | |
| FBXL3 | 173 | SNX10 | 172 | LMTK2 | 29 | NCOA2 | 2 | | |
| FBXO16 | 173 | SLC35B1 | 172 | NFATC2 | 29 | ASCL5 | 2 | | |
| CITED1 | 173 | FGF3 | 172 | TERT | 29 | SERPINB7 | 2 | | |
| DNAAF3 | 173 | AGR2 | 172 | UGGT2 | 29 | PCDH20 | 2 | | |
| DLEU7 | 173 | RIN2 | 172 | CYP2B6 | 29 | PHKG1 | 2 | | |
| FBXO6 | 173 | CHAD | 172 | NUTM2G | 29 | ANXA5 | 2 | | |
| CUL4A | 173 | SLC50A1 | 172 | PNP | 28 | PLA2G2A | 2 | | |
| CPVL | 173 | DHRS7B | 172 | ABLIM2 | 27 | ATP5A1 | 2 | | |
| CPN1 | 173 | C5orf15 | 172 | CSF1 | 27 | TFAP2A | 2 | | |
| CPD | 173 | HPS4 | 171 | PRSS33 | 27 | SS18 | 2 | | |

TABLE 3-continued

Frequency of genes appearing in the top 500 most correlated genes.

| Gene Name | #of times used | Gene Name | #of times used | Gene Name | #of times used | Gene Name | #of times used | Gene Name | #of times used |
|---|---|---|---|---|---|---|---|---|---|
| CRYBB3 | 173 | HGD | 171 | RBM12B | 27 | TMEM220 | 2 | | |
| CSF3R | 173 | LGR5 | 171 | REG4 | 26 | ZNF614 | 2 | | |
| CTSB | 173 | RNF17 | 171 | LMTK3 | 26 | DIRC2 | 2 | | |
| CTSD | 173 | SLC39A5 | 171 | NDUFC2 | 26 | ZNF326 | 2 | | |
| CTSE | 173 | PRB3 | 171 | SLC6A8 | 25 | ZDHHC20 | 2 | | |
| CTSL | 173 | PAFAH1B1 | 171 | TNNT1 | 25 | WNT10A | 2 | | |
| CTSS | 173 | CPT2 | 171 | MRO | 25 | FBXO41 | 2 | | |
| CXCL16 | 173 | COX10 | 171 | PPARA | 24 | URI1 | 2 | | |
| DIAPH3 | 173 | BEX2 | 171 | GRHL3 | 24 | GEMIN4 | 2 | | |
| CXCR2 | 173 | NUP88 | 171 | THRA | 24 | CDR2 | 2 | | |
| COQ2 | 173 | PCK1 | 171 | CDK18 | 23 | GOLIM4 | 2 | | |
| CYBA | 173 | SCGB2A2 | 171 | RPL14 | 23 | TOP1MT | 2 | | |
| CYP2F1 | 173 | LAMTOR5 | 171 | MYL12A | 23 | GPR182 | 2 | | |
| COPS3 | 173 | MPC1 | 171 | ACO1 | 23 | HAVCR2 | 2 | | |
| CYP4F2 | 173 | CDC16 | 171 | APOO | 22 | MAP7 | 2 | | |
| CYSTM1 | 173 | CCL4L1 | 171 | C1orf195 | 22 | TMEM237 | 2 | | |
| DACH1 | 173 | IGF1R | 171 | TAS2R43 | 22 | LPCAT1 | 2 | | |
| DGKH | 173 | C17orf49 | 171 | TRAF3IP1 | 22 | INTS6 | 2 | | |
| DHRS7 | 173 | S100A6 | 171 | SPDYC | 22 | C7orf55 | 2 | | |
| CHRFAM7A | 173 | ARGLU1 | 171 | BTD | 21 | KLKB1 | 2 | | |
| FCER1G | 173 | OOEP | 171 | ZNF587 | 20 | L3HYPDH | 2 | | |
| KRT40 | 173 | RBM39 | 171 | POU5F1 | 20 | CAMTA2 | 2 | | |
| CD68 | 173 | PLA2G6 | 170 | STAMBPL1 | 20 | TCIRG1 | 2 | | |
| HBEGF | 173 | DHRS12 | 170 | S100A16 | 20 | LPIN2 | 2 | | |
| HINT2 | 173 | DNAJC1 | 170 | SMAD7 | 19 | SKIL | 1 | | |
| CD84 | 173 | FRMD3 | 170 | TFAP4 | 19 | ZSCAN21 | 1 | | |
| HOXA2 | 173 | VPS53 | 170 | NOXO1 | 19 | SYN3 | 1 | | |
| HOXA6 | 173 | SERPINA1 | 170 | RGL4 | 19 | ZNF507 | 1 | | |
| HPSE | 173 | PER2 | 170 | ADAM21 | 19 | TAS2R20 | 1 | | |
| HSPA1A | 173 | KLRF2 | 169 | SCIN | 19 | SPCS1 | 1 | | |
| HSPH1 | 173 | LAG3 | 169 | SDR42E1 | 19 | WARS | 1 | | |
| HUNK | 173 | PPP1R15A | 169 | TMEM102 | 19 | TSEN2 | 1 | | |
| IFI30 | 173 | FER1L5 | 169 | CDHR3 | 18 | UPP1 | 1 | | |
| IHH | 173 | PLD2 | 169 | AZGP1 | 18 | TSPY4 | 1 | | |
| GZF1 | 173 | MUC15 | 168 | SMOX | 18 | SH3BP4 | 1 | | |
| IL1R2 | 173 | WRAP53 | 168 | OSER1 | 18 | RNF6 | 1 | | |
| IL22RA1 | 173 | VSIG10 | 168 | CAMK2D | 17 | SEC61A2 | 1 | | |
| IPO5 | 173 | IGSF22 | 168 | MORN1 | 17 | SMCHD1 | 1 | | |
| IQCG | 173 | ATP6V1B2 | 167 | SRR | 17 | SLC5A6 | 1 | | |
| IZUMO2 | 173 | CRHR2 | 167 | SHROOM2 | 17 | TMEM205 | 1 | | |
| KBTBD6 | 173 | RAP1GAP2 | 167 | C7orf55-LUC7L2 | 17 | SEH1L | 1 | | |
| KIAA0226L | 173 | VNN2 | 166 | AMELX | 16 | AFTPH | 1 | | |
| KIF16B | 173 | DDX60L | 166 | TM4SF19 | 16 | CRB2 | 1 | | |
| CD14 | 173 | C12orf75 | 166 | NES | 16 | BTN2A2 | 1 | | |
| KRT39 | 173 | ZNF551 | 166 | FIGF | 16 | RNF215 | 1 | | |
| H2AFZ | 173 | FRMD1 | 166 | MOCS2 | 16 | CISD1 | 1 | | |
| GRN | 173 | LAPTM5 | 166 | RALGAPA2 | 15 | HNRNPA1L2 | 1 | | |
| FCGR1A | 173 | BTBD18 | 166 | TK2 | 15 | CDADC1 | 1 | | |
| GAS6 | 173 | ZSWIM3 | 165 | MTRF1 | 15 | HIRA | 1 | | |
| FCGR2A | 173 | TPSAB1 | 165 | GTF2IRD1 | 15 | GPR157 | 1 | | |
| FCGR3B | 173 | CTSC | 165 | PALM3 | 15 | GLS | 1 | | |
| FCN3 | 173 | UBE2L6 | 165 | ENG | 15 | GDPD1 | 1 | | |
| FECH | 173 | GPANK1 | 165 | C22orf23 | 15 | FER1L6 | 1 | | |
| FOXH1 | 173 | ZNF48 | 164 | ZNF646 | 15 | FBXO44 | 1 | | |
| FPR1 | 173 | HSD3B7 | 164 | TJP2 | 15 | CHRNG | 1 | | |
| FRRS1 | 173 | MICU1 | 164 | PLCB4 | 14 | CISD2 | 1 | | |
| FTCD | 173 | SUGP2 | 164 | TMEM62 | 14 | KLK8 | 1 | | |
| FUCA1 | 173 | DOCK9 | 164 | TGIF2LX | 14 | FAM25G | 1 | | |
| G6PC3 | 173 | MRPS7 | 164 | CEP76 | 13 | FAM105A | 1 | | |
| GCM2 | 173 | USP54 | 164 | OVOL2 | 13 | ENTPD6 | 1 | | |
| CDHR1 | 173 | RMND5A | 164 | SERPIND1 | 13 | EIF4A1 | 1 | | |
| CEP192 | 173 | P4HB | 164 | LGR6 | 13 | EID3 | 1 | | |
| GDPD5 | 173 | SLC22A3 | 163 | GUCY2C | 13 | DNAJC21 | 1 | | |
| CENPJ | 173 | PABPC1 | 162 | UBOX5 | 13 | CYP4F12 | 1 | | |
| CELA2B | 173 | TMEM211 | 162 | LARP6 | 12 | CXXC5 | 1 | | |

Example 4—Predication Model for Metastasis of Colon and Rectosigmoid Junction Cancers The model presented in Example 3 was prepared using expression data obtained using multiple RNA expression pipelines. To evaluate the results of model training on data obtained using a single RNA expression pipeline, a subset of 106 of the 173 training subjects used in Example 3, for which RNA expression data was generated using the same RNA expression pipeline, was used to train a second model following the same procedure as in Example 3.

Figure 21:
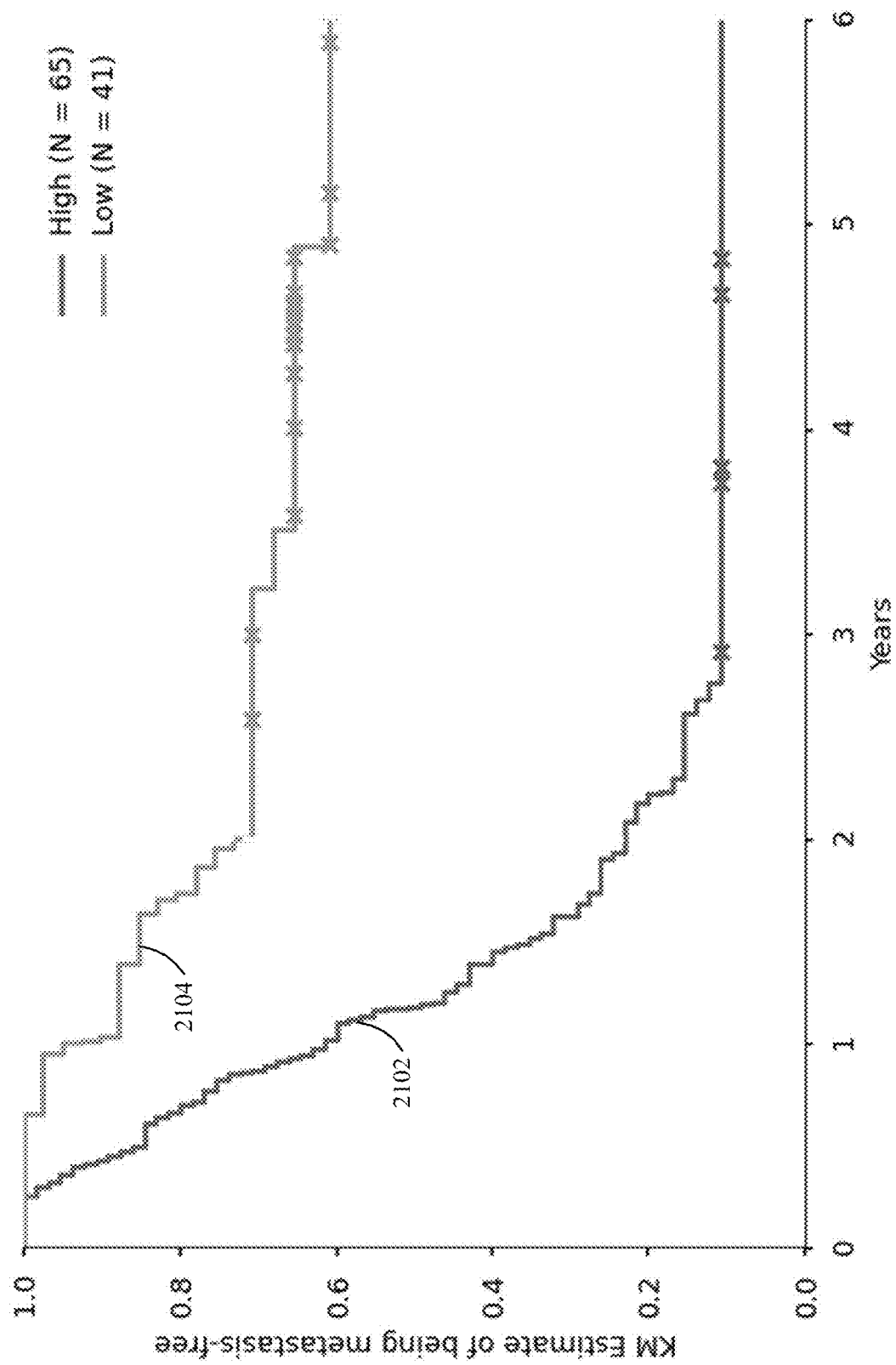
FIG. 21 illustrates survival curves of a survival model showing predicted metastasis-free survival for high-risk patients (2102) and low-risk patients (2104), in accordance with some embodiments of the present disclosure.

Survival curves of the model showing predicted metastasis-free survival for high-risk patients (2102) and low-risk patients (2104) are illustrated in FIG. 21. The hazard ratio comparing the predicted high-risk group to the low-risk group is 5.20 (2.9-9.32).

The risk status for a patient was determined using a risk score threshold, which can be selected between 0% and 100% of the total possible model output (e.g., 0 to 1 for a model in which 1 represents 100% chance of metastasis). In this example, the risk threshold was determined by using the percentile from ranked predictions that corresponds to the metastasis rate of the training cohort. That is, if 74% of patients in the cohort experienced metastasis, the risk threshold is set as the predicted probability at the $26^{th}$ percentile. For instance, FIG. 19B illustrates a histogram of model scores output from an entire training cohort in which 74% of the training subjects experienced metastasis. The model score at the $26^{th}$ percentile (between 0.3 and 0.4) is set as the risk threshold.

Example 5—RNA Expression-Based Predication Model for Metastasis of Colorectal Cancer RNA expression data obtained from tumor samples from 173 subjects with colon or rectosigmoid junction cancer was used to train a Cox Proportional Hazard model for time without metastasis of the cancer. Briefly, the inclusion criteria for selection of the training subjects was: the subject had a primary colon or rectosigmoid junction cancer diagnosis, RNA sequence data from tissue collected from the primary colorectal tumor was available, the primary colorectal cancer was not a recurrence, subjects with positive margins were excluded, subjects with metastases recorded within 30 days of sample collection were excluded, subjects staged with stage 4 cancer were excluded, patients without evidence of future metastasis must have at least two years of follow-up medical records available from members of the subject's cancer treatment team, fresh-frozen tissue samples were excluded, subjects staged with stage 1 cancer were excluded, non-adenocarcinomas were excluded, samples taken from biopsies were excluded (only samples obtained from resections were used), subjects with metastases recorded within 90 days of sample collection or who were determined to be likely metastatic at the time of sample collection were excluded, and subjects undergoing systematic treatment for an additional primary cancer within two years of the colon cancer diagnosis were excluded.

Figure 22:
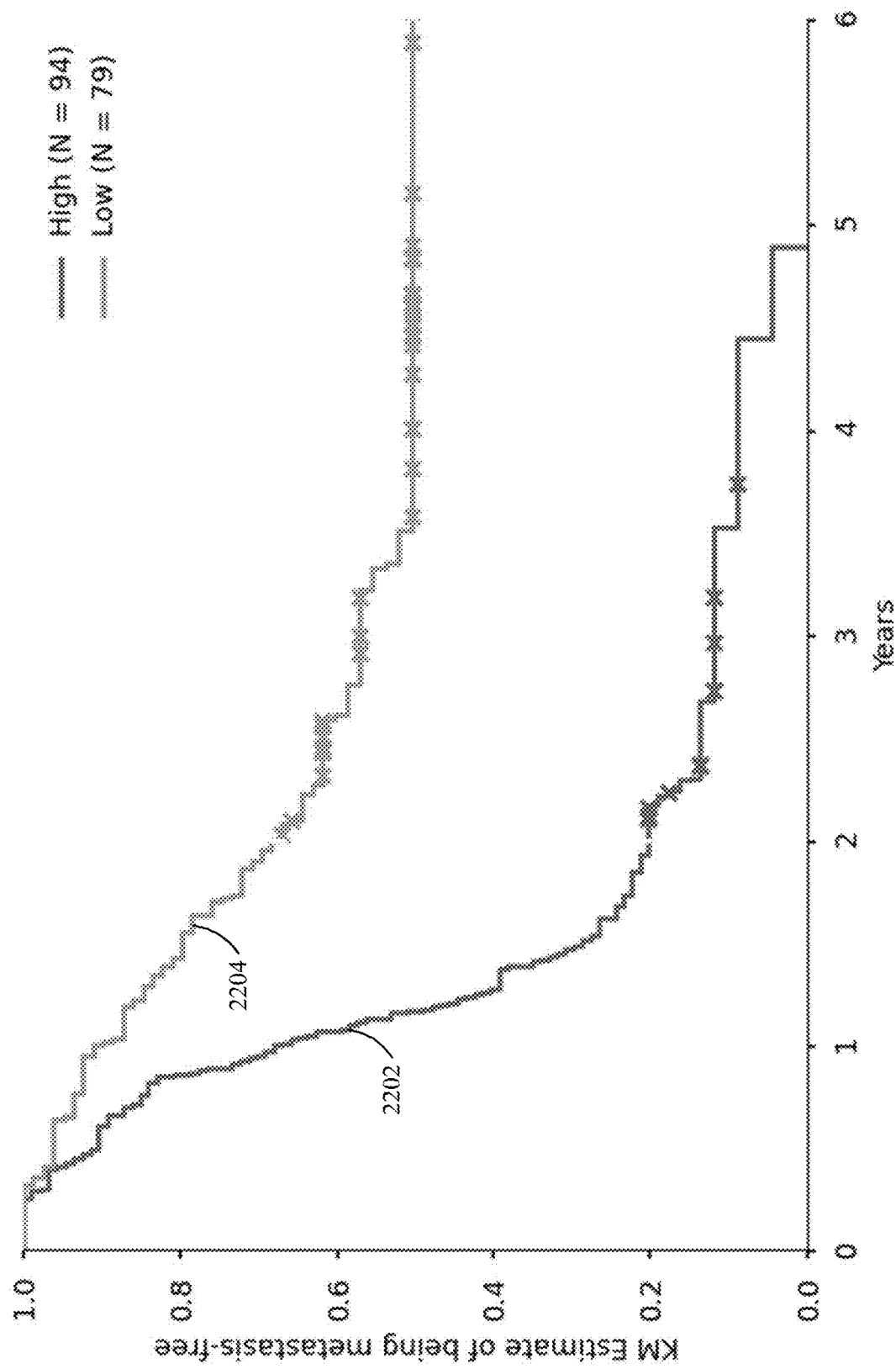
FIG. 22 illustrates survival curves of a survival model showing predicted metastasis-free survival for high-risk patients (2202) and low-risk patients (2204), in accordance with some embodiments of the present disclosure.
Figure 23:
FIG. 23 illustrates an example report generated based on the analysis of patient data using a predictive model of metastasis, in accordance with some embodiments of the disclosure.

Briefly, RNA expression data was normalized to transcripts per million (TPM) for all genes. The top 100 most correlated genes were then identified for each training run by Spearman Rank correlation. The data from a single patient was removed from the training cohort and a model was fit. The process was then repeated for all the patients within the cohort. The results of this is the establishment of one model for every patient in the training cohort, and one prediction for every patient in the training cohort. A brief summary of model training is shown below:

Model Description:
 CV framework:
  Model Performance Evaluation:
   LeaveOneOut: 173 Splits
  Feature Selection:
   SurvivalSplitter, 5 Splits
 Feature Generation:
  Overall:
   Drop Column with Zero Variance
  Cross-Validated
   Drop Columns with a Low Expression (Median Expression <0)
   Keep Top 100 Features Most correlated (Spearman) with metastasis
   PowerTransforms
   Kernel PCA (Cosine Kernel) Keep First 20 Columns
   StandardScaler
 Model type:
  Cox Proportional Hazard Regression
 Hyperparameter search method and space:
  None Survival curves of the model showing predicted metastasis-free survival for high-risk patients (2202) and low-risk patients (2204) are illustrated in FIG. 22. The hazard ratio comparing the predicted high-risk group to the low-risk group is 4.21 (2.81-6.32).

The risk status for a patient was determined using a risk score threshold, which can be selected between 0% and 100% of the total possible model output (e.g., 0 to 1 for a model in which 1 represents 100% chance of metastasis). In this example, the risk threshold was determined by using the percentile from ranked predictions that corresponds to the metastasis rate of the training cohort. That is, if 74% of patients in the cohort experienced metastasis, the risk threshold is set as the predicted probability at the $26^{th}$ percentile. For instance, FIG. 19B illustrates a histogram of model scores output from an entire training cohort in which 74% of the training subjects experienced metastasis. The model score at the $26^{th}$ percentile (between 0.3 and 0.4) is set as the risk threshold.

Example 6—Multi-Modal Modeling Or Metastasis of Colorectal Cancer

To evaluate the effect of combining feature types on the ability to model metastases, a stepladder analysis, where features were added to subsequent model builds, was performed. Briefly, pathology data, tumor imaging data, DNA sequencing data, and RNA expression data was obtained from tumor samples from 146 subjects with colon or rectosigmoid junction cancer, and used to train a series of Cox Proportional Hazard model for time without metastasis of the cancer. Briefly, the inclusion criteria for selection of the training subjects was: the subject had a primary colon or rectosigmoid junction cancer diagnosis, RNA sequence data from tissue collected from the primary colorectal tumor was available, the primary colorectal cancer was not a recurrence, subjects with positive margins were excluded, subjects with metastases recorded within 30 days of sample collection were excluded, subjects staged with stage 4 cancer were excluded, patients without evidence of future metastasis must have at least two years of follow-up medical records available from members of the subject's cancer treatment team, fresh-frozen tissue samples were excluded, subjects staged with stage 1 cancer were excluded, non-adenocarcinomas were excluded, samples taken from biopsies were excluded (only samples obtained from resections were used), subjects with metastases recorded within 90 days of sample collection or who were determined to be likely metastatic at the time of sample collection were excluded, and subjects undergoing systematic treatment for an additional primary cancer within two years of the colon cancer diagnosis were excluded.

A brief summary of data preprocessing and model training is shown below:

Model Description:
  CV framework:
    Model Performance Evaluation:
      LeaveOneOut: 146 Splits
    Feature Selection:
      StratifiedKFold: 5 Splits, stratified on 2 year metastasis binary label
  Preprocessing:
    Binary encode gender
    Ordinal encode stage, N stage, and T stage as corresponding integer in [0, 1, 2, 3, 4]
    Binary encode histopath grade as 0=low grade, 1=high grade
    RNA gene expression transformed as log 2(TPM)
    Binary encode DNA features as 1=somatic pathogenic gene variant, 0=no somatic pathogenic gene variant
    Drop any columns missing all values or with zero variance
  Feature selection and inline preprocessing:
    RNA features
      Drop genes below 25th percentile of variance
      Select top 500 genes by Spearman correlation with target observed (uncensored) duration until metastasis
      Apply standard scaling (z-score) transformation
    DNA features
      Drop gene variants below 25th percentile of variance
      Extract top 8 most important features as ranked by fitting a RandomForestClassifier (2000 estimators, max depth 2, max samples 0.8) on the 2 year binary label for metastasis
    Imaging features
      Select top 100 imaging features by Spearman correlation with target observed (uncensored) duration until metastasis
      QuantileTransform features into a uniform distribution in range [−1, 1]
    Clinical features
      Apply standard scaling (z-score) transformation to age at sample collection; mean fill any missing age
      Fill any missing T stage and N stage using k-NearestNeighbors based on all other stage data
      Mean encode histology and histopath grade, such that each category value is replaced by the mean duration until metastasis within each value group
      Apply standard scaling (z-score) transformation to all clinical features
  Dimensionality reduction:
    RNA
      Singular Value Decomposition of standard scaled top 500 duration correlated genes from feature selection; retain top 20 (largest magnitude singular values) components; mean center each SVD component
    DNA
      No dimensionality reduction
    Imaging
      Singular Value Decomposition of uniform distribution features in range [−1, 1]; retain top 20 (largest magnitude singular values) components; mean center each SVD component
    Clinical
      No dimensionality reduction
  Model type:
    Cox Proportional Hazards model (lifelines python package)
    Baseline hazard predicted by spline
    L2 coefficient regularization
    Apply power calibration transformation of predictions such that the baseline survival probability equals 0.5 at 2 years
  Hyperparameter search method and space:
    Grid search maximizing the c-index of the concatenation of out-of-fold predictions in the StratifiedKFold inner cross validation loop:
      L2 regularization parameter: [0.2, 0.02, 0.002, 0.0002]

Four predictive models were trained: (i) clinical data only, (ii) clinical data and imaging data, (iii) clinical data, imaging data, and DNA somatic mutation data, and (iv) clinical data, imaging data, DNA somatic mutation data, and RNA expression data. As shown in Table 4, below, evaluation of the four models indicates that there is an additive benefit to the addition of each type of data to the predictive model, across all three metrics considered.

TABLE 4

Analysis of Cox Proportional Hazards predictive of metastases in colon or rectosigmoid junction cancer.

|  | Clinical | Clinical + Imaging | Clinical + Imaging + DNA | Clinical + Imaging + DNA + RNA |
| --- | --- | --- | --- | --- |
| Hazard ratio | 1.41 (0.98-2.02) | 1.71 (1.18-2.49) | 1.91 (1.32-2.78) | 2.76 (1.88-4.05) |
| C-index | 0.542 | 0.5855 | 0.596 | 0.641 |
| AUROC | 0.568 | 0.678 | 0.718 | 0.756 |

Example 7—RNA Expression-Based Predication Model for Metastasis of Non-Small Cell Lung Cancer (NSCLC)

RNA expression data obtained from tumor samples from subjects with NSCLC can be used to train a Cox Proportional Hazard model for time without metastasis of the cancer. In a first training, inclusion criteria includes: the subject has a primary lung cancer diagnosis with NSCLC histology, RNA sequence data from tissue collected from the primary lung tumor was available, subjects with metastases recorded within 90 days of sample collection were excluded, subjects staged with stage 4 cancer were excluded, patients without evidence of future metastasis must have at least two years of follow-up medical records available, and fresh-frozen tissue samples were excluded.

In a second training, inclusion criteria includes: the subject has a primary lung cancer diagnosis with NSCLC histology, RNA sequence data from tissue collected from the primary lung tumor was available, subjects with metastases recorded within 90 days of sample collection were excluded, subjects staged with stage 3 or stage 4 cancer were excluded, patients without evidence of future metastasis must have at least two years of follow-up medical records available, and fresh-frozen tissue samples were excluded, patients undergoing systemic treatment for an additional primary cancer within 2 years of NSCLC diagnosis (except for hormone therapy) were excluded, samples taken from recurrences were excluded (only include samples taken from initial diagnosis), patients with squamous histologies were excluded, patients who did not receive resections were excluded, patients with positive surgical margins were excluded, and EGFR positive patients were excluded.

Some trainings are performed according to the methodologies outlined in any one of Examples 1-5. Other trainings are performed using other known methodologies for training survival models.

Example 8—Multi-Modal Modeling for Metastasis of Non-Small Cell Lung Cancer (NSCLC)

Various combinations of pathology data, tumor imaging data, DNA sequencing data, and RNA expression data are used to train a model, e.g., a survival model, for predicting metastasis. inclusion criteria includes: the subject has a primary lung cancer diagnosis with NSCLC histology, RNA sequence data from tissue collected from the primary lung tumor was available, subjects with metastases recorded within 90 days of sample collection were excluded, subjects staged with stage 4 cancer were excluded, patients without evidence of future metastasis must have at least two years of follow-up medical records available, and fresh-frozen tissue samples were excluded.

In a second training, inclusion criteria includes: the subject has a primary lung cancer diagnosis with NSCLC histology, RNA sequence data from tissue collected from the primary lung tumor was available, subjects with metastases recorded within 90 days of sample collection were excluded, subjects staged with stage 3 or stage 4 cancer were excluded, patients without evidence of future metastasis must have at least two years of follow-up medical records available, and fresh-frozen tissue samples were excluded, patients undergoing systemic treatment for an additional primary cancer within 2 years of NSCLC diagnosis (except for hormone therapy) were excluded, samples taken from recurrences were excluded (only include samples taken from initial diagnosis), patients with squamous histologies were excluded, patients who did not receive resections were excluded, patients with positive surgical margins were excluded, and EGFR positive patients were excluded.

Some trainings are performed according to the methodologies outlined in Example 6. Other trainings are performed using other known methodologies for training survival models.

CONCLUSION

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may include a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

What is claimed is:

1. A method for predicting metastasis of a non-small cell lung cancer (NSCLC) in a subject, comprising:
at a computer system having one or more processors, and memory storing one or more programs for execution by the one or more processors:
(A) obtaining, in electronic format, a plurality of at least 10,000 sequence reads, wherein the plurality of sequence reads is obtained for a plurality of RNA molecules from a sample of the NSCLC obtained from the subject;
(B) determining from the plurality of at least 10,000 sequence reads, a plurality of data elements for the subject's NSCLC comprising:
a first set of sequence features comprising relative abundance values for the expression of a plurality of at least 30 genes in the sample of the NSCLC obtained from the subject; and
(C) applying, to the plurality of data elements for the subject's NSCLC comprising the first set of sequence features comprising relative abundance values for the expression of the plurality of at least 30 genes, one or more models that are collectively trained to provide a respective one or more indications of whether the NSCLC will metastasize in the subject,
thereby predicting whether the NSCLC will metastasize.

2. The method of claim 1, wherein the plurality of data elements further comprises one or more personal characteristics about the subject selected from the group consisting of age, gender, and race and wherein the (C) applying includes applying the one or more personal characteristics about the subject to the one or more models.

3. The method of claim 1, wherein the plurality of data elements further comprises one or more clinical features related to the diagnosis or treatment of the NSCLC in the subject selected from the group consisting of a stage of the NSCLC, a histopathological grade of the NSCLC, a therapy administered to the subject, a symptom associated with NSCLC or metastasis thereof, and a comorbidity with the NSCLC and wherein the (C) applying includes applying the one or more clinical features to the one or more models.

4. The method of claim 1, wherein the plurality of data elements further comprises one or more temporal features related to the diagnosis or treatment of the NSCLC in the subject selected from the group consisting of a first temporal element indicating a duration of time since a diagnosis for the NSCLC, a second temporal element indicating a duration of time since an administration of a therapy to the subject, a third temporal element indicating a duration of time since an experience of a symptom associated with NSCLC or metastasis thereof, and a fourth temporal element indicating a duration of time since an experience of a comorbidity with the NSCLC and wherein the (C) applying includes applying the one or more temporal features to the one or more models.

5. The method of claim 1, wherein the plurality of at least 30 genes comprises at least 20 genes selected from the group consisting of the genes listed in Table 2.

6. The method of claim 1, wherein the plurality of at least 30 genes is no more than 250 genes.

7. The method of claim 1, wherein the plurality of data elements further comprises a single-sample gene set enrichment analysis (ssGSEA) score for the transcriptional profile of the NSCLC and wherein the (C) applying includes applying the single-sample gene set enrichment analysis (ssGSEA) score to the one or more models.

8. The method of claim 1, wherein the plurality of data elements further comprises a smoking status or a menopausal status of the subject and wherein the (C) applying includes applying the smoking status or the menopausal status to the one or more models.

9. The method of claim 1, wherein the plurality of data elements further comprises a physical characteristic of the sample of the NSCLC and wherein the (C) applying includes applying the physical characteristic to the one or more models.

10. The method of claim 1, wherein the plurality of data elements further comprises a mutational status for one or more genes in the sample of the NSCLC and wherein the (C) applying includes applying the mutational status for the one or more genes to the one or more models.

11. The method of claim 10, wherein the mutational status is for a gene selected from the group consisting of the genes listed in Table 2.

12. The method of claim 1, wherein the plurality of data elements further comprises a mutational status for one or more genes determined from genomic fragments of a non-cancerous tissue of the subject and wherein the (C) applying includes applying the mutational status for the one or more genes to the one or more models.

13. The method of claim 1, wherein the plurality of data elements further comprises a copy number status for one or more genomic regions associated with NSCLC and wherein the (C) applying includes applying the copy number status for the one or more genomic regions to the one or more models.

14. The method of claim 1, wherein the one or more models is a set of models that are collectively trained to provide, for each respective tissue in a plurality of tissues, a corresponding set of indications, in the one or more indications, of whether the NSCLC will metastasize to the respective tissue in the subject, wherein the corresponding set of indications includes a corresponding indication for each respective time horizon in a corresponding plurality of time horizons.

15. The method of claim 14, wherein the set of models comprises, for each respective tissue in the plurality of tissues, a respective subset of models, wherein each respective model, in the respective subset of models, is trained to provide a respective indication of whether the NSCLC in the subject will metastasize to the respective tissue in the subject within a respective time horizon in the corresponding plurality of time horizons.

16. The method of claim 14, wherein:
the corresponding plurality of time horizons for each respective tissue in the plurality of tissues is the same plurality of time horizons; and
the set of models comprises, for each respective time horizon in the plurality of time horizons, a respective model trained to provide, for each respective tissue in the plurality of tissues, a corresponding indication of whether the NSCLC in the subject will metastasize to the respective tissue in the subject within the respective time horizon.

17. The method of claim 14, wherein the set of models comprises, for each respective tissue in the plurality of tissues, a corresponding model trained to provide, for each respective time horizon in the corresponding plurality of time horizons, a corresponding indication of whether the NSCLC in the subject will metastasize to the respective tissue in the subject within the respective time horizon.

18. The method of claim 14, wherein:
the set of models comprises a respective model trained to provide, for each respective time horizon in a plurality of time horizons, a respective indication of whether the NSCLC will metastasize to any tissue in the subject; and
the plurality of indications of whether the NSCLC will metastasize includes, for each respective time horizon in the plurality of time horizons, a corresponding indication of whether the NSCLC will metastasize to any tissue in the subject.

19. The method of claim 14, wherein the plurality of tissues comprises adrenal gland tissue, bone tissue, brain tissue, and liver tissue.

20. The method of claim 14, the method further comprising:
(D) generating a clinical report comprising the one or more indications of whether the NSCLC will metastasize; and
(E) displaying the clinical report in a graphical user interface (GUI), wherein the GUI comprises an anatomical representation of a body and a first affordance configured for switching between respective time horizons in the plurality of time horizons, the displaying comprising:
displaying a first rendering of metastatic predictions comprising, for each respective tissue in the plurality of tissues, a corresponding visual representation of the respective indication, in the plurality of indications, corresponding to whether the NSCLC in the subject will metastasize to the respective tissue within a first respective time horizon, in the corresponding plurality of time horizons, wherein the rendering is superposed upon the anatomical representation of the body; and
responsive to receiving a user input corresponding to the first affordance on the GUI, replacing display of the first rendering of metastatic predictions with display of a second rendering of metastatic predictions comprising, for each respective tissue in the plurality of tissues, a corresponding visual representation of the respective indication, in the plurality of indications, corresponding to whether the NSCLC in the subject will metastasize to the respective tissue within a second respective time horizon in the corresponding plurality of time horizons, wherein the rendering is superposed upon the anatomical representation of the body.

21. The method of claim 1, wherein the one or more models comprises a trained survival function.

22. The method of claim 1, the method further comprising:
when the one or more indications of whether the NSCLC will metastasize satisfies a first threshold risk for metastasis of the NSCLC, administering a first therapy tailored for treatment of metastatic NSCLC; and
when the one or more indications of whether the cancer will metastasize does not satisfy the first threshold risk for metastasis of the NSCLC, administering a second therapy tailored for treatment of non-metastatic NSCLC.

23. The method of claim 1, the method further comprising, prior to the (C) applying, training the one or more models using (i) values for the corresponding plurality of data elements across a plurality of training subjects that have NSCLC, wherein a portion of the plurality of training subjects have metastasized NSCLC and a portion of the training subjects have NSCLC that has not metastasized, and wherein the corresponding plurality of data elements serve as independent variables in the training and (ii) a corresponding indication for each respective training subject in the plurality of training subjects, of whether the respective training subject's NSCLC metastasized, wherein the indication serves as a dependent variable in the training thereby obtaining the one or more models that are collectively trained to provide a respective one or more indications of whether the NSCLC will metastasize in a subject.

24. The method of claim 1, the method further comprising generating a clinical report comprising the one or more indications of whether the NSCLC will metastasize.

25. The method of claim 1, wherein the plurality of at least 10,000 sequence reads is at least 100,000 sequence reads.

26. The method of claim 1, wherein the plurality of at least 10,000 sequence reads is at least 1,000,000 sequence reads.

27. A computer system having one or more processors, and memory storing one or more programs for execution by the one or more processors, the one or more programs comprising instructions for performing a method for predicting metastasis of a non-small cell lung cancer (NSCLC) in a subject, the method comprising:
(A) obtaining, in electronic format, a plurality of at least 10,000 sequence reads, wherein the plurality of sequence reads is obtained for a plurality of RNA molecules from a sample of the NSCLC obtained from the subject;
(B) determining from the plurality of at least 10,000 sequence reads, a plurality of data elements for the subject's NSCLC comprising:
a first set of sequence features comprising relative abundance values for the expression of a plurality of at least 30 genes in the sample of the NSCLC obtained from the subject; and
(C) applying, to the plurality of data elements for the subject's NSCLC comprising the first set of sequence features comprising relative abundance values for the expression of the plurality of at least 30 genes, one or more models that are collectively trained to provide a respective one or more indications of whether the NSCLC will metastasize in the subject, thereby predicting whether the NSCLC will metastasize.

28. The computer system of claim 27, wherein the plurality of data elements further comprises one or more personal characteristics about the subject selected from the group consisting of age, gender, and race and wherein the (C) applying includes applying the one or more personal characteristics about the subject to the one or more models.

29. The computer system of claim 27, wherein the plurality of data elements further comprises one or more clinical features related to the diagnosis or treatment of the NSCLC in the subject selected from the group consisting of a stage of the NSCLC, a histopathological grade of the NSCLC, a therapy administered to the subject, a symptom associated with NSCLC or metastasis thereof, and a comorbidity with the NSCLC and wherein the (C) applying includes applying the one or more clinical features to the one or more models.

30. The computer system of claim 27, wherein the plurality of data elements further comprises one or more temporal features related to the diagnosis or treatment of the NSCLC in the subject selected from the group consisting of a first temporal element indicating a duration of time since a diagnosis for the NSCLC, a second temporal element indicating a duration of time since an administration of a therapy to the subject, a third temporal element indicating a duration of time since an experience of a symptom associated with NSCLC or metastasis thereof, and a fourth temporal element indicating a duration of time since an experience of a comorbidity with the NSCLC and wherein the (C) applying includes applying the one or more temporal features to the one or more models.

31. The computer system of claim 27, wherein the plurality of at least 30 genes comprises at least 20 genes selected from the group consisting of the genes listed in Table 2.

32. The computer system of claim 27, wherein the plurality of at least 30 genes is no more than 250 genes.

33. The computer system of claim 27, wherein the plurality of data elements further comprises a single-sample gene set enrichment analysis (ssGSEA) score for the transcriptional profile of the NSCLC and wherein the (C) applying includes applying the single-sample gene set enrichment analysis (ssGSEA) score to the one or more models.

34. The computer system of claim 27, wherein the plurality of data elements further comprises a smoking status or a menopausal status of the subject and wherein the (C) applying includes applying the smoking status or the menopausal status to the one or more models.

35. The computer system of claim 27, wherein the plurality of data elements further comprises a physical characteristic of the sample of the NSCLC and wherein the (C) applying includes applying the physical characteristic to the one or more models.

36. The computer system of claim 27, wherein the plurality of data elements further comprises a mutational status for one or more genes in the sample of the NSCLC and wherein the (C) applying includes applying the mutational status for the one or more genes to the one or more models.

37. The computer system of claim 36, wherein the mutational status is for a gene selected from the group consisting of the genes listed in Table 2.

38. The computer system of claim 27, wherein the plurality of data elements further comprises a mutational status for one or more genes determined from genomic fragments of a non-cancerous tissue of the subject and wherein the (C) applying includes applying the mutational status for the one or more genes to the one or more models.

39. The computer system of claim 27, wherein the plurality of data elements further comprises a copy number status for one or more genomic regions associated with NSCLC and wherein the (C) applying includes applying the copy number status for the one or more genomic regions to the one or more models.

40. The computer system of claim 27, wherein the one or more models is a set of models that are collectively trained to provide, for each respective tissue in a plurality of tissues, a corresponding set of indications, in the one or more indications, of whether the NSCLC will metastasize to the respective tissue in the subject, wherein the corresponding set of indications includes a corresponding indication for each respective time horizon in a corresponding plurality of time horizons.

41. The computer system of claim 40, wherein the set of models comprises, for each respective tissue in the plurality of tissues, a respective subset of models, wherein each respective model, in the respective subset of models, is trained to provide a respective indication of whether the NSCLC in the subject will metastasize to the respective tissue in the subject within a respective time horizon in the corresponding plurality of time horizons.

42. The computer system of claim 40, wherein:
the corresponding plurality of time horizons for each respective tissue in the plurality of tissues is the same plurality of time horizons; and
the set of models comprises, for each respective time horizon in the plurality of time horizons, a respective model trained to provide, for each respective tissue in the plurality of tissues, a corresponding indication of whether the NSCLC in the subject will metastasize to the respective tissue in the subject within the respective time horizon.

43. The computer system of claim 40, wherein the set of models comprises, for each respective tissue in the plurality of tissues, a corresponding model trained to provide, for each respective time horizon in the corresponding plurality of time horizons, a corresponding indication of whether the NSCLC in the subject will metastasize to the respective tissue in the subject within the respective time horizon.

44. The computer system of claim 40, wherein:
the set of models comprises a respective model trained to provide, for each respective time horizon in a plurality of time horizons, a respective indication of whether the NSCLC will metastasize to any tissue in the subject; and
the plurality of indications of whether the NSCLC will metastasize includes, for each respective time horizon in the plurality of time horizons, a corresponding indication of whether the NSCLC will metastasize to any tissue in the subject.

45. The computer system of claim 40, wherein the plurality of tissues comprises adrenal gland tissue, bone tissue, brain tissue, and liver tissue.

46. The computer system of claim 40, wherein the one or more programs further comprise instructions for:
(D) generating a clinical report comprising the one or more indications of whether the NSCLC will metastasize; and
(E) displaying the clinical report in a graphical user interface (GUI), wherein the GUI comprises an anatomical representation of a body and a first affordance configured for switching between respective time horizons in the plurality of time horizons, the displaying comprising:
displaying a first rendering of metastatic predictions comprising, for each respective tissue in the plurality of tissues, a corresponding visual representation of the respective indication, in the plurality of indications, corresponding to whether the NSCLC in the subject will metastasize to the respective tissue within a first respective time horizon, in the corresponding plurality of time horizons, wherein the rendering is superposed upon the anatomical representation of the body; and
responsive to receiving a user input corresponding to the first affordance on the GUI, replacing display of the first rendering of metastatic predictions with display of a second rendering of metastatic predictions comprising, for each respective tissue in the plurality of tissues, a corresponding visual representation of the respective indication, in the plurality of indications, corresponding to whether the NSCLC in the subject will metastasize to the respective tissue within a second respective time horizon in the corresponding plurality of time horizons, wherein the rendering is superposed upon the anatomical representation of the body.

47. The computer system of claim 27, wherein the one or more models comprises a trained survival function.

48. The computer system of claim 27, wherein the one or more programs further comprise instructions for, prior to the (C) applying, training the one or more models using (i) values for the corresponding plurality of data elements across a plurality of training subjects that have NSCLC, wherein a portion of the plurality of training subjects have metastasized NSCLC and a portion of the training subjects have NSCLC that has not metastasized, and wherein the corresponding plurality of data elements serve as independent variables in the training and (ii) a corresponding indication for each respective training subject in the plurality of training subjects, of whether the respective training subject's NSCLC metastasized, wherein the indication serves as a dependent variable in the training thereby obtaining the one or more models that are collectively trained to provide a respective one or more indications of whether the NSCLC will metastasize in a subject.

49. The computer system of claim 27, wherein the one or more programs further comprise instructions for generating a clinical report comprising the one or more indications of whether the NSCLC will metastasize.

50. The computer system of claim 27, wherein the plurality of at least 10,000 sequence reads is at least 100,000 sequence reads.

51. The computer system of claim 27, wherein the plurality of at least 10,000 sequence reads is at least 1,000,000 sequence reads.

52. A non-transitory computer readable storage medium storing one or more programs configured for execution by a computer, the one or more programs comprising instructions for carrying out a method for predicting metastasis of a non-small cell lung cancer (NSCLC) in a subject, the method comprising:
  (A) obtaining, in electronic format, a plurality of at least 10,000 sequence reads, wherein the plurality of sequence reads is obtained for a plurality of RNA molecules from a sample of the NSCLC obtained from the subject;
  (B) determining from the plurality of at least 10,000 sequence reads, a plurality of data elements for the subject's NSCLC comprising:
    a first set of sequence features comprising relative abundance values for the expression of a plurality of at least 30 genes in the sample of the NSCLC obtained from the subject; and
  (C) applying, to the plurality of data elements for the subject's NSCLC comprising the first set of sequence features comprising relative abundance values for the expression of the plurality of at least 30 genes, one or more models that are collectively trained to provide a respective one or more indications of whether the NSCLC will metastasize in the subject, thereby predicting whether the NSCLC will metastasize.

53. The non-transitory computer readable storage medium of claim 52, wherein the plurality of data elements further comprises one or more personal characteristics about the subject selected from the group consisting of age, gender, and race and wherein the (C) applying includes applying the one or more personal characteristics about the subject to the one or more models.

54. The non-transitory computer readable storage medium of claim 52, wherein the plurality of data elements further comprises one or more clinical features related to the diagnosis or treatment of the NSCLC in the subject selected from the group consisting of a stage of the NSCLC, a histopathological grade of the NSCLC, a therapy administered to the subject, a symptom associated with NSCLC or metastasis thereof, and a comorbidity with the NSCLC and wherein the (C) applying includes applying the one or more clinical features to the one or more models.

55. The non-transitory computer readable storage medium of claim 52, wherein the plurality of data elements further comprises one or more temporal features related to the diagnosis or treatment of the NSCLC in the subject selected from the group consisting of a first temporal element indicating a duration of time since a diagnosis for the NSCLC, a second temporal element indicating a duration of time since an administration of a therapy to the subject, a third temporal element indicating a duration of time since an experience of a symptom associated with NSCLC or metastasis thereof, and a fourth temporal element indicating a duration of time since an experience of a comorbidity with the NSCLC and wherein the (C) applying includes applying the one or more temporal features to the one or more models.

56. The non-transitory computer readable storage medium of claim 52, wherein the plurality of at least 30 genes comprises at least 20 genes selected from the group consisting of the genes listed in Table 2.

57. The non-transitory computer readable storage medium of claim 52, wherein the plurality of at least 30 genes is no more than 250 genes.

58. The non-transitory computer readable storage medium of claim 52, wherein the plurality of data elements further comprises a single-sample gene set enrichment analysis (ssGSEA) score for the transcriptional profile of the NSCLC and wherein the (C) applying includes applying the single-sample gene set enrichment analysis (ssGSEA) score to the one or more models.

59. The non-transitory computer readable storage medium of claim 52, wherein the plurality of data elements further comprises a smoking status or a menopausal status of the subject and wherein the (C) applying includes applying the smoking status or the menopausal status to the one or more models.

60. The non-transitory computer readable storage medium of claim 52, wherein the plurality of data elements further comprises a physical characteristic of the sample of the NSCLC and wherein the (C) applying includes applying the physical characteristic to the one or more models.

61. The non-transitory computer readable storage medium of claim 52, wherein the plurality of data elements further comprises a mutational status for one or more genes in the sample of the NSCLC and wherein the (C) applying includes applying the mutational status for the one or more genes to the one or more models.

62. The non-transitory computer readable storage medium of claim 61, wherein the mutational status is for a gene selected from the group consisting of the genes listed in Table 2.

63. The non-transitory computer readable storage medium of claim 52, wherein the plurality of data elements further comprises a mutational status for one or more genes determined from genomic fragments of a non-cancerous tissue of the subject and wherein the (C) applying includes applying the mutational status for the one or more genes to the one or more models.

64. The non-transitory computer readable storage medium of claim 52, wherein the plurality of data elements further comprises a copy number status for one or more genomic regions associated with NSCLC and wherein the (C) applying includes applying the copy number status for the one or more genomic regions to the one or more models.

65. The non-transitory computer readable storage medium of claim 52, wherein the one or more models is a set of models that are collectively trained to provide, for each respective tissue in a plurality of tissues, a corresponding set of indications, in the one or more indications, of whether the NSCLC will metastasize to the respective tissue in the subject, wherein the corresponding set of indications includes a corresponding indication for each respective time horizon in a corresponding plurality of time horizons.

66. The non-transitory computer readable storage medium of claim 65, wherein the set of models comprises, for each respective tissue in the plurality of tissues, a respective subset of models, wherein each respective model, in the respective subset of models, is trained to provide a respective indication of whether the NSCLC in the subject will metastasize to the respective tissue in the subject within a respective time horizon in the corresponding plurality of time horizons.

67. The non-transitory computer readable storage medium of claim 65, wherein:
the corresponding plurality of time horizons for each respective tissue in the plurality of tissues is the same plurality of time horizons; and
the set of models comprises, for each respective time horizon in the plurality of time horizons, a respective model trained to provide, for each respective tissue in the plurality of tissues, a corresponding indication of whether the NSCLC in the subject will metastasize to the respective tissue in the subject within the respective time horizon.

68. The non-transitory computer readable storage medium of claim 65, wherein the set of models comprises, for each respective tissue in the plurality of tissues, a corresponding model trained to provide, for each respective time horizon in the corresponding plurality of time horizons, a corresponding indication of whether the NSCLC in the subject will metastasize to the respective tissue in the subject within the respective time horizon.

69. The non-transitory computer readable storage medium of claim 65, wherein:
the set of models comprises a respective model trained to provide, for each respective time horizon in a plurality of time horizons, a respective indication of whether the NSCLC will metastasize to any tissue in the subject; and
the plurality of indications of whether the NSCLC will metastasize includes, for each respective time horizon in the plurality of time horizons, a corresponding indication of whether the NSCLC will metastasize to any tissue in the subject.

70. The non-transitory computer readable storage medium of claim 65, wherein the plurality of tissues comprises adrenal gland tissue, bone tissue, brain tissue, and liver tissue.

71. The non-transitory computer readable storage medium of claim 65, wherein the one or more programs further comprise instructions for:
(D) generating a clinical report comprising the one or more indications of whether the NSCLC will metastasize; and (E) displaying the clinical report in a graphical user interface (GUI), wherein the GUI comprises an anatomical representation of a body and a first affordance configured for switching between respective time horizons in the plurality of time horizons, the displaying comprising:
displaying a first rendering of metastatic predictions comprising, for each respective tissue in the plurality of tissues, a corresponding visual representation of the respective indication, in the plurality of indications, corresponding to whether the NSCLC in the subject will metastasize to the respective tissue within a first respective time horizon, in the corresponding plurality of time horizons, wherein the rendering is superposed upon the anatomical representation of the body; and
responsive to receiving a user input corresponding to the first affordance on the GUI, replacing display of the first rendering of metastatic predictions with display of a second rendering of metastatic predictions comprising, for each respective tissue in the plurality of tissues, a corresponding visual representation of the respective indication, in the plurality of indications, corresponding to whether the NSCLC in the subject will metastasize to the respective tissue within a second respective time horizon in the corresponding plurality of time horizons, wherein the rendering is superposed upon the anatomical representation of the body.

72. The non-transitory computer readable storage medium of claim 52, wherein the one or more models comprises a trained survival function.

73. The non-transitory computer readable storage medium of claim 52, wherein the one or more programs further comprise instructions for, prior to the (C) applying, training the one or more models using (i) values for the corresponding plurality of data elements across a plurality of training subjects that have NSCLC, wherein a portion of the plurality of training subjects have metastasized NSCLC and a portion of the training subjects have NSCLC that has not metastasized, and wherein the corresponding plurality of data elements serve as independent variables in the training and (ii) a corresponding indication for each respective training subject in the plurality of training subjects, of whether the respective training subject's NSCLC metastasized, wherein the indication serves as a dependent variable in the training thereby obtaining the one or more models that are collectively trained to provide a respective one or more indications of whether the NSCLC will metastasize in a subject.

74. The non-transitory computer readable storage medium of claim 52, wherein the one or more programs further comprise instructions for generating a clinical report comprising the one or more indications of whether the NSCLC will metastasize.

75. The non-transitory computer readable storage medium of claim 52, wherein the plurality of at least 10,000 sequence reads is at least 100,000 sequence reads.

76. The non-transitory computer readable storage medium of claim 52, wherein the plurality of at least 10,000 sequence reads is at least 1,000,000 sequence reads.

* * * * *